United States Patent
Burkhardt et al.

(10) Patent No.: US 6,870,016 B1
(45) Date of Patent: Mar. 22, 2005

(54) POLYMERIZATION PROCESS AND POLYMER COMPOSITION

(75) Inventors: Terry J. Burkhardt, Kingwood, TX (US); James R. Hart, Pasadena, TX (US); William T. Haygood, Houston, TX (US); Robert T. Li, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 280 days.

(21) Appl. No.: 09/896,494

(22) Filed: Jun. 29, 2001

Related U.S. Application Data

(60) Provisional application No. 60/215,597, filed on Jun. 30, 2000.

(51) Int. Cl.⁷ .............................. C08F 4/64; C08F 4/68; C08F 4/69; C08F 4/642
(52) U.S. Cl. ...................... 526/127; 526/134; 526/160; 526/161; 526/166; 526/172; 526/943
(58) Field of Search ................................ 526/127, 134, 526/160, 943

(56) References Cited

U.S. PATENT DOCUMENTS

| | | | |
|---|---|---|---|
| 5,753,769 A | 5/1998 | Ueda et al. | |
| 5,770,753 A | 6/1998 | Küber et al. | |
| 5,789,634 A | 8/1998 | Sullivan et al. | |
| 5,840,644 A | 11/1998 | Küber et al. | |
| 5,936,053 A | 8/1999 | Fukuoka et al. | |
| 6,500,949 B2 * | 12/2002 | Campbell et al. | 544/64 |
| 6,686,055 B2 * | 2/2004 | Tanaka et al. | 428/516 |

FOREIGN PATENT DOCUMENTS

| | | | | |
|---|---|---|---|---|
| CA | 2191661 | * | 2/1997 | |
| CA | 2191661 | | 6/1997 | |
| EP | 0 629 632 A | | 12/1994 | |
| EP | 0 646 624 A | | 4/1995 | |
| EP | 0 704 461 A | | 4/1996 | |
| EP | 0 704 463 A | | 4/1996 | |
| EP | 0 776 913 A | | 6/1997 | |
| EP | 0 816 395 A | | 1/1998 | |
| EP | 0 846 696 A | | 6/1998 | |
| EP | 0 775 148 B | | 8/1999 | |
| WO | WO 98/40331 | | 9/1998 | |
| WO | WO 98/40416 | | 9/1998 | |
| WO | WO 98/40419 | | 9/1998 | |
| WO | WO 99/12943 | * | 3/1999 | |
| WO | WO 99/33881 | | 7/1999 | |
| WO | WO 99/42497 | | 8/1999 | |
| WO | WO 00/20462 | | 4/2000 | |
| WO | WO 01/14388 | | 3/2001 | C07F/7/00 |

OTHER PUBLICATIONS

U.S. Appl. No. 09/620,046, filed Jul. 19, 2000 (Inventors Mathew C. Kuchta, Udo M. Stehling, Robert T. Li, William T. Haygood, Jr. & Terry J. Burkhardt), entitled "Metallocene Compositions". (2000B039A).

U.S. Appl. No. 09/620,359, filed Jul. 19, 2000 (Inventors Mathew C. Kuchta, Udo M. Stehling, Robert T. Li, William T. Haygood, Jr. & Terry J. Burkhardt), entitled "Metallocene Compositions". (2000B039B).

U.S. Appl. No. 09/620,341, filed Jul. 19, 2000 (Inventors Mathew C. Kuchta, Udo M. Stehling, Robert T. Li, William T. Haygood, Jr. & Terry J. Burkhardt), entitled "Metallocene Compositions". (2000B039C).

U.S. Appl. No. 09/619,751, filed Jul. 19, 2000 (Inventors Mathew C. Kuchta, Udo M. Stehling, Robert T. Li, William T. Haygood, Jr. & Terry J. Burkhardt), entitled "Metallocene Compositions". (2000B039D).

U.S. Appl. No. 09/619,757, filed Jul. 19, 2000 (Inventors Mathew C. Kuchta, Udo M. Stehling, Robert T. Li, William T. Haygood, Jr. & Terry J. Burkhardt), entitled "Metallocene Compositions". (2000B039E).

U.S. Appl. No. 09/620,613, filed Jul. 19, 2000 (Inventors Mathew C. Kuchta, Udo M. Stehling, Robert T. Li, William T. Haygood, Jr. & Terry J. Burkhardt), entitled "Metallocene Compositions". (2000B039F).

(List continued on next page.)

*Primary Examiner*—Roberto Rabago
(74) *Attorney, Agent, or Firm*—Paige Schmidt

(57) ABSTRACT

Olefin polymerization processes using catalyst systems based on metallocenes and olefin, in particular, propylene polymers obtainable thereby. The metallocenes may be represented by the formula:

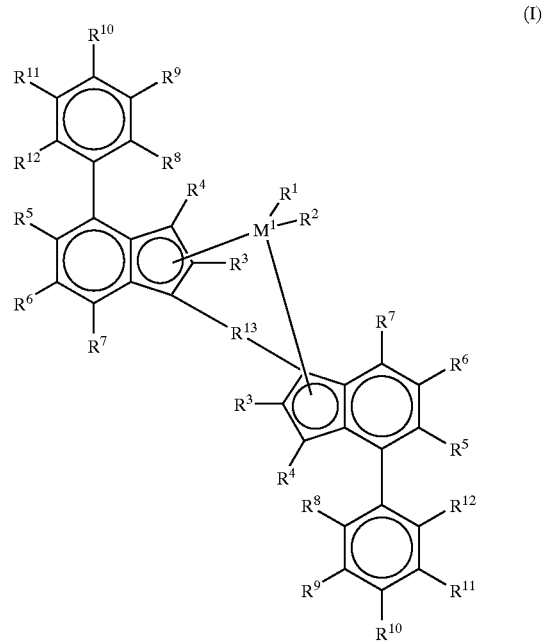

wherein $M^1$ preferably is zirconium or hafnium; and $R^{12}$ is different from hydrogen.

36 Claims, No Drawings

OTHER PUBLICATIONS

U.S. Appl. No. 09/620,175, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions". (2000B040A).

U.S. Appl. No. 09/619,759, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions". (2000B040B).

U.S. Appl. No. 09/619,748, filed Jul. 19, 2001 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions". (2000B040C).

U.S. Appl. No. 09/620,304, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions". (2000B040D).

U.S. Appl. No. 09/620,522, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions". (2000B040E).

U.S. Appl. No. 09/619,752, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions". (2000B040F).

U.S. Appl. No. 09/619,750, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions". (2000B040G).

U.S. Appl. No. 09/619,749, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions". (2000B040H).

U.S. Appl. No. 09/620,303, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions". (2000B040I).

U.S. Appl. No. 09/619,764, filed Jul. 19, 2000 (Inventors Mathew C. Kuchta, Udo M. Stehling Robert T. Li, William T. Haygood, Jr. James R. Hart, James Charles Vizzini & Terry J. Burkhardt), entitled "Metallocene Compositions". (2000B040J).

U.S. Appl. No. 09/620,302, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions". (2000B040K).

U.S. Appl. No. 09/620,198, filed Jul. 19, 2000 (Inventors Mathew C. Kuchta, Udo M. Stehling, Robert T. Li, William T. Haygood, Jr. James R. Hart, James Charles Vizzini & Terry J. Burkhardt), entitled "Metallocene Compositions". (2000B040L).

D.P. Krut'ko et al., "Synthesis and photoinduced isomerization of ansa–{$\eta^5$, $\eta^5$,–[1,1'–(1–silacyclopent–3–ene3–1m, 1–diyl)bis(indenyl)]}–dichlorozirconium. The crystal structure of its meso form"—*Russian Chemical Bulletin* vol. 47 (11), Nov., 1998—pp. 2280–2285.

Woei–Min Tsai et al., "Silolene–Bridged Zirconocenium Polymerization Catalysts" *Journal of Polymer Science, Part A: Polymer Chemistry*, vol. 32, pp. 149–158 (1994).

U.S. Appl. No. Not Yet Assigned, filed Jun. 29, 2001 (Inventors Terry J. Burkhardt, James R. Hart, William T. Haygood, Jr., and Robert T. Li), entitled "Metallocene and Catalyst Compositions". (2001B070).

* cited by examiner

POLYMERIZATION PROCESS AND POLYMER COMPOSITION

CROSS-REFERENCE TO RELATED APPLICATIONS

The present application claims priority under 35 U.S.C. § 119 of Provisional Application U.S. Ser. No. 60/215,597 filed Jun. 30, 2000, the disclosure of which is expressly incorporated herein by reference in its entirety.

FIELD

This invention relates to metallocene compounds and their use in the preparation of catalyst compositions for olefin polymerization, particularly propylene homo- and copolymerization. The present invention also relates to polymerisation processes using such catalyst compositions and polymer compositions obtainable by these processes.

BACKGROUND

The use of metallocene compositions in olefin polymerization is well known. Metallocenes containing substituted, bridged indenyl derivatives are noted for their ability to produce isotactic propylene polymers having high isotacticity and narrow molecular weight distribution. Considerable effort has been made toward obtaining metallocene produced propylene polymers having ever-higher molecular weight and melting point and, thus, ever better strength (impact) properties, while maintaining suitable catalyst activity.

Toward this end researchers have found that there is a direct relationship between the way in which a metallocene is substituted and the molecular structure of the resulting polymer. For the substituted, bridged indenyl type metallocenes, it is now well established that the type and arrangement of substituents on the indenyl groups, as well as the type of bridge connecting the indenyl groups, determines such polymer attributes as molecular weight and melting point.

For example, U.S. Pat. Nos. 5,840,644 and 5,770,753, incorporated herein by reference in their entireties, describe certain metallocenes containing aryl-substituted indenyl derivatives as ligands, which are said to provide propylene polymers having high isotacticity, narrow molecular weight distribution and very high molecular weight.

Likewise, U.S. Pat. No. 5,936,053, incorporated herein by reference in its entirety, describes certain metallocene compounds said to be useful for producing high molecular weight propylene polymers. These metallocenes have a specific hydrocarbon substituent at the 2 position and an unsubstituted aryl substituent at the 4 position on each indenyl group of the metallocene compound.

WO 98/40419 and WO 99/42497 both describe certain supported catalyst systems for producing propylene polymers having high melting point. Metallocene compositions and their activators are often combined with a support material in order to obtain a catalyst system that is less likely to cause reactor fouling. However, it is known that supported metallocene catalyst systems tend to result in a polymer having lower melting point than would otherwise be obtained if the metallocene were not supported.

Much of the current research in this area has been directed toward using metallocene catalyst systems under commercially relevant process conditions, to obtain propylene polymers having melting points higher than known metallocene catalyst systems and close to, or as high as, propylene polymers obtained using conventional, Ziegler-Natta catalyst systems. The present inventors have discovered metallocene compounds that not only have this capability, but retain it upon supportation.

Additionally, it would be desirable to have available metallocenes which not only afford propylene homopolymers having high melting points of (i.e., high stereotacticity), but also elastomeric copolymers having the high molecular weights required for the production of, e.g., impact copolymers, thereby making possible the production of satisfactory in situ blends of, e.g., propylene homopolymer and ethylene-propylene rubbers (EPR's) with a single catalyst composition in a single reactor or in a series of two or more reactors. The present inventors have found metallocene compounds which in combination with a cocatalyst (activator) make both propylene homopolymers having high melting points and elastomeric copolymers that are suitable for the production of impact copolymers in combination with these propylene homopolymers.

SUMMARY OF THE INVENTION

The present invention relates to novel metallocene compounds capable of providing propylene homo- and copolymers having high melting point and high molecular weight. The present invention further relates to metallocene catalyst compositions comprising one or more of these compounds and one or more activators or cocatalysts, and optionally, support material, and to the use of such catalyst compositions in polymerization, in particular propylene polymerization.

In one aspect, the present invention provides metallocene compounds represented by formula (I):

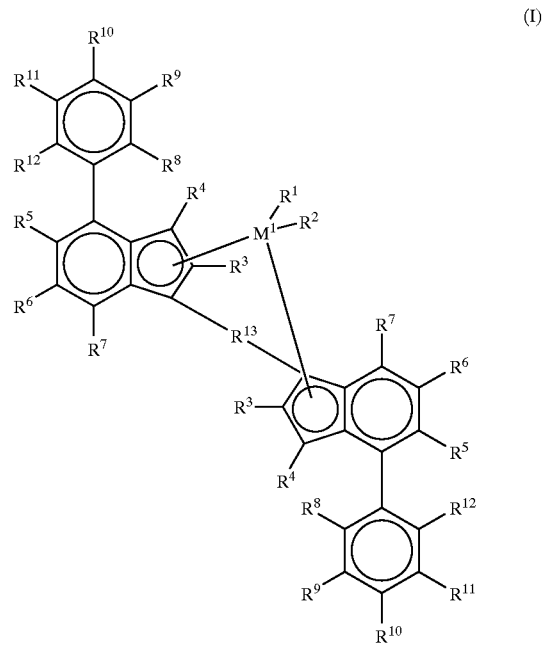

wherein:
M$^1$ is selected from titanium, zirconium, hafnium, vanadium, niobium, tantalum, chromium, molybdenum and tungsten;
R$^1$ and R$^2$ are selected from hydrogen, halogen, hydroxy, C$_1$–C$_{10}$ alkyl groups, C$_1$–C$_{10}$ alkoxy groups, C$_6$–C$_{14}$ aryl groups, C$_6$–C$_{14}$ aryloxy groups, C$_2$–C$_{10}$ alkenyl groups, $C_7$–$C_{40}$ arylalkyl groups, $C_7$–$C_{40}$ alkylaryl groups and $C_7$–$C_{40}$ arylalkenyl groups; or $R^1$ and $R^2$ are joined together to form a $C_4$–$C_{40}$ alkanediyl group or a conjugated diene ligand which is coordinated to $M^1$ in a metallacyclopentene fashion; or $R^1$ and $R^2$ represent a conjugated diene, optionally substituted with one or more groups independently selected from hydrocarbyl, trihydrocarbylsilyl and trihydrocarbylsilylhydrocarbyl groups, said diene having a total of up to 40 atoms not counting hydrogen and forming a π complex with $M^1$;

$R^3$ is selected from hydrogen, halogen, $C_1$–$C_{10}$ alkyl groups, $C_6$–$C_{14}$ aryl groups, $C_2$–$C_{10}$ alkenyl groups, $C_7$–$C_{40}$ arylalkyl groups, $C_7$–$C_{40}$ alkylaryl groups, $C_8$–$C_{40}$ arylalkenyl groups, and —NR'$_2$, —SR', —OR', —SiR'$_3$, —OSiR'$_3$ and —PR'$_2$ radicals wherein each R' is independently selected from halogen, $C_1$–$C_{10}$ alkyl groups and $C_6$–$C_{14}$ aryl groups; provided that if $R^1$ and $R^2$ both are halogen and $R^{13}$ is dimethylsilanediyl, $R^3$ is different from methyl and ethyl;

$R^4$, $R^5$, $R^6$ and $R^7$ are each independently selected from hydrogen, halogen, $C_1$–$C_{10}$ alkyl groups, $C_6$–$C_{14}$ aryl groups, $C_2$–$C_{10}$ alkenyl groups, $C_7$–$C_{40}$ arylalkyl groups, $C_7$–$C_{40}$ alkylaryl groups, $C_8$–$C_{40}$ arylalkenyl groups, and —NR'$_2$, —SR', —OR', —SiR'$_3$, —OSiR'$_3$ and —PR'$_2$ radicals wherein each R' is independently selected from halogen, $C_1$–$C_{10}$ alkyl groups and $C_6$–$C_{14}$ aryl groups; or two or more adjacent radicals $R^5$, $R^6$ and $R^7$ together with the atoms connecting them may form one or more rings; $R^8$, $R^9$, $R^{10}$ and $R^{11}$ are each independently as defined for $R^4$, $R^5$, $R^6$ and $R^7$, provided that two or more adjacent radicals $R^{8,}$ $R^9$, $R^{10}$ and $R^{11}$ together with the atoms connecting them may form one or more rings;

$R^{12}$ is selected from halogen, $C_1$–$C_{10}$ alkyl groups, $C_6$–$C_{14}$ aryl groups, $C_2$–$C_{10}$ alkenyl groups, $C_7$–$C_{40}$ arylalkyl groups, $C_7$–$C_{40}$ alkylaryl groups, $C_8$–$C_{40}$ arylalkenyl groups, and —NR'$_2$, —SR', —OR', —SiR'$_3$, —OSiR'$_3$ and —PR'$_2$ radicals wherein each R' is independently selected from halogen, $C_1$–$C_{10}$ alkyl groups and $C_6$–$C_{14}$ aryl groups;

$R^{13}$ is selected from

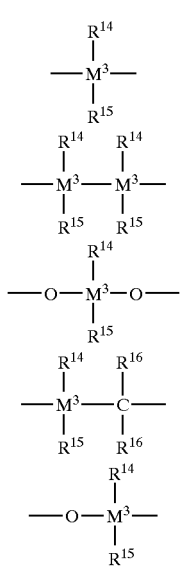

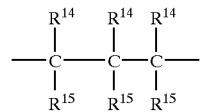

—B($R^{14}$)—, —Al($R^{14}$)—, —Ge—, —Sn—, —O—, —S—, —SO—, —SO$_2$—, —N($R^{14}$)—, —CO—, —P($R^{14}$)— —P(O)($R^{14}$)—, —B(N$R^{14}R^{15}$)— and —B[N(Si$R^{14}R^{15}R^{16}$)$_2$]—;

wherein:

$R^{14}$, $R^{15}$ and $R^{16}$ are each independently selected from hydrogen, halogen, $C_1$–$C_{20}$ alkyl groups, $C_6$–$C_{30}$ aryl groups, $C_1$–$C_{20}$ alkoxy groups, $C_2$–$C_{20}$ alkenyl groups, $C_7$–$C_{40}$ arylalkyl groups, $C_8$–$C_{40}$ arylalkenyl groups and $C_7$–$C_{40}$ alkylaryl groups, or $R^{14}$ and $R^{15}$, together with the atom(s) connecting them, form a ring; and $M^3$ is selected from carbon, silicon, germanium and tin; or $R^{13}$ is represented by the formula

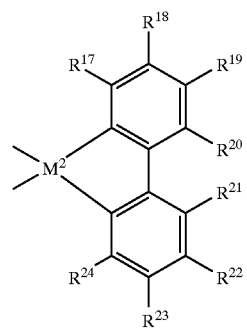

wherein:

$R^{17}$, $R^{18}$, $R^{19}$, $R^{20}$, $R^{21}$, $R^{22}$, $R^{23}$ and $R^{24}$ are each independently selected from hydrogen, halogen, hydroxy, $C_1$–$C_{10}$ alkyl groups, $C_1$–$C_{10}$ alkoxy groups, $C_6$–$C_{14}$ aryl groups, $C_6$–$C_{14}$ aryloxy groups, $C_2$–$C_{10}$ alkenyl groups, $C_7$–$C_{40}$ arylalkyl groups, $C_7$–$C_{40}$ alkylaryl groups and $C_8$–$C_{40}$ arylalkenyl groups; or two or more adjacent radicals $R^{17}$, $R^{18}$, $R^{19}$, $R^{20}$, $R^{21}$, $R^{22}$, $R^{23}$ and $R^{24}$, including $R^{20}$ and $R^{21}$, together with the atoms connecting them, form one or more rings; and $M^2$ represents one or more carbon atoms, or a silicon, germanium or tin atom.

In preferred embodiments of the above compound, $M^1$ is selected from titanium, zirconium and hafnium and $R^1$ and $R^2$ are selected from chlorine, $C_1$–$C_6$ alkyl groups, $C_6$–$C_{10}$ aryl groups, $C_7$–$C_{12}$ arylalkyl groups and $C_7$–$C_{12}$ alkylaryl groups.

$R^3$ may be a $C_3$–$C_6$ alkyl group such as, e.g., a branched $C_3$–$C_4$ alkyl group and, in particular, an isopropyl group, or may be a phenyl group.

Preferably at least one of $R^4$ and $R^8$, and most preferred both of them, represent hydrogen atoms.

In the above formula, $M^3$ may be selected from carbon and silicon, and $R^{14}$, $R^{15}$ and $R^{16}$ may independently be selected from $C_1$–$C_4$ alkyl groups and $C_6$–$C_{10}$ aryl groups. Moreover, when $R^{13}$ is represented by the formula

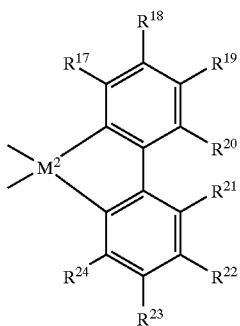

$R^{17}$, $R^{18}$, $R^{19}$, $R^{20}$, $R^{21}$, $R^{22}$, $R^{23}$ and $R^{24}$ may each be hydrogen, with $M^2$ representing a silicon atom.

$R^{12}$ may be selected from $C_1$–$C_6$ alkyl groups and $C_6$–$C_{10}$ aryl groups, a preferred meaning being phenyl. In another embodiment, $R^{11}$ is different from hydrogen and may represent, e.g., a $C_1$–$C_4$ alkyl group.

Particularly preferred compounds of the above formula include those wherein $R^1$ and $R^2$ are selected from chlorine, methyl, neopentyl and benzyl, $R^3$ is selected from $C_3$–$C_4$ alkyl groups, each of $R^4$ and $R^8$ is hydrogen, and $R^{12}$ is selected from $C_1$–$C_4$ alkyl groups and $C_6$–$C_{10}$ aryl groups; wherein $R^3$ is selected from branched $C_3$–$C_4$ alkyl groups and $R^{12}$ is selected from $C_6$–$C_{10}$ aryl groups; wherein $R^3$ is selected from isopropyl isobutyl, sec-butyl, tert-butyl and phenyl groups, and $R^{12}$ is selected from n-propyl, isopropyl, n-butyl, isobutyl, sec-butyl, tert-butyl, phenyl, tolyl, benzyl and naphthyl groups; and wherein $M^1$ is selected from zirconium and hafnium; $R^1$ and $R^2$ are selected from chlorine, $C_1$–$C_3$ alkyl groups and $C_6$–$C_{10}$ aryl groups; $R^3$ is selected from $C_3$–$C_6$ alkyl groups and $C_6$–$C_{10}$ aryl groups; $R^4$ and $R^8$ are hydrogen; $R^5$, $R^6$, $R^7$, $R^9$, $R^{10}$ and $R^{11}$ are each independently selected from hydrogen, halogen and $C_1$–$C_3$ alkyl groups; $R^{12}$ is selected from $C_3$–$C_6$ alkyl groups and $C_6$–$C_{10}$ aryl groups; and $R^{13}$ is selected from di($C_1$–$C_4$ alkyl)silanediyl, diphenylsilanediyl, ($C_1$–$C_4$ alkyl) phenylsilanediyl, diphenylmethanediyl and $C_2$–$C_4$ alkanediyl and alkenediyl radicals, and groups of the formula R

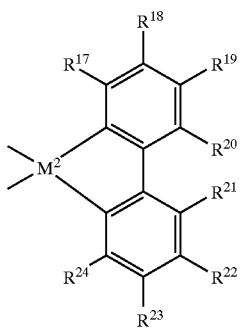

wherein:

$R^{17}$, $R^{18}$, $R^{19}$, $R^{20}$, $R^{21}$, $R^{22}$, $R^{23}$ and $R^{24}$ are each independently selected from hydrogen, halogen and $C_1$–$C_3$ alkyl groups, and $M^2$ represents a carbon or silicon atom.

In another aspect $R^{13}$ may selected from di($C_1$–$C_4$ alkyl) silanediyl, diphenylsilanediyl, ($C_1$–$C_4$ alkyl) phenylsilanediyl, $C_2$–$C_4$ alkanediyl and alkenediyl, di($C_1$–$C_4$ alkyl)amidoborane and bis[tri($C_1$–$C_4$ alkyl)silyl] amidoborane radicals.

Other preferred compounds of the above formula may comprise not more than 2% of the meso isomer.

In another aspect the metallocenes of this invention are represented by the above formula (I), wherein:

$M^1$ is selected from titanium, zirconium, hafnium, vanadium, niobium, tantalum, chromium, molybdenum and tungsten;

$R^1$ and $R^2$ are selected from hydrogen, halogen, hydroxy, $C_1$–$C_{10}$ alkyl groups, $C_1$–$C_{10}$ alkoxy groups, $C_6$–$C_{14}$ aryl groups, $C_6$–$C_{14}$ aryloxy groups, $C_2$–$C_{10}$ alkenyl groups, $C_7$–$C_{40}$ arylalkyl groups, $C_7$–$C_{40}$ alkylaryl groups and $C_7$–$C_{40}$ arylalkenyl groups; or $R^1$ and $R^2$ are joined together to form an alkanediyl group or a conjugated $C_4$–$C_{40}$ diene ligand which is coordinated to $M^1$ in a metallacyclopentene fashion; or $R^1$ and $R^2$ represent a conjugated diene, optionally substituted with one or more groups independently selected from hydrocarbyl, trihydrocarbylsilyl and trihydrocarbylsilylhydrocarbyl groups, said diene having a total of up to 40 atoms not counting hydrogen and forming a π complex with $M^1$;

$R^3$ is selected from hydrogen, halogen, $C_1$–$C_{10}$ alkyl groups, $C_6$–$C_{14}$ aryl groups, $C_2$–$C_{10}$ alkenyl groups, $C_7$–$C_{40}$ arylalkyl groups, $C_7$–$C_{40}$ alkylaryl groups, $C_8$–$C_{40}$ arylalkenyl groups, and —$NR'_2$, —$SR'$, —$OR'$, —$SiR'_3$, —$OSiR'_3$ and —$PR'_2$ radicals wherein each R' is independently selected from halogen, $C_1$–$C_{10}$ alkyl groups and $C_6$–$C_{14}$ aryl groups;

$R^4$, $R^5$, $R^6$ and $R_7$ are each independently selected from hydrogen, halogen, $C_1$–$C_{10}$ alkyl groups, $C_6$–$C_{14}$ aryl groups, $C_2$–$C_{10}$ alkenyl groups, $C_7$–$C_{40}$ arylalkyl groups, $C_7$–$C_{40}$ alkylaryl groups, $C_8$–$C_{40}$ arylalkenyl groups, and —$NR'_2$, —$SR'$, —$OR'$, —$SiR'_3$, —$OSiR'_3$ and —$PR'_2$ radicals wherein each R' is independently selected from halogen, $C_1$–$C_{10}$ alkyl groups and $C_6$–$C_{14}$ aryl groups; or two or more adjacent radicals $R^5$, $R^6$ and $R^7$ together with the atoms connecting them may form one or more rings; $R^8$, $R^9$, $R^{10}$ and $R^{11}$ are each independently as defined for $R^4$, $R^5$, $R^6$ and $R^7$ provided that two or more adjacent radicals $R^8$, $R^9$, $R^{10}$ and $R^{11}$ together with the atoms connecting them may form one or more rings;

$R^{12}$ is selected from halogen, $C_1$–$C_{10}$ alkyl groups, $C_6$–$C_{14}$ aryl groups, $C_2$–$C_{10}$ alkenyl groups, $C_7$–$C_{40}$ arylalkyl groups, $C_7$–$C_{40}$ alkylaryl groups, $C_8$–$C_{40}$ arylalkenyl groups, and —$NR'_2$, —$SR'$, —$OR'$, —$SiR'_3$, —$OSiR'_3$ and —$PR'_2$ radicals wherein each R' is independently selected from halogen, $C_1$–$C_{10}$ alkyl groups and $C_6$–$C_{14}$ aryl groups;

$R^{13}$ is selected from di($C_6$–$C_{12}$ aryl))silanediyl, ($C_1$–$C_6$ alkyl)($C_6$–$C_{12}$ aryl)silanediyl, and groups of the formula

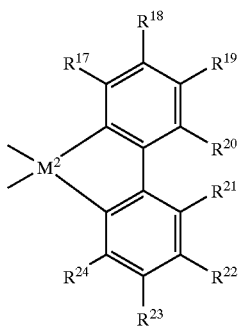

wherein:

$R^{17}$, $R^{18}$, $R^{19}$, $R^{20}$, $R^{21}$, $R^{22}$, $R^{23}$ and $R^{24}$ are each independently selected from hydrogen, halogen, hydroxy, $C_1$–$C_{10}$ alkyl groups, $C_1$–$C_{10}$ alkoxy groups, $C_6$–$C_{14}$ aryl groups, $C_6$–$C_{14}$ aryloxy groups, $C_2$–$C_{10}$ alkenyl groups, $C_7$–$C_{40}$ arylalkyl groups, $C_7$–$C_{40}$ alkylaryl groups and $C_8$–$C_{40}$ arylalkenyl groups; or two or more adjacent radicals $R^{17}$, $R^{18}$, $R^{19}$, $R^{20}$, $R^{22}$, $R^{22}$, $R^{23}$ and $R^{24}$, including $R^{20}$ and $R^{21}$, together with the atoms connecting them, form one or more rings; and $M^2$ represents a carbon, silicon or germanium atom.

Preferred embodiments of these compounds are those already given above.

The present invention also provides a catalyst composition which comprises the product of a compound of at least one of the above metallocene compounds of the present invention and a cocatalyst. The cocatalyst may be a compound comprising a noncoordinating anion (e.g., a noncoordinating anion comprising at least one unit of the formula —B($C_6F_5$)$_3$) and/or may be an alumoxane, e.g., methylalumoxane. The catalyst composition may comprises a support material, e.g., an inorganic material such as silica, alumina, silica-alumina and magnesium chloride.

Preferred support materials include silica having a surface area ranging from 10 to 700 m$^2$/g, a total pore volume ranging from 0.1 to 4.0 cc/g and an average particle size ranging from 10 to 500 μm.

Another aspect of the present invention is a polymerization process which comprises contacting, under polymerization conditions, one or more ethylenically unsaturated monomers and a catalyst composition as defined above.

The ethylenically unsaturated monomers preferably are selected from monoolefins, diolefins and mixtures thereof. Illustrative and non-limiting examples of suitable monoolefins are compounds of the formula $R^aCR=CHR^b$ wherein $R^a$ and $R^b$ are each independently selected from hydrogen, alkyl and alkenyl radicals having 1 to 14 carbon atoms or, together with the carbon atoms to which they are connected, form a ring having 4 to 8 carbon atoms. Preferred monoolefins include ethylene and α-olefins having from 3 to 12 carbon atoms such as, e.g., propylene, 1-butene, 4-methyl-1-pentene, 1-hexene, 1-octene and mixtures thereof. In a preferred embodiment, the ethylenically unsaturated monomers consist essentially of ethylene and propylene.

In one aspect of the above process the temperature ranges from about 30° C. to about 80° C. In another aspect, the process is carried out at a pressure ranging from about 5 to about 64 bar.

The present invention also provides a polymer composition comprising: (a) propylene polymer comprising at least about 99% by weight of units derived from propylene and having a melting point of at least about 155° C.; and (b) olefin copolymer comprising from about 40 to about 70% by weight of units derived from propylene and having an intrinsic viscosity of at least about 1.8; the composition made with a single catalyst composition. Component (a) may be a homopolypropylene or a copolymer of propylene and at least one monoolefin selected from ethylene and α-olefins having from 4 to 12 carbon atoms, the copolymer containing at least about 99.5% by weight of units derived from propylene. Component (b) may contain from about 30 to about 60% by weight of ethylene and/or components (a) and (b) together may contain a total of about 1.5 to about 20% by weight of ethylene.

In a preferred composition of the present invention component (a) has a melting point of at least about 156° C., more preferred at least about 157° C., and/or component (b) has an intrinsic viscosity of at least about 2.0, more preferred at least about 2.2. The composition preferably has a molecular weight distribution, $M_w/M_n$, of not higher than about 3.5, more preferably not higher than about 3.0.

In another preferred embodiment the catalyst composition used to make the polymer composition is based on a bridged zirconocene compound.

DETAILED DESCRIPTION

In the following detailed description, unless otherwise stated, all percentages, parts, ratios, etc., are by weight.

Also, unless otherwise stated, a reference to a compound or component includes the compound or component by itself, its individual stereoisomers and any mixtures thereof, of as well as any combination with other compounds or components, such as mixtures of compounds.

Further, when an amount, concentration, or other value or parameter, is given as a list of upper preferable values and lower preferable values, this is to be understood as specifically disclosing all ranges formed from any pair of an upper preferred value and a lower preferred value, regardless whether ranges are separately disclosed.

Additionally, as utilized herein, the following terms have the meanings indicated below.

The term "product" in connection with the catalyst composition of the present invention includes any species that is different in any respect from the completely independent and individual materials, i.e., the metallocene compound (catalyst precursor) and the cocatalyst (activator). By way of illustrative, non-limiting example, these individual materials may have interacted or even reacted, giving rise to a contact product and/or reaction product.

The term "alkyl", means a straight-chain, branched-chain or cyclic alkyl radical. Examples of such radicals include, but are not limited to, methyl, ethyl, n-propyl, isopropyl, n-butyl, isobutyl, sec-butyl, tert-butyl, pentyl, iso-amyl, hexyl, 2-ethylhexyl, octyl, cyclopentyl, cyclohexyl and the like. The cyclic alkyl radicals may be substituted with one or more straight-chain and/or branched-chain alkyl radicals (i.e., may be alkylcycloalkyl radicals such as, e.g., methylcyclohexyl etc.). Conversely, the straight-chain and branched-chain alkyl radicals may be substituted with one or more cyclic alkyl radicals (i.e., may be cycloalkylalkyl radicals such as cyclohexylmethyl etc.). Moreover, unless indicated otherwise, the above alkyl radicals may be substituted by one or more groups preferably and independently selected from halogen (e.g., F, Cl, Br), alkoxy (e.g., methoxy, ethoxy, propoxy, butoxy and the like), hydroxy, amino, monoalkylamino (e.g., methylamino, ethylamino, propylamino and the like) and dialkylamino (e.g., dimethylamino, diethylamino, dipropylamino, diisopropylamino, piperidino and the like) and trihydrocarbylsilyl (e.g., trimethylsilyl, triphenylsilyl and the like).

The term "alkenyl" means "alkyl" as defined above having one or more double and/or triple bonds. Examples of alkenyl radicals include, but are not limited to, ethenyl, propenyl, allyl, butenyl, propargyl, 1,4-butadienyl, isopropenyl, cyclopentenyl, cyclohexenyl, cyclooctenyl, cyclopentadienyl, cyclohexadienyl, cyclooctadienyl and the like.

The term "alkoxy" means an alkyl or alkenyl ether radical wherein the terms "alkyl" and "alkenyl" are as defined above. Examples of suitable alkyl ether radicals include, but are not limited to, methoxy, ethoxy, n-propoxy, isopropoxy, n-butoxy, iso-butoxy, sec-butoxy, tert-butoxy, allyloxy, trifluoromethoxy and the like.

The term "aryl" means an aromatic radical, for example, a phenyl, naphthyl, azulenyl, phenanthryl or anthracenyl radical and the like which optionally contains one or more (e.g., 2 or 3) heteroatoms (preferably selected from N, O and S and combinations thereof) in the ring and/or carries one or more identical or different substituents, for example, alkoxy, aryl, halogen, hydroxy, amino, monoalkylamino, dialkylamino, nitro, trihydrocarbylsilyl, alkyl-CO, alkylsulfonyl, alkyl-OCO etc., these terms being as defined herein. Illustrative, non-limiting examples of aryl radicals are phenyl, naphthyl, fluorenyl, chlorophenyl, dichlorophenyl, fluorophenyl, perfluorophenyl, hydroxyphenyl, anisyl, biphenyl, nitrophenyl, acetylphenyl, aminophenyl, pyridyl, pyridazyl, quinolyl, and the like. When carbon numbers are given herein for aryl radicals, ring heteroatoms are counted as carbon atoms.

The term "aryloxy" means an aryl ether radical wherein the term "aryl" is as defined above.

The term "alkylaryl" means an aryl radical carrying at least one alkyl and/or alkenyl radical as ring substituent, the terms "aryl", "alkyl" and "alkenyl" being as defined above. Illustrative, non-limiting examples of alkylaryl groups are tolyl, xylyl, mesityl, ethylphenyl, trifluoromethylphenyl, vinylphenyl, cumyl, methylpyridyl and the like.

The term "arylalkyl" means an alkyl radical carrying at least one aryl group wherein the terms "aryl" and "alkyl" are as defined above, provided that the aryl radical may have one or more alkyl substituents. Illustrative, non-limiting examples of arylalkyl groups are benzyl, phenethyl, diphenyl methyl, tolyl methyl, naphthylmethyl and the like.

The term "arylalkenyl" means an alkenyl radical carrying at least one aryl substituent wherein the terms "aryl" and "alkenyl" are as defined above, provided that the aryl radical may have one or more alkyl substituents. Illustrative, non-limiting examples of arylalkenyl groups are styryl, methylstyryl, phenylpropenyl, 1-phenyl-1,4-butadienyl and the like.

The term "halogen" means fluorine, chlorine, bromine and iodine.

The term "hydrocarbyl" encompasses alkyl, alkenyl, arylalkyl, arylalkenyl and alkylaryl groups as defined above. Preferred hydrocarbyl groups comprise 1 to 20, more preferred 1 to 10, and most preferred 1 to 6 carbon atoms. Illustrative, non-limiting examples are methyl, ethyl, propyl and phenyl.

Unless specified otherwise herein, preferred meanings of the various groups defined above are:

Alkyl: linear and branched alkyl groups having 1 to 8, particularly 1 to 6, and even more preferred, 1 to 4 carbon atoms (such as, e.g., methyl, ethyl, propyl and isopropyl). If present, substituents are preferably selected from halogen and alkoxy, more preferred from F, Cl, methoxy and ethoxy, most preferred from F and Cl.

Alkoxy: the preferred alkyl groups connected to an oxygen atom, more preferred methoxy and ethoxy.

Alkenyl: linear and branched alkenyl groups having 2 to 8, particularly 2 to 6, and even more preferred, 2 to 4 carbon atoms (such as, e.g., vinyl, allyl, and 2-butenyl). If present, substituents are preferably selected from halogen and alkoxy, more preferred from F, Cl, methoxy and ethoxy, most preferred from F and Cl.

Aryl: aryl groups containing 6 to 12, more preferred 6 to 10 carbon atoms, such as, e.g., phenyl, naphthyl and biphenyl. Preferably no heteroatoms are present in the ring system. If present, substituents are preferably selected from halogen and alkoxy, more preferred from F, Cl, methoxy and ethoxy, most, preferred from F and Cl.

Aryloxy: the preferred aryl groups attached to an oxygen atom. Most preferred are phenoxy and naphthoxy.

Arylalkyl and alkylaryl: the preferred aryl groups in combination with the preferred alkyl groups, the total number of carbon atoms being 7 to 20, more preferred 7 to 12. Particularly preferred examples include benzyl, phenethyl, tolyl and xylyl.

Arylalkenyl: the preferred aryl groups in combination with the preferred alkenyl groups, the total number of carbon atoms being 8 to 20, more preferred 8 to 12. Particularly preferred examples include styryl and chlorostyryl.

Halogen: F, Cl and Br, more preferred F and Cl.

Preferred meanings of the various constituents of the compounds of formula (I) above are as follows, it being understood that these preferred meanings are defined as above, including the preferred embodiments of a particular meaning. For example, "alkyl" means an alkyl group as defined above, preferred meanings thereof being also as defined above.

$M^1$: titanium, zirconium, hafnium; more preferred are zirconium and hafnium, with zirconium being most preferred.

$R^1$ and $R^2$: halogen (more preferred Cl and Br), alkyl (more preferred methyl and neopentyl), aryl (more preferred phenyl), alkylaryl (more preferred tolyl) and arylalkyl (more preferred benzyl); or $R^1$ and $R^2$ are joined together to form a $C_{4-6}$ alkanediyl group or a conjugated $C_4$–$C_6$ diene ligand which is coordinated to $M^1$ in a metallacycloalkane or -cycloalkene fashion; or $R^1$ and $R^2$ represent a conjugated diene, optionally substituted with one or more groups independently selected from alkyl, aryl, trialkylsilyl and trialkylsilylalkyl groups, said diene having a total of up to 30, e.g., up to 24 atoms not counting hydrogen and forming a π complex with $M^1$. Illustrative, non-limiting examples of conjugated dienes are 1,4-diphenyl-1,3-butadiene, 1,3-pentadiene, 2-methyl-1,3-pentadiene, 2,4-hexadiene, 1-phenyl-1,3-pentadiene, 1,4-dibenzyl-1,3-butadiene, 1,4-ditolyl-1,3-butadiene, 1,4-bis(trimethylsilyl)-1,3-butadiene, and 1,4-dinaphthyl-1,3-butadiene. While $R^1$ and $R^2$ may be different, they are preferably the same. The most preferred meanings of $R^1$ and $R^2$ are Cl and methyl.

$R^3$: alkyl, aryl, alkylaryl and arylalkyl. More preferred meanings are methyl, ethyl, n-propyl, isopropyl, n-butyl, isobutyl, sec-butyl, tert-butyl, phenyl, naphthyl, tolyl and benzyl, even more preferred isopropyl, benzyl and phenyl. Most preferred is isopropyl.

$R^4$, $R^5$, $R^6$ and $R^7$: hydrogen, alkyl and aryl (particularly phenyl), more preferred hydrogen and alkyl. Illustrative, non-limiting examples are hydrogen, methyl and ethyl. For $R^4$ a particularly preferred meaning is hydrogen. In another preferred embodiment, all of $R^4$, $R^5$, $R^6$ and $R^7$ are hydrogen.

$R^8$, $R^9$, $R^{10}$ and $R^{11}$: hydrogen, alkyl, arylalkyl (particularly benzyl) and aryl (particularly phenyl), more preferred hydrogen and alkyl. Illustrative, non-limiting examples are hydrogen, methyl and ethyl. For $R^8$ a particularly preferred meaning is hydrogen. In another preferred embodiment, all of $R^8$, $R^9$, $R^{10}$ and $R^{11}$ are hydrogen. While in still another preferred embodiment at least one of $R^9$ and $R^{11}$ is different from hydrogen, it is particularly preferred for $R^{11}$ to be different from hydrogen when $R^{12}$ represents methyl or ethyl.

$R^{12}$: alkyl, aryl, alkylaryl, arylalkyl and trialkylsilyl. More preferred meanings are methyl ethyl, n-propyl, isopropyl, n-butyl, isobutyl, sec-butyl, tert-butyl, phenyl, naphthyl, (o-, m- and p-)tolyl, benzyl and trimethylsilyl, in particular, isopropyl and phenyl. Most preferred is phenyl.

$R^{13}$: dialkylsilanediyl, diarylsilanedlyl, (aryl)(alkyl) silanediyl, amidoborane, alkylene, arylalkylene and arylene, the latter groups being derived from the defined alkyl, arylalkyl and aryl radicals. More preferred as alkyl and aryl groups are methyl, ethyl, propyl, butyl and phenyl. More preferred alkylene, arylalkylene and arylene radicals are ethylene, propylene, butylene, phenylmethylene and diphenylmethylene as well as phenylene. More preferred dialkylsilanediyl, diarylsilanediyl and (aryl)(alkyl)silanediyl radicals are dimethylsilanediyl, diethylsilanediyl, dipropylsilanediyl, dibutylsilanediyl, methylphenylsilanediyl and diphenylsilanediyl. More preferred amidoborane radicals are dialkylamidoborane, diarylamidoborane and bis(trialkylsilyl)amidoborane radicals. Illustrative, non-limiting examples thereof are dimethylamidoborane, diethylamidoborane, diisopropylamidoborane, diphenylamidoborane and bis(trimethylsilyl)amidoborane. Other preferred meanings of $R^{13}$ are 9-fluorenyl and 9-silafluorenyl. $R^{13}$ is usually connected to the 1-positions of the indenyl ring systems.

The following are particularly preferred metallocenes:

dimethylsilanediylbis{1-[2-n-propyl, 4-(2-methylphenyl)indenyl]}zirconium dichloride;
dimethylsilanediylbis{1-[2-isopropyl, 4-(2-methylphenyl)indenyl]}zirconium dichloride;
dimethylsilanediylbis{1-[2-n-butyl, 4-(2-methylphenyl)indenyl]}zirconium dichloride;
dimethylsilanediylbis{1-[2-isobutyl, 4-(2-methylphenyl)indenyl]}zirconium dichloride;
dimethylsilanediylbis{1-[2-sec-butyl, 4-(2-methylphenyl)indenyl]}zirconium dichloride;
dimethylsilanediylbis{1-[2-tert-butyl, 4-(2-methylphenyl)indenyl]}zirconium dichloride;
dimethylsilanediylbis{1-[2-phenyl, 4-(2-methylphenyl)indenyl]}zirconium dichloride;
dimethylsilanediylbis{1-[2-n-propyl, 4-(2-ethylphenyl)indenyl]}zirconium dichloride;
dimethylsilanediylbis{1-[2-isopropyl, 4-(2-ethylphenyl)indenyl]}zirconium dichloride;
dimethylsilanediylbis{1-[2-n-butyl, 4-(2-ethylphenyl)indenyl]}zirconium dichloride;
dimethylsilanediylbis{1-[2-isobutyl, 4-(2-ethylphenyl)indenyl]}zirconium dichloride;
dimethylsilanediylbis{1-[2-sec-butyl, 4-(2-ethylphenyl)indenyl]}zirconium dichloride;
dimethylsilanediylbis{1-[2-tert-butyl, 4-(2-ethylphenyl)indenyl]}zirconium dichloride;
dimethylsilanediylbis{1-[2-phenyl, 4-(2-ethylphenyl)indenyl]}zirconium dichloride;
dimethylsilanediylbis{1-[2-n-propyl, 4-(2-n-propylphenyl)indenyl]}zirconium dichloride;
dimethylsilanediylbis{1-[2-isopropyl, 4-(2-n-propylphenyl)indenyl]}zirconium dichloride;
dimethylsilanediylbis{1-[2-n-butyl, 4-(2-n-propylphenyl)indenyl]}zirconium dichloride;
dimethylsilanediylbis{1-[2-isobutyl, 4-(2-n-propylphenyl)indenyl]}zirconium dichloride;
dimethylsilanediylbis{1-[2-sec-butyl, 4-(2-n-propylphenyl)indenyl]}zirconium dichloride;
dimethylsilanediylbis{1-[2-tert-butyl, 4-(2-n-propylphenyl)indenyl]}zirconium dichloride;
dimethylsilanediylbis{1-[2-phenyl, 4-(2-n-propylphenyl)indenyl]}zirconium dichloride;
dimethylsilanediylbis{1-[2-n-propyl, 4-(2-isopropylphenyl)indenyl]}zirconium dichloride;
dimethylsilanediylbis{1-[2-isopropyl, 4-(2-isopropylphenyl)indenyl]}zirconium dichloride;
dimethylsilanediylbis{1-[2-n-butyl, 4-(2-isopropylphenyl)indenyl]}zirconium dichloride;
dimethylsilanediylbis{1-[2-isobutyl, 4-(2-isopropylphenyl)indenyl]}zirconium dichloride;
dimethylsilanediylbis{1-[2-sec-butyl, 4-(2-isopropylphenyl)indenyl]}zirconium dichloride;
dimethylsilanediylbis{1-[2-tert-butyl, 4-(2-isopropylphenyl)indenyl]}zirconium dichloride;
dimethylsilanediylbis{1-[2-phenyl, 4-(2-isopropylphenyl)indenyl]}zirconium dichloride;
dimethylsilanediylbis{1-[2-n-propyl, 4-(2-n-butylphenyl)indenyl]}zirconium dichloride;
dimethylsilanediylbis{1-[2-isopropyl, 4-(2-n-butylphenyl)indenyl]}zirconium dichloride;
dimethylsilanediylbis{1-[2-n-butyl, 4-(2-n-butylphenyl)indenyl]}zirconium dichloride;
dimethylsilanediylbis{1-[2-isobutyl, 4-(2-n-butylphenyl)indenyl]}zirconium dichloride;
dimethylsilanediylbis{1-[2-sec-butyl, 4-(2-n-butylphenyl)indenyl]}zirconium dichloride;
dimethylsilanediylbis{1-[2-tert-butyl, 4-(2-n-butylphenyl)indenyl]}zirconium dichloride;
dimethylsilanediylbis{1-[2-phenyl, 4-(2-n-butylphenyl)indenyl]}zirconium dichloride;
dimethylsilanediylbis{1-[2-n-propyl, 4-(2-isobutylphenyl)indenyl]}zirconium dichloride;
dimethylsilanediylbis{1-[2-isopropyl, 4-(2-isobutylphenyl)indenyl]}zirconium dichloride;
dimethylsilanediylbis{1-[2-n-butyl, 4-(2-isobutylphenyl)indenyl]}zirconium dichloride;
dimethylsilanediylbis{1-[2-isobutyl, 4-(2-isobutylphenyl)indenyl]}zirconium dichloride;
dimethylsilanediylbis{1-[2-sec-butyl, 4-(2-isobutylphenyl)indenyl]}zirconium dichloride;
dimethylsilanediylbis{1-[2-tert-butyl, 4-(2-isobutylphenyl)indenyl]}zirconium dichloride;
dimethylsilanediylbis{1-[2-phenyl, 4-(2-isobutylphenyl)indenyl]}zirconium dichloride;
dimethylsilanediylbis{1-[2-n-propyl, 4-(2-sec-butylphenyl)indenyl]}zirconium dichloride;
dimethylsilanediylbis{1-[2-isopropyl, 4-(2-sec-butylphenyl)indenyl]}zirconium dichloride;
dimethylsilanediylbis{1-[2-n-butyl, 4-(2-sec-butylphenyl)indenyl]}zirconium dichloride;
dimethylsilanediylbis{1-[2-isobutyl, 4-(2-sec-butylphenyl)indenyl]}zirconium dichloride;
dimethylsilanediylbis{1-[2-sec-butyl, 4-(2-sec-butylphenyl)indenyl]}zirconium dichloride;

dimethylsilanediylbis{1-[2-tert-butyl, 4-(2-sec-butylphenyl)indenyl]}zirconium dichloride;
dimethylsilanediylbis{1-[2-phenyl, 4-(2-sec-butylphenyl)indenyl]}zirconium dichloride;
dimethylsilanediylbis{1-[2-n-propyl, 4-(2-tert-butylphenyl)indenyl]}zirconium dichloride;
dimethylsilanediylbis{1-[2-isopropyl, 4-(2-tert-butylphenyl)indenyl]}zirconium dichloride;
dimethylsilanediylbis{1-[2-n-butyl, 4-(2-tert-butylphenyl)indenyl]}zirconium dichloride;
dimethylsilanediylbis{1-[2-isobutyl, 4-(2-tert-butylphenyl)indenyl]}zirconium dichloride;
dimethylsilanediylbis{1-[2-sec-butyl 4-(2-tert-butylphenyl)indenyl]}zirconium dichloride;
dimethylsilanediylbis{1-[2-tert-butyl, 4-(2-tert-butylphenyl)indenyl]}zirconium dichloride;
dimethylsilanediylbis{1-[2-phenyl, 4-(2-tert-butylphenyl)indenyl]}zirconium dichloride;
dimethylsilanediylbis{1-[2-n-propyl, 4-(2-biphenyl)indenyl]}zirconium dichloride;
dimethylsilanediylbis{1-[2-isopropyl, 4-(2-biphenyl)indenyl]}zirconium dichloride;
dimethylsilanediylbis{1-[2-n-butyl, 4-(2-biphenyl)indenyl]}zirconium dichloride;
dimethylsilanediylbis{1-[2-isobutyl, 4-(2-biphenyl)indenyl]}zirconium dichloride;
dimethylsilanediylbis{1-[2-sec-butyl, 4-(2-biphenyl)indenyl]}zirconium dichloride;
dimethylsilanediylbis{1-[2-tert-butyl, 4-(2-biphenyl)indenyl]}zirconium dichloride;
dimethylsilanediylbis{1-[2-phenyl, 4-(2-biphenyl)indenyl]}zirconium dichloride;
dimethylsilanediylbis{1-[2-n-propyl, 4-(2-α-naphthylphenyl)indenyl]}zirconium dichloride;
dimethylsilanediylbis{1-[2-isopropyl, 4-(2-α-naphthylphenyl)indenyl]}zirconium dichloride;
dimethylsilanediylbis{1-[2-n-butyl, 4-(2-α-naphthylphenyl)indenyl]}zirconium dichloride;
dimethylsilanediylbis{1-[2-isobutyl, 4-(2-α-naphthylphenyl)indenyl]}zirconium dichloride;
dimethylsilanediylbis{1-[2-sec-butyl, 4-(2-α-naphthylphenyl)indenyl]}zirconium dichloride;
dimethylsilanediylbis{1-[2-tert-butyl, 4-(2-α-naphthylphenyl)indenyl]}zirconium dichloride;
dimethylsilanediylbis{1-[2-phenyl, 4-(2-α-naphthylphenyl)indenyl]}zirconium dichloride;
dimethylsilanediylbis{1-[2-n-propyl, 4-(2-β-naphthylphenyl)indenyl]}zirconium dichloride;
dimethylsilanediylbis{1-[2-isopropyl, 4-(2-β-naphthylphenyl)indenyl]}zirconium dichloride;
dimethylsilanediylbis{1-[2-n-butyl, 4-(2-β-naphthylphenyl)indenyl]}zirconium dichloride:
dimethylsilanediylbis{1-[2-isobutyl, 4-(2-β-naphthylphenyl)indenyl]}zirconium dichloride;
dimethylsilanediylbis{1-[2-sec-butyl, 4-(2-β-naphthylphenyl)indenyl]}zirconium dichloride:
dimethylsilanediylbis{1-[2-tert-butyl, 4-(2-β-naphthylphenyl)indenyl]}zirconium dichloride;
dimethylsilanediylbis{1-[2-phenyl, 4-(2-β-naphthylphenyl)indenyl]}zirconium dichloride;
dimethylsilanediylbis{1-[2-n-propyl, 4-(2-trifluoromethylphenyl)indenyl]}-zirconium dichloride;
dimethylsilanediylbis{1-[2-isopropyl, 4-(2-trifluoromethylphenyl)indenyl]}-zirconium dichloride;
dimethylsilanediylbis{1-[2-n-butyl, 4-(2-trifluoromethylphenyl)indenyl]}-zirconium dichloride;
dimethylsilanediylbis{1-[2-isobutyl, 4-(2-trifluoromethylphenyl)indenyl]}-zirconium dichloride;
dimethylsilanediylbis{1-[2-sec-butyl, 4-(2-trifluoromethylphenyl)indenyl]}-zirconium dichloride;
dimethylsilanediylbis{1-[2-tert-butyl, 4-(2-trifluoromethylphenyl)indenyl]}-zirconium dichloride;
dimethylsilanediylbis{1-[2-phenyl, 4-(2-trifluoromethylphenyl)indenyl]}-zirconium dichloride;
dimethylsilanediylbis{1-[2-n-propyl, 4-(2-trimethylsilylphenyl)indenyl]}-zirconium dichloride;
dimethylsilanediylbis{1-[2-isopropyl, 4-(2-trimethylsilylphenyl)indenyl]}-zirconium dichloride;
dimethylsilanediylbis{1-[2-n-butyl, 4-(2-trimethylsilylphenyl)indenyl]}-zirconium dichloride;
dimethylsilanediylbis{1-[2-isobutyl, 4-(2-trimethysilylphenyl)indenyl]}-zirconium dichloride;
dimethylsilanediylbis{1-[2-sec-butyl, 4-(2-trimethylsilylphenyl)indenyl]}-zirconium dichloride;
dimethylsilanediylbis{1-[2-tert-butyl, 4-(2-trimethylsilylphenyl)indenyl]}-zirconium dichloride;
dimethylsilanediylbis{1-[2-phenyl, 4-(2-trimethylsilylphenyl)indenyl]}-zirconium dichloride;
dimethylsilanediylbis{1-[2-n-propyl, 4-(2,3-dimethylphenyl)indenyl]}zirconium dichloride;
dimethylsilanediylbis{1-[2-isopropyl, 4-(2,3-dimethylphenyl)indenyl]}zirconium dichloride;
dimethylsilanediylbis{1-[2-n-butyl, 4-(2,3-dimethylphenyl)indenyl]}zirconium dichloride;
dimethylsilanediylbis{1-[2-isobutyl, 4-(2,3-dimethylphenyl)indenyl]}zirconium dichloride;
dimethylsilanediylbis{1-[2-sec-butyl, 4-(2,3-dimethylphenyl)indenyl]}zirconium dichloride;
dimethylsilanediylbis{1-[2-tert-butyl, 4-(2,3-dimethylphenyl)indenyl]}zirconium dichloride;
dimethylsilanediylbis{1-[2-phenyl, 4-(2,3-dimethylphenyl)indenyl]}zirconium dichloride;
dimethylsilanediylbis{1-[2-n-propyl, 4-(2,3,4-trimethylphenyl)indenyl]}zirconium dichloride;
dimethylsilanediylbis{1-[2-isopropyl, 4-(2,3,4-trimethylphenyl)indenyl]}zirconium dichloride;
dimethylsilanediylbis{1-[2-n-butyl, 4-(2,3,4-trimethylphenyl)indenyl]}zirconium dichloride;
dimethylsilanediylbis{1-[2-isobutyl, 4-(2,3,4-trimethylphenyl)indenyl]}zirconium dichloride;
dimethylsilanediylbis{1-[2-sec-butyl, 4-(2,3,4-trimethylphenyl)indenyl]}zirconium dichloride;
dimethylsilanediylbis{1-[2-tert-butyl, 4-(2,3,4-trimethylphenyl)indenyl]}zirconium dichloride;
dimethylsilanediylbis{1-[2-phenyl, 4-(2,3,4-trimethylphenyl)indenyl]}zirconium dichloride;
dimethylsilanediylbis{1-[2-n-propyl, 4-(2,3,5-trimethylphenyl)indenyl]}zirconium dichloride;
dimethylsilanediylbis{1-[2-isopropyl, 4-(2,3,5-trimethylphenyl)indenyl]}zirconium dichloride;
dimethylsilanediylbis{1-[2-n-butyl, 4-(2,3,5-trimethylphenyl)indenyl]}zirconium dichloride;
dimethylsilanediylbis{1-[2-isobutyl, 4-(2,3,5-trimethylphenyl)indenyl]}zirconium dichloride;
dimethylsilanediylbis{1-[2-sec-butyl, 4-(2,3,5-trimethylphenyl)indenyl]}zirconium dichloride;
dimethylsilanediylbis{1-[2-tert-butyl, 4-(2,3,5-trimethylphenyl)indenyl]}zirconium dichloride;
dimethylsilanediylbis{1-[2-phenyl, 4-(2,3,5-trimethylphenyl)indenyl]}zirconium dichloride;
dimethylsilanediylbis{1-[2-n-propyl, 4-(2-methylphenyl)indenyl]}zirconium dimethyl;
dimethylsilanediylbis{1-[2-isopropyl, 4-(2-methylphenyl)indenyl]}zirconium dimethyl;
dimethylsilanediylbis{1-[2-n-butyl, 4-(2-methylphenyl)indenyl]}zirconium dimethyl;

dimethylsilanediylbis{1-[2-isobutyl, 4-(2-methylphenyl)indenyl]}zirconium dimethyl;
dimethylsilanediylbis{1-[2-sec-butyl, 4-(2-methylphenyl)indenyl]}zirconium dimethyl;
dimethylsilanediylbis{1-[2-tert-butyl, 4-(2-methylphenyl)indenyl]}zirconium dimethyl;
dimethylsilanediylbis{1-[2-phenyl, 4-(2-methylphenyl)indenyl]}zirconium dimethyl;
dimethylsilanediylbis{1-[2-n-propyl, 4-(2-ethylphenyl)indenyl]}zirconium dimethyl;
dimethylsilanediylbis{1-[2-isopropyl, 4-(2-ethylphenyl)indenyl]}zirconium dimethyl;
dimethylsilanediylbis{1-[2-n-butyl, 4-(2-ethylphenyl)indenyl]}zirconium dimethyl;
dimethylsilanediylbis{1-[2-isobutyl, 4-(2-ethylphenyl)indenyl]}zirconium dimethyl;
dimethylsilanediylbis{1-[2-sec-butyl, 4-(2-ethylphenyl)indenyl]}zirconium dimethyl;
dimethylsilanediylbis{1- [2-tert-butyl, 4-(2-ethylphenyl)indenyl]}zirconium dimethyl;
dimethylsilanediylbis{1-[2-phenyl, 4-(2-ethylphenyl)indenyl]}zirconium dimethyl;
dimethylsilanediylbis{1-[2-n-propyl, 4-(2-n-propylphenyl)indenyl]}zirconium dimethyl;
dimethylsilanediylbis{1-[2-isopropyl, 4-(2-n-propylphenyl)indenyl]}zirconium dimethyl;
dimethylsilanediylbis{1-[2-n-butyl, 4-(2-n-propylphenyl)indenyl]}zirconium dimethyl;
dimethylsilanediylbis{1-[2-isobutyl, 4-(2-n-propylphenyl)indenyl]}zirconium dimethyl;
dimethylsilanediylbis{1-[2-sec-butyl, 4-(2-n-propylphenyl)indenyl]}zirconium dimethyl;
dimethylsilanediylbis{1-[2-tert-butyl, 4-(2-n-propylphenyl)indenyl]}zirconium dimethyl;
dimethylsilanediylbis{1-[2-phenyl, 4-(2-n-propylphenyl)indenyl]}zirconium dimethyl;
dimethylsilanediylbis{1-[2-n-propyl, 4-(2-isopropylphenyl)indenyl]}zirconium dimethyl;
dimethylsilanediylbis{1-[2-isopropyl, 4-(2-isopropylphenyl)indenyl]}zirconium dimethyl;
dimethylsilanediylbis{1-[2-n-butyl, 4-(2-isopropylphenyl)indenyl]}zirconium dimethyl;
dimethylsilanediylbis{1-[2-isobutyl, 4-(2-isopropylphenyl)indenyl]}zirconium dimethyl;
dimethylsilanediylbis{1-[2-sec-butyl, 4-(2-isopropylphenyl)indenyl]}zirconium dimethyl;
dimethylsilanediylbis{1-[2-tert-butyl, 4-(2-isopropylphenyl)indenyl]}zirconium dimethyl;
dimethylsilanediylbis{1-[2-phenyl, 4-(2-isopropylphenyl)indenyl]}zirconium dimethyl;
dimethylsilanediylbis{1-[2-n-propyl, 4-(2-n-butylphenyl)indenyl]}zirconium dimethyl;
dimethylsilanediylbis{1-[2-isopropyl, 4-(2-n-butylphenyl)indenyl]}zirconium dimethyl;
dimethylsilanediylbis{1-[2-n-butyl, 4-(2-n-butylphenyl)indenyl]}zirconium dimethyl;
dimethylsilanediylbis{1-[2-isobutyl, 4-(2-n-butylphenyl)indenyl]}zirconium dimethyl;
dimethylsilanediylbis{1-[2-sec-butyl, 4-(2-n-butylphenyl)indenyl]}zirconium dimethyl;
dimethylsilanediylbis{1-[2-tert-butyl, 4-(2-n-butylphenyl)indenyl]}zirconium dimethyl;
dimethylsilanediylbis{1-[2-phenyl, 4-(2-n-butylphenyl)indenyl]}zirconium dimethyl;
dimethylsilanediylbis{1-[2-n-propyl, 4-(2-isobutylphenyl)indenyl]}zirconium dimethyl;
dimethylsilanediylbis{1-[2-isopropyl, 4-(2-isobutylphenyl)indenyl]}zirconium dimethyl;
dimethylsilanediylbis{1-[2-n-butyl, 4-(2-isobutylphenyl)indenyl]}zirconium dimethyl;
dimethylsilanediylbis{1-[2-isobutyl, 4-(2-isobutylphenyl)indenyl}zirconium dimethyl;
dimethylsilanediylbis{1-[2-sec-butyl, 4-(2-isobutylphenyl)indenyl]}zirconium dimethyl;
dimethylsilanediylbis{1-[2-tert-butyl, 4-(2-isobutylphenyl)indenyl]}zirconium dimethyl;
dimethylsilanediylbis{1-[2-phenyl, 4-(2-isobutylphenyl)indenyl]}zirconium dimethyl;
dimethylsilanediylbis{1-[2-n-propyl, 4-(2-sec-butylphenyl)indenyl]}zirconium dimethyl;
dimethylsilanediylbis{1-[2-isopropyl, 4-(2-sec-butylphenyl)indenyl]}zirconium dimethyl;
dimethylsilanediylbis{1-[2-n-butyl, 4-(2-sec-butylphenyl)indenyl]}zirconium dimethyl;
dimethylsilanediylbis{1-[2-isobutyl, 4-(2-sec-butylphenyl)indenyl]}zirconium dimethyl;
dimethylsilanediylbis{1-[2-sec-butyl, 4-(2-sec-butylphenyl)indenyl]}zirconium dimethyl;
dimethylsilanediylbis{1-[2-tert-butyl, 4-(2-sec-butylphenyl)indenyl]}zirconium dimethyl;
dimethylsilanediylbis{1-[2-phenyl, 4-(2-sec-butylphenyl)indenyl]}zirconium dimethyl;
dimethylsilanediylbis{1-[2-n-propyl, 4-(2-tert-butylphenyl)indenyl]}zirconium dimethyl;
dimethylsilanediylbis{1-[2-isopropyl, 4-(2-tert-butylphenyl)indenyl]}zirconium dimethyl;
dimethylsilanediylbis{1-[2-n-butyl, 4-(2-tert-butylphenyl)indenyl]}zirconium dimethyl;
dimethylsilanediylbis{1-[2-isobutyl, 4-(2-tert-butylphenyl)indenyl]}zirconium dimethyl;
dimethylsilanediylbis{1-[2-sec-butyl, 4-(2-tert-butylphenyl)indenyl]}zirconium dimethyl;
dimethylsilanediylbis{1-[2-tert-butyl, 4-(2-tert-butylphenyl)indenyl]}zirconium dimethyl;
dimethylsilanediylbis{1-[2-phenyl, 4-(2-tert-butylphenyl)indenyl]}zirconium dimethyl;
dimethylsilanediylbis{1-[2-n-propyl, 4-(2-biphenyl)indenyl]}zirconium dimethyl;
dimethylsilanediylbis{1-[2-isopropyl, 4-(2-biphenyl)indenyl]}zirconium dimethyl;
dimethylsilanediylbis{1-[2-n-butyl, 4-(2-biphenyl)indenyl]}zirconium dimethyl;
dimethylsilanediylbis{1-[2-isobutyl, 4-(2-biphenyl)indenyl]}zirconium dimethyl;
dimethylsilanediylbis{1-[2-sec-butyl, 4-(2-biphenyl)indenyl]}zirconium dimethyl;
dimethylsilanediylbis{1-[2-tert-butyl, 4-(2-biphenyl)indenyl]}zirconium dimethyl;
dimethylsilanediylbis{1-[2-phenyl, 4-(2-biphenyl)indenyl]}zirconium dimethyl;
dimethylsilanediylbis{1-[2-n-propyl, 4-(2α-naphthylphenyl)indenyl]}zirconium dimethyl;
dimethylsilanediylbis{1-[2-isopropyl, 4-(2-α-naphthylphenyl)indenyl]}zirconium dimethyl;
dimethylsilanediylbis{1-[2-n-butyl, 4-(2-α-naphthylphenyl)indenyl]}zirconium dimethyl;
dimethylsilanediylbis{1-[2-isobutyl, 4-(2-α-naphthylphenyl)indenyl]}zirconium dimethyl;
dimethylsilanediylbis{1-[2-sec-butyl, 4-(2-α-naphthylphenyl)indenyl]}zirconium dimethyl;
dimethylsilanediylbis{1-[2-tert-butyl, 4-(2-α-naphthylphenyl)indenyl]}zirconium dimethyl;
dimethylsilanediylbis{1-[2-phenyl, 4-(2-α-naphthylphenyl)indenyl]}zirconium dimethyl;
dimethylsilanediylbis{1-[2-n-propyl, 4-(2-β-naphthylphenyl)indenyl]}zirconium dimethyl;

dimethylsilanediylbis{1-1-[2-isopropyl, 4-(2-β-naphthylphenyl)indenyl]}zirconium dimethyl;
dimethylsilanediylbis{1-[2-n-butyl, 4-(2-β-naphthylphenyl)indenyl]}zirconium dimethyl;
dimethylsilanediylbis{1-[2-isobutyl, 4-(2-β-naphthylphenyl)indenyl]}zirconium dimethyl;
dimethylsilanediylbis{1-[2-sec-butyl, 4-(2-β-naphthylphenyl)indenyl]}zirconium dimethyl;
dimethylsilanediylbis{1-[2-tert-butyl, 4-(2-β-naphthylphenyl)indenyl]}zirconium dimethyl;
dimethylsilanediylbis{1-[2-phenyl, 4-(2-β-naphthylphenyl)indenyl]}zirconium dimethyl;
dimethylsilanediylbis{1-[2-n-propyl, 4-(2-trifluoromethylphenyl)indenyl]}-zirconium dimethyl;
dimethylsilanediylbis{1-[2-isopropyl, 4-(2-trifluoromethylphenyl)indenyl]}-zirconium dimethyl;
dimethylsilanediylbis{1-[2-n-butyl, 4-(2-trifluoromethylphenyl)indenyl]}-zirconium dimethyl;
dimethylsilanediylbis{1-[2-isobutyl, 4-(2-trifluoromethylphenyl)indenyl]}-zirconium dimethyl;
dimethylsilanediylbis{1-[2-sec-butyl, 4-(2-trifluoromethylphenyl)indenyl]}-zirconium dimethyl;
dimethylsilanediylbis{1-[2-tert-butyl, 4-(2-trifluoromethylphenyl)indenyl]}-zirconium dimethyl;
dimethylsilanediylbis{1-[2-phenyl, 4-(2-trifluoromethylphenyl)indenyl]}-zirconium dimethyl;
dimethylsilanediylbis{1-[2-n-propyl, 4-(2-trimethylsilylphenyl)indenyl]}-zirconium dimethyl;
dimethylsilanediylbis{1-[2-isopropyl, 4-(2-trimethylsilylphenyl)indenyl]}-zirconium dimethyl;
dimethylsilanediylbis{1-[2-n-butyl, 4-(2-trimethylsilylphenyl)indenyl]}-zirconium dimethyl;
dimethylsilanediylbis{1-[2-isobutyl, 4-(2-trimethylsilylphenyl)indenyl]}-zirconium dimethyl;
dimethylsilanediylbis{1-[2-sec-butyl, 4-(2-trimethylsilylphenyl)indenyl]}-zirconium dimethyl;
dimethylsilanediylbis{1-[2-tert-butyl, 4-(2-trimethylsilylphenyl)indenyl]}-zirconium dimethyl;
dimethylsilanediylbis{1-[2-phenyl, 4-(2-trimethylsilylphenyl)indenyl]}-zirconium dimethyl;
dimethylsilanediylbis{1-[2-n-propyl, 4-(2,3-dimethylphenyl)indenyl]}zirconium dimethyl;
dimethylsilanediylbis{1-[2-isopropyl, 4-(2,3-dimethylphenyl)indenyl]}zirconium dimethyl;
dimethylsilanediylbis{1-[2-n-butyl, 4-(2,3-dimethylphenyl)indenyl]}zirconium dimethyl;
dimethylsilanediylbis{1-[2-isobutyl, 4-(2,3-dimethylphenyl)indenyl]}zirconium dimethyl;
dimethylsilanediylbis{1-[2-sec-butyl, 4-(2,3dimethylphenyl)indenyl]}zirconium dimethyl;
dimethylsilanediylbis{1-[2-tert-butyl, 4-(2,3-dimethylphenyl)indenyl]}zirconium dimethyl;
dimethylsilanediylbis{1-[2-phenyl, 4-(2,3-dimethylphenyl)indenyl]}zirconium dimethyl;
dimethylsilanediylbis{1-[2-n-propyl, 4-(2,3,4-trimethylphenyl)indenyl]}zirconium dimethyl;
dimethylsilanediylbis{1-[2-isopropyl, 4-(2,3,4-trimethylphenyl)indenyl]}zirconium dimethyl;
dimethylsilanediylbis{1-[2-n-butyl, 4-(2,3,4-trimethylphenyl)indenyl]}zirconium dimethyl;
dimethylsilanediylbis{1-[2-isobutyl, 4-(2,3,4-trimethylphenyl)indenyl]}zirconium dimethyl;
dimethylsilanediylbis{1-[2-sec-butyl, 4-(2,3,4-trimethylphenyl)indenyl]}zirconium dimethyl;
dimethylsilanediylbis{1-[2-tert-butyl, 4-(2,3,4-trimethylphenyl)indenyl]}zirconium dimethyl;
dimethylsilanediylbis{1-[2-phenyl, 4-(2,3,4-trimethylphenyl)indenyl]}zirconium dimethyl;
dimethylsilanediylbis{1-[2-n-propyl, 4-(2,3,5-trimethylphenyl)indenyl]}zirconium dimethyl;
dimethylsilanediylbis{1-[2-isopropyl, 4-(2,3,5-trimethylphenyl)indenyl]}zirconium dimethyl;
dimethylsilanediylbis{1-[2-n-butyl, 4-(2,3,5-trimethylphenyl)indenyl]}zirconium dimethyl;
dimethylsilanediylbis{1-[2-isobutyl, 4-(2,3,5-trimethylphenyl)indenyl]}zirconium dimethyl;
dimethylsilanediylbis{1-[2-sec-butyl, 4-(2,3,5-trimethylphenyl)indenyl]}zirconium dimethyl;
dimethylsilanediylbis{1-[2-tert-butyl, 4-(2,3,5-trimethylphenyl)indenyl]}zirconium dimethyl;
dimethylsilanediylbis{1-[2-phenyl, 4-(2,3,5-trimethylphenyl)indenyl]}zirconium dimethyl;
dimethylsilanediylbis{1-[2-n-propyl, 4-(2-methylphenyl)indenyl]}hafnium dichloride;
dimethylsilanediylbis{1-[2-isopropyl, 4-(2-methylphenyl)indenyl]}hafnium dichloride;
dimethylsilanediylbis{1-[2-n-butyl, 4-(2-methylphenyl)indenyl]}hafnium dichloride;
dimethylsilanediylbis{1-[2-isobutyl, 4-(2-methylphenyl)indenyl]}hafnium dichloride;
dimethylsilanediylbis{1-[2-sec-butyl, 4-(2-methylphenyl)indenyl]}hafnium dichloride;
dimethylsilanediylbis{1-[2-tert-butyl, 4-(2-methylphenyl)indenyl]}hafnium dichloride;
dimethylsilanediylbis{1-[2-phenyl, 4-(2-methylphenyl)indenyl]}hafnium dichloride;
dimethylsilanediylbis{1-[2-n-propyl, 4-(2-ethylphenyl)indenyl]}hafnium dichloride;
dimethylsilanediylbis{1-[2-isopropyl, 4-(2-ethylphenyl)indenyl]}hafnium dichloride;
dimethylsilanediylbis{1-[2-n-butyl, 4-(2-ethylphenyl)indenyl]}hafnium dichloride;
dimethylsilanediylbis{1-[2-isobutyl, 4-(2-ethylphenyl)indenyl]}hafnium dichloride;
dimethylsilanediylbis{1-[2-sec-butyl, 4-(2-ethylphenyl)indenyl]}hafnium dichloride;
dimethylsilanediylbis{1-[2-tert-butyl, 4-(2-ethylphenyl)indenyl]}hafnium dichloride;
dimethylsilanediylbis{1-[2-phenyl, 4-(2-ethylphenyl)indenyl]}hafnium dichloride;
dimethylsilanediylbis{1-[2-n-propyl, 4-(2-n-propylphenyl)indenyl]}hafnium dichloride;
dimethylsilanediylbis{1-[2-isopropyl, 4-(2-n-propylphenyl)indenyl]}hafnium dichloride;
dimethylsilanediylbis{1-[2-n-butyl, 4-(2-n-propylphenyl)indenyl]}hafnium dichloride;
dimethylsilanediylbis{1-[2-isobutyl, 4-(2-n-propylphenyl)indenyl]}hafnium dichloride;
dimethylsilanediylbis{1-[2-sec-butyl, 4-(2-n-propylphenyl)indenyl]}hafnium dichloride;
dimethylsilanediylbis{1-[2-tert-butyl, 4-(2-n-propylphenyl)indenyl]}hafnium dichloride;
dimethylsilanediylbis{1-[2-phenyl, 4-(2-n-propylphenyl)indenyl]}hafnium dichloride;
dimethylsilanediylbis{1-[2-n-propyl, 4-(2-isopropylphenyl)indenyl]}hafnium dichloride;
dimethylsilanediylbis{1-[2-isopropyl, 4-(2-isopropylphenyl)indenyl]}hafnium dichloride;
dimethylsilanediylbis{1-[2-n-butyl, 4-(2-isopropylphenyl)indenyl]}hafnium dichloride;
dimethylsilanediylbis{1-[2-isobutyl, 4-(2-isopropylphenyl)indenyl]}hafnium dichloride;
dimethylsilanediylbis{1-[2-sec-butyl, 4-(2-isopropylphenyl)indenyl]}hafnium dichloride;
dimethylsilanediylbis{1-[2-tert-butyl, 4-(2-isopropylphenyl)indenyl]}hafnium dichloride;

dimethylsilanediylbis{1-[2-phenyl, 4-(2-isopropylphenyl)indenyl]}hafnium dichloride;
dimethylsilanediylbis{1-[2-n-propyl, 4-(2-n-butylphenyl)indenyl]}hafnium dichloride;
dimethylsilanediylbis{1-[2-isopropyl, 4-(2-n-butylphenyl)indenyl]}hafnium dichloride;
dimethylsilanediylbis{1-[2-n-butyl, 4-(2-n-butylphenyl)indenyl]}hafnium dichloride;
dimethylsilanediylbis{1-[2-isobutyl, 4-(2-n-butylphenyl)indenyl]}hafnium dichloride;
dimethylsilanediylbis{1-[2-sec-butyl, 4-(2-n-butylphenyl)indenyl]}hafnium dichloride;
dimethylsilanediylbis{1-[2-tert-butyl, 4-(2-n-butylphenyl)indenyl]}hafnium dichloride;
dimethylsilanediylbis{1-[2-phenyl, 4-(2-n-butylphenyl)indenyl]}hafnium dichloride;
dimethylsilanediylbis{1-[2-n-propyl, 4-(2-isobutylphenyl)indenyl]}hafnium dichloride;
dimethylsilanediylbis{1-[2-isopropyl, 4-(2-isobutylphenyl)indenyl]}hafnium dichloride;
dimethylsilanediylbis{1-[2-n-butyl, 4-(2-isobutylphenyl)indenyl]}hafnium dichloride;
dimethylsilanediylbis{1-[2-isobutyl, 4-(2-isobutylphenyl)indenyl]}hafnium dichloride;
dimethylsilanediylbis{1-[2-sec-butyl, 4-(2-isobutylphenyl)indenyl]}hafnium dichloride;
dimethylsilanediylbis{1-[2-tert-butyl, 4-(2-isobutylphenyl)indenyl]}hafnium dichloride;
dimethylsilanediylbis{1-[2-phenyl, 4-(2-isobutylphenyl)indenyl]}hafnium dichloride;
dimethylsilanediylbis{1-[2-n-propyl, 4-(2-sec-butylphenyl)indenyl]}hafnium dichloride;
dimethylsilanediylbis{1-[2-isopropyl, 4-(2-sec-butylphenyl)indenyl]}hafnium dichloride;
dimethylsilanediylbis{1-[2-n-butyl, 4-(2-sec-butylphenyl)indenyl]}hafnium dichloride;
dimethylsilanediylbis{1-[2-isobutyl, 4-(2-sec-butylphenyl)indenyl]}hafnium dichloride;
dimethylsilanediylbis{1-[2-sec-butyl, 4-(2-sec-butylphenyl)indenyl]}hafnium dichloride;
dimethylsilanediylbis{1-[2-tert-butyl, 4-(2-sec-butylphenyl)indenyl]}hafnium dichloride;
dimethylsilanediylbis{1-[2-phenyl, 4-(2-sec-butylphenyl)indenyl]}hafnium dichloride;
dimethylsilanediylbis{1-[2-n-propyl, 4-(2-tert-butylphenyl)indenyl]}hafnium dichloride;
dimethylsilanediylbis{1-[2-isopropyl, 4-(2-tert-butylphenyl)indenyl]}hafnium dichloride;
dimethylsilanediylbis{1-[2-n-butyl, 4-(2-tert-butylphenyl)indenyl]}hafnium dichloride;
dimethylsilanediylbis{1-[2-isobutyl, 4-(2-tert-butylphenyl)indenyl]}hafnium dichloride;
dimethylsilanediylbis{1-[2-sec-butyl, 4-(2-tert-butylphenyl)indenyl]}hafnium dichloride;
dimethylsilanediylbis{1-[2-tert-butyl, 4-(2-tert-butylphenyl)indenyl]}hafnium dichloride;
dimethylsilanediylbis{1-[2-phenyl, 4-(2-tert-butylphenyl)indenyl]}hafnium dichloride;
dimethylsilanediylbis{1-[2-n-propyl, 4-(2-biphenyl)indenyl]}hafnium dichloride;
dimethylsilanediylbis{1-[2-isopropyl, 4-(2-biphenyl)indenyl]}hafnium dichloride;
dimethylsilanediylbis{1-[2-n-butyl, 4-(2-biphenyl)indenyl]}hafnium dichloride;
dimethylsilanediylbis{1-[2-isobutyl, 4-(2-biphenyl)indenyl]}hafnium dichloride;
dimethylsilanediylbis{1-[2-sec-butyl, 4,2-biphenyl)indenyl]}hafnium dichloride;
dimethylsilanediylbis{1-[2-tert-butyl, 4-(2-biphenyl)indenyl]}hafnium dichloride;
dimethylsilanediylbis{1-[2-phenyl, 4-(2-biphenyl)indenyl]}hafnium dichloride;
dimethylsilanediylbis{1-[2-n-propyl, 4-(2-α-naphthylphenyl)indenyl]}hafnium dichloride;
dimethylsilanediylbis{1-[2-isopropyl, 4-(2-α-naphthylphenyl)indenyl]}hafnium dichloride;
dimethylsilanediylbis{1-[2-n-butyl, 4-(2-α-naphthylphenyl)indenyl]}hafnium dichloride;
dimethylsilanediylbis{1-[2-isobutyl, 4-(2-α-naphthylphenyl)indenyl]}hafnium dichloride;
dimethylsilanediylbis{1-[2-sec-butyl, 4-(2-α-naphthylphenyl)indenyl]}hafnium dichloride;
dimethylsilanediylbis{1-[2-tert-butyl, 4-(2-α-naphthylphenyl)indenyl]}hafnium dichloride;
dimethylsilanediylbis{1-[2-phenyl, 4-(2-α-naphthylphenyl)indenyl]}hafnium dichloride;
dimethylsilanediylbis{1-[2-n-propyl, 4-(2-β-naphthylphenyl)indenyl]}hafnium dichloride;
dimethylsilanediylbis{1-[2-isopropyl, 4-(2-β-naphthylphenyl)indenyl]}hafnium dichloride;
dimethylsilanediylbis{1-[2-n-butyl, 4-(2-β-naphthylphenyl)indenyl]}hafnium dichloride;
dimethylsilanediylbis{1-[2-isobutyl, 4-(2-β-naphthylphenyl)indenyl]}hafnium dichloride;
dimethylsilanediylbis{1-[2-sec-butyl, 4-(2-β-naphthylphenyl)indenyl]}hafnium dichloride;
dimethylsilanediylbis{1-[2-tert-butyl, 4-(2-β-naphthylphenyl)indenyl]}hafnium dichloride;
dimethylsilanediylbis{1-[2-phenyl, 4-(2-β-naphthylphenyl)indenyl]}hafnium dichloride;
dimethylsilanediylbis{1-[2-n-propyl, 4-(2-trifluoromethylphenyl)indenyl]}-hafnium dichloride;
dimethylsilanediylbis{1-[2-isopropyl, 4-(2-trifluoromethylphenyl)indenyl]}-hafnium dichloride;
dimethylsilanediylbis{1-[2-n-butyl, 4-(2-trifluoromethylphenyl)indenyl]}-hafnium dichloride;
dimethylsilanediylbis{1-[2-isobutyl, 4-(2-trifluoromethylphenyl)indenyl]}-hafnium dichloride;
dimethylsilanediylbis{1-[2-sec-butyl, 4-(2-trifluoromethylphenyl)indenyl]}-hafnium dichloride;
dimethylsilanediylbis{1-[2-tert-butyl, 4-(2-trifluoromethylphenyl)indenyl]}-hafnium dichloride;
dimethylsilanediylbis{1-[2-phenyl, 4-(2-trifluoromethylphenyl)indenyl]}-hafnium dichloride;
dimethylsilanediylbis{1-[2-n-propyl, 4-(2-trimethylsilylphenyl)indenyl]}hafnium dichloride;
dimethylsilanediylbis{1-[2-isopropyl, 4-(2-trimethylsilylphenyl)indenyl]}-hafnium dichloride;
dimethylsilanediylbis{1-[2-n-butyl, 4-(2-trimethylsilylphenyl)indenyl]}hafnium dichloride;
dimethylsilanediylbis{1-[2-isobutyl, 4-(2-trimethylsilylphenyl)indenyl]}hafnium dichloride;
dimethylsilanediylbis{1-[2-sec-butyl, 4-(2-trimethylsilylphenyl)indenyl]}-hafnium dichloride;
dimethylsilanediylbis{1-[2-tert-butyl, 4-(2-trimethylsilylphenyl)indenyl]}-hafnium dichloride;
dimethylsilanediylbis{1-[2-phenyl, 4-(2-trimethylsilylphenyl)indenyl]}hafnium dichloride;
dimethylsilanediylbis{1-[2-n-propyl, 4-(2,3-dimethylphenyl)indenyl]}hafnium dichloride;
dimethylsilanediylbis{1-[2-isopropyl, 4-(2,3-dimethylphenyl)indenyl]}hafnium dichloride;
dimethylsilanediylbis{1-[2-n-butyl, 4-(2,3-dimethylphenyl)indenyl]}hafnium dichloride;
dimethylsilanediylbis{1-[2-isobutyl, 4-(2,3-dimethylphenyl)indenyl]}hafnium dichloride;

dimethylsilanediylbis{1-[2-sec-butyl, 4-(2,3-dimethylphenyl)indenyl]}hafnium dichloride;
dimethylsilanediylbis{1-[2-tert-butyl, 4-(2,3-dimethylphenyl)indenyl]}hafnium dichloride;
dimethylsilanediylbis{1-[2-phenyl, 4-(2,3-dimethylphenyl)indenyl]}hafnium dichloride;
dimethylsilanediylbis{1-[2-n-propyl, 4-(2,3,4-trimethylphenyl)indenyl]}hafnium dichloride;
dimethylsilanediylbis{1-[2-isopropyl, 4-(2,3,4-trimethylphenyl)indenyl]}hafnium dichloride;
dimethylsilanediylbis{1-[2-n-butyl, 4-(2,3,4-trimethylphenyl)indenyl]}hafnium dichloride;
dimethylsilanediylbis{1-[2-isobutyl, 4-(2,3,4-trimethylphenyl)indenyl]}hafnium dichloride;
dimethylsilanediylbis{1-[2-sec-butyl, 4-(2,3,4-trimethylphenyl)indenyl]}hafnium dichloride;
dimethylsilanediylbis{1-[2-tert-butyl, 4-(2,3,4-trimethylphenyl)indenyl]}hafnium dichloride;
dimethylsilanediylbis{1-[2-phenyl, 4-(2,3,4-trimethylphenyl)indenyl]}hafnium dichloride;
dimethylsilanediylbis{1-[2-n-propyl, 4-(2,3,5-trimethylphenyl)indenyl]}hafnium dichloride;
dimethylsilanediylbis{1-[2-isopropyl, 4-(2,3,5-trimethylphenyl)indenyl]}hafnium dichloride;
dimethylsilanediylbis{1-[2-n-butyl, 4-(2,3,5-trimethylphenyl)indenyl]}hafnium dichloride;
dimethylsilanediylbis{1-[2-isobutyl, 4-(2,3,5-trimethylphenyl)indenyl]}hafnium dichloride;
dimethylsilanediylbis{1-[2-sec-butyl, 4-(2,3,5-trimethylphenyl)indenyl]}hafnium dichloride;
dimethylsilanediylbis{1-[2-tert-butyl, 4-(2,3,5-trimethylphenyl)indenyl]}hafnium dichloride;
dimethylsilanediylbis{1-[2-phenyl, 4-(2,3,5-trimethylphenyl)indenyl]}hafnium dichloride;
dimethylsilanediylbis{1-[2-n-propyl, 4-(2-methylphenyl)indenyl]}hafnium dimethyl;
dimethylsilanediylbis{1-[2-isopropyl, 4-(2-methylphenyl)indenyl]}hafnium dimethyl;
dimethylsilanediylbis{1-[2-n-butyl, 4-(2-methylphenyl)indenyl]}hafnium dimethyl;
dimethylsilanediylbis{1-[2-isobutyl, 4-(2-methylphenyl)indenyl]}hafnium dimethyl;
dimethylsilanediylbis{1-[2-sec-butyl, 4-(2-methylphenyl)indenyl]}hafnium dimethyl;
dimethylsilanediylbis{1-[2-tert-butyl, 4-(2-methylphenyl)indenyl]}hafnium dimethyl;
dimethylsilanediylbis{1-[2-phenyl, 4-(2-methylphenyl)indenyl]}hafnium dimethyl;
dimethylsilanediylbis{1-[2-n-propyl, 4-(2-ethylphenyl)indenyl]}hafnium dimethyl;
dimethylsilanediylbis{1-[2-isopropyl, 4-(2-ethylphenyl)indenyl]}hafnium dimethyl;
dimethylsilanediylbis{1-[2-n-butyl, 4-(2-ethylphenyl)indenyl]}hafnium dimethyl;
dimethylsilanediylbis{1-[2-isobutyl, 4-(2-ethylphenyl)indenyl]}hafnium dimethyl;
dimethylsilanediylbis{1-[2-sec-butyl, 4-(2-ethylphenyl)indenyl]}hafnium dimethyl;
dimethylsilanediylbis{1-[2-tert-butyl, 4-(2-ethylphenyl)indenyl]}hafnium dimethyl;
dimethylsilanediylbis{1-[2-phenyl, 4-(2-ethylphenyl)indenyl]}hafnium dimethyl;
dimethylsilanediylbis{1-[2-n-propyl, 4-(2-n-propylphenyl)indenyl]}hafnium dimethyl;
dimethylsilanediylbis{1-[2-isopropyl, 4-(2-n-propylphenyl)indenyl]}hafnium dimethyl;
dimethylsilanediylbis{1-[2-n-butyl, 4-(2-n-propylphenyl)indenyl]}hafnium dimethyl;
dimethylsilanediylbis{1-[2-isobutyl, 4-(2-n-propylphenyl)indenyl]}hafnium dimethyl;
dimethylsilanediylbis{1-[2-sec-butyl, 4-(2-n-propylphenyl)indenyl]}hafnium dimethyl;
dimethylsilanediylbis{1-[2-tert-butyl, 4-(2-n-propylphenyl)indenyl]}hafnium dimethyl;
dimethylsilanediylbis{1-[2-phenyl, 4-(2-n-propylphenyl)indenyl]}hafnium dimethyl;
dimethylsilanediylbis{1-[2-n-propyl, 4-(2-isopropylphenyl)indenyl]}hafnium dimethyl;
dimethylsilanediylbis{1-[2-isopropyl, 4-(2-isopropylphenyl)indenyl]}hafnium dimethyl;
dimethylsilanediylbis{1-[2-n-butyl, 4-(2-isopropylphenyl)indenyl]}hafnium dimethyl;
dimethylsilanediylbis{1-[2-isobutyl, 4-(2-isopropylphenyl)indenyl]}hafnium dimethyl;
dimethylsilanediylbis{1-[2-sec-butyl, 4-(2-isopropylphenyl)indenyl]}hafnium dimethyl;
dimethylsilanediylbis{1-[2-tert-butyl, 4-(2-isopropylphenyl)indenyl]}hafnium dimethyl;
dimethylsilanediylbis{1-[2-phenyl, 4-(2-isopropylphenyl)indenyl]}hafnium dimethyl;
dimethylsilanediylbis{1-[2-n-propyl, 4-(2-n-butylphenyl)indenyl]}hafnium dimethyl;
dimethylsilanediylbis{1-[2-isopropyl, 4-(2-n-butylphenyl)indenyl]}hafnium dimethyl;
dimethylsilanediylbis{1-[2-n-butyl, 4-(2-n-butylphenyl)indenyl]}hafnium dimethyl;
dimethylsilanediylbis{1-[2-isobutyl, 4-(2-n-butylphenyl)indenyl]}hafnium dimethyl;
dimethylsilanediylbis{1-[2-sec-butyl 4-(2-n-butylphenyl)indenyl]}hafnium dimethyl;
dimethylsilanediylbis{1-[2-tert-butyl, 4-(2-n-butylphenyl)indenyl]}hafnium dimethyl;
dimethylsilanediylbis{1-[2-phenyl, 4-(2-n-butylphenyl)indenyl]}hafnium dimethyl;
dimethylsilanediylbis{1-[2-n-propyl, 4-(2-isobutylphenyl)indenyl]}hafnium dimethyl;
dimethylsilanediylbis{1-[2-isopropyl, 4-(2-isobutylphenyl)indenyl]}hafnium dimethyl;
dimethylsilanediylbis{1-[2-n-butyl, 4-(2-isobutylphenyl)indenyl]}hafnium dimethyl;
dimethylsilanediylbis{1-[2-isobutyl, 4-(2-isobutylphenyl)indenyl]}hafnium dimethyl;
dimethylsilanediylbis{1-[2-sec-butyl, 4-(2-isobutylphenyl)indenyl]}hafnium dimethyl;
dimethylsilanediylbis{1-[2-tert-butyl, 4-(2-isobutylphenyl)indenyl]}hafnium dimethyl;
dimethylsilanediylbis{1-[2-phenyl, 4-(2-isobutylphenyl)indenyl}hafnium dimethyl;
dimethylsilanediylbis{1-[2-n-propyl, 4-(2-sec-butylphenyl)indenyl]}hafnium dimethyl;
dimethylsilanediylbis{1-[2-isopropyl, 4-(2-sec-butylphenyl)indenyl]}hafnium dimethyl;
dimethylsilanediylbis{1-[2-n-butyl, 4-(2-sec-butylphenyl)indenyl]}hafnium dimethyl;
dimethylsilanediylbis{1-[2-isobutyl, 4-(2-sec-butylphenyl)indenyl]}hafnium dimethyl;
dimethylsilanediylbis{1-[2-sec-butyl, 4-(2-sec-butylphenyl)indenyl]}hafnium dimethyl;
dimethylsilanediylbis{1-[2-tert-butyl, 4-(2-sec-butylphenyl)indenyl]}hafnium dimethyl;
dimethylsilanediylbis{1-[2-phenyl, 4-(2-sec-butylphenyl)indenyl]}hafnium dimethyl;
dimethylsilanediylbis{1-[2-n-propyl, 4-(2-tert-butylphenyl)indenyl]}hafnium dimethyl;
dimethylsilanediylbis{1-[2-isopropyl, 4-(2-tert-butylphenyl)indenyl]}hafnium dimethyl;

dimethylsilanediylbis{1-[2-n-butyl, 4-(2-tert-butylphenyl)indenyl]}hafnium dimethyl;
dimethylsilanediylbis{1-[2-isobutyl, 4-(2-tert-butylphenyl)indenyl]}hafnium dimethyl;
dimethylsilanediylbis{1-[2-sec-butyl, 4-(2-tert-butylphenyl)indenyl]}hafnium dimethyl;
dimethylsilanediylbis{1-[2-tert-butyl, 4-(2-tert-butylphenyl)indenyl]}hafnium dimethyl;
dimethylsilanediylbis{1-[2-phenyl, 4-(2-tert-butylphenyl)indenyl]}hafnium dimethyl;
dimethylsilanediylbis{1-[2-n-propyl, 4-(2-biphenyl)indenyl]}hafnium dimethyl;
dimethylsilanediylbis{1-[2-isopropyl, 4-(2-biphenyl)indenyl]}hafnium dimethyl;
dimethylsilanediylbis{1-[2-n-butyl, 4-(2-biphenyl)indenyl]}hafnium dimethyl;
dimethylsilanediylbis{1-[2-isobutyl, 4-(2-biphenyl)indenyl]}hafnium dimethyl;
dimethylsilanediylbis{1-[2-sec-butyl, 4-(2-biphenyl)indenyl]}hafnium dimethyl;
dimethylsilanediylbis{1-[2-tert-butyl, 4-(2-biphenyl)indenyl]}hafnium dimethyl;
dimethylsilanediylbis{1-[2-phenyl, 4-(2-biphenyl)indenyl]}hafnium dimethyl;
dimethylsilanediylbis{1-[2-n-propyl, 4-(2-α-naphthylphenyl)indenyl]}hafnium dimethyl;
dimethylsilanediylbis{1-[2-isopropyl, 4-(2-α-naphthylphenyl)indenyl]}hafnium dimethyl;
dimethylsilanediylbis{1-[2-n-butyl, 4-(2-α-naphthylphenyl)indenyl]}hafnium dimethyl;
dimethylsilanediylbis{1-[2-isobutyl, 4-(2-α-naphthylphenyl)indenyl]}hafnium dimethyl;
dimethylsilanediylbis{1-[2-sec-butyl, 4-(2-α-naphthylphenyl)indenyl]}hafnium dimethyl;
dimethylsilanediylbis{1-[2-tert-butyl, 4-(2-α-naphthylphenyl)indenyl]}hafnium dimethyl;
dimethylsilanediylbis{1-[2-phenyl, 4-(2-α-naphthylphenyl)indenyl]}hafnium dimethyl;
dimethylsilanediylbis{1-[2-n-propyl, 4-(2-β-naphthylphenyl)indenyl]}hafnium dimethyl;
dimethylsilanediylbis{1-[2-isopropyl, 4-(2-β-naphthylphenyl)indenyl]}hafnium dimethyl;
dimethylsilanediylbis{1-[2-n-butyl, 4-(2-β-naphthylphenyl)indenyl]}hafnium dimethyl;
dimethylsilanediylbis{1-[2-isobutyl, 4-(2-β-naphthylphenyl)indenyl]}hafnium dimethyl;
dimethylsilanediylbis{1-[2-sec-butyl, 4-(2-β-naphthylphenyl)indenyl]}hafnium dimethyl;
dimethylsilanediylbis{1-[2-tert-butyl, 4-(2-β-naphthylphenyl)indenyl]}hafnium dimethyl;
dimethylsilanediylbis{1-[2-phenyl, 4-(2-β-naphthylphenyl)indenyl]}hafnium dimethyl;
dimethylsilanediylbis{1-[2-n-propyl, 4-(2-trifluoromethylphenyl)indenyl]}-hafnium dimethyl;
dimethylsilanediylbis{1-[2-isopropyl, 4-(2-trifluoromethylphenyl)indenyl]}-hafnium dimethyl;
dimethylsilanediylbis{1-[2-n-butyl, 4-(2-trifluoromethylphenyl)indenyl]}-hafnium dimethyl;
dimethylsilanediylbis{1-[2-isobutyl, 4-(2-trifluoromethylphenyl)indenyl]}-hafnium dimethyl;
dimethylsilanediylbis{1-[2-sec-butyl, 4-(2-trifluoromethylphenyl)indenyl]}-hafnium dimethyl;
dimethylsilanediylbis{1-[2-tert-butyl, 4-(2-trifluoromethylphenyl)indenyl]}-hafnium dimethyl;
dimethylsilanediylbis{1-[2-phenyl, 4-(2-trifluoromethylphenyl)indenyl]}-hafnium dimethyl;
dimethylsilanediylbis{1-[2-n-propyl, 4-(2-trimethylsilylphenyl)indenyl]}hafnium dimethyl;
dimethylsilanediylbis{1-[2-isopropyl, 4-(2-trimethylsilylphenyl)indenyl]}hafnium dimethyl;
dimethylsilanediylbis{1-[2-n-butyl, 4-(2-trimethylsilylphenyl)indenyl]}hafnium dimethyl;
dimethylsilanediylbis{1-[2-isobutyl, 4-(2-trimethylsilylphenyl)indenyl]}hafnium dimethyl;
dimethylsilanediylbis{1-[2-sec-butyl, 4-(2-trimethylsilylphenyl)indenyl]}hafnium dimethyl;
dimethylsilanediylbis{1-[2-tert-butyl, 4-(2-trimethylsilylphenyl)indenyl]}hafnium dimethyl;
dimethylsilanediylbis{1-[2-phenyl, 4-(2-trimethylsilylphenyl)indenyl]}hafnium dimethyl;
dimethylsilanediylbis{1-[2-n-propyl, 4-(2,3-dimethylphenyl)indenyl]}hafnium dimethyl;
dimethylsilanediylbis{1-[2-isopropyl, 4-(2,3dimethylphenyl)indenyl]}hafnium dimethyl;
dimethylsilanediylbis{1-[2-n-butyl, 4-(2,3-dimethylphenyl)indenyl]}hafnium dimethyl;
dimethylsilanediylbis{1-[2-isobutyl, 4-(2,3-dimethylphenyl)indenyl]}hafnium dimethyl;
dimethylsilanediylbis{1-[2-sec-butyl, 4-(2,3-dimethylphenyl)indenyl]}hafnium dimethyl;
dimethylsilanediylbis{1-[2-tert-butyl, 4-(2,3-dimethylphenyl)indenyl]}hafnium dimethyl;
dimethylsilanediylbis{1-[2-phenyl, 4-(2,3-dimethylphenyl)indenyl]}hafnium dimethyl;
dimethylsilanediylbis{1-[2-n-propyl, 4-(2,3,4-trimethylphenyl)indenyl]}hafnium dimethyl;
dimethylsilanediylbis{1-[2-isopropyl, 4-(2,3,4-trimethylphenyl)indenyl]}hafnium dimethyl;
dimethylsilanediylbis{1-[2-n-butyl, 4-(2,3,4-trimethylphenyl)indenyl]}hafnium dimethyl;
dimethylsilanediylbis{1-[2-isobutyl, 4-(2,3,4-trimethylphenyl)indenyl]}hafnium dimethyl;
dimethylsilanediylbis{1-[2-sec-butyl, 4-(2,3,4-trimethylphenyl)indenyl]}hafnium dimethyl;
dimethylsilanediylbis{1-[2-tert-butyl, 4-(2,3,4-trimethylphenyl)indenyl]}hafnium dimethyl;
dimethylsilanediylbis{1-[2-phenyl, 4-(2,3,4-trimethylphenyl)indenyl]}hafnium dimethyl;
dimethylsilanediylbis{1-[2-n-propyl, 4-(2,3,5-trimethylphenyl)indenyl]}hafnium dimethyl;
dimethylsilanediylbis{1-[2-isopropyl, 4-(2,3,5-trimethylphenyl)indenyl]}hafnium dimethyl;
dimethylsilanediylbis{1-[2-n-butyl, 4-(2,3,5-trimethylphenyl)indenyl]}hafnium dimethyl;
dimethylsilanediylbis{1-[2-isobutyl, 4-(2,3,5-trimethylphenyl)indenyl]}hafnium dimethyl;
dimethylsilanediylbis{1-[2-sec-butyl, 4-(2,3,5-trimethylphenyl)indenyl]}hafnium dimethyl;
dimethylsilanediylbis{1-[2-tert-butyl, 4-(2,3,5-trimethylphenyl)indenyl]}hafnium dimethyl;
dimethylsilanediylbis{1-[2-phenyl, 4-(2,3,5-trimethylphenyl)indenyl]}hafnium dimethyl;
9-silafluorenediylbis{1-[2-methyl, 4-(2-methylphenyl)indenyl]}zirconium dichloride:
9-silafluorenediylbis{1-[2-ethyl, 4-(2-methylphenyl)indenyl]}zirconium dichloride;
9-silafluorenediylbis{1-[2-n-propyl, 4-(2-methylphenyl)indenyl]}zirconium dichloride;
9-silafluorenediylbis{1-[2-isopropyl, 4-(2-methylphenyl)indenyl]}zirconium dichloride;
9-silafluorenediylbis{1-[2-n-butyl, 4-(2-methylphenyl)indenyl]}zirconium dichloride;
9-silafluorenediylbis{1-[2-isobutyl, 4-(2-methylphenyl)indenyl]}zirconium dichloride;
9-silafluorenediylbis{1-[2-sec-butyl, 4-(2-methylphenyl)indenyl]}zirconium dichloride;

9-silafluorenediylbis{1-[2-tert-butyl, 4-(2-methylphenyl) indenyl]}zirconium dichloride;
9-silafluorenediylbis{1-[2-phenyl, 4-(2-methylphenyl) indenyl]}zirconium dichloride;
9-silafluorenediylbis{1-[2-methyl, 4-(2-ethylphenyl) indenyl]}zirconium dichloride;
9-silafluorenediylbis{1-[2-ethyl, 4-(2-ethylphenyl)indenyl]}zirconium dichloride;
9-silafluorenediylbis{1-[2-n-propyl, 4-(2-ethylphenyl) indenyl]}zirconium dichloride;
9-silafluorenediylbis{1-[2-isopropyl, 4-(2-ethylphenyl) indenyl]}zirconium dichloride;
9-silafluorenediylbis{1-[2-n-butyl, 4-(2-ethylphenyl) indenyl]}zirconium dichloride;
9-silafluorenediylbis{1-[2-isobutyl, 4-(2-ethylphenyl) indenyl]}zirconium dichloride;
9-silafluorenediylbis{1-[2-sec-butyl, 4-(2-ethylphenyl) indenyl]}zirconium dichloride;
9-silafluorenediylbis{1-[2-tert-butyl, 4-(2-ethylphenyl) indenyl]}zirconium dichloride,
9-silafluorenediylbis{1-[2-phenyl, 4-(2-ethylphenyl) indenyl]}zirconium dichloride;
9-silafluorenediylbis{1-[2-methyl, 4-(2-n-propylphenyl) indenyl]}zirconium dichloride;
9-silafluorenediylbis{1-[2-ethyl, 4-(2-n-propylphenyl) indenyl]}zirconium dichloride;
9-silafluorenediylbis{1-[2-n-propyl, 4-(2-n-propylphenyl) indenyl]}zirconium dichloride;
9-silafluorenediylbis{1-[2-isopropyl, 4-(2-n-propylphenyl) indenyl]}zirconium dichloride;
9-silafluorenediylbis{1-[2-n-butyl, 4-(2-n-propylphenyl) indenyl]}zirconium dichloride;
9-silafluorenediylbis{1-[2-isobutyl, 4-(2-n-propylphenyl) indenyl]}zirconium dichloride;
9-silafluorenediylbis{1-[2-sec-butyl, 4-(2-n-propylphenyl) indenyl]}zirconium dichloride;
9-silafluorenediylbis{1-[2-tert-butyl, 4-(2-n-propylphenyl) indenyl]}zirconium dichloride;
9-silafluorenediylbis{1-[2-phenyl, 4-(2-n-propylphenyl) indenyl]}zirconium dichloride;
9-silafluorenediylbis{1-[2-methyl, 4-(2-isopropylphenyl) indenyl]}zirconium dichloride;
9-silafluorenediylbis{1-[2-ethyl, 4-(2-isopropylphenyl) indenyl]}zirconium dichloride;
9-silafluorenediylbis{1-[2-n-propyl, 4-(2-isopropylphenyl) indenyl]}zirconium dichloride;
9-silafluorenediylbis{1-[2-isopropyl, 4-(2-isopropylphenyl) indenyl]}zirconium dichloride;
9-silafluorenediylbis{1-[2-n-butyl, 4-(2-isopropylphenyl) indenyl]}zirconium dichloride;
9-silafluorenediylbis{1-[2-isobutyl, 4-(2-isopropylphenyl) indenyl]}zirconium dichloride;
9-silafluorenediylbis{1-[2-sec-butyl, 4-(2-isopropylphenyl) indenyl]}zirconium dichloride;
9-silafluorenediylbis{1-[2-tert-butyl, 4-(2-isopropylphenyl) indenyl]}zirconium dichloride;
9-silafluorenediylbis{1-[2-phenyl, 4-(2-isopropylphenyl) indenyl]}zirconium dichloride;
9-silafluorenediylbis{1-[2-methyl, 4-(2-n-butylphenyl) indenyl]}zirconium dichloride;
9-silafluorenediylbis{1-[2-ethyl, 4-(2-n-butylphenyl) indenyl]}zirconium dichloride;
9-silafluorenediylbis{1-[2-n-propyl, 4-(2-n-butylphenyl) indenyl]}zirconium dichloride;
9-silafluorenediylbis{1-[2-isopropyl, 4-(2-n-butylphenyl) indenyl]}zirconium dichloride;
9-silafluorenediylbis{1-[2-n-butyl, 4-(2-n-butylphenyl) indenyl]}zirconium dichloride;
9-silafluorenediylbis{1-[2-isobutyl, 4-(2-n-butylphenyl) indenyl]}zirconium dichloride;
9-silafluorenediylbis{1-[2-sec-butyl, 4-(2-n-butylphenyl) indenyl]}zirconium dichloride;
9-silafluorenediylbis{1-[2-tert-butyl, 4-(2-n-butylphenyl) indenyl]}zirconium dichloride;
9-silafluorenediylbis{1-[2-phenyl, 4-(2-n-butylphenyl) indenyl]}zirconium dichloride;
9-silafluorenediylbis{1-[2-methyl, 4-(2-isobutylphenyl) indenyl]}zirconium dichloride;
9-silafluorenediylbis{1-[2-ethyl, 4-(2-isobutylphenyl) indenyl]}zirconium dichloride;
9-silafluorenediylbis{1-[2-n-propyl, 4-(2-isobutylphenyl) indenyl]}zirconium dichloride;
9-silafluorenediylbis{1-[2-isopropyl, 4-(2-isobutylphenyl) indenyl]}zirconium dichloride;
9-silafluorenediylbis{1-[2-n-butyl, 4-(2-isobutylphenyl) indenyl]}zirconium dichloride;
9-silafluorenediylbis{1-[2-isobutyl, 4-(2-isobutylphenyl) indenyl]}zirconium dichloride;
9-silafluorenediylbis{1-[2-sec-butyl, 4-(2-isobutylphenyl) indenyl]}zirconium dichloride;
9-silafluorenediylbis{1-[2-tert-butyl, 4-(2-isobutylphenyl) indenyl]}zirconium dichloride;
9-silafluorenediylbis{1-[2-phenyl, 4-(2-isobutylphenyl) indenyl]}zirconium dichloride;
9-silafluorenediylbis{1-[2-methyl, 4-(2-sec-butylphenyl) indenyl]}zirconium dichloride;
9-silafluorenediylbis{1-[2-ethyl, 4-(2-sec-butylphenyl) indenyl]}zirconium dichloride;
9-silafluorenediylbis{1-[2-n-propyl, 4-(2-sec-butylphenyl) indenyl]}zirconium dichloride;
9-silafluorenediylbis{1-[2-isopropyl, 4-(2-sec-butylphenyl) indenyl]}zirconium dichloride;
9-silafluorenediylbis{1-[2-n-butyl, 4-(2-sec-butylphenyl) indenyl]}zirconium dichloride;
9-silafluorenediylbis{1-[2-isobutyl, 4-(2-sec-butylphenyl) indenyl]}zirconium dichloride;
9-silafluorenediylbis{1-[2-sec-butyl, 4-(2-sec-butylphenyl) indenyl]}zirconium dichloride;
9-silafluorenediylbis{1-[2-tert-butyl, 4-(2-sec-butylphenyl) indenyl]}zirconium dichloride;
9-silafluorenediylbis{1-[2-phenyl, 4-(2-sec-butylphenyl) indenyl]}zirconium dichloride;
9-silafluorenediylbis{1-[2-methyl, 4-(2-tert-butylphenyl) indenyl]}zirconium dichloride;
9-silafluorenediylbis{1-[2-ethyl, 4-(2-tert-butylphenyl) indenyl]}zirconium dichloride,
9-silafluorenediylbis{1-[2-n-propyl, 4-(2-tert-butylphenyl) indenyl]}zirconium dichloride;
9-silafluorenediylbis{1-[2-isopropyl, 4-(2-tert-butylphenyl) indenyl]}zirconium dichloride;
9-silafluorenediylbis{1-[2-n-butyl, 4-(2-tert-butylphenyl) indenyl]}zirconium dichloride;
9-silafluorenediylbis{1-[2-isobutyl, 4-(2-tert-butylphenyl) indenyl]}zirconium dichloride;
9-silafluorenediylbis{1-[2-sec-butyl, 4-(2-tert-butylphenyl) indenyl]}zirconium dichloride;
9-silafluorenediylbis{1-[2-tert-butyl, 4-(2-tert-butylphenyl) indenyl]}zirconium dichloride;
9-silafluorenediylbis{1-[2-phenyl, 4-(2-tert-butylphenyl) indenyl]}zirconium dichloride;
9-silafluorenediylbis{1-[2-methyl, 4-(2-biphenyl)indenyl]}zirconium dichloride;
9-silafluorenediylbis{1-[2-ethyl, 4-(2-biphenyl)indenyl]}zirconium dichloride;
9-silafluorenediylbis{1-[2-n-propyl, 4-(2-biphenyl) indenyl]} zirconium dichloride;

9-silafluorenediylbis{1-[2-isopropyl, 4-(2-biphenyl)indenyl]}zirconium dichloride;
9-silafluorenediylbis{1-[2-n-butyl, 4-(2-biphenyl)indenyl]}zirconium dichloride;
9-silafluorenediylbis{1-[2-isobutyl, 4-(2-biphenyl)indenyl]} zirconium dichloride;
9-silafluorenediylbis{1-[2-sec-butyl, 4-(2-biphenyl)indenyl]} zirconium dichloride;
9-silafluorenediylbis{1-[2-tert-butyl, 4-(2-biphenyl)indenyl]}zirconium dichloride;
9-silafluorenediylbis{1-[2-phenyl, 4-(2-biphenyl)indenyl]}zirconium dichloride;
9-silafluorenediylbis{1-[2-n-propyl, 4-(2-α-naphthylphenyl)indenyl]}zirconium dichloride;
9-silafluorenediylbis{1-[2-isopropyl, 4-(2-α-naphthylphenyl)indenyl]}zirconium dichloride;
9-silafluorenediylbis{1-[2-n-butyl, 4-(2-α-naphthylphenyl)indenyl]}zirconium dichloride;
9-silafluorenediylbis{1-[2-isobutyl, 4-(2-α-naphthylphenyl)indenyl]}zirconium dichloride;
9-silafluorenediylbis{1-[2-sec-butyl, 4-(2-α-naphthylphenyl)indenyl]}zirconium dichloride;
9-silafluorenediylbis{1-[2-tert-butyl, 4-(2-α-naphthylphenyl)indenyl}zirconium dichloride;
9-silafluorenediylbis{1-[2-phenyl, 4-(2-α-naphthylphenyl)indenyl]}zirconium dichloride;
9-silafluorenediylbis{1-[2-n-propyl, 4-(2-β-naphthylphenyl)indenyl]}zirconium dichloride;
9-silafluorenediylbis{-[2-isopropyl, 4-(2-β-naphthylphenyl)indenyl]}zirconium dichloride;
9-silafluorenediylbis{1-[2-n-butyl, 4-(2-β-naphthylphenyl)indenyl]}zirconium dichloride;
9-silafluorenediylbis{1-[2-isobutyl, 4-(2-β-naphthylphenyl)indenyl]}zirconium dichloride;
9-silafluorenediylbis{1-[2-sec-butyl, 4-(2-β-naphthylphenyl)indenyl]}zirconium dichloride;
9-silafluorenediylbis{1-[2-tert-butyl, 4-(2-β-naphthylphenyl)indenyl]}zirconium dichloride;
9-silafluorenediylbis{1-[2-phenyl, 4-(2-β-naphthylphenyl)indenyl]}zirconium dichloride;
9-silafluorenediylbis{1-[2-methyl, 4-(2-trifluoromethylphenyl)indenyl]}zirconium dichloride;
9-silafluorenediylbis{1-[2-ethyl, 4-(2-trifluoromethylphenyl)indenyl]}zirconium dichloride;
9-silafluorenediylbis{1-[2-n-propyl, 4-(2-trifluoromethylphenyl)indenyl]}-zirconium dichloride;
9-silafluorenediylbis{1-[2-isopropyl, 4-(2-trifluoromethylphenyl)indenyl]}-zirconium dichloride;
9-silafluorenediylbis{1-[2-n-butyl, 4-(2-trifluoromethylphenyl)indenyl]}-zirconium dichloride;
9-silafluorenediylbis{1-[2-isobutyl, 4-(2-trifluoromethylphenyl)indenyl]}-zirconium dichloride;
9-silafluorenediylbis{1-[2-sec-butyl, 4-(2-trifluoromethylphenyl)indenyl]}-zirconium dichloride;
9-silafluorenediylbis{1-[2-tert-butyl, 4-(2-trifluoromethylphenyl)indenyl]}-zirconium dichloride;
9-silafluorenediylbis{1-[2-phenyl, 4-(2-trifluoromethylphenyl)indenyl]}-zirconium dichloride
9-silafluorenediylbis{1-[2-methyl, 4-(2-trimethylsilylphenyl)indenyl]}zirconium dichloride;
9-silafluorenediylbis{1-[2-ethyl, 4-(2-trimethylsilylphenyl)indenyl]}zirconium dichloride;
9-silafluorenediylbis{1-[2-n-propyl, 4-(2-trimethylsilylphenyl)indenyl]}-zirconium dichloride;
9-silafluorenediylbis{1-[2-isopropyl, 4-(2-trimethylsilylphenyl)indenyl]}-zirconium dichloride;
9-silafluorenediylbis{1-[2-n-butyl, 4-(2-trimethylsilylphenyl)indenyl]}-zirconium dichloride;
9-silafluorenediylbis{1-[2-isobutyl, 4-(2-trimethylsilylphenyl)indenyl]}-zirconium dichloride;
9-silafluorenediylbis{1-[2-sec-butyl, 4-(2-trimethylsilylphenyl)indenyl]}-zirconium dichloride;
9-silafluorenediylbis{1-[2-tert-butyl, 4-(2-trimethylsilylphenyl)indenyl]}-zirconium dichloride;
9-silafluorenediylbis{1-[2-phenyl, 4-(2-trimethylsilylphenyl)indenyl]}-zirconium dichloride;
9-silafluorenediylbis{1-[2-n-propyl, 4-(2,3-dimethylphenyl)indenyl]}zirconium dichloride;
9-silafluorenediylbis{1-[2-isopropyl, 4-(2,3-dimethylphenyl)indenyl]}zirconium dichloride;
9-silafluorenediylbis{1-[2-n-butyl, 4-(2,3-dimethylphenyl)indenyl]}zirconium dichloride;
9-silafluorenediylbis{1-[2-isobutyl, 4-(2,3-dimethylphenyl)indenyl]}zirconium dichloride;
9-silafluorenediylbis{1-[2-sec-butyl, 4-(2,3-dimethylphenyl)indenyl]}zirconium dichloride;
9-silafluorenediylbis{1-[2-tert-butyl, 4-(2,3-dimethylphenyl)indenyl]}zirconium dichloride;
9-silafluorenediylbis{1-[2-phenyl, 4-(2,3-dimethylphenyl)indenyl]}zirconium dichloride;
9-silafluorenediylbis{1-[2-n-propyl, 4-(2,3,4-trimethylphenyl)indenyl]}zirconium dichloride;
9-silafluorenediylbis{1-[2-isopropyl, 4-(2,3,4-trimethylphenyl)indenyl]}zirconium dichloride;
9-silafluorenediylbis{1-[2-n-butyl, 4-(2,3,4-trimethylphenyl)indenyl]}zirconium dichloride;
9-silafluorenediylbis{1-[2-isobutyl, 4-(2,3,4-trimethylphenyl)indenyl]}zirconium dichloride;
9-silafluorenediylbis{1-[2-sec-butyl, 4-(2,3,4-trimethylphenyl)indenyl]}zirconium dichloride;
9-silafluorenediylbis{1-[2-tert-butyl, 4-(2,3,4-trimethylphenyl)indenyl]}zirconium dichloride;
9-silafluorenediylbis{1-[2-phenyl, 4-(2,3,4-trimethylphenyl)indenyl]}zirconium dichloride;
9-silafluorenediylbis{1-[2-n-propyl, 4-(2,3,5-trimethylphenyl)indenyl]}zirconium dichloride;
9-silafluorenediylbis{1-[2-isopropyl, 4-(2,3,5-trimethylphenyl)indenyl]}zirconium dichloride;
9-silafluorenediylbis{1-[2-n-butyl, 4-(2,3,5-trimethylphenyl)indenyl]}zirconium dichloride;
9-silafluorenediylbis{1-[2-isobutyl, 4-(2,3,5-trimethylphenyl)indenyl]}zirconium dichloride;
9-silafluorenediylbis{1-[2-sec-butyl, 4-(2,3,5-trimethylphenyl)indenyl]}zirconium dichloride;
9-silafluorenediylbis{1-[2-tert-butyl, 4-(2,3,5-trimethylphenyl)indenyl]}zirconium dichloride;
9-silafluorenediylbis{1-[2-phenyl, 4-(2,3,5-trimethylphenyl)indenyl]}zirconium dichloride;
9-silafluorenediylbis{1-[2-n-propyl, 4-(2-methylphenyl)indenyl]}zirconium dimethyl;
9-silafluorenediylbis{1-[2-isopropyl, 4-(2-methylphenyl)indenyl]}zirconium dimethyl;
9-silafluorenediylbis{1-[2-n-butyl, 4-(2-methylphenyl)indenyl]}zirconium dimethyl;
9-silafluorenediylbis{1-[2-isobutyl, 4-(2-methylphenyl)indenyl]}zirconium dimethyl;
9-silafluorenediylbis{1-[2-sec-butyl, 4-(2-methylphenyl)indenyl]}zirconium dimethyl;
9-silafluorenediylbis{1-[2-tert-butyl, 4-(2-methylphenyl)indenyl]}zirconium dimethyl;
9-silafluorenediylbis{1-[2-phenyl, 4-(2-methylphenyl)indenyl]}zirconium dimethyl;
9-silafluorenediylbis{1-[2-n-propyl, 4-(2-ethylphenyl)indenyl]}zirconium dimethyl;
9-silafluorenediylbis{1-[2-isopropyl, 4-(2-ethylphenyl)indenyl]}zirconium dimethyl;

9-silafluorenediylbis{1-[2-n-butyl, 4-(2-ethylphenyl)indenyl]}zirconium dimethyl;
9-silafluorenediylbis{1-[2-isobutyl, 4-(2-ethylphenyl)indenyl]}zirconium dimethyl;
9-silafluorenediylbis{1-[2-sec-butyl, 4-(2-ethylphenyl)indenyl]}zirconium dimethyl;
9-silafluorenediylbis{1-[2-tert-butyl, 4-(2-ethylphenyl)indenyl]}zirconium dimethyl;
9-silafluorenediylbis{1-[2-phenyl, 4-(2-ethylphenyl)indenyl]}zirconium dimethyl;
9-silafluorenediylbis{1-[2-n-propyl, 4-(2-n-propylphenyl)indenyl]}zirconium dimethyl;
9-silafluorenediylbis{1-[2-isopropyl, 4-(2-n-propylphenyl)indenyl]}zirconium dimethyl;
9-silafluorenediylbis{1-[2-n-butyl, 4-(2-n-propylphenyl)indenyl]}zirconium dimethyl;
9-silafluorenediylbis{1-[2-isobutyl, 4-(2-n-propylphenyl)indenyl]}zirconium dimethyl;
9-silafluorenediylbis{1-[2-sec-butyl, 4-(2-n-propylphenyl)indenyl]}zirconium dimethyl;
9-silafluorenediylbis{1-[2-tert-butyl, 4-(2-n-propylphenyl)indenyl]}zirconium dimethyl;
9-silafluorenediylbis{1-[2-phenyl, 4-(2-n-propylphenyl)indenyl]}zirconium dimethyl;
9-silafluorenediylbis{1-[2-n-propyl, 4-(2-isopropylphenyl)indenyl]}zirconium dimethyl;
9-silafluorenediylbis{1-[2-isopropyl, 4-(2-isopropylphenyl)indenyl]}zirconium dimethyl;
9-silafluorenediylbis{1-[2-n-butyl, 4-(2-isopropylphenyl)indenyl]}zirconium dimethyl;
9-silafluorenediylbis{1-[2-isobutyl, 4-(2-isopropylphenyl)indenyl]}zirconium dimethyl;
9-silafluorenediylbis{1-[2-sec-butyl, 4-(2-isopropylphenyl)indenyl]}zirconium dimethyl;
9-silafluorenediylbis{1-[2-tert-butyl, 4-(2-isopropylphenyl)indenyl]}zirconium dimethyl;
9-silafluorenediylbis{1-[2-phenyl, 4-(2-isopropylphenyl)indenyl]}zirconium dimethyl;
9-silafluorenediylbis{1-[2-n-propyl, 4-(2-n-butylphenyl)indenyl]}zirconium dimethyl;
9-silafluorenediylbis{1-[2-isopropyl, 4-(2-n-butylphenyl)indenyl]}zirconium dimethyl;
9-silafluorenediylbis{1-[2-n-butyl, 4-(2-n-butylphenyl)indenyl]}zirconium dimethyl;
9-silafluorenediylbis{1-[2-isobutyl, 4-(2-n-butylphenyl)indenyl]}zirconium dimethyl;
9-silafluorenediylbis{1-[2-sec-butyl, 4-(2-n-butylphenyl)indenyl]}zirconium dimethyl;
9-silafluorenediylbis{1-[2-tert-butyl, 4-(2-n-butylphenyl)indenyl]}zirconium dimethyl;
9-silafluorenediylbis{1-[2-phenyl, 4-(2-n-butylphenyl)indenyl]}zirconium dimethyl;
9-silafluorenediylbis{1-[2-n-propyl, 4-(2-isobutylphenyl)indenyl]}zirconium dimethyl;
9-silafluorenediylbis{1-[2-isopropyl, 4-(2-isobutylphenyl)indenyl]}zirconium dimethyl;
9-silafluorenediylbis{1-[2-n-butyl, 4-(2-isobutylphenyl)indenyl]}zirconium dimethyl;
9-silafluorenediylbis{1-[2-isobutyl, 4-(2-isobutylphenyl)indenyl]}zirconium dimethyl;
9-silafluorenediylbis{1-[2-sec-butyl, 4-(2-isobutylphenyl)indenyl]}zirconium dimethyl;
9-silafluorenediylbis{1-[2-tert-butyl, 4-(2-isobutylphenyl)indenyl]}zirconium dimethyl;
9-silafluorenediylbis{1-[2-phenyl, 4-(2-isobutylphenyl)indenyl]}zirconium dimethyl;
9-silafluorenediylbis{1-[2-n-propyl, 4-(2-sec-butylphenyl)indenyl]}zirconium dimethyl;
9-silafluorenediylbis{1-[2-isopropyl, 4-(2-sec-butylphenyl)indenyl]}zirconium dimethyl;
9-silafluorenediylbis{1-[2-n-butyl, 4-(2-sec-butylphenyl)indenyl]}zirconium dimethyl;
9-silafluorenediylbis{1-[2-isobutyl, 4-(2-sec-butylphenyl)indenyl]}zirconium dimethyl;
9-silafluorenediylbis{1-[2-sec-butyl, 4-(2-sec-butylphenyl)indenyl]}zirconium dimethyl;
9-silafluorenediylbis{1-[2-tert-butyl, 4-(2-sec-butylphenyl)indenyl]}zirconium dimethyl;
9-silafluorenediylbis{1-[2-phenyl, 4-(2-sec-butylphenyl)indenyl]}zirconium dimethyl;
9-silafluorenediylbis{1-[2-n-propyl, 4-(2-tert-butylphenyl)indenyl]}zirconium dimethyl;
9-silafluorenediylbis{1-[2-isopropyl, 4-(2-tert-butylphenyl)indenyl]}zirconium dimethyl;
9-silafluorenediylbis{1-[2-n-butyl, 4-(2-tert-butylphenyl)indenyl]}zirconium dimethyl;
9-silafluorenediylbis{1-[2-isobutyl, 4-(2-tert-butylphenyl)indenyl]}zirconium dimethyl;
9-silafluorenediylbis{1-[2-sec-butyl, 4-(2-tert-butylphenyl)indenyl]}zirconium dimethyl;
9-silafluorenediylbis{1-[2-tert-butyl, 4-(2-tert-butylphenyl)indenyl]}zirconium dimethyl;
9-silafluorenediylbis{1-[2-phenyl, 4-(2-tert-butylphenyl)indenyl]}zirconium dimethyl;
9-silafluorenediylbis{1-[2-n-propyl, 4-(2-biphenyl)indenyl]} zirconium dimethyl;
9-silafluorenediylbis{1-[2-isopropyl, 4-(2-biphenyl)indenyl]}zirconium dimethyl;
9-silafluorenediylbis{1-[2-n-butyl, 4-(2-biphenyl)indenyl]} zirconium dimethyl;
9-silafluorenediylbis{1-[2-isobutyl, 4-(2-biphenyl)indenyl]}zirconium dimethyl;
9-silafluorenediylbis{1-[2-sec-butyl, 4-(2-biphenyl)indenyl]}zirconium dimethyl;
9-silafluorenediylbis{1-[2-tert-butyl, 4-(2-biphenyl)indenyl]}zirconium dimethyl;
9-silafluorenediylbis{1-[2-phenyl, 4-(2-biphenyl)indenyl]}zirconium dimethyl;
9-silafluorenediylbis{1-[2-n-propyl, 4-(2-α-naphthylphenyl)indenyl]}zirconium dimethyl;
9-silafluorenediylbis{1-[2-isopropyl, 4-(2-α-naphthylphenyl)indenyl]}zirconium dimethyl;
9-silafluorenediylbis{1-[2-n-butyl, 4-(2-α-naphthylphenyl)indenyl]}zirconium dimethyl;
9-silafluorenediylbis{1-[2-isobutyl, 4-(2-α-naphthylphenyl)indenyl]}zirconium dimethyl;
9-silafluorenediylbis{1-[2-sec-butyl, 4-(2-α-naphthylphenyl)indenyl]}zirconium dimethyl;
9-silafluorenediylbis{1-[2-tert-butyl, 4-(2-α-naphthylphenyl)indenyl]}zirconium dimethyl;
9-silafluorenediylbis{1-[2-phenyl, 4-(2-α-naphthylphenyl)indenyl]}zirconium dimethyl;
9-silafluorenediylbis{1-[2-n-propyl, 4-(2-β-naphthylphenyl)indenyl]}zirconium dimethyl;
9-silafluorenediylbis{1-[2-isopropyl, 4-(2-β-naphthylphenyl)indenyl]}zirconium dimethyl;
9-silafluorenediylbis{1-[2-n-butyl, 4-(2-β-naphthylphenyl)indenyl]}zirconium dimethyl;
9-silafluorenediylbis{1-[2-isobutyl, 4-(2-β-naphthylphenyl)indenyl]}zirconium dimethyl;
9-silafluorenediylbis{1-[2-sec-butyl, 4-(2-β-naphthylphenyl)indenyl]}zirconium dimethyl;
9-silafluorenediylbis{1-[2-tert-butyl, 4-(2-β-naphthylphenyl)indenyl]}zirconium dimethyl;
9-silafluorenediylbis{1-[2-phenyl, 4-(2-β-naphthylphenyl)indenyl]}zirconium dimethyl;

9-silafluorenediylbis{1-[2-n-propyl, 4-(2-trifluoromethylphenyl)indenyl]}zirconium dimethyl;
9-silafluorenediylbis{1-[2-isopropyl, 4-(2-trifluoromethylphenyl)indenyl]}zirconium dimethyl;
9-silafluorenediylbis{1-[2-n-butyl, 4-(2-trifluoromethylphenyl)indenyl]}zirconium dimethyl;
9-silafluorenediylbis{1-[2-isobutyl, 4-(2-trifluoromethylphenyl)indenyl]}zirconium dimethyl;
9-silafluorenediylbis{1-[2-sec-butyl, 4-(2-trifluoromethylphenyl)indenyl]}zirconium dimethyl;
9-silafluorenediylbis{1-[2-tert-butyl, 4-(2-trifluoromethylphenyl)indenyl]}zirconium dimethyl;
9-silafluorenediylbis{1-[2-phenyl, 4-(2-trifluoromethylphenyl)indenyl]}zirconium dimethyl;
9-silafluorenediylbis{1-[2-n-propyl, 4-(2-trimethylsilylphenyl)indenyl]}zirconium dimethyl;
9-silafluorenediylbis{1-[2-isopropyl, 4-(2-trimethylsilylphenyl)indenyl]}zirconium dimethyl;
9-silafluorenediylbis{1-[2-n-butyl, 4-(2-trimethylsilylphenyl)indenyl]}zirconium dimethyl;
9-silafluorenediylbis{1-[2-isobutyl, 4-(2-trimethylsilylphenyl)indenyl]}zirconium dimethyl;
9-silafluorenediylbis{1-[2-sec-butyl, 4-(2-trimethylsilylphenyl)indenyl]}zirconium dimethyl;
9-silafluorenediylbis{1-[2-tert-butyl, 4-(2-trimethylsilylphenyl)indenyl]}zirconium dimethyl;
9-silafluorenediylbis{1-[2-phenyl, 4-(2-trimethylsilylphenyl)indenyl]}zirconium dimethyl;
9-silafluorenediylbis{1-[2-n-propyl, 4-(2,3-dimethylphenyl)indenyl]}zirconium dimethyl;
9-silafluorenediylbis{1-[2-isopropyl, 4-(2,3-dimethylphenyl)indenyl]}zirconium dimethyl;
9-silafluorenediylbis{1-[2-n-butyl, 4-(2,3-dimethylphenyl)indenyl]}zirconium dimethyl;
9-silafluorenediylbis{1-[2-isobutyl, 4-(2,3-dimethylphenyl)indenyl]}zirconium dimethyl;
9-silafluorenediylbis{1-[2-sec-butyl, 4-(2,3-dimethylphenyl)indenyl]}zirconium dimethyl;
9-silafluorenediylbis{1-[2-tert-butyl, 4-(2,3-dimethylphenyl)indenyl]}zirconium dimethyl;
9-silafluorenediylbis{1-[2-phenyl, 4-(2,3-dimethylphenyl)indenyl]}zirconium dimethyl;
9-silafluorenediylbis{1-[2-n-propyl, 4-(2,3,4-trimethylphenyl)indenyl]}zirconium dimethyl;
9-silafluorenediylbis{1-[2-isopropyl, 4-(2,3,4-trimethylphenyl)indenyl]}zirconium dimethyl;
9-silafluorenediylbis{1-[2-n-butyl, 4-(2,3,4-trimethylphenyl)indenyl]}zirconium dimethyl;
9-silafluorenediylbis{1-[2-isobutyl, 4-(2,3,4-trimethylphenyl)indenyl]}zirconium dimethyl;
9-silafluorenediylbis{1-[2-sec-butyl, 4-(2,3,4-trimethylphenyl)indenyl]}zirconium dimethyl;
9-silafluorenediylbis{1-[2-tert-butyl, 4-(2,3,4-trimethylphenyl)indenyl]}zirconium dimethyl;
9-silafluorenediylbis{1-[2-phenyl, 4-(2,3,4-trimethylphenyl)indenyl]}zirconium dimethyl;
9-silafluorenediylbis{1-[2-n-propyl, 4-(2,3,5-trimethylphenyl)indenyl]}zirconium dimethyl;
9-silafluorenediylbis{1-[2-isopropyl, 4-(2,3,5-trimethylphenyl)indenyl]}zirconium dimethyl;
9-silafluorenediylbis{1-[2-n-butyl, 4-(2,3,5-trimethylphenyl)indenyl]}zirconium dimethyl;
9-silafluorenediylbis{1-[2-isobutyl, 4-(2,3,5-trimethylphenyl)indenyl]}zirconium dimethyl;
9-silafluorenediylbis{1-[2-sec-butyl, 4-(2,3,5-trimethylphenyl)indenyl]}zirconium dimethyl;
9-silafluorenediylbis{1-[2-tert-butyl, 4-(2,3,5-trimethylphenyl)indenyl]}zircon dimethyl;
9-silafluorenediylbis{1-[2-phenyl, 4-(2,3,5-trimethylphenyl)indenyl]}zirconium dimethyl;
9-silafluorenediylbis{1-[2-n-propyl, 4-(2-methylphenyl)indenyl]}hafnium dichloride;
9-silafluorenediylbis{1-[2-isopropyl, 4-(2-methylphenyl)indenyl]}hafnium dichloride;
9-silafluorenediylbis{1-[2-n-butyl, 4-(2-methylphenyl)indenyl]}hafnium dichloride;
9-silafluorenediylbis{1-[2-isobutyl, 4-(2-methylphenyl)indenyl]}hafnium dichloride;
9-silafluorenediylbis{1-[2-sec-butyl, 4-(2-methylphenyl)indenyl]}hafnium dichloride;
9-silafluorenediylbis{1-[2-tert-butyl, 4-(2-methylphenyl)indenyl]}hafnium dichloride;
9-silafluorenediylbis{1-[2-phenyl, 4-(2-methylphenyl)indenyl]}hafnium dichloride;
9-silafluorenediylbis{1-[2-n-propyl, 4-(2-ethylphenyl)indenyl]}hafnium dichloride;
9-silafluorenediylbis{1-[2-isopropyl, 4-(2-ethylphenyl)indenyl]}hafnium dichloride;
9-silafluorenediylbis{1-[2-n-butyl, 4-(2-ethylphenyl)indenyl]}hafnium dichloride;
9-silafluorenediylbis{1-[2-isobutyl, 4-(2-ethylphenyl)indenyl]}hafnium dichloride;
9-silafluorenediylbis{1-[2-sec-butyl, 4-(2-ethylphenyl)indenyl]}hafnium dichloride;
9-silafluorenediylbis{1-[2-tert-butyl, 4-(2-ethylphenyl)indenyl]}hafnium dichloride;
9-silafluorenediylbis{1-[2-phenyl, 4-(2-ethylphenyl)indenyl]}hafnium dichloride;
9-silafluorenediylbis{1-[2-n-propyl, 4-(2-n-propylphenyl)indenyl]}hafnium dichloride;
9-silafluorenediylbis{1-[2-isopropyl, 4-(2-n-propylphenyl)indenyl]}hafnium dichloride;
9-silafluorenediylbis{1-[2-n-butyl, 4-(2-n-propylphenyl)indenyl]}hafnium dichloride;
9-silafluorenediylbis{1-[2-isobutyl, 4-(2-n-propylphenyl)indenyl]}hafnium dichloride;
9-silafluorenediylbis{1-[2-sec-butyl, 4-(2-n-propylphenyl)indenyl]}hafnium dichloride;
9-silafluorenediylbis{1-[2-tert-butyl, 4-(2-n-propylphenyl)indenyl]}hafnium dichloride;
9-silafluorenediylbis{1-[2-phenyl, 4-(2-n-propylphenyl)indenyl]}hafnium dichloride;
9-silafluorenediylbis{1-[2-n-propyl, 4-(2-isopropylphenyl)indenyl]}hafnium dichloride;
9-silafluorenediylbis{1-[2-isopropyl, 4-(2-isopropylphenyl)indenyl]}hafnium dichloride;
9-silafluorenediylbis{1-[2-n-butyl, 4-(2-isopropylphenyl)indenyl]}hafnium dichloride;
9-silafluorenediylbis{1-[2-isobutyl, 4-(2-isopropylphenyl)indenyl]}hafnium dichloride;
9-silafluorenediylbis{1-[2-sec-butyl, 4-(2-isopropylphenyl)indenyl]}hafnium dichloride;
9-silafluorenediylbis{1-[2-tert-butyl, 4-(2-isopropylphenyl)indenyl]}hafnium dichloride;
9-silafluorenediylbis{1-[2-phenyl, 4-(2-isopropylphenyl)indenyl]}hafnium dichloride;
9-silafluorenediylbis{1-[2-n-propyl, 4-(2-n-butylphenyl)indenyl]}hafnium dichloride;
9-silafluorenediylbis{1-[2-isopropyl, 4-(2-n-butylphenyl)indenyl]}hafnium dichloride;
9-silafluorenediylbis{1-[2-n-butyl, 4-(2-n-butylphenyl)indenyl]}hafnium dichloride;
9-silafluorenediylbis{1-[2-isobutyl, 4-(2-n-butylphenyl)indenyl]}hafnium dichloride;
9-silafluorenediylbis{1-[2-sec-butyl, 4-(2-n-butylphenyl)indenyl]}hafnium dichloride;

9-silafluorenediylbis{1-[2-tert-butyl, 4-(2-n-butylphenyl)indenyl]}hafnium dichloride;
9-silafluorenediylbis{1-[2-phenyl, 4-(2-n-butylphenyl)indenyl]}hafnium dichloride;
9-silafluorenediylbis{1-[2-n-propyl, 4-(2-isobutylphenyl)indenyl]}hafnium dichloride;
9-silafluorenediylbis{1-[2-isopropyl, 4-(2-isobutylphenyl)indenyl]}hafnium dichloride;
9-silafluorenediylbis{1-[2-n-butyl, 4-(2-isobutylphenyl)indenyl]}hafnium dichloride;
9-silafluorenediylbis{1-[2-isobutyl, 4-(2-isobutylphenyl)indenyl]}hafnium dichloride;
9-silafluorenediylbis{1-[2-sec-butyl, 4-(2-isobutylphenyl)indenyl]}hafnium dichloride;
9-silafluorenediylbis{1-[2-tert-butyl, 4-(2-isobutylphenyl)indenyl]}hafnium dichloride;
9-silafluorenediylbis{1-[2-phenyl, 4-(2-isobutylphenyl)indenyl]}hafnium dichloride;
9-silafluorenediylbis{1-[2-n-propyl, 4-(2-sec-butylphenyl)indenyl]}hafnium dichloride;
9-silafluorenediylbis{1-[2-isopropyl, 4-(2-sec-butylphenyl)indenyl]}hafnium dichloride;
9-silafluorenediylbis{1-[2-n-butyl, 4-(2-sec-butylphenyl)indenyl]}hafnium dichloride;
9-silafluorenediylbis{1-[2-isobutyl, 4-(2-sec-butylphenyl)indenyl]}hafnium dichloride;
9-silafluorenediylbis{1-[2-sec-butyl, 4-(2-sec-butylphenyl)indenyl]}hafnium dichloride;
9-silafluorenediylbis{1-[2-tert-butyl, 4-(2-sec-butylphenyl)indenyl]}hafnium dichloride;
9-silafluorenediylbis{1-[2-phenyl, 4-(2-sec-butylphenyl)indenyl]}hafnium dichloride;
9-silafluorenediylbis{1-[2-n-propyl, 4-(2-tert-butylphenyl)indenyl]}hafnium dichloride;
9-silafluorenediylbis{1-[2-isopropyl, 4-(2-tert-butylphenyl)indenyl]}hafnium dichloride;
9-silafluorenediylbis{1-[2-n-butyl, 4-(2-tert-butylphenyl)indenyl]}hafnium dichloride;
9-silafluorenediylbis{1-[2-isobutyl, 4-(2-tert-butylphenyl)indenyl]}hafnium dichloride;
9-silafluorenediylbis{1-[2-sec-butyl, 4-(2-tert-butylphenyl)indenyl]}hafnium dichloride;
9-silafluorenediylbis{1-[2-tert-butyl, 4-(2-tert-butylphenyl)indenyl]}hafnium dichloride;
9-silafluorenediylbis{1-[2-phenyl, 4-(2-tert-butylphenyl)indenyl]}hafnium dichloride;
9-silafluorenediylbis{1-[2-n-propyl, 4-(2-biphenyl)indenyl]} hafnium dichloride;
9-silafluorenediylbis{1-[2-isopropyl, 4-(2-biphenyl)indenyl]}hafnium dichloride;
9-silafluorenediylbis{1-[2-n-butyl, 4-(2-biphenyl)indenyl]} hafnium dichloride;
9-silafluorenediylbis{1-[2-isobutyl, 4-(2-biphenyl)indenyl]} hafnium dichloride;
9-silafluorenediylbis{1-[2-sec-butyl, 4-(2-biphenyl)indenyl]} hafnium dichloride;
9-silafluorenediylbis{1-[2-tert-butyl, 4-(2biphenyl)indenyl]} hafnium dichloride;
9-silafluorenediylbis{1-[2-phenyl, 4-(2-biphenyl)indenyl]}hafnium dichloride;
9-silafluorenediylbis{1-[2-n-propyl, 4-(2-α-naphthylphenyl)indenyl]}hafnium dichloride;
9-silafluorenediylbis{1-[2-isopropyl, 4-(2-α-naphthylphenyl)indenyl]}hafnium dichloride;
9-silafluorenediylbis{1-[2-n-butyl, 4-(2-α-naphthylphenyl)indenyl]}hafnium dichloride;
9-silafluorenediylbis{1-[2-isobutyl, 4-(2-α-naphthylphenyl)indenyl]}hafnium dichloride;
9-silafluorenediylbis{1-[2-sec-butyl, 4-(2-α-naphthylphenyl)indenyl]}hafnium dichloride;
9-silafluorenediylbis{1-[2-tert-butyl, 4-(2-α-naphthylphenyl)indenyl]}hafnium dichloride;
9-silafluorenediylbis{1-[2-phenyl, 4-(2-α-naphthylphenyl)indenyl]}hafnium dichloride;
9-silafluorenediylbis{1-[2-n-propyl, 4-(2-β-naphthylphenyl)indenyl]}hafnium dichloride;
9-silafluorenediylbis{1-[2-isopropyl, 4-(2-β-naphthylphenyl)indenyl]}hafnium dichloride;
9-silafluorenediylbis{1-[2-n-butyl, 4-(2-β-naphthylphenyl)indenyl]}hafnium dichloride;
9-silafluorenediylbis{1-[2-isobutyl, 4-(2-β-naphthylphenyl)indenyl]}hafnium dichloride;
9-silafluorenediylbis{1-[2-sec-butyl, 4-(2-β-naphthylphenyl)indenyl]}hafnium dichloride;
9-silafluorenediylbis{1-[2-tert-butyl, 4-(2-β-naphthylphenyl)indenyl]}hafnium dichloride;
9-silafluorenediylbis{1-[2-phenyl, 4-(2-β-naphthylphenyl)indenyl]}hafnium dichloride;
9-silafluorenediylbis{1-[2-n-propyl, 4-(2-trifluoromethylphenyl)indenyl]}hafnium dichloride;
9-silafluorenediylbis{1-[2-isopropyl, 4-(2-trifluoromethylphenyl)indenyl]}hafnium dichloride;
9-silafluorenediylbis{1-[2-n-butyl, 4-(2-trifluoromethylphenyl)indenyl]}hafnium dichloride;
9-silafluorenediylbis{1-[2-isobutyl, 4-(2-trifluoromethylphenyl)indenyl]}hafnium dichloride;
9-silafluorenediylbis{1-[2-sec-butyl, 4-(2-trifluoromethylphenyl)indenyl]}hafnium dichloride;
9-silafluorenediylbis{1-[2-tert-butyl, 4-(2-trifluoromethylphenyl)indenyl]}hafnium dichloride;
9-silafluorenediylbis{1-[2-phenyl, 4-(2-trifluoromethylphenyl)indenyl]}hafnium dichloride;
9-silafluorenediylbis{1-[2-n-propyl, 4-(2-trimethylsilylphenyl)indenyl]}hafnium dichloride;
9-silafluorenediylbis{1-[2-isopropyl, 4-(2-trimethylsilylphenyl)indenyl]}hafnium dichloride;
9-silafluorenediylbis{1-[2-n-butyl, 4-(2-trimethylsilylphenyl)indenyl]}hafnium dichloride;
9-silafluorenediylbis{1-[2-isobutyl, 4-(2-trimethylsilylphenyl)indenyl]}hafnium dichloride;
9-silafluorenediylbis{1-[2-sec-butyl 4-(2-trimethylsilylphenyl)indenyl]}hafnium dichloride;
9-silafluorenediylbis{1-[2-tert-butyl, 4-(2-trimethylsilylphenyl)indenyl]}hafnium dichloride;
9-silafluorenediylbis{1-[2-phenyl, 4-(2-trimethylsilylphenyl)indenyl]}hafnium dichloride;
9-silafluorenediylbis{1-[2-n-propyl, 4-(2,3-dimethylphenyl)indenyl]}hafnium dichloride;
9-silafluorenediylbis{1-[2-isopropyl, 4-(2,3-dimethylphenyl)indenyl]}hafnium dichloride;
9-silafluorenediylbis{1-[2-n-butyl, 4-(2,3-dimethylphenyl)indenyl]}hafnium dichloride;
9-silafluorenediylbis{1-[2-isobutyl, 4-(2,3-dimethylphenyl)indenyl]}hafnium dichloride;
9-silafluorenediylbis{1-[2-sec-butyl, 4-(2,3-dimethylphenyl)indenyl]}hafnium dichloride;
9-silafluorenediylbis{1-[2-tert-butyl, 4-(2,3-dimethylphenyl)indenyl]}hafnium dichloride;
9-silafluorenediylbis{1-[2-phenyl, 4-(2,3-dimethylphenyl)indenyl]}hafnium dichloride;
9-silafluorenediylbis{1-[2-n-propyl, 4-(2,3,4-trimethylphenyl)indenyl]}hafnium dichloride;
9-silafluorenediylbis{1-[2-isopropyl, 4-(2,3,4-trimethylphenyl)indenyl]}hafnium dichloride;
9-silafluorenediylbis{1-[2-n-butyl, 4-(2,3,4-trimethylphenyl)indenyl]}hafnium dichloride;

9-silafluorenediylbis{1-[2-isobutyl, 4-(2,3,4-trimethylphenyl)indenyl]}hafnium dichloride;
9-silafluorenediylbis{1-[2-sec-butyl, 4-(2,3,4-trimethylphenyl)indenyl]}hafnium dichloride;
9-silafluorenediylbis{1-[2-tert-butyl, 4-(2,3,4-trimethylphenyl)indenyl]}hafnium dichloride;
9-silafluorenediylbis{1-[2-phenyl, 4-(2,3,4-trimethylphenyl)indenyl]}hafnium dichloride;
9-silafluorenediylbis{1-[2-n-propyl, 4-(2,3,5-trimethylphenyl)indenyl]}hafnium dichloride;
9-silafluorenediylbis{1-[2-isopropyl, 4-(2,3,5-trimethylphenyl)indenyl]}hafnium dichloride;
9-silafluorenediylbis{1-[2-n-butyl, 4-(2,3,5-trimethylphenyl)indenyl]}hafnium dichloride;
9-silafluorenediylbis{1-[2-isobutyl, 4-(2,3,5-trimethylphenyl)indenyl]}hafnium dichloride;
9-silafluorenediylbis{1-[2-sec-butyl, 4-(2,3,5-trimethylphenyl)indenyl]}hafnium dichloride;
9-silafluorenediylbis{1-[2-tert-butyl, 4-(2,3,5-trimethylphenyl)indenyl]}hafnium dichloride;
9-silafluorenediylbis{1-[2-phenyl, 4-(2,3,5-trimethylphenyl)indenyl]}hafnium dichloride;
9-silafluorenediylbis{1-[2-n-propyl, 4-(2-methylphenyl)indenyl]}hafnium dimethyl;
9-silafluorenediylbis{1-[2-isopropyl, 4-(2-methylphenyl)indenyl]}hafnium dimethyl;
9-silafluorenediylbis{1-[2-n-butyl, 4-(2-methylphenyl)indenyl]}hafnium dimethyl;
9-silafluorenediylbis{1-[2-isobutyl, 4-(2-methylphenyl)indenyl]}hafnium dimethyl;
9-silafluorenediylbis{1-[2-sec-butyl, 4-(2-methylphenyl)indenyl]}hafnium dimethyl;
9-silafluorenediylbis{1-[2-tert-butyl, 4-(2-methylphenyl)indenyl]}hafnium dimethyl;
9-silafluorenediylbis{1-[2-phenyl, 4-(2-methylphenyl)indenyl]}hafnium dimethyl;
9-silafluorenediylbis{1-[2-n-propyl, 4-(2-ethylphenyl)indenyl]}hafnium dimethyl;
9-silafluorenediylbis{1-[2-isopropyl, 4-(2-ethylphenyl)indenyl]}hafnium dimethyl;
9-silafluorenediylbis{1-[2-n-butyl, 4-(2-ethylphenyl)indenyl]}hafnium dimethyl;
9-silafluorenediylbis{1-[2-isobutyl, 4-(2-ethylphenyl)indenyl]}hafnium dimethyl;
9-silafluorenediylbis{1-[2-sec-butyl, 4-(2-ethylphenyl)indenyl]}hafnium dimethyl;
9-silafluorenediylbis{1-[2-tert-butyl, 4-(2-ethylphenyl)indenyl]}hafnium dimethyl;
9-silafluorenediylbis{1-[2-phenyl, 4-(2-ethylphenyl)indenyl]}hafnium dimethyl;
9-silafluorenediylbis{1-[2-n-propyl, 4-(2-n-propylphenyl)indenyl]}hafnium dimethyl;
9-silafluorenediylbis{1-[2-isopropyl, 4-(2-n-propylphenyl)indenyl]}hafnium dimethyl;
9-silafluorenediylbis{1-[2-n-butyl, 4-(2-n-propylphenyl)indenyl]}hafnium dimethyl;
9-silafluorenediylbis{1-[2-isobutyl, 4-(2-n-propylphenyl)indenyl]}hafnium dimethyl;
9-silafluorenediylbis{1-[2-sec-butyl, 4-(2-n-propylphenyl)indenyl]}hafnium dimethyl;
9-silafluorenediylbis{1-[2-tert-butyl, 4-(2-n-propylphenyl)indenyl]}hafnium dimethyl;
9-silafluorenediylbis{1-[2-phenyl, 4-(2-n-propylphenyl)indenyl]}hafnium dimethyl;
9-silafluorenediylbis{1-[2-n-propyl, 4-(2-isopropylphenyl)indenyl]}hafnium dimethyl;
9-silafluorenediylbis{1-[2-isopropyl, 4-(2-isopropylphenyl)indenyl]}hafnium dimethyl;
9-silafluorenediylbis{1-[2-n-butyl, 4-(2-isopropylphenyl)indenyl]}hafnium dimethyl;
9-silafluorenediylbis{1-[2-isobutyl, 4-(2-isopropylphenyl)indenyl]}hafnium dimethyl;
9-silafluorenediylbis{1-[2-sec-butyl, 4-(2-isopropylphenyl)indenyl]}hafnium dimethyl;
9-silafluorenediylbis{1-[2-tert-butyl, 4-(2-isopropylphenyl)indenyl]}hafnium dimethyl;
9-silafluorenediylbis{1-[2-phenyl, 4-(2-isopropylphenyl)indenyl]}hafnium dimethyl;
9-silafluorenediylbis{1-[2-n-propyl, 4-(2-n-butylphenyl)indenyl]}hafnium dimethyl;
9-silafluorenediylbis{1-[2-isopropyl, 4-(2-n-butylphenyl)indenyl]}hafnium dimethyl;
9-silafluorenediylbis{1-[2-n-butyl, 4-(2-n-butylphenyl)indenyl]}hafnium dimethyl;
9-silafluorenediylbis{1-[2-isobutyl, 4-(2-n-butylphenyl)indenyl]}hafnium dimethyl;
9-silafluorenediylbis{1-[2-sec-butyl, 4-(2-n-butylphenyl)indenyl]}hafnium dimethyl;
9-silafluorenediylbis{1-[2-tert-butyl, 4-(2-n-butylphenyl)indenyl]}hafnium dimethyl;
9-silafluorenediylbis{1-[2-phenyl, 4-(2-n-butylphenyl)indenyl]}hafnium dimethyl;
9-silafluorenediylbis{1-[2-n-propyl, 4-(2-isobutylphenyl)indenyl]}hafnium dimethyl,
9-silafluorenediylbis{1-[2-isopropyl, 4-(2-isobutylphenyl)indenyl]}hafnium dimethyl;
9-silafluorenediylbis{1-[2-n-butyl, 4-(2-isobutylphenyl)indenyl]}hafnium dimethyl;
9-silafluorenediylbis{1-[2-isobutyl, 4-(2-isobutylphenyl)indenyl]}hafnium dimethyl;
9-silafluorenediylbis{1-[2-sec-butyl, 4-(2-isobutylphenyl)indenyl]}hafnium dimethyl;
9-silafluorenediylbis{1-[2-tert-butyl, 4-(2-isobutylphenyl)indenyl]}hafnium dimethyl;
9-silafluorenediylbis{1-[2-phenyl, 4-(2-isobutylphenyl)indenyl]}hafnium dimethyl;
9-silafluorenediylbis{1-[2-n-propyl, 4-(2-sec-butylphenyl)indenyl]}hafnium dimethyl;
9-silafluorenediylbis{1-[2-isopropyl, 4-(2-sec-butylphenyl)indenyl]}hafnium dimethyl;
9-silafluorenediylbis{1-[2-n-butyl, 4-(2-sec-butylphenyl)indenyl]}hafnium dimethyl;
9-silafluorenediylbis{1-[2-isobutyl, 4-(2-sec-butylphenyl)indenyl]}hafnium dimethyl;
9-silafluorenediylbis{1-[2-sec-butyl, 4-(2-sec-butylphenyl)indenyl]}hafnium dimethyl;
9-silafluorenediylbis{1-[2-tert-butyl, 4-(2-sec-butylphenyl)indenyl]}hafnium dimethyl;
9-silafluorenediylbis{1-[2-phenyl, 4-(2-sec-butylphenyl)indenyl]}hafnium dimethyl;
9-silafluorenediylbis{1-[2-n-propyl, 4-(2-tert-butylphenyl)indenyl]}hafnium dimethyl;
9-silafluorenediylbis{1-[2-isopropyl, 4-(2-tert-butylphenyl)indenyl]}hafnium dimethyl;
9-silafluorenediylbis{1-[2-n-butyl, 4-(2-tert-butylphenyl)indenyl]}hafnium dimethyl;
9-silafluorenediylbis{1-[2-isobutyl, 4-(2-tert-butylphenyl)indenyl]}hafnium dimethyl;
9-silafluorenediylbis{1-[2-sec-butyl, 4-(2-tert-butylphenyl)indenyl]}hafnium dimethyl;
9-silafluorenediylbis{1-[2-tert-butyl, 4-(2-tert-butylphenyl)indenyl]}hafnium dimethyl;
9-silafluorenediylbis{1-[2-phenyl, 4-(2-tert-butylphenyl)indenyl]}hafnium dimethyl;
9-silafluorenediylbis{1-[2-n-propyl, 4-(2-biphenyl)indenyl]} hafnium dimethyl;

9-silafluorenediylbis{1-[2-isopropyl, 4-(2-biphenyl) indenyl]}hafnium dimethyl;
9-silafluorenediylbis{1-[2-n-butyl, 4-(2-biphenyl)indenyl]} hafnium dimethyl;
9-silafluorenediylbis{1-[2-isobutyl, 4-(2-biphenyl) indenyl]} hafnium dimethyl;
9-silafluorenediylbis{1-[2-sec-butyl, 4-(2-biphenyl) indenyl]} hafnium dimethyl;
9-silafluorenediylbis{1-[2-tert-butyl, 4-(2-biphenyl) indenyl]}hafnium dimethyl;
9-silafluorenediylbis{1-[2-phenyl, 4-(2-biphenyl)indenyl]} hafnium dimethyl;
9-silafluorenediylbis{1-[2-n-propyl, 4-(2-α-naphthylphenyl)indenyl]}hafnium dimethyl;
9-silafluorenediylbis{1-[2-isopropyl, 4-(2-α-naphthylphenyl)indenyl]}hafnium dimethyl;
9-silafluorenediylbis{1-[2-n-butyl, 4-(2-α-naphthylphenyl) indenyl]}hafnium dimethyl;
9-silafluorenediylbis{1-[2-isobutyl, 4-(2-α-naphthylphenyl) indenyl]}hafnium dimethyl;
9-silafluorenediylbis{1-[2-sec-butyl, 4-(2-α-naphthylphenyl)indenyl]}hafnium dimethyl;
9-silafluorenediylbis{1-[2-tert-butyl, 4-(2-α-naphthylphenyl)indenyl]}hafnium dimethyl;
9-silafluorenediylbis{1-[2-phenyl, 4-(2-α-naphthylphenyl) indenyl]}hafnium dimethyl;
9-silafluorenediylbis{1-[2-n-propyl, 4-(2-β-naphthylphenyl)indenyl]}hafnium dimethyl;
9-silafluorenediylbis{1-[2-isopropyl, 4-(2-β-naphthylphenyl)indenyl]}hafnium dimethyl;
9-silafluorenediylbis{1-[2-n-butyl, 4-(2-β-naphthylphenyl) indenyl]}hafnium dimethyl;
9-silafluorenediylbis{1-[2-isobutyl, 4-(2-β-naphthylphenyl) indenyl]}hafnium dimethyl;
9-silafluorenediylbis{1-[2-sec-butyl, 4-(2-β-naphthylphenyl)indenyl]}hafnium dimethyl;
9-silafluorenediylbis{1-[2-tert-butyl, 4-(2-β-naphthylphenyl)indenyl]}hafnium dimethyl;
9-silafluorenediylbis{1-[2-phenyl, 4-(2-β-naphthylphenyl) indenyl]}hafnium dimethyl;
9-silafluorenediylbis{1-[2-n-propyl, 4-(2-trifluoromethylphenyl)indenyl]}hafnium dimethyl;
9-silafluorenediylbis{1-[2-isopropyl, 4-(2-trifluoromethylphenyl)indenyl]}hafnium dimethyl;
9-silafluorenediylbis{1-[2-n-butyl, 4-(2-trifluoromethylphenyl)indenyl]}hafnium dimethyl;
9-silafluorenediylbis{1-[2-isobutyl, 4-(2-trifluoromethylphenyl)indenyl]}hafnium dimethyl;
9-silafluorenediylbis{1-[2-sec-butyl, 4-(2-trifluoromethylphenyl)indenyl]}hafnium dimethyl;
9-silafluorenediylbis{1-[2-tert-butyl, 4-(2-trifluoromethylphenyl)indenyl]}hafnium dimethyl;
9-silafluorenediylbis{1-[2-phenyl, 4-(2-trifluoromethylphenyl)indenyl]}hafnium dimethyl;
9-silafluorenediylbis{1-[-2-n-propyl, 4-(2-trimethylsilylphenyl)indenyl]}hafnium dimethyl;
9-silafluorenediylbis{1-[2-isopropyl, 4-(2-trimethylsilylphenyl)indenyl]}hafnium dimethyl;
9-silafluorenediylbis{1-[2-n-butyl, 4-(2-trimethylsilylphenyl)indenyl]}hafnium dimethyl;
9-silafluorenediylbis{1-[2-isobutyl, 4-(2-trimethylsilylphenyl)indenyl]}hafnium dimethyl;
9-silafluorenediylbis{1-[2-sec-butyl, 4-(2-trimethylsilylphenyl)indenyl]}hafnium dimethyl;
9-silafluorenediylbis{1-[2-tert-butyl, 4-(2-trimethylsilylphenyl)indenyl]}hafnium dimethyl;
9-silafluorenediylbis{1-[2-phenyl, 4-(2-trimethylsilylphenyl)indenyl]}hafnium dimethyl;
9-silafluorenediylbis{1-[2-n-propyl, 4-(2,3-dimethylphenyl) indenyl]}hafnium dimethyl;
9-silafluorenediylbis{1-[2-isopropyl, 4-(2,3-dimethylphenyl)indenyl]}hafnium dimethyl;
9-silafluorenediylbis{1-[2-n-butyl, 4-(2,3-dimethylphenyl) indenyl]}hafnium dimethyl;
9-silafluorenediylbis{1-[2-isobutyl, 4-(2,3-dimethylphenyl) indenyl]}hafnium dimethyl;
9-silafluorenediylbis{1-[2-sec-butyl, 4-(2,3-dimethylphenyl)indenyl]}hafnium dimethyl;
9-silafluorenediylbis{1-[2-tert-butyl, 4-(2,3-dimethylphenyl)indenyl]}hafnium dimethyl;
9-silafluorenediylbis{1-[2-phenyl, 4-(2,3-dimethylphenyl) indenyl]}hafnium dimethyl;
9-silafluorenediylbis{1-[2-n-propyl, 4-(2,3,4-trimethylphenyl)indenyl]}hafnium dimethyl;
9-silafluorenediylbis{1-[2-isopropyl, 4-(2,3,4-trimethylphenyl)indenyl]}hafnium dimethyl;
9-silafluorenediylbis{1-[2-n-butyl, 4-(2,3,4-trimethylphenyl)indenyl]}hafnium dimethyl;
9-silafluorenediylbis{1-[2-isobutyl, 4-(2,3,4-trimethylphenyl)indenyl]}hafnium dimethyl;
9-silafluorenediylbis{1-[2-sec-butyl, 4-(2,3,4-trimethylphenyl)indenyl]}hafnium dimethyl;
9-silafluorenediylbis{1-[2-tert-butyl, 4-(2,3,4-trimethylphenyl)indenyl]}hafnium dimethyl;
9-silafluorenediylbis{1-[2-phenyl, 4-(2,3,4-trimethylphenyl)indenyl]}hafnium dimethyl;
9-silafluorenediylbis{1-[2-n-propyl, 4-(2,3,5-trimethylphenyl)indenyl]}hafnium dimethyl;
9-silafluorenediylbis{1-[2-isopropyl, 4-(2,3,5-trimethylphenyl)indenyl]}hafnium dimethyl;
9-silafluorenediylbis{1-[2-n-butyl, 4-(2,3,5-trimethylphenyl)indenyl]}hafnium dimethyl;
9-silafluorenediylbis{1-[2-isobutyl, 4-(2,3,5-trimethylphenyl)indenyl]}hafnium dimethyl;
9-silafluorenediylbis{1-[2-sec-butyl, 4-(2,3,5-trimethylphenyl)indenyl]}hafnium dimethyl;
9-silafluorenediylbis{1-[2-tert-butyl, 4-(2,3,5-trimethylphenyl)indenyl]}hafnium dimethyl;
9-silafluorenediylbis{1-[2-phenyl, 4-(2,3,5-trimethylphenyl)indenyl]}hafnium dimethyl;
dimethylamidoboranebis{1-[2-n-propyl, 4-(2-methylphenyl)indenyl]}zirconium dichloride;
dimethylamidoboranebis{1-[2-isopropyl, 4-(2-methylphenyl)indenyl]}zirconium dichloride;
dimethylamidoboranebis{1-[2-n-butyl, 4-(2-methylphenyl) indenyl]}zirconium dichloride;
dimethylamidoboranebis{1-[2-isobutyl, 4-(2-methylphenyl) indenyl]}zirconium dichloride;
dimethylamidoboranebis{1-[2-sec-butyl, 4-(2-methylphenyl)indenyl]}zirconium dichloride;
dimethylamidoboranebis{1-[2-tert-butyl, 4-(2-methylphenyl)indenyl]}zirconium dichloride;
dimethylamidoboranebis{1-[2-phenyl, 4-(2-methylphenyl) indenyl]}zirconium dichloride;
dimethylamidoboranebis{1-[2-n-propyl, 4-(2-ethylphenyl) indenyl]}zirconium dichloride;
dimethylamidoboranebis{1-[2-isopropyl, 4-(2-ethylphenyl) indenyl]}zirconium dichloride;
dimethylamidoboranebis{1-[2-n-butyl, 4-(2-ethylphenyl) indenyl]}zirconium dichloride;
dimethylamidoboranebis{1-[2-isobutyl, 4-(2-ethylphenyl) indenyl]}zirconium dichloride;
dimethylamidoboranebis{1-2-sec-butyl, 4-(2-ethylphenyl) indenyl]}zirconium dichloride;
dimethylamidoboranebis{1-[2-tert-butyl, 4-(2-ethylphenyl) indenyl]}zirconium dichloride;

dimethylamidoboranebis{1-[2-phenyl, 4-(2-ethylphenyl)indenyl]}zirconium dichloride;
dimethylamidoboranebis{1-[2-n-propyl, 4-(2-n-propylphenyl)indenyl]}zirconium dichloride;
dimethylamidoboranebis{1-[2-isopropyl, 4-(2-n-propylphenyl)indenyl]}zirconium dichloride;
dimethylamidoboranebis{1-[2-n-butyl, 4-(2-n-propylphenyl)indenyl]}zirconium dichloride;
dimethylamidoboranebis{1-[2-isobutyl, 4-(2-n-propylphenyl)indenyl]}zirconium dichloride;
dimethylamidoboranebis{1-[2-sec-butyl, 4-(2-n-propylphenyl)indenyl]}zirconium dichloride;
dimethylamidoboranebis{1-[2-tert-butyl, 4-(2-n-propylphenyl)indenyl]}zirconium dichloride;
dimethylamidoboranebis{1-[2-phenyl, 4-(2-n-propylphenyl)indenyl]}zirconium dichloride;
dimethylamidoboranebis{1-[2-n-propyl, 4-(2-isopropylphenyl)indenyl]}zirconium dichloride;
dimethylamidoboranebis{1-[2-isopropyl, 4-(2-isopropylphenyl)indenyl]}zirconium dichloride;
dimethylamidoboranebis{1-[2-n-butyl, 4-(2-isopropylphenyl)indenyl]}zirconium dichloride;
dimethylamidoboranebis{1-[2-isobutyl, 4-(2-isopropylphenyl)indenyl]}zirconium dichloride;
dimethylamidoboranebis{1-[2-sec-butyl, 4-(2-isopropylphenyl)indenyl]}zirconium dichloride;
dimethylamidoboranebis{1-[2-tert-butyl, 4-(2-isopropylphenyl)indenyl]}zirconium dichloride;
dimethylamidoboranebis{1-[2-phenyl, 4-(2-isopropylphenyl)indenyl]}zirconium dichloride;
dimethylamidoboranebis{1-[2-n-propyl, 4-(2-n-butylphenyl)indenyl]}zirconium dichloride;
dimethylamidoboranebis{1-[2-isopropyl, 4-(2-n-butylphenyl)indenyl]}zirconium dichloride;
dimethylamidoboranebis{1-[2-n-butyl, 4-(2-n-butylphenyl)indenyl]}zirconium dichloride;
dimethylamidoboranebis{1-[2-isobutyl, 4-(2-n-butylphenyl)indenyl]}zirconium dichloride;
dimethylamidoboranebis{1-[2-sec-butyl, 4-(2-n-butylphenyl)indenyl]}zirconium dichloride;
dimethylamidoboranebis{1-[2-tert-butyl, 4-(2-n-butylphenyl)indenyl]}zirconium dichloride;
dimethylamidoboranebis{1-[2-phenyl, 4-(2-n-butylphenyl)indenyl]}zirconium dichloride;
dimethylamidoboranebis{1-[2-n-propyl, 4-(2-isobutylphenyl)indenyl]}zirconium dichloride;
dimethylamidoboranebis{1-[2-isopropyl, 4-(2-isobutylphenyl)indenyl]}zirconium dichloride;
dimethylamidoboranebis{1-[2-n-butyl, 4-(2-isobutylphenyl)indenyl]}zirconium dichloride;
dimethylamidoboranebis{1-[2-isobutyl, 4-(2-isobutylphenyl)indenyl]}zirconium dichloride;
dimethylamidoboranebis{1-[2-sec-butyl, 4-(2-isobutylphenyl)indenyl]}zirconium dichloride;
dimethylamidoboranebis{1-[2-tert-butyl, 4-(2-isobutylphenyl)indenyl]}zirconium dichloride;
dimethylamidoboranebis{1-[2-phenyl, 4-(2-isobutylphenyl)indenyl]}zirconium dichloride;
dimethylamidoboranebis{1-[2-n-propyl, 4-(2-sec-butylphenyl)indenyl]}zirconium dichloride;
dimethylamidoboranebis{1-[2-isopropyl, 4-(2-sec-butylphenyl)indenyl]}zirconium dichloride;
dimethylamidoboranebis{1-[2-n-butyl, 4-(2-sec-butylphenyl)indenyl]}zirconium dichloride;
dimethylamidoboranebis{1-[2-isobutyl, 4-(2-sec-butylphenyl)indenyl]}zirconium dichloride;
dimethylamidoboranebis{1-[2-sec-butyl, 4-(2-sec-butylphenyl)indenyl]}zirconium dichloride;
dimethylamidoboranebis{1-[2-tert-butyl, 4-(2-sec-butylphenyl)indenyl]}zirconium dichloride;
dimethylamidoboranebis{1-[2-phenyl, 4-(2-sec-butylphenyl)indenyl]}zirconium dichloride;
dimethylamidoboranebis{1-[2-n-propyl, 4-(2-tert-butylphenyl)indenyl]}zirconium dichloride;
dimethylamidoboranebis{1-[2-isopropyl, 4-(2-tert-butylphenyl)indenyl]}zirconium dichloride;
dimethylamidoboranebis{1-[2-n-butyl, 4-(2-tert-butylphenyl)indenyl]}zirconium dichloride;
dimethylamidoboranebis{1-[2-isobutyl, 4-(2-tert-butylphenyl)indenyl]}zirconium dichloride;
dimethylamidoboranebis{1-[2-sec-butyl, 4-(2-tert-butylphenyl)indenyl]}zirconium dichloride;
dimethylamidoboranebis{1-[2-tert-butyl, 4-(2-tert-butylphenyl)indenyl]}zirconium dichloride;
dimethylamidoboranebis{1-[2-phenyl, 4-(2-tert-butylphenyl)indenyl]}zirconium dichloride;
dimethylamidoboranebis{1-[2-n-propyl, 4-(2-biphenyl)indenyl]}zirconium dichloride;
dimethylamidoboranebis{1-[2-isopropyl, 4-(2-biphenyl)indenyl]}zirconium dichloride;
dimethylamidoboranebis{1-[2-n-butyl, 4-(2-biphenyl)indenyl]}zirconium dichloride;
dimethylamidoboranebis{1-[2-isobutyl, 4-(2-biphenyl)indenyl]}zirconium dichloride;
dimethylamidoboranebis{1-[2-sec-butyl, 4-(2-biphenyl)indenyl]}zirconium dichloride;
dimethylamidoboranebis{1-[2-tert-butyl, 4-(2-biphenyl)indenyl]}zirconium dichloride;
dimethylamidoboranebis{1-[2-phenyl, 4-(2-biphenyl)indenyl]}zirconium dichloride;
dimethylamidoboranebis{1-[2-n-propyl, 4-(2-α-naphthylphenyl)indenyl]}zirconium dichloride;
dimethylamidoboranebis{1-[2-isopropyl, 4-(2-α-naphthylphenyl)indenyl]}zirconium dichloride;
dimethylamidoboranebis{1-[2-n-butyl, 4-(2-α-naphthylphenyl)indenyl]}zirconium dichloride;
dimethylamidoboranebis{1-[2-isobutyl, 4-(2-α-naphthylphenyl)indenyl]}zirconium dichloride;
dimethylamidoboranebis{1-[2-sec-butyl, 4-(2-α-naphthylphenyl)indenyl]}zirconium dichloride;
dimethylamidoboranebis{1-[2-tert-butyl, 4-(2-α-naphthylphenyl)indenyl]}zirconium dichloride;
dimethylamidoboranebis{1-[2-phenyl, 4-(2-α-naphthylphenyl)indenyl]}zirconium dichloride;
dimethylamidoboranebis{1-[2-n-propyl, 4-(2-β-naphthylphenyl)indenyl]}zirconium dichloride;
dimethylamidoboranebis{1-[2-isopropyl, 4-(2-β-naphthylphenyl)indenyl]}zirconium dichloride;
dimethylamidoboranebis{1-[2-n-butyl, 4-(2-β-naphthylphenyl)indenyl]}zirconium dichloride;
dimethylamidoboranebis{1-[2-isobutyl, 4-(2-β-naphthylphenyl)indenyl]}zirconium dichloride;
dimethylamidoboranebis{1-[2-sec-butyl, 4-(2-β-naphthylphenyl)indenyl]}zirconium dichloride;
dimethylamidoboranebis{1-[2-tert-butyl, 4-(2-β-naphthylphenyl)indenyl]}zirconium dichloride;
dimethylamidoboranebis{1-[2-phenyl, 4-(2-β-naphthylphenyl)indenyl]}zirconium dichloride;
dimethylamidoboranebis{1-[2-n-propyl, 4-(2-trifluoromethylphenyl)indenyl]}-zirconium dichloride;
dimethylamidoboranebis{1-[2-isopropyl, 4-(2-trifluoromethylphenyl)indenyl]}-zirconium dichloride;
dimethylamidoboranebis{1-[2-n-butyl, 4-(2-trifluoromethylphenyl)indenyl]}-zirconium dichloride;
dimethylamidoboranebis{1-[2-isobutyl, 4-(2-trifluoromethylphenyl)indenyl]}-zirconium dichloride;

dimethylamidoboranebis{1-[2-sec-butyl, 4-(2-trifluoromethylphenyl)indenyl]}-zirconium dichloride;
dimethylamidoboranebis{1-[2-tert-butyl, 4-(2-fluoromethylphenyl)indenyl]}-zirconium dichloride;
dimethylamidoboranebis{1-[2-phenyl, 4-(2-trifluoromethylphenyl)indenyl]}-zirconium dichloride;
dimethylamidoboranebis{1-[2-n-propyl, 4-(2,3-dimethylphenyl)indenyl]}zirconium dichloride;
dimethylamidoboranebis{1-[2-isopropyl, 4-(2,3-dimethylphenyl)indenyl]}zirconium dichloride;
dimethylamidoboranebis{1-[2-n-butyl, 4-(2,3-dimethylphenyl)indenyl]}zirconium dichloride;
dimethylamidoboranebis{1-[2-isobutyl, 4-(2,3-dimethylphenyl)indenyl]}zirconium dichloride;
dimethylamidoboranebis{1-[2-sec-butyl, 4-(2,3-dimethylphenyl)indenyl]}zirconium dichloride;
dimethylamidoboranebis{1-[2-tert-butyl, 4-(2,3-dimethylphenyl)indenyl]}zirconium dichloride;
dimethylamidoboranebis{1-[2-phenyl, 4-(2,3-dimethylphenyl)indenyl]}zirconium dichloride;
dimethylamidoboranebis{1-[2-n-propyl, 4-(2,3,4-trimethylphenyl)indenyl]}zirconium dichloride;
dimethylamidoboranebis{1-[2-isopropyl, 4-(2,3,4-trimethylphenyl)indenyl]}zirconium dichloride;
dimethylamidoboranebis{1-[2-n-butyl, 4-(2,3,4-trimethylphenyl)indenyl]}zirconium dichloride;
dimethylamidoboranebis{1-[2-isobutyl, 4-(2,3,4-trimethylphenyl)indenyl]}zirconium dichloride;
dimethylamidoboranebis{1-[2-sec-butyl, 4-(2,3,4-trimethylphenyl)indenyl]}zirconium dichloride;
dimethylamidoboranebis{1-[2-tert-butyl, 4-(2,3,4-trimethylphenyl)indenyl]}zirconium dichloride;
dimethylamidoboranebis{1-[2-phenyl, 4-(2,3,4-trimethylphenyl)indenyl]}zirconium dichloride;
dimethylamidoboranebis{1-[2-n-propyl, 4-(2,3,5-trimethylphenyl)indenyl]}zirconium dichloride;
dimethylamidoboranebis{1-[2-isopropyl, 4-(2,3,5-trimethylphenyl)indenyl]}zirconium dichloride;
dimethylamidoboranebis{1-[2-n-butyl, 4-(2,3,5-trimethylphenyl)indenyl]}zirconium dichloride;
dimethylamidoboranebis{1-[2-isobutyl, 4-(2,3,5-trimethylphenyl)indenyl]}zirconium dichloride;
dimethylamidoboranebis{1-[2-sec-butyl, 4-(2,3,5-trimethylphenyl)indenyl]}zirconium dichloride;
dimethylamidoboranebis{1-[2-tert-butyl, 4-(2,3,5-trimethylphenyl)indenyl]}zirconium dichloride;
dimethylamidoboranebis{1-[2-phenyl, 4-(2,3,5-trimethylphenyl)indenyl]}zirconium dichloride;
dimethylamidoboranebis{1-[2-n-propyl, 4-(2-methylphenyl)indenyl]}zirconium dimethyl;
dimethylamidoboranebis{1-[2-isopropyl, 4-(2-methylphenyl)indenyl]}zirconium dimethyl;
dimethylamidoboranebis{1-[2-n-butyl, 4-(2-methylphenyl)indenyl]}zirconium dimethyl;
dimethylamidoboranebis{1-[2-isobutyl, 4-(2-methylphenyl)indenyl]}zirconium dimethyl;
dimethylamidoboranebis{1-[2-sec-butyl, 4-(2-methylphenyl)indenyl]}zirconium dimethyl;
dimethylamidoboranebis{1-[2-tert-butyl, 4-(2-methylphenyl)indenyl]}zirconium dimethyl;
dimethylamidoboranebis{1-[2-phenyl, 4-(2-methylphenyl)indenyl]}zirconium dimethyl;
dimethylamidoboranebis{1-[2-n-propyl, 4-(2-ethylphenyl)indenyl]}zirconium dimethyl;
dimethylamidoboranebis{1-[2-isopropyl, 4-(2-ethylphenyl)indenyl]}zirconium dimethyl;
dimethylamidoboranebis{1-[2-n-butyl, 4-(2-ethylphenyl)indenyl]}zirconium dimethyl;
dimethylamidoboranebis{1-[2-isobutyl, 4-(2-ethylphenyl)indenyl]}zirconium dimethyl;
dimethylamidoboranebis{1-[2-sec-butyl, 4-(2-ethylphenyl)indenyl]}zirconium dimethyl;
dimethylamidoboranebis{1-[2-tert-butyl, 4-(2-ethylphenyl)indenyl]}zirconium dimethyl;
dimethylamidoboranebis{1-[2-phenyl, 4-(2-ethylphenyl)indenyl]}zirconium dimethyl;
dimethylamidoboranebis{1-[2-n-propyl, 4-(2-n-propylphenyl)indenyl]}zirconium dimethyl;
dimethylamidoboranebis{1-[2-isopropyl, 4-(2-n-propylphenyl)indenyl]}zirconium dimethyl;
dimethylamidoboranebis{1-[2-n-butyl, 4-(2-n-propylphenyl)indenyl]}zirconium dimethyl;
dimethylamidoboranebis{1-[2-isobutyl, 4-(2-n-propylphenyl)indenyl]}zirconium dimethyl;
dimethylamidoboranebis{1-[2-sec-butyl, 4-(2-n-propylphenyl)indenyl]}zirconium dimethyl;
dimethylamidoboranebis{1-[2-tert-butyl, 4-(2-n-propylphenyl)indenyl]}zirconium dimethyl;
dimethylamidoboranebis{1-[2-phenyl, 4-(2-n-propylphenyl)indenyl]}zirconium dimethyl;
dimethylamidoboranebis{1-[2-n-propyl, 4-(2-isopropylphenyl)indenyl]}zirconium dimethyl;
dimethylamidoboranebis{1-[2-isopropyl, 4-(2-isopropylphenyl)indenyl]}zirconium dimethyl;
dimethylamidoboranebis{1-[2-n-butyl, 4-(2-isopropylphenyl)indenyl]}zirconium dimethyl;
dimethylamidoboranebis{1-[2-isobutyl, 4-(2-isopropylphenyl)indenyl]}zirconium dimethyl;
dimethylamidoboranebis{1-[2-sec-butyl, 4-(2-isopropylphenyl)indenyl]}zirconium dimethyl;
dimethylamidoboranebis{1-[2-tert-butyl, 4-(2-isopropylphenyl)indenyl]}zirconium dimethyl;
dimethylamidoboranebis{1-[2-phenyl, 4-(2-isopropylphenyl)indenyl]}zirconium dimethyl;
dimethylamidoboranebis{1-[2-n-propyl, 4-(2-n-butylphenyl)indenyl]}zirconium dimethyl;
dimethylamidoboranebis{1-[2-isopropyl, 4-(2-n-butylphenyl)indenyl]}zirconium dimethyl;
dimethylamidoboranebis{1-[2-n-butyl, 4-(2-n-butylphenyl)indenyl]}zirconium dimethyl;
dimethylamidoboranebis{1-[2-isobutyl, 4-(2-n-butylphenyl)indenyl]}zirconium dimethyl;
dimethylamidoboranebis{1-[2-sec-butyl, 4-(2-n-butylphenyl)indenyl]}zirconium dimethyl;
dimethylamidoboranebis{1-[2-tert-butyl, 4-(2-n-butylphenyl)indenyl]}zirconium dimethyl;
dimethylamidoboranebis{1-[2-phenyl, 4-(2-n-butylphenyl)indenyl]}zirconium dimethyl;
dimethylamidoboranebis{1-[2-n-propyl, 4-(2-isobutylphenyl)indenyl]}zirconium dimethyl;
dimethylamidoboranebis{1-[2-isopropyl, 4-(2-isobutylphenyl)indenyl]}zirconium dimethyl;
dimethylamidoboranebis{1-[2-n-butyl, 4-(2-isobutylphenyl)indenyl]}zirconium dimethyl;
dimethylamidoboranebis{1-[2-isobutyl, 4-(2-isobutylphenyl)indenyl]}zirconium dimethyl;
dimethylamidoboranebis{1-[2-sec-butyl, 4-(2-isobutylphenyl)indenyl]}zirconium dimethyl;
dimethylamidoboranebis{1-[2-tert-butyl, 4-(2-isobutylphenyl)indenyl]}zirconium dimethyl;
dimethylamidoboranebis{1-[2-phenyl, 4-(2-isobutylphenyl)indenyl]}zirconium dimethyl;
dimethylamidoboranebis{1-[2-n-propyl, 4-(2-sec-butylphenyl)indenyl]}zirconium dimethyl;
dimethylamidoboranebis{1-[2-isopropyl, 4-(2-sec-butylphenyl)indenyl]}zirconium dimethyl;

dimethylamidoboranebis{1-[2-n-butyl, 4-(2-sec-butylphenyl)indenyl]}zirconium dimethyl;
dimethylamidoboranebis{1-[2-isobutyl, 4-(2-sec-butylphenyl)indenyl]}zirconium dimethyl;
dimethylamidoboranebis{1-[2-sec-butyl, 4-(2-sec-butylphenyl)indenyl]}zirconium dimethyl;
dimethylamidoboranebis{1-[2-tert-butyl, 4-(2-sec-butylphenyl)indenyl]}zirconium dimethyl;
dimethylamidoboranebis{1-[2-phenyl, 4-(2-sec-butylphenyl)indenyl]}zirconium dimethyl;
dimethylamidoboranebis{1-[2-n-propyl, 4-(2-tert-butylphenyl)indenyl]}zirconium dimethyl;
dimethylamidoboranebis{1-[2-isopropyl, 4-(2-tert-butylphenyl)indenyl]}zirconium dimethyl;
dimethylamidoboranebis{1-[2-n-butyl, 4-(2-tert-butylphenyl)indenyl]}zirconium dimethyl;
dimethylamidoboranebis{1-[2-isobutyl, 4-(2-tert-butylphenyl)indenyl]}zirconium dimethyl;
dimethylamidoboranebis{1-[2-sec-butyl, 4-(2-tert-butylphenyl)indenyl]}zirconium dimethyl;
dimethylamidoboranebis{1-[2-tert-butyl, 4-(2-tert-butylphenyl)indenyl]}zirconium dimethyl;
dimethylamidoboranebis{1-[2-phenyl, 4-(2-tert-butylphenyl)indenyl]}zirconium dimethyl;
dimethylamidoboranebis{1-[2-n-propyl, 4-(2-biphenyl)indenyl]}zirconium dimethyl;
dimethylamidoboranebis{1-[2-isopropyl, 4-(2-biphenyl)indenyl]}zirconium dimethyl;
dimethylamidoboranebis{1-[2-n-butyl, 4-(2-biphenyl)indenyl]}zirconium dimethyl;
dimethylamidoboranebis{1-[2-isobutyl, 4-(2-biphenyl)indenyl]}zirconium dimethyl;
dimethylamidoboranebis{1-[2-sec-butyl, 4-(2-biphenyl)indenyl]}zirconium dimethyl;
dimethylamidoboranebis{1-[2-tert-butyl, 4-(2-biphenyl)indenyl]}zirconium dimethyl;
dimethylamidoboranebis{1-[2-phenyl, 4-(2-biphenyl)indenyl]}zirconium dimethyl;
dimethylamidoboranebis{1-[2-n-propyl, 4-(2-α-naphthylphenyl)indenyl]}zirconium dimethyl;
dimethylamidoboranebis{1-[2-isopropyl, 4-(2-α-naphthylphenyl)indenyl]}zirconium dimethyl;
dimethylamidoboranebis{1-[2-n-butyl, 4-(2-α-naphthylphenyl)indenyl]}zirconium dimethyl;
dimethylamidoboranebis{1-[2-isobutyl, 4-(2-α-naphthylphenyl)indenyl]}zirconium dimethyl;
dimethylamidoboranebis{1-[2-sec-butyl, 4-(2-α-naphthylphenyl)indenyl]}zirconium dimethyl;
dimethylamidoboranebis{1-[2-tert-butyl, 4-(2-α-naphthylphenyl)indenyl]}zirconium dimethyl;
dimethylamidoboranebis{1-[2-phenyl, 4-(2-α-naphthylphenyl)indenyl]}zirconium dimethyl;
dimethylamidoboranebis{1-[2-n-propyl, 4-(2-β-naphthylphenyl)indenyl])zirconium dimethyl;
dimethylamidoboranebis{1-[2-isopropyl, 4-(2-β-naphthylphenyl)indenyl]}zirconium dimethyl;
dimethylamidoboranebis{1-[2-n-butyl, 4-(2-β-naphthylphenyl)indenyl]}zirconium dimethyl;
dimethylamidoboranebis{1-[2-isobutyl, 4-(2-β-naphthylphenyl)indenyl]}zirconium dimethyl;
dimethylamidoboranebis{1-[2-sec-butyl, 4-(2-β-naphthylphenyl)indenyl]}zirconium dimethyl;
dimethylamidoboranebis{1-[2-tert-butyl, 4-(2-β-naphthylphenyl)indenyl]}zirconium dimethyl;
dimethylamidoboranebis{1-[2-phenyl, 4-(2-β-naphthylphenyl)indenyl]}zirconium dimethyl;
dimethylamidoboranebis{1-[2-n-propyl, 4-(2-trifluoromethylphenyl)indenyl]}-zirconium dimethyl;
dimethylamidoboranebis{1-[2-isopropyl, 4-(2-trifluoromethylphenyl)indenyl]}-zirconium dimethyl;
dimethylamidoboranebis{1-[2-n-butyl, 4-(2-trifluoromethylphenyl)indenyl]}-zirconium dimethyl;
dimethylamidoboranebis{1-[2-isobutyl, 4-(2-trifluoromethylphenyl)indenyl]}-zirconium dimethyl;
dimethylamidoboranebis{1-[2-sec-butyl, 4-(2-trifluoromethylphenyl)indenyl]}-zirconium dimethyl;
dimethylamidoboranebis{1-[2-tert-butyl, 4-(2-trifluoromethylphenyl)indenyl]}-zirconium dimethyl;
dimethylamidoboranebis{1-[2-phenyl, 4-(2-trifluoromethylphenyl)indenyl]}-zirconium dimethyl;
dimethylamidoboranebis{1-[2-n-propyl, 4-(2,3-dimethylphenyl)indenyl]}zirconium dimethyl;
dimethylamidoboranebis{1-[2-isopropyl, 4-(2,3-dimethylphenyl)indenyl]}zirconium dimethyl;
dimethylamidoboranebis{1-[2-n-butyl, 4-(2,3-dimethylphenyl)indenyl]}zirconium dimethyl;
dimethylamidoboranebis{1-[2-isobutyl, 4-(2,3-dimethylphenyl)indenyl]}zirconium dimethyl;
dimethylamidoboranebis{1-[2-sec-butyl, 4-(2,3-dimethylphenyl)indenyl]}zirconium dimethyl;
dimethylamidoboranebis{1-[2-tert-butyl, 4-(2,3-dimethylphenyl)indenyl]}zirconium dimethyl;
dimethylamidoboranebis{1-[2-phenyl, 4-(2,3-dimethylphenyl)indenyl]}zirconium dimethyl;
dimethylamidoboranebis{1-[2-n-propyl, 4-(2,3,4-trimethylphenyl)indenyl]}zirconium dimethyl;
dimethylamidoboranebis{1-[2-isopropyl, 4-(2,3,4-trimethylphenyl)indenyl]}zirconium dimethyl;
dimethylamidoboranebis{1-[2-n-butyl, 4-(2,3,4-trimethylphenyl)indenyl]}zirconium dimethyl;
dimethylamidoboranebis{1-[2-isobutyl, 4-(2,3,4-trimethylphenyl)indenyl]}zirconium dimethyl;
dimethylamidoboranebis{1-[2-sec-butyl, 4-(2,3,4-trimethylphenyl)indenyl]}zirconium dimethyl;
dimethylamidoboranebis{1-[2-tert-butyl, 4-(2,3,4-trimethylphenyl)indenyl]}zirconium dimethyl;
dimethylamidoboranebis{1-[2-phenyl, 4-(2,3,4-trimethylphenyl)indenyl]}zirconium dimethyl;
dimethylamidoboranebis{1-[2-n-propyl, 4-(2,3,5-trimethylphenyl)indenyl]}zirconium dimethyl;
dimethylamidoboranebis{1-[2-isopropyl, 4-(2,3,5-trimethylphenyl)indenyl]}zirconium dimethyl;
dimethylamidoboranebis{1-[2-n-butyl, 4-(2,3,5-trimethylphenyl)indenyl]}zirconium dimethyl;
dimethylamidoboranebis{1-[2-isobutyl, 4-(2,3,5-trimethylphenyl)indenyl]}zirconium dimethyl;
dimethylamidoboranebis{1-[2-sec-butyl, 4-(2,3,5-trimethylphenyl)indenyl]}zirconium dimethyl;
dimethylamidoboranebis{1-[2-tert-butyl, 4-(2,3,5-trimethylphenyl)indenyl]}zirconium dimethyl;
dimethylamidoboranebis{1-[2-phenyl, 4-(2,3,5-trimethylphenyl)indenyl]}zirconium dimethyl;
dimethylamidoboranebis{1-[2-n-propyl, 4-(2-methylphenyl)indenyl]}hafnium dichloride;
dimethylamidoboranebis{1-[2-isopropyl, 4-(2-methylphenyl)indenyl]}hafnium dichloride;
dimethylamidoboranebis{1-[2-n-butyl, 4-(2-methylphenyl)indenyl]}hafnium dichloride;
dimethylamidoboranebis{1-[2-isobutyl, 4-(2-methylphenyl)indenyl]}hafnium dichloride;
dimethylamidoboranebis{1-[2-sec-butyl, 4-(2-methylphenyl)indenyl]}hafnium dichloride;
dimethylamidoboranebis{1-[2-tert-butyl, 4-(2-methylphenyl)indenyl]}hafnium dichloride;
dimethylamidoboranebis{1-[2-phenyl, 4-(2-methylphenyl)indenyl]}hafnium dichloride;

dimethylamidoboranebis{1-[2-n-propyl, 4-(2-ethylphenyl)indenyl]}hafnium dichloride;
dimethylamidoboranebis{1-[2-isopropyl, 4-(2-ethylphenyl)indenyl]}hafnium dichloride;
dimethylamidoboranebis{1-[2-n-butyl, 4-(2-ethylphenyl)indenyl]}hafnium dichloride;
dimethylamidoboranebis{1-[2-isobutyl, 4-(2-ethylphenyl)indenyl]}hafnium dichloride;
dimethylamidoboranebis{1-[2-sec-butyl, 4-(2-ethylphenyl)indenyl]}hafnium dichloride;
dimethylamidoboranebis{1-[2-tert-butyl, 4-(2-ethylphenyl)indenyl]}hafnium dichloride;
dimethylamidoboranebis{1-[2-phenyl, 4-(2-ethylphenyl)indenyl]}hafnium dichloride;
dimethylamidoboranebis{1-[2-n-propyl, 4-(2-n-propylphenyl)indenyl]}hafnium dichloride;
dimethylamidoboranebis{1-[2-isopropyl, 4-(2-n-propylphenyl)indenyl]}hafnium dichloride;
dimethylamidoboranebis{1-[2-n-butyl, 4-(2-n-propylphenyl)indenyl]}hafnium dichloride;
dimethylamidoboranebis{1-[2-isobutyl, 4-(2-n-propylphenyl)indenyl]}hafnium dichloride;
dimethylamidoboranebis{1-[2-sec-butyl, 4-(2-n-propylphenyl)indenyl]}hafnium dichloride;
dimethylamidoboranebis{1-[2-tert-butyl, 4-(2-n-propylphenyl)indenyl]}hafnium dichloride;
dimethylamidoboranebis{1-[2-phenyl, 4-(2-n-propylphenyl)indenyl]}hafnium dichloride;
dimethylamidoboranebis{1-[2-n-propyl, 4-(2-isopropylphenyl)indenyl]}hafnium dichloride;
dimethylamidoboranebis{1-[2-isopropyl, 4-(2-isopropylphenyl)indenyl]}hafnium dichloride;
dimethylamidoboranebis{1-[2-n-butyl, 4-(2-isopropylphenyl)indenyl]}hafnium dichloride;
dimethylamidoboranebis{1-[2-isobutyl, 4-(2-isopropylphenyl)indenyl]}hafnium dichloride;
dimethylamidoboranebis{1-[2-sec-butyl, 4-(2-isopropylphenyl)indenyl]}hafnium dichloride;
dimethylamidoboranebis{1-[2-tert-butyl, 4-(2-isopropylphenyl)indenyl]}hafnium dichloride;
dimethylamidoboranebis{1-[2-phenyl, 4-(2-isopropylphenyl)indenyl]}halnium dichloride;
dimethylamidoboranebis{1-[2-n-propyl, 4-(2-n-butylphenyl)indenyl]}hafnium dichloride;
dimethylamidoboranebis{1-[2-isopropyl, 4-(2-n-butylphenyl)indenyl]}hafnium dichloride;
dimethylamidoboranebis{1-[2-n-butyl, 4-(2-n-butylphenyl)indenyl]}hafnium dichloride;
dimethylamidoboranebis{1-[2-isobutyl, 4-(2-n-butylphenyl)indenyl]}hafnium dichloride;
dimethylamidoboranebis{1-[2-sec-butyl, 4-(2-n-butylphenyl)indenyl]}hafnium dichloride;
dimethylamidoboranebis{1-[2-tert-butyl, 4-(2-n-butylphenyl)indenyl]}hafnium dichloride;
dimethylamidoboranebis{1-[2-phenyl, 4-(2-n-butylphenyl)indenyl]}hafnium dichloride;
dimethylamidoboranebis{1-[2-n-propyl, 4-(2-isobutylphenyl)indenyl]}hafnium dichloride;
dimethylamidoboranebis{1-[2-isopropyl, 4-(2-isobutylphenyl)indenyl]}hafnium dichloride;
dimethylamidoboranebis{1-[2-n-butyl, 4-(2-isobutylphenyl)indenyl]}hafnium dichloride;
dimethylamidoboranebis{1-[2-isobutyl, 4-(2-isobutylphenyl)indenyl]}hafnium dichloride;
dimethylamidoboranebis{1-[2-sec-butyl, 4-(2-isobutylphenyl)indenyl]}hafnium dichloride;
dimethylamidoboranebis{1-[2-tert-butyl, 4-(2-isobutylphenyl)indenyl]}hafnium dichloride;
dimethylamidoboranebis{1-[2-phenyl, 4-(2-isobutylphenyl)indenyl]}hafnium dichloride;
dimethylamidoboranebis{1-[2-n-propyl, 4-(2-sec-butylphenyl)indenyl]}hafnium dichloride;
dimethylamidoboranebis{1-[2-isopropyl, 4-(2-sec-butylphenyl)indenyl]}hafnium dichloride;
dimethylamidoboranebis{1-[2-n-butyl, 4-(2-sec-butylphenyl)indenyl]}hafnium dichloride;
dimethylamidoboranebis{1-[2-isobutyl, 4-(2-sec-butylphenyl)indenyl]}hafnium dichloride;
dimethylamidoboranebis{1-[2-sec-butyl, 4-(2-sec-butylphenyl)indenyl]}hafnium dichloride;
dimethylamidoboranebis{1-[2-tert-butyl, 4-(2-sec-butylphenyl)indenyl]}hafnium dichloride;
dimethylamidoboranebis{1-[2-phenyl, 4-(2-sec-butylphenyl)indenyl]}hafnium dichloride;
dimethylamidoboranebis{1-[2-n-propyl, 4-(2-tert-butylphenyl)indenyl]}hafnium dichloride;
dimethylamidoboranebis{1-[2-isopropyl, 4-(2-tert-butylphenyl)indenyl]}hafnium dichloride;
dimethylamidoboranebis{1-[2-n-butyl, 4-(2-tert-butylphenyl)indenyl]}hafnium dichloride;
dimethylamidoboranebis{1-[2-isobutyl, 4-(2-tert-butylphenyl)indenyl]}hafnium dichloride;
dimethylamidoboranebis{1-[2-sec-butyl, 4-(2-tert-butylphenyl)indenyl]}hafnium dichloride;
dimethylamidoboranebis{1-[2-tert-butyl, 4-(2-tert-butylphenyl)indenyl]}hafnium dichloride;
dimethylamidoboranebis{1-[2-phenyl, 4-(2-tert-butylphenyl)indenyl]}hafnium dichloride;
dimethylamidoboranebis{1-[2-n-propyl, 4-(2-biphenyl)indenyl]}hafnium dichloride;
dimethylamidoboranebis{1-[2-isopropyl, 4-(2-biphenyl)indenyl]}hafnium dichloride;
dimethylamidoboranebis{1-[2-n-butyl, 4-(2-biphenyl)indenyl]}hafnium dichloride;
dimethylamidoboranebis{1-[2-isobutyl, 4-(2-biphenyl)indenyl]}halnium dichloride;
dimethylamidoboranebis{1-[2-sec-butyl, 4-(2-biphenyl)indenyl]}hafnium dichloride;
dimethylamidoboranebis{1-[2-tert-butyl, 4-(2-biphenyl)indenyl]}hafnium dichloride;
dimethylamidoboranebis{1-[2-phenyl, 4-(2-biphenyl)indenyl]}haffium dichloride;
dimethylamidoboranebis{1-[2-n-propyl, 4-(2-α-naphthylphenyl)indenyl]}hafnium dichloride;
dimethylamidoboranebis{1-[2-isopropyl, 4-(2-α-naphthylphenyl)indenyl]}hafnium dichloride;
dimethylamidoboranebis{1-[2-n-butyl, 4-(2-α-naphthylphenyl)indenyl]}hafnium dichloride;
dimethylamidoboranebis{1-[2-isobutyl, 4-(2-α-naphthylphenyl)indenyl]}hafnium dichloride;
dimethylamidoboranebis{1-[2-sec-butyl, 4-(2-α-naphthylphenyl)indenyl]}hafnium dichloride;
dimethylamidoboranebis{1-[2-tert-butyl, 4-(2-α-naphthylphenyl)indenyl]}hafnium dichloride;
dimethylamidoboranebis{1-[2-phenyl, 4-(2-α-naphthylphenyl)indenyl]}hafnium dichloride;
dimethylamidoboranebis{1-[2-n-propyl, 4-(2-β-naphthylphenyl)indenyl]}hafnium dichloride;
dimethylamidoboranebis{1-[2-isopropyl, 4-(2-β-naphthylphenyl)indenyl]}hafnium dichloride;
dimethylamidoboranebis{1-[2-n-butyl, 4-(2-β-naphthylphenyl)indenyl]}hafnium dichloride;
dimethylamidoboranebis{1-[2-isobutyl, 4-(2-β-naphthylphenyl)indenyl]}hafnium dichloride;
dimethylamidoboranebis{1-[2-sec-butyl, 4-(2-β-naphthylphenyl)indenyl]}hafnium dichloride;

dimethylamidoboranebis{1-[2-tert-butyl, 4-(2-β-naphthylphenyl)indenyl]}hafnium dichloride;
dimethylamidoboranebis{1-[2-phenyl, 4-(2-β-naphthylphenyl)indenyl]}hafnium dichloride;
dimethylamidoboranebis{1-[2-n-propyl, 4-(2-trifluoromethylphenyl)indenyl]}-hafnium dichloride;
dimethylamidoboranebis{1-[2-isopropyl, 4-(2-trifluoromethylphenyl)indenyl]}-hafnium dichloride;
dimethylamidoboranebis{1-[2-n-butyl, 4-(2-trifluoromethylphenyl)indenyl]}-hafnium dichloride;
dimethylamidoboranebis{1-[2-isobutyl, 4-(2-trifluoromethylphenyl)indenyl]}-hafnium dichloride;
dimethylamidoboranebis{1-[2-sec-butyl, 4-(2-trifluoromethylphenyl)indenyl]}-hafnium dichloride;
dimethylamidoboranebis{1-[2-tert-butyl, 4-(2-trifluoromethylphenyl)indenyl]}-hafnium dichloride;
dimethylamidoboranebis{1-[2-phenyl, 4-(2-trifluoromethylphenyl)indenyl]}-hafnium dichloride;
dimethylamidoboranebis{1-[2-n-propyl, 4-(2,3-dimethylphenyl)indenyl]}hafnium dichloride;
dimethylamidoboranebis{1-[2-isopropyl, 4-(2,3-dimethylphenyl)indenyl]}hafnium dichloride;
dimethylamidoboranebis{1-[2-n-butyl, 4-(2,3-dimethylphenyl)indenyl]}hafnium dichloride;
dimethylamidoboranebis{1-[2-isobutyl, 4-(2,3-dimethylphenyl)indenyl]}hafnium dichloride;
dimethylamidoboranebis{1-[2-sec-butyl, 4-(2,3-dimethylphenyl)indenyl]}hafnium dichloride;
dimethylamidoboranebis{1-[2-tert-butyl, 4-(2,3-dimethylphenyl)indenyl]}hafnium dichloride;
dimethylamidoboranebis{1-[2-phenyl, 4-(2,3-dimethylphenyl)indenyl]}hafnium dichloride;
dimethylamidoboranebis{1-[2-n-propyl, 4-(2,3,4-trimethylphenyl)indenyl]}hafnium dichloride;
dimethylamidoboranebis{1-[2-isopropyl, 4-(2,3,4-trimethylphenyl)indenyl]}hafnium dichloride;
dimethylamidoboranebis{1-[2-n-butyl, 4-(2,3,4-trimethylphenyl)indenyl]}hafnium dichloride;
dimethylamidoboranebis{1-[2-isobutyl, 4-(2,3,4-trimethylphenyl)indenyl]}hafnium dichloride;
dimethylamidoboranebis{1-[2-sec-butyl, 4-(2,3,4-trimethylphenyl)indenyl]}hafnium dichloride;
dimethylamidoboranebis{1-[2-tert-butyl, 4-(2,3,4-trimethylphenyl)indenyl]}hafnium dichloride;
dimethylamidoboranebis{1-[2-phenyl, 4-(2,3,4-trimethylphenyl)indenyl]}hafnium dichloride;
dimethylamidoboranebis{1-[2-n-propyl, 4-(2,3,5-trimethylphenyl)indenyl]}hafnium dichloride;
dimethylamidoboranebis{1-[2-isopropyl, 4-(2,3,5-trimethylphenyl)indenyl]}hafnium dichloride;
dimethylamidoboranebis{1-[2-n-butyl, 4-(2,3,5-trimethylphenyl)indenyl]}hafnium dichloride;
dimethylamidoboranebis{1-[2-isobutyl, 4-(2,3,5-trimethylphenyl)indenyl]}hafnium dichloride;
dimethylamidoboranebis{1-[2-sec-butyl, 4-(2,3,5-trimethylphenyl)indenyl]}hafnium dichloride;
dimethylamidoboranebis{1-[2-tert-butyl, 4-(2,3,5-trimethylphenyl)indenyl]}hafnium dichloride;
dimethylamidoboranebis{1-[2-phenyl, 4-(2,3,5-trimethylphenyl)indenyl]}hafnium dichloride;
dimethylamidoboranebis{1-[2-n-propyl, 4-(2-methylphenyl)indenyl]}hafnium dimethyl;
dimethylamidoboranebis{1-[2-isopropyl, 4-(2-methylphenyl)indenyl)}hafnium dimethyl;
dimethylamidoboranebis{1-[2-n-butyl, 4-(2-methylphenyl)indenyl]}hafnium dimethyl;
dimethylamidoboranebis{1-[2-isobutyl, 4-(2-methylphenyl)indenyl]}hafnium dimethyl;
dimethylamidoboranebis{1-[2-sec-butyl, 4-(2-methylphenyl)indenyl]}hafnium dimethyl;
dimethylamidoboranebis{1-[2-tert-butyl, 4-(2-methylphenyl)indenyl]}hafnium dimethyl;
dimethylamidoboranebis{1-[2-phenyl, 4-(2-methylphenyl)indenyl]}hafnium dimethyl;
dimethylamidoboranebis{1-[2-n-propyl, 4-(2-ethylphenyl)indenyl]}hafnium dimethyl;
dimethylamidoboranebis{1-[2-isopropyl, 4-(2-ethylphenyl)indenyl]}hafnium dimethyl;
dimethylamidoboranebis{1-[2-n-butyl, 4-(2-ethylphenyl)indenyl]}hafnium dimethyl;
dimethylamidoboranebis{1-[2-isobutyl, 4-(2-ethylphenyl)indenyl]}hafnium dimethyl;
dimethylamidoboranebis{1-[2-sec-butyl, 4-(2-ethylphenyl)indenyl]}hafnium dimethyl;
dimethylamidoboranebis{1-[2-tert-butyl, 4-(2-ethylphenyl)indenyl]}hafnium dimethyl;
dimethylamidoboranebis{1-[2-phenyl, 4-(2-ethylphenyl)indenyl]}hafnium dimethyl;
dimethylamidoboranebis{1-[2-n-propyl, 4-(2-n-propylphenyl)indenyl]}hafnium dimethyl;
dimethylamidoboranebis{1-[2-isopropyl, 4-(2-n-propylphenyl)indenyl]}hafnium dimethyl;
dimethylamidoboranebis{1-[2-n-butyl, 4-(2-n-propylphenyl)indenyl]}hafnium dimethyl;
dimethylamidoboranebis{1-[2-isobutyl, 4-(2-n-propylphenyl)indenyl]}hafnium dimethyl;
dimethylamidoboranebis{1-[2-sec-butyl, 4-(2-n-propylphenyl)indenyl]}hafnium dimethyl;
dimethylamidoboranebis{1-[2-tert-butyl, 4-(2-n-propylphenyl)indenyl]}hafnium dimethyl;
dimethylamidoboranebis{1-[2-phenyl, 4-(2-n-propylphenyl)indenyl]}hafnium dimethyl;
dimethylamidoboranebis{1-[2-n-propyl, 4-(2-isopropylphenyl)indenyl]}hafnium dimethyl;
dimethylamidoboranebis{1-[2-isopropyl, 4-(2-isopropylphenyl)indenyl]}hafnium dimethyl;
dimethylamidoboranebis{1-[2-n-butyl, 4-(2-isopropylphenyl)indenyl]}hafnium dimethyl;
dimethylamidoboranebis{1-[2-isobutyl, 4-(2-isopropylphenyl)indenyl]}hafnium dimethyl;
dimethylamidoboranebis{1-[2-sec-butyl, 4-(2-isopropylphenyl)indenyl]}hafnium dimethyl;
dimethylamidoboranebis{1-[2-tert-butyl, 4-(2-isopropylphenyl)indenyl]}hafnium dimethyl;
dimethylamidoboranebis{1-[2-phenyl, 4-(2-isopropylphenyl)indenyl]}hafnium dimethyl;
dimethylamidoboranebis{1-[2-n-propyl, 4-(2-n-butylphenyl)indenyl]}hafnium dimethyl;
dimethylamidoboranebis{1-[2-isopropyl, 4-(2-n-butylphenyl)indenyl]}hafnium dimethyl;
dimethylamidoboranebis{1-[2-n-butyl, 4-(2-n-butylphenyl)indenyl]}hafnium dimethyl;
dimethylamidoboranebis{1-[2-isobutyl, 4-(2-n-butylphenyl)indenyl]}hafnium dimethyl;
dimethylamidoboranebis{1-[2-sec-butyl, 4-(2-n-butylphenyl)indenyl]}hafnium dimethyl;
dimethylamidoboranebis{1-[2-tert-butyl, 4-(2-n-butylphenyl)indenyl]}hafnium dimethyl;
dimethylamidoboranebis{1-[2-phenyl, 4-(2-n-butylphenyl)indenyl]}hafnium dimethyl;
dimethylamidoboranebis{1-[2-n-propyl, 4-(2-isobutylphenyl)indenyl]}hafnium dimethyl;
dimethylamidoboranebis{1-[2-isopropyl, 4-(2-isobutylphenyl)indenyl]}hafnium dimethyl;
dimethylamidoboranebis{1-[2-n-butyl, 4-(2-isobutylphenyl)indenyl]}hafnium dimethyl;

dimethylamidoboranebis{1-[2-isobutyl, 4-(2-isobutylphenyl)indenyl]}hafnium dimethyl;
dimethylamidoboranebis{1-[2-sec-butyl, 4-(2-isobutylphenyl)indenyl]}hafnium dimethyl;
dimethylamidoboranebis{1-[2-tert-butyl, 4-(2-isobutylphenyl)indenyl]}hafnium dimethyl;
dimethylamidoboranebis{1-[2-phenyl, 4-(2-isobutylphenyl)indenyl]}hafnium dimethyl;
dimethylamidoboranebis{1-[2-n-propyl, 4-(2-sec-butylphenyl)indenyl]}hafnium dimethyl;
dimethylamidoboranebis{1-[2-isopropyl, 4-(2-sec-butylphenyl)indenyl]}hafnium dimethyl;
dimethylamidoboranebis{1-[2-n-butyl, 4-(2-sec-butylphenyl)indenyl]}hafnium dimethyl;
dimethylamidoboranebis{1-[2-isobutyl, 4-(2-sec-butylphenyl)indenyl]}hafnium dimethyl;
dimethylamidoboranebis{1-[2-sec-butyl, 4-(2-sec-butylphenyl)indenyl]}hafnium dimethyl;
dimethylamidoboranebis{1-[2-tert-butyl, 4-(2-sec-butylphenyl)indenyl]}hafnium dimethyl;
dimethylamidoboranebis{1-[2-phenyl, 4-(2-sec-butylphenyl)indenyl]}hafnium dimethyl;
dimethylamidoboranebis{1-[2-n-propyl, 4-(2-tert-butylphenyl)indenyl]}hafnium dimethyl;
dimethylamidoboranebis{1-[2-isopropyl, 4-(2-tert-butylphenyl)indenyl]}hafnium dimethyl;
dimethylamidoboranebis{1-[2-n-butyl, 4-(2-tert-butylphenyl)indenyl]}hafnium dimethyl;
dimethylamidoboranebis{1-12-isobutyl, 4-(2-tert-butylphenyl)indenyl]}hafnium dimethyl;
dimethylamidoboranebis{1-[2-sec-butyl, 4-(2-tert-butylphenyl)indenyl]}hafnium dimethyl;
dimethylamidoboranebis{1-[2-tert-butyl, 4-(2-tert-butylphenyl)indenyl]}hafnium dimethyl;
dimethylamidoboranebis{1-[2-phenyl, 4-(2-tert-butylphenyl)indenyl]}hafnium dimethyl;
dimethylamidoboranebis{1-[2-n-propyl, 4-(2-biphenyl)indenyl]}hafnium dimethyl;
dimethylamidoboranebis{1-[2-isopropyl, 4-(2-biphenyl)indenyl]}hafnium dimethyl;
dimethylamidoboranebis{1-[2-n-butyl, 4-(2-biphenyl)indenyl]}hafnium dimethyl;
dimethylamidoboranebis{1-[2-isobutyl, 4-(2-biphenyl)indenyl]}hafnium dimethyl;
dimethylamidoboranebis{1-[2-sec-butyl, 4-(2-biphenyl)indenyl]}hafnium dimethyl;
dimethylamidoboranebis{1-[2-tert-butyl, 4-(2-biphenyl)indenyl]}hafnium dimethyl;
dimethylamidoboranebis{1-[2-phenyl, 4-(2-biphenyl)indenyl]}hafnium dimethyl;
dimethylamidoboranebis{1-[2-n-propyl, 4-(2-α-naphthylphenyl)indenyl]}hafnium dimethyl;
dimethylamidoboranebis{1-[2-isopropyl, 4-(2-α-naphthylphenyl)indenyl]}hafnium dimethyl;
dimethylamidoboranebis{1-[2-n-butyl, 4-(2-α-naphthylphenyl)indenyl]}hafnium dimethyl;
dimethylamidoboranebis{1-[2-isobutyl, 4-(2-α-naphthylphenyl)indenyl]}hafnium dimethyl;
dimethylamidoboranebis{1-[2-sec-butyl, 4-(2-α-naphthylphenyl)indenyl]}hafnium dimethyl;
dimethylamidoboranebis{1-[2-tert-butyl, 4-(2-α-naphthylphenyl)indenyl]}hafnium dimethyl;
dimethylamidoboranebis{1-[2-phenyl, 4-(2-α-naphthylphenyl)indenyl]}hafnium dimethyl;
dimethylamidoboranebis{1-[2-n-propyl, 4-(2-β-naphthylphenyl)indenyl]}hafnium dimethyl;
dimethylamidoboranebis{1-[2-isopropyl, 4-(2-β-naphthylphenyl)indenyl]}hafnium dimethyl;
dimethylamidoboranebis{1-[2-n-butyl, 4-(2-β-naphthylphenyl)indenyl]}hafnium dimethyl;
dimethylamidoboranebis{1-[2-isobutyl, 4-(2-β-naphthylphenyl)indenyl]}hafnium dimethyl;
dimethylamidoboranebis{1-[2-sec-butyl, 4-(2-β-naphthylphenyl)indenyl]}hafnium dimethyl;
dimethylamidoboranebis{1-[2-tert-butyl, 4-(2-β-naphthylphenyl)indenyl]}hafnium dimethyl;
dimethylamidoboranebis{1-[2-phenyl, 4-(2-β-naphthylphenyl)indenyl]}hafnium dimethyl;
dimethylamidoboranebis{1-[2-n-propyl, 4-(2-trifluoromethylphenyl)indenyl]}-hafnium dimethyl;
dimethylamidoboranebis{1-[2-isopropyl, 4-(2-trifluoromethylphenyl)indenyl]}-hafnium dimethyl;
dimethylamidoboranebis{1-[2-n-butyl, 4-(2-trifluoromethylphenyl)indenyl]}-hafnium dimethyl;
dimethylamidoboranebis{1-[2-isobutyl, 4-(2-trifluoromethylphenyl)indenyl]}-hafnium dimethyl;
dimethylamidoboranebis{1-[2-sec-butyl, 4-(2-trifluoromethylphenyl)indenyl]}-hafnium dimethyl;
dimethylamidoboranebis{1-[2-tert-butyl, 4-(2-trifluoromethylphenyl)indenyl]}-hafnium dimethyl;
dimethylamidoboranebis{1-[2-phenyl, 4-(2-trifluoromethylphenyl)indenyl]}-hafnium dimethyl;
dimethylamidoboranebis{1-[2-n-propyl, 4-(2,3-dimethylphenyl)indenyl]}hafnium dimethyl;
dimethylamidoboranebis{1-[2-isopropyl, 4-(2,3-dimethylphenyl)indenyl]}hafnium dimethyl,
dimethylamidoboranebis{1-[2-n-butyl, 4-(2,3-dimethylphenyl)indenyl]}hafnium dimethyl;
dimethylamidoboranebis{1-[2-isobutyl, 4-(2,3-dimethylphenyl)indenyl]}hafnium dimethyl;
dimethylamidoboranebis{1-[2-sec-butyl, 4-(2,3-dimethylphenyl)indenyl]}hafnium dimethyl;
dimethylamidoboranebis{1-[2-tert-butyl, 4-(2,3-dimethylphenyl)indenyl]}hafnium dimethyl;
dimethylamidoboranebis{1-[2-phenyl, 4-(2,3-dimethylphenyl)indenyl]}hafnium dimethyl;
dimethylamidoboranebis{1-[2-n-propyl, 4-(2,3,4-trimethylphenyl)indenyl]}hafnium dimethyl;
dimethylamidoboranebis{1-[2-isopropyl, 4-(2,3,4-trimethylphenyl)indenyl]}hafnium dimethyl;
dimethylamidoboranebis{1-[2-n-butyl, 4-(2,3,4-trimethylphenyl)indenyl]}hafnium dimethyl;
dimethylamidoboranebis{1-[2-isobutyl, 4-(2,3,4-trimethylphenyl)indenyl]}hafnium dimethyl;
dimethylamidoboranebis{1-[2-sec-butyl, 4-(2,3,4-trimethylphenyl)indenyl]}hafnium dimethyl;
dimethylamidoboranebis{1-[2-tert-butyl, 4-(2,3,4-trimethylphenyl)indenyl]}hafnium dimethyl;
dimethylamidoboranebis{1-[2-phenyl, 4-(2,3,4-trimethylphenyl)indenyl]}hafnium dimethyl;
dimethylamidoboranebis{1-[2-n-propyl, 4-(2,3,5-trimethylphenyl)indenyl]}hafnium dimethyl;
dimethylamidoboranebis{1-[2-isopropyl, 4-(2,3,5-trimethylphenyl)indenyl]}hafnium dimethyl;
dimethylamidoboranebis{1-[2-n-butyl, 4-(2,3,5-trimethylphenyl)indenyl]}hafnium dimethyl;
dimethylamidoboranebis{1-[2-isobutyl, 4-(2,3,5-trimethylphenyl)indenyl]}hafnium dimethyl;
dimethylamidoboranebis{1-[2-sec-butyl, 4-(2,3,5-trimethylphenyl)indenyl]}hafnium dimethyl;
dimethylamidoboranebis{-2-tert-butyl, 4-(2,3,5-trimethylphenyl)indenyl]}hafnium dimethyl;
dimethylamidoboranebis{1-[2-phenyl, 4-(2,3,5-trimethylphenyl)indenyl]}hafnium dimethyl;
diisopropylamidoboranebis{1-[2-n-propyl, 4-(2-methylphenyl)indenyl]}hafnium dichloride;

diisopropylamidoboranebis{1-[2-isopropyl, 4-(2-methylphenyl)indenyl]}hafnium dichloride;
diisopropylamidoboranebis{1-[2-n-butyl, 4-(2-methylphenyl)indenyl]}hafnium dichloride;
diisopropylamidoboranebis{1-[2-isobutyl, 4-(2-methylphenyl)indenyl]}hafnium dichloride;
diisopropylamidoboranebis{1-[2-sec-butyl, 4-(2-methylphenyl)indenyl]}hafnium dichloride;
diisopropylamidoboranebis{1-[2-tert-butyl, 4-(2-methylphenyl)indenyl]}hafnium dichloride;
diisopropylamidoboranebis{1-[2-phenyl, 4-(2-methylphenyl)indenyl]}hafnium dichloride;
diisopropylamidoboranebis{1-[2-n-propyl, 4-(2-ethylphenyl)indenyl]}hafnium dichloride;
diisopropylamidoboranebis{1-[2-isopropyl, 4-(2-ethylphenyl)indenyl]}hafnium dichloride;
diisopropylamidoboranebis{1-[2-n-butyl, 4-(2-ethylphenyl)indenyl]}hafnium dichloride;
diisopropylamidoboranebis{1-[2-isobutyl, 4-(2-ethylphenyl)indenyl]}hafnium dichloride;
diisopropylamidoboranebis{1-[2-sec-butyl, 4-(2-ethylphenyl)indenyl]}hafnium dichloride;
diisopropylamidoboranebis{1-[2-tert-butyl, 4-(2-ethylphenyl)indenyl]}hafnium dichloride;
diisopropylamidoboranebis{1-[2-phenyl, 4-(2-ethylphenyl)indenyl]}hafnium dichloride;
diisopropylamidoboranebis{1-[2-n-propyl, 4-(2-n-propylphenyl)indenyl]}hafnium dichloride;
diisopropylamidoboranebis{1-[2-isopropyl, 4-(2-n-propylphenyl)indenyl]}hafnium dichloride;
diisopropylamidoboranebis{1-[2-n-butyl, 4-(2-n-propylphenyl)indenyl]}hafnium dichloride;
diisopropylamidoboranebis{1-[2-isobutyl, 4-(2-n-propylphenyl)indenyl]}hafnium dichloride;
diisopropylamidoboranebis{1-[2-sec-butyl, 4-(2-n-propylphenyl)indenyl]}hafnium dichloride;
diisopropylamidoboranebis{1-[2-tert-butyl, 4-(2-n-propylphenyl)indenyl]}hafnium dichloride;
diisopropylamidoboranebis{1-[2-phenyl, 4-(2-n-propylphenyl)indenyl]}hafnium dichloride;
diisopropylamidoboranebis{1-[2-n-propyl, 4-(2-isopropylphenyl)indenyl]}hafnium dichloride;
diisopropylamidoboranebis{1-[2-isopropyl, 4-(2-isopropylphenyl)indenyl]}hafnium dichloride;
diisopropylamidoboranebis{1-[2-n-butyl, 4-(2-isopropylphenyl)indenyl]}hafnium dichloride;
diisopropylamidoboranebis{1-[2-isobutyl, 4-(2-isopropylphenyl)indenyl]}hafnium dichloride;
diisopropylamidoboranebis{1-[2-sec-butyl, 4-(2-isopropylphenyl)indenyl]}hafnium dichloride;
diisopropylamidoboranebis{1-[2-tert-butyl, 4-(2-isopropylphenyl)indenyl]}hafnium dichloride;
diisopropylamidoboranebis{1-[2-phenyl, 4-(2-isopropylphenyl)indenyl]}hafnium dichloride;
diisopropylamidoboranebis{1-[2-n-propyl, 4-(2-n-butylphenyl)indenyl]}hafnium dichloride;
diisopropylamidoboranebis{1-[2-isopropyl, 4-(2-n-butylphenyl)indenyl]}hafnium dichloride;
diisopropylamidoboranebis{1-[2-n-butyl, 4-(2-n-butylphenyl)indenyl]}hafnium dichloride;
diisopropylamidoboranebis{1-[2-isobutyl, 4-(2-n-butylphenyl)indenyl]}hafnium dichloride;
diisopropylamidoboranebis{1-[2-sec-butyl, 4-(2-n-butylphenyl)indenyl]}hafnium dichloride;
diisopropylamidoboranebis{1-[2-tert-butyl, 4-(2-n-butylphenyl)indenyl]}hafnium dichloride;
diisopropylamidoboranebis{1-[2-phenyl, 4-(2-n-butylphenyl)indenyl]}hafnium dichloride;
diisopropylamidoboranebis{1-[2-n-propyl, 4-(2-isobutylphenyl)indenyl]}hafnium dichloride;
diisopropylamidoboranebis{1-[2-isopropyl, 4-(2-isobutylphenyl)indenyl]}hafnium dichloride;
diisopropylamidoboranebis{1-[2-n-butyl, 4-(2-isobutylphenyl)indenyl]}hafnium dichloride;
diisopropylamidoboranebis{1-[2-isobutyl, 4-(2-isobutylphenyl)indenyl]}hafnium dichloride;
diisopropylamidoboranebis{1-[2-sec-butyl, 4-(2-isobutylphenyl)indenyl]}hafnium dichloride;
diisopropylamidoboranebis{1-[2-tert-butyl, 4-(2-isobutylphenyl)indenyl]}hafnium dichloride;
diisopropylamidoboranebis{1-[2-phenyl, 4-(2-isobutylphenyl)indenyl]}hafnium dichloride;
diisopropylamidoboranebis{1-[2-n-propyl, 4-(2-sec-butylphenyl)indenyl]}hafnium dichloride;
diisopropylamidoboranebis{1-[2-isopropyl, 4-(2-sec-butylphenyl)indenyl]}hafnium dichloride;
diisopropylamidoboranebis{1-[2-n-butyl, 4-(2-sec-butylphenyl)indenyl]}hafnium dichloride;
diisopropylamidoboranebis{1-[2-isobutyl, 4-(2-sec-butylphenyl)indenyl]}hafnium dichloride;
diisopropylamidoboranebis{1-[2-sec-butyl, 4-(2-sec-butylphenyl)indenyl]}hafnium dichloride;
diisopropylamidoboranebis{1-[2-tert-butyl, 4-(2-sec-butylphenyl)indenyl]}hafnium dichloride;
diisopropylamidoboranebis{1-[2-phenyl, 4-(2-sec-butylphenyl)indenyl]}hafnium dichloride;
diisopropylamidoboranebis{1-[2-n-propyl, 4-(2-tert-butylphenyl)indenyl]}hafnium dichloride;
diisopropylamidoboranebis{1-[2-isopropyl, 4-(2-tert-butylphenyl)indenyl]}hafnium dichloride;
diisopropylamidoboranebis{1-[2-n-butyl, 4-(2-tert-butylphenyl)indenyl]}hafnium dichloride;
diisopropylamidoboranebis{1-[2-isobutyl, 4-(2-tert-butylphenyl)indenyl]}hafnium dichloride;
diisopropylamidoboranebis{1-[2-sec-butyl, 4-(2-tert-butylphenyl)indenyl]}hafnium dichloride;
diisopropylamidoboranebis{1-[2-tert-butyl, 4-(2-tert-butylphenyl)indenyl]}hafnium dichloride;
diisopropylamidoboranebis{1-[2-phenyl, 4-(2-tert-butylphenyl)indenyl]}hafnium dichloride;
diisopropylamidoboranebis{1-[2-n-propyl, 4-(2-biphenyl)indenyl]}hafnium dichloride;
diisopropylamidoboranebis{1-[2-isopropyl, 4-(2-biphenyl)indenyl]}hafnium dichloride;
diisopropylamidoboranebis{1-[2-n-butyl, 4-(2-biphenyl)indenyl]}hafnium dichloride;
diisopropylamidoboranebis{1-[2-isobutyl, 4-(2-biphenyl)indenyl]}hafnium dichloride;
diisopropylamidoboranebis{1-[2-sec-butyl, 4-(2-biphenyl)indenyl]}hafnium dichloride;
diisopropylamidoboranebis{1-[2-tert-butyl, 4-(2-biphenyl)indenyl]}hafnium dichloride;
diisopropylamidoboranebis{1-[2-phenyl, 4-(2-biphenyl)indenyl]}hafnium dichloride;
diisopropylamidoboranebis{1-[2-n-propyl, 4-(2-α-naphthylphenyl)indenyl]}hafnium dichloride;
diisopropylamidoboranebis{1-[2-isopropyl, 4-(2-α-naphthylphenyl)indenyl]}hafnium dichloride;
diisopropylamidoboranebis{1-[2-n-butyl, 4-(2-α-naphthylphenyl)indenyl]}hafnium dichloride;
diisopropylamidoboranebis{1-[2-isobutyl, 4-(2-α-naphthylphenyl)indenyl]}hafnium dichloride;
diisopropylamidoboranebis{1-[2-sec-butyl, 4-(2-α-naphthylphenyl)indenyl]}hafnium dichloride;
diisopropylamidoboranebis{1-[2-tert-butyl, 4-(2-α-naphthylphenyl)indenyl]}hafnium dichloride;

diisopropylamidoboranebis{1-[2-phenyl, 4-(2-α-naphthylphenyl)indenyl]}hafnium dichloride;
diisopropylamidoboranebis{1-[2-n-propyl, 4-(2-β-naphthylphenyl)indenyl]}hafnium dichloride;
diisopropylamidoboranebis{1-[2-isopropyl, 4-(2-β-naphthylphenyl)indenyl]}hafnium dichloride;
diisopropylamidoboranebis{1-[2-n-butyl, 4-(2-β-naphthylphenyl)indenyl]}hafnium dichloride;
diisopropylamidoboranebis{1-[2-isobutyl, 4-(2-β-naphthylphenyl)indenyl]}hafnium dichloride;
diisopropylamidoboranebis{1-[2-sec-butyl, 4-(2-β-naphthylphenyl)indenyl]}hafnium dichloride;
diisopropylamidoboranebis{1-[2-tert-butyl, 4-(2-β-naphthylphenyl)indenyl]}hafnium dichloride;
diisopropylamidoboranebis{1-[2-phenyl, 4-(2-β-naphthylphenyl)indenyl]}hafnium dichloride;
diisopropylamidoboranebis{1-[2-n-propyl, 4-(2-trifluoromethylphenyl)indenyl]}-hafnium dichloride;
diisopropylamidoboranebis{1-[2-isopropyl, 4-(2-trifluoromethylphenyl)indenyl[}-hafnium dichloride;
diisopropylamidoboranebis{1-[2-n-butyl, 4-(2-trifluoromethylphenyl)indenyl]}-hafnium dichloride;
diisopropylamidoboranebis{1-[2-isobutyl, 4-(2-trifluoromethylphenyl)indenyl]}-hafnium dichloride;
diisopropylamidoboranebis{1-[2-sec-butyl, 4-(2-trifluoromethylphenyl)indenyl]}-hafnium dichloride;
diisopropylamidoboranebis{1-[2-tert-butyl, 4-(2-trifluoromethylphenyl)indenyl]}-hafnium dichloride;
diisopropylamidoboranebis{1-[2-phenyl, 4-(2-trifluoromethylphenyl)indenyl]}-hafnium dichloride;
diisopropylamidoboranebis{1-[2-n-propyl, 4-(2,3-dimethylphenyl)indenyl]}hafnium dichloride;
diisopropylamidoboranebis{1-[2-isopropyl, 4-(2,3-dimethylphenyl)indenyl]}hafnium dichloride;
diisopropylamidoboranebis{1-[2-n-butyl, 4-(2,3-dimethylphenyl)indenyl]}hafnium dichloride;
diisopropylamidoboranebis{1-[2-isobutyl, 4-(2,3-dimethylphenyl)indenyl]}hafnium dichloride;
diisopropylamidoboranebis{1-[2-sec-butyl, 4-(2,3-dimethylphenyl)indenyl]}hafnium dichloride;
diisopropylamidoboranebis{1-[2-tert-butyl, 4-(2,3-dimethylphenyl)indenyl]}hafnium dichloride;
diisopropylamidoboranebis{1-[2-phenyl, 4-(2,3-dimethylphenyl)indenyl]}hafnium dichloride;
diisopropylamidoboranebis{1-[2-n-propyl, 4-(2,3,4-trimethylphenyl)indenyl]}hafnium dichloride;
diisopropylamidoboranebis{1-[2-isopropyl, 4-(2,3,4-trimethylphenyl)indenyl]}hafnium dichloride;
diisopropylamidoboranebis{1-[2-n-butyl, 4-(2,3,4-trimethylphenyl)indenyl]}hafnium dichloride;
diisopropylamidoboranebis{1-[2-isobutyl, 4-(2,3,4-trimethylphenyl)indenyl]}hafnium dichloride;
diisopropylamidoboranebis{1-[2-sec-butyl, 4-(2,3,4-trimethylphenyl)indenyl]}hafnium dichloride;
diisopropylamidoboranebis{1-[2-tert-butyl, 4-(2,3,4-trimethylphenyl)indenyl]}hafnium dichloride;
diisopropylamidoboranebis{1-[2-phenyl, 4-(2,3,4-trimethylphenyl)indenyl]}hafnium dichloride;
diisopropylamidoboranebis{1-[2-n-propyl, 4-(2,3,5-trimethylphenyl)indenyl]}hafnium dichloride;
diisopropylamidoboranebis{1-[2-isopropyl, 4-(2,3,5-trimethylphenyl)indenyl]}hafnium dichloride;
diisopropylamidoboranebis{1-[2-n-butyl, 4-(2,3,5-trimethylphenyl)indenyl]}hafnium dichloride;
diisopropylamidoboranebis{1-[2-isobutyl, 4-(2,3,5-trimethylphenyl)indenyl]}hafnium dichloride;
diisopropylamidoboranebis{1-[2-sec-butyl, 4-(2,3,5-trimethylphenyl)indenyl]}hafnium dichloride;
diisopropylamidoboranebis{1-[2-tert-butyl, 4-(2,3,5-trimethylphenyl)indenyl]}hafnium dichloride;
diisopropylamidoboranebis{1-[2-phenyl, 4-(2,3,5-trimethylphenyl)indenyl]}hafnium dichloride;
diisopropylamidoboranebis{1-[2-n-propyl, 4-(2-methylphenyl)indenyl]}hafnium dimethyl;
diisopropylamidoboranebis{1-[2-isopropyl, 4-(2-methylphenyl)indenyl]}hafnium dimethyl;
diisopropylamidoboranebis{1-[2-n-butyl, 4-(2-methylphenyl)indenyl]}hafnium dimethyl;
diisopropylamidoboranebis{1-[2-isobutyl, 4-(2-methylphenyl)indenyl]}hafnium dimethyl;
diisopropylamidoboranebis{1-[2-sec-butyl, 4-(2-methylphenyl)indenyl}hafnium dimethyl;
diisopropylamidoboranebis{1-[2-tert-butyl, 4-(2-methylphenyl)indenyl]}hafnium dimethyl;
diisopropylamidoboranebis{1-[2-phenyl, 4-(2-methylphenyl)indenyl]}hafnium dimethyl;
diisopropylamidoboranebis{1-[2-n-propyl, 4-(2-ethylphenyl)indenyl]}hafnium dimethyl;
diisopropylamidoboranebis{1-[2-isopropyl, 4-(2-ethylphenyl)indenyl]}hafnium dimethyl;
diisopropylamidoboranebis{1-[2-n-butyl, 4-(2-ethylphenyl)indenyl]}hafnium dimethyl;
diisopropylamidoboranebis{1-[2-isobutyl, 4-(2-ethylphenyl)indenyl]}hafnium dimethyl;
diisopropylamidoboranebis{1-[2-sec-butyl, 4-(2-ethylphenyl)indenyl]}hafnium dimethyl;
diisopropylamidoboranebis{1-[2-tert-butyl, 4-(2-ethylphenyl)indenyl]}hafnium dimethyl;
diisopropylamidoboranebis{1-[2-phenyl, 4-(2-ethylphenyl)indenyl]}hafnium dimethyl;
diisopropylamidoboranebis{1-[2-n-propyl, 4-(2-n-propylphenyl)indenyl]}hafnium dimethyl;
diisopropylamidoboranebis{1-[2-isopropyl, 4-(2-n-propylphenyl)indenyl]}hafnium dimethyl;
diisopropylamidoboranebis{1-[2-n-butyl, 4-(2-n-propylphenyl)indenyl]}hafnium dimethyl;
diisopropylamidoboranebis{1-[2-isobutyl, 4-(2-n-propylphenyl)indenyl]}hafnium dimethyl;
diisopropylamidoboranebis{1-[2-sec-butyl, 4-(2-n-propylphenyl)indenyl]}hafnium dimethyl;
diisopropylamidoboranebis{1-[2-tert-butyl, 4-(2-n-propylphenyl)indenyl]}hafnium dimethyl;
diisopropylamidoboranebis{1-[2-phenyl, 4-(2-n-propylphenyl)indenyl]}hafnium dimethyl;
diisopropylamidoboranebis{1-[2-n-propyl, 4-(2-isopropylphenyl)indenyl]}hafnium dimethyl;
diisopropylamidoboranebis{1-[2-isopropyl, 4-(2-isopropylphenyl)indenyl]}hafnium dimethyl;
diisopropylamidoboranebis{1-[2-n-butyl, 4-(2-isopropylphenyl)indenyl]}hafnium dimethyl;
diisopropylamidoboranebis{1-[2-isobutyl, 4-(2-isopropylphenyl)indenyl]}hafnium dimethyl;
diisopropylamidoboranebis{1-[2-sec-butyl, 4-(2-isopropylphenyl)indenyl]}hafnium dimethyl;
diisopropylamidoboranebis{1-[2-tert-butyl, 4-(2-isopropylphenyl)indenyl]}hafnium dimethyl;
diisopropylamidoboranebis{1-[2-phenyl, 4-(2-isopropylphenyl)indenyl]}hafnium dimethyl;
diisopropylamidoboranebis{1-[2-n-propyl, 4-(2-n-butylphenyl)indenyl]}hafnium dimethyl;
diisopropylamidoboranebis{1-[2-isopropyl, 4-(2-n-butylphenyl)indenyl]}hafnium dimethyl;
diisopropylamidoboranebis{1-[2-n-butyl, 4-(2-n-butylphenyl)indenyl]}hafnium dimethyl;
diisopropylamidoboranebis{1-[2-isobutyl, 4-(2-n-butylphenyl)indenyl]}hafnium dimethyl;

diisopropylamidoboranebis{1-[2-sec-butyl, 4-(2-n-butylphenyl)indenyl]}hafnium dimethyl;
diisopropylamidoboranebis{1-[2-tert-butyl, 4-(2-n-butylphenyl)indenyl]}hafnium dimethyl;
diisopropylamidoboranebis{1-[2-phenyl, 4-(2-n-butylphenyl)indenyl]}hafnium dimethyl;
diisopropylamidoboranebis{1-[2-n-propyl, 4-(2-isobutylphenyl)indenyl]}hafnium dimethyl;
diisopropylamidoboranebis{1-[2-isopropyl, 4-(2-isobutylphenyl)indenyl]}hafnium dimethyl;
diisopropylamidoboranebis{1-[2-n-butyl, 4-(2-isobutylphenyl)indenyl]}hafnium dimethyl;
diisopropylamidoboranebis{1-[2-isobutyl, 4-(2-isobutylphenyl)indenyl]}hafnium dimethyl;
diisopropylamidoboranebis{1-[2-sec-butyl, 4-(2-isobutylphenyl)indenyl]}hafnium dimethyl;
diisopropylamidoboranebis{1-[2-tert-butyl, 4-(2-isobutylphenyl)indenyl]}hafnium dimethyl;
diisopropylamidoboranebis{1-[2-phenyl, 4-(2-isobutylphenyl)indenyl]}hafnium dimethyl;
diisopropylamidoboranebis{1-[2-n-propyl, 4-(2-sec-butylphenyl)indenyl]}hafnium dimethyl;
diisopropylamidoboranebis{1-[2-isopropyl, 4-(2-sec-butylphenyl)indenyl]}hafnium dimethyl;
diisopropylamidoboranebis{1-[2-n-butyl, 4-(2-sec-butylphenyl)indenyl]}hafnium dimethyl;
diisopropylamidoboranebis{1-[2-isobutyl, 4-(2-sec-butylphenyl)indenyl]}hafnium dimethyl;
diisopropylamidoboranebis{1-[2-sec-butyl, 4-(2-sec-butylphenyl)indenyl]}hafnium dimethyl;
diisopropylamidoboranebis{1-[2-tert-butyl, 4-(2-sec-butylphenyl)indenyl]}hafnium dimethyl;
diisopropylamidoboranebis{1-[2-phenyl, 4-(2-sec-butylphenyl)indenyl]}hafnium dimethyl;
diisopropylamidoboranebis{1-[2-n-propyl, 4-(2-tert-butylphenyl)indenyl]}hafnium dimethyl;
diisopropylamidoboranebis{1-[2-isopropyl, 4-(2-tert-butylphenyl)indenyl]}hafnium dimethyl;
diisopropylamidoboranebis{1-[2-n-butyl, 4-(2-tert-butylphenyl)indenyl]}hafnium dimethyl;
diisopropylamidoboranebis{1-[2-isobutyl, 4-(2-tert-butylphenyl)indenyl]}hafnium dimethyl;
diisopropylamidoboranebis{1-[2-sec-butyl, 4-(2-tert-butylphenyl)indenyl]}hafnium dimethyl;
diisopropylamidoboranebis{1-[2-tert-butyl, 4-(2-tert-butylphenyl)indenyl]}hafnium dimethyl;
diisopropylamidoboranebis{1-[2-phenyl, 4-(2-tert-butylphenyl)indenyl]}hafnium dimethyl;
diisopropylamidoboranebis{1-[2-n-propyl, 4-(2-biphenyl)indenyl]}hafnium dimethyl;
diisopropylamidoboranebis{1-[2-isopropyl, 4-(2-biphenyl)indenyl]}hafnium dimethyl;
diisopropylamidoboranebis{1-[2-n-butyl, 4-(2-biphenyl)indenyl]}hafnium dimethyl;
diisopropylamidoboranebis{1-[2-isobutyl, 4-(2-biphenyl)indenyl]}hafnium dimethyl;
diisopropylamidoboranebis{1-[2-sec-butyl, 4-(2-biphenyl)indenyl]}hafnium dimethyl;
diisopropylamidoboranebis{1-[2-tert-butyl, 4-(2-biphenyl)indenyl]}hafnium dimethyl;
diisopropylamidoboranebis{1-[2-phenyl, 4-(2-biphenyl)indenyl]}hafnium dimethyl;
diisopropylamidoboranebis{1-[2-n-propyl, 4-(2-α-naphthylphenyl)indenyl)}hafnium dimethyl;
diisopropylamidoboranebis{1-[2-isopropyl, 4-(2-α-naphthylphenyl)indenyl]}hafnium dimethyl;
diisopropylamidoboranebis{1-[2-n-butyl, 4-(2-α-naphthylphenyl)indenyl]}hafnium dimethyl;
diisopropylamidoboranebis{1-[2-isobutyl, 4-(2-α-naphthylphenyl)indenyl]}hafnium dimethyl;
diisopropylamidoboranebis{1-[2-sec-butyl, 4-(2-α-naphthylphenyl)indenyl]}hafnium dimethyl;
diisopropylamidoboranebis{1-[2-tert-butyl, 4-(2-α-naphthylphenyl)indenyl]}hafnium dimethyl;
diisopropylamidoboranebis{1-[2-phenyl, 4-(2-α-naphthylphenyl)indenyl]}hafnium dimethyl;
diisopropylamidoboranebis{1-[2-n-propyl, 4-(2-β-naphthylphenyl)indenyl]}hafnium dimethyl;
diisopropylamidoboranebis{1-[2-isopropyl, 4-(2-β-naphthylphenyl)indenyl]}hafnium dimethyl;
diisopropylamidoboranebis{1-[2-n-butyl, 4-(2-β-naphthylphenyl)indenyl]}hafnium dimethyl;
diisopropylamidoboranebis{1-[2-isobutyl, 4-(2-β-naphthylphenyl)indenyl]}hafnium dimethyl;
diisopropylamidoboranebis{1-[2-sec-butyl, 4-(2-β-naphthylphenyl)indenyl]}hafnium dimethyl;
diisopropylamidoboranebis{1-[2-tert-butyl, 4-(2-β-naphthylphenyl)indenyl]}hafnium dimethyl;
diisopropylamidoboranebis{1-[2-phenyl, 4-(2-β-naphthylphenyl)indenyl]}hafnium dimethyl;
diisopropylamidoboranebis{1-[2-n-propyl, 4-(2-trifluoromethylphenyl)indenyl]}-hafnium dimethyl;
diisopropylamidoboranebis{1-[2-isopropyl, 4-(2-trifluoromethylphenyl)indenyl]}-hafnium dimethyl;
diisopropylamidoboranebis{1-[2-n-butyl, 4-(2-trifluoromethylphenyl)indenyl]}-hafnium dimethyl;
diisopropylamidoboranebis{1-[2-isobutyl, 4-(2-trifluoromethylphenyl)indenyl]}-hafnium dimethyl;
diisopropylamidoboranebis{1-[2-sec-butyl, 4-(2-trifluoromethylphenyl)indenyl]}-hafnium dimethyl;
diisopropylamidoboranebis{1-[2-tert-butyl, 4-(2-trifluoromethylphenyl)indenyl]}-hafnium dimethyl;
diisopropylamidoboranebis{1-[2-phenyl, 4-(2-trifluoromethylphenyl)indenyl]}-hafnium dimethyl;
diisopropylamidoboranebis{1-[2-n-propyl, 4-(2,3-dimethylphenyl)indenyl]}hafnium dimethyl;
diisopropylamidoboranebis{1-[2-isopropyl, 4-(2,3-dimethylphenyl)indenyl]}hafnium dimethyl;
diisopropylamidoboranebis{1-[2-n-butyl, 4-(2,3-dimethylphenyl)indenyl]}hafnium dimethyl;
diisopropylamidoboranebis{1-[2-isobutyl, 4-(2,3-dimethylphenyl)indenyl]}hafnium dimethyl;
diisopropylamidoboranebis{1-[2-sec-butyl, 4-(2,3-dimethylphenyl)indenyl]}hafnium dimethyl;
diisopropylamidoboranebis{1-[2-tert-butyl, 4-(2,3-dimethylphenyl)indenyl]}hafnium dimethyl;
diisopropylamidoboranebis{1-[2-phenyl, 4-(2,3-dimethylphenyl)indenyl]}hafnium dimethyl;
diisopropylamidoboranebis{1-[2-n-propyl, 4-(2,3,4-trimethylphenyl)indenyl]}hafnium dimethyl;
diisopropylamidoboranebis{1-[2-isopropyl, 4-(2,3,4-trimethylphenyl)indenyl]}hafnium dimethyl;
diisopropylamidoboranebis{1-[2-n-butyl, 4-(2,3,4-trimethylphenyl)indenyl]}hafnium dimethyl;
diisopropylamidoboranebis{1-[2-isobutyl, 4-(2,3,4-trimethylphenyl)indenyl]}hafnium dimethyl;
diisopropylamidoboranebis{1-[2-sec-butyl, 4-(2,3,4-trimethylphenyl)indenyl]}hafnium dimethyl;
diisopropylamidoboranebis{1-[2-tert-butyl, 4-(2,3,4-trimethylphenyl)indenyl]}hafnium dimethyl;
diisopropylamidoboranebis{1-[2-phenyl, 4-(2,3,4-trimethylphenyl)indenyl]}hafnium dimethyl;
diisopropylamidoboranebis{1-[2-n-propyl, 4-(2,3,5-trimethylphenyl)indenyl]}hafnium dimethyl;
diisopropylamidoboranebis{1-[2-isopropyl, 4-(2,3,5-trimethylphenyl)indenyl]}hafnium dimethyl;

diisopropylamidoboranebis{1-[2-n-butyl, 4-(2,3,5-trimethylphenyl)indenyl]}hafnium dimethyl;
diisopropylamidoboranebis{1-[2-isobutyl, 4-(2,3,5-trimethylphenyl)indenyl]}hafnium dimethyl;
diisopropylamidoboranebis{1-[2-sec-butyl, 4-(2,3,5-trimethylphenyl)indenyl]}hafnium dimethyl;
diisopropylamidoboranebis{1-[2-tert-butyl, 4-(2,3,5-trimethylphenyl)indenyl]}hafnium dimethyl;
diisopropylamidoboranebis{1-[2-phenyl, 4-(2,3,5-trimethylphenyl)indenyl]}hafnium dimethyl;
diisopropylamidoboranebis{1-[2-n-propyl, 4-(2-methylphenyl)indenyl]}zirconium dichloride;
diisopropylamidoboranebis{1-[2-isopropyl, 4-(2-methylphenyl)indenyl]}zirconium dichloride;
diisopropylamidoboranebis{1-[2-n-butyl, 4-(2-methylphenyl)indenyl]}zirconium dichloride;
diisopropylamidoboranebis{1-[2-isobutyl, 4-(2-methylphenyl)indenyl]}zirconium dichloride;
diisopropylamidoboranebis{1-[2-sec-butyl, 4-(2-methylphenyl)indenyl]}zirconium dichloride;
diisopropylamidoboranebis{1-[2-tert-butyl, 4-(2-methylphenyl)indenyl]}zirconium dichloride;
diisopropylamidoboranebis{1-[2-phenyl, 4-(2-methylphenyl)indenyl]}zirconium dichloride;
diisopropylamidoboranebis{1-[2-n-propyl, 4-(2-ethylphenyl)indenyl]}zirconium dichloride;
diisopropylamidoboranebis{1-[2-isopropyl, 4-(2-ethylphenyl)indenyl]}zirconium dichloride;
diisopropylamidoboranebis{1-[2-n-butyl, 4-(2-ethylphenyl)indenyl]}zirconium dichloride;
diisopropylamidoboranebis{1-[2-isobutyl, 4-(2-ethylphenyl)indenyl]}zirconium dichloride;
diisopropylamidoboranebis{1-[2-sec-butyl, 4-(2-ethylphenyl)indenyl]}zirconium dichloride;
diisopropylamidoboranebis{1-[2-tert-butyl, 4-(2-ethylphenyl)indenyl]}zirconium dichloride;
diisopropylamidoboranebis{1-[2-phenyl, 4-(2-ethylphenyl)indenyl]}zirconium dichloride;
diisopropylamidoboranebis{1-[2-n-propyl, 4-(2-n-propylphenyl)indenyl]}zirconium dichloride;
diisopropylamidoboranebis{1-[2-isopropyl, 4-(2-n-propylphenyl)indenyl]}zirconium dichloride;
diisopropylamidoboranebis{1-[2-n-butyl, 4-(2-n-propylphenyl)indenyl]}zirconium dichloride;
diisopropylamidoboranebis{1-[2-isobutyl, 4-(2-n-propylphenyl)indenyl]}zirconium dichloride;
diisopropylamidoboranebis{1-[2-sec-butyl, 4-(2-n-propylphenyl)indenyl]}zirconium dichloride;
diisopropylamidoboranebis{1-[2-tert-butyl, 4-(2-n-propylphenyl)indenyl]}zirconium dichloride;
diisopropylamidoboranebis{1-[2-phenyl, 4-(2-n-propylphenyl)indenyl]}zirconium dichloride;
diisopropylamidoboranebis{1-[2-n-propyl, 4-(2-isopropylphenyl)indenyl]}zirconium dichloride;
diisopropylamidoboranebis{1-[2-isopropyl, 4-(2-isopropylphenyl)indenyl]}zirconium dichloride;
diisopropylamidoboranebis{1-[2-n-butyl, 4-(2-isopropylphenyl)indenyl]}zirconium dichloride;
diisopropylamidoboranebis{1-[2-isobutyl, 4-(2-isopropylphenyl)indenyl]}zirconium dichloride;
diisopropylamidoboranebis{1-[2-sec-butyl, 4-(2-isopropylphenyl)indenyl]}zirconium dichloride;
diisopropylamidoboranebis{1-[2-tert-butyl, 4-(2-isopropylphenyl)indenyl]}zirconium dichloride;
diisopropylamidoboranebis{1-[2-phenyl, 4-(2-isopropylphenyl)indenyl]}zirconium dichloride;
diisopropylamidoboranebis{1-[2-n-propyl 4-(2-n-butylphenyl)indenyl]}zirconium dichloride;
diisopropylamidoboranebis{1-[2-isopropyl, 4-(2-n-butylphenyl)indenyl]}zirconium dichloride;
diisopropylamidoboranebis{1-[2-n-butyl, 4-(2-n-butylphenyl)indenyl]}zirconium dichloride;
diisopropylamidoboranebis{1-[2-isobutyl, 4-(2-n-butylphenyl)indenyl]}zirconium dichloride;
diisopropylamidoboranebis{1-[2-sec-butyl, 4-(2-n-butylphenyl)indenyl]}zirconium dichloride;
diisopropylamidoboranebis{1-[2-tert-butyl, 4-(2-n-butylphenyl)indenyl]}zirconium dichloride;
diisopropylamidoboranebis{1-[2-phenyl, 4-(2-n-butylphenyl)indenyl]}zirconium dichloride;
diisopropylamidoboranebis{1-[2-n-propyl, 4-(2-isobutylphenyl)indenyl]}zirconium dichloride;
diisopropylamidoboranebis{1-[2-isopropyl, 4-(2-isobutylphenyl)indenyl]}zirconium dichloride;
diisopropylamidoboranebis{1-[2-n-butyl, 4-(2-isobutylphenyl)indenyl]}zirconium dichloride;
diisopropylamidoboranebis{1-[2-isobutyl, 4-(2-isobutylphenyl)indenyl]}zirconium dichloride;
diisopropylamidoboranebis{1-[2-sec-butyl, 4-(2-isobutylphenyl)indenyl]}zirconium dichloride;
diisopropylamidoboranebis{1-[2-tert-butyl, 4-(2-isobutylphenyl)indenyl]}zirconium dichloride;
diisopropylamidoboranebis{1-[2-phenyl, 4-(2-isobutylphenyl)indenyl]}zirconium dichloride;
diisopropylamidoboranebis{1-[2-n-propyl, 4-(2-sec-butylphenyl)indenyl]}zirconium dichloride;
diisopropylamidoboranebis{1-[2-isopropyl, 4-(2-sec-butylphenyl)indenyl]}zirconium dichloride;
diisopropylamidoboranebis{1-[2-n-butyl, 4-(2-sec-butylphenyl)indenyl]}zirconium dichloride;
diisopropylamidoboranebis{1-[2-isobutyl, 4-(2-sec-butylphenyl)indenyl]}zirconium dichloride;
diisopropylamidoboranebis{1-[2-sec-butyl, 4-(2-sec-butylphenyl)indenyl]}zirconium dichloride;
diisopropylamidoboranebis{1-[2-tert-butyl, 4-(2-sec-butylphenyl)indenyl]}zirconium dichloride;
diisopropylamidoboranebis{1-[2-phenyl, 4-(2-sec-butylphenyl)indenyl]}zirconium dichloride;
diisopropylamidoboranebis{1-[2-n-propyl, 4-(2-tert-butylphenyl)indenyl]}zirconium dichloride;
diisopropylamidoboranebis{1-[2-isopropyl, 4-(2-tert-butylphenyl)indenyl]}zirconium dichloride;
diisopropylamidoboranebis{1-[2-n-butyl, 4-(2-tert-butylphenyl)indenyl]}zirconium dichloride;
diisopropylamidoboranebis{1-[2-isobutyl, 4-(2-tert-butylphenyl)indenyl]}zirconium dichloride;
diisopropylamidoboranebis{1-[2-sec-butyl, 4-(2-tert-butylphenyl)indenyl]}zirconium dichloride;
diisopropylamidoboranebis{1-[2-tert-butyl, 4-(2-tert-butylphenyl)indenyl]}zirconium dichloride;
diisopropylamidoboranebis{1-[2-phenyl, 4-(2-tert-butylphenyl)indenyl]}zirconium dichloride;
diisopropylamidoboranebis{1-[2-n-propyl, 4-(2-biphenyl)indenyl]}zirconium dichloride;
diisopropylamidoboranebis{1-[2-isopropyl, 4-(2-biphenyl)indenyl]}zirconium dichloride;
diisopropylamidoboranebis{1-[2-n-butyl, 4-(2-biphenyl)indenyl]}zirconium dichloride;
diisopropylamidoboranebis{1-[2-isobutyl, 4-(2-biphenyl)indenyl]}zirconium dichloride;
diisopropylamidoboranebis{1-[2-sec-butyl, 4-(2-biphenyl)indenyl]}zirconium dichloride;
diisopropylamidoboranebis{1-[2-tert-butyl, 4-(2-biphenyl)indenyl]}zirconium dichloride;
diisopropylamidoboranebis{1-[2-phenyl, 4-(2-biphenyl)indenyl]}zirconium dichloride;

diisopropylamidoboranebis{1-[2-n-propyl, 4-(2-α-naphthylphenyl)indenyl]}zirconium dichloride;
diisopropylamidoboranebis{1-[2-isopropyl, 4-(2-α-naphthylphenyl)indenyl]}zirconium dichloride;
diisopropylamidoboranebis{1-[2-n-butyl, 4-(2-α-naphthylphenyl)indenyl]}zirconium dichloride;
diisopropylamidoboranebis{1-[2-isobutyl, 4-(2-α-naphthylphenyl)indenyl]}zirconium dichloride;
diisopropylamidoboranebis{1-[2-sec-butyl, 4-(2-α-naphthylphenyl)indenyl]}zirconium dichloride;
diisopropylamidoboranebis{1-[2-tert-butyl, 4-(2-α-naphthylphenyl)indenyl]}zirconium dichloride;
diisopropylamidoboranebis{1-[2-phenyl, 4-(2-α-naphthylphenyl)indenyl]}zirconium dichloride;
diisopropylamidoboranebis{1-[2-n-propyl, 4-(2-β-naphthylphenyl)indenyl]}zirconium dichloride;
diisopropylamidoboranebis{1-[2-isopropyl, 4-(2-β-naphthylphenyl)indenyl]}zirconium dichloride;
diisopropylamidoboranebis{1-[2-n-butyl, 4-(2-β-naphthylphenyl)indenyl]}zirconium dichloride;
diisopropylamidoboranebis{1-[2-isobutyl, 4-(2-β-naphthylphenyl)indenyl]}zirconium dichloride;
diisopropylamidoboranebis{1-[2-sec-butyl, 4-(2-β-naphthylphenyl)indenyl]}zirconium dichloride;
diisopropylamidoboranebis{1-[2-tert-butyl, 4-(2-β-naphthylphenyl)indenyl]}zirconium dichloride;
diisopropylamidoboranebis{1-[2-phenyl, 4-(2-β-naphthylphenyl)indenyl]}zirconium dichloride;
diisopropylamidoboranebis{1-[2-n-propyl, 4-(2-trifluoromethylphenyl)indenyl]}-zirconium dichloride;
diisopropylamidoboranebis{1-[2-isopropyl, 4-(2-trifluoromethylphenyl)indenyl]}-zirconium dichloride;
diisopropylamidoboranebis{1-[2-n-butyl, 4-(2-trifluoromethylphenyl)indenyl]}-zirconium dichloride;
diisopropylamidoboranebis{1-[2-isobutyl, 4-(2-trifluoromethylphenyl)indenyl]}-zirconium dichloride;
diisopropylamidoboranebis{1-[2-sec-butyl, 4-(2-trifluoromethylphenyl)indenyl]}-zirconium dichloride;
diisopropylamidoboranebis{1-[2-tert-butyl, 4-(2-trifluoromethylphenyl)indenyl]}-zirconium dichloride;
diisopropylamidoboranebis{1-[2-phenyl, 4-(2-trifluoromethylphenyl)indenyl]}-zirconium dichloride;
diisopropylamidoboranebis{1-[2-n-propyl, 4-(2,3-dimethylphenyl)indenyl]}zirconium dichloride;
diisopropylamidoboranebis{1-[2-isopropyl, 4-(2,3-dimethylphenyl)indenyl]}zirconium dichloride;
diisopropylamidoboranebis{1-[2-n-butyl, 4-(2,3-dimethylphenyl)indenyl]}zirconium dichloride;
diisopropylamidoboranebis{1-[2-isobutyl, 4-(2,3-dimethylphenyl)indenyl]}zirconium dichloride;
diisopropylamidoboranebis{1-[2-sec-butyl, 4-(2,3-dimethylphenyl)indenyl]}zirconium dichloride;
diisopropylamidoboranebis{1-[2-tert-butyl, 4-(2,3-dimethylphenyl)indenyl]}zirconium dichloride;
diisopropylamidoboranebis{1-[2-phenyl, 4-(2,3-dimethylphenyl)indenyl]}zirconium dichloride;
diisopropylamidoboranebis{1-[2-n-propyl, 4-(2,3,4-trimethylphenyl)indenyl]}zirconium dichloride;
diisopropylamidoboranebis{1-[2-isopropyl, 4-(2,3,4-trimethylphenyl)indenyl]}zirconium dichloride;
diisopropylamidoboranebis{1-[2-n-butyl, 4-(2,3,4-trimethylphenyl)indenyl]}zirconium dichloride;
diisopropylamidoboranebis{1-[2-isobutyl, 4-(2,3,4-trimethylphenyl)indenyl]}zirconium dichloride;
diisopropylamidoboranebis{1-[2-sec-butyl, 4-(2,3,4-trimethylphenyl)indenyl]}zirconium dichloride;
diisopropylamidoboranebis{1-[2-tert-butyl, 4-(2,3,4-trimethylphenyl)indenyl]}zirconium dichloride;
diisopropylamidoboranebis{1-[2-phenyl, 4-(2,3,4-trimethylphenyl)indenyl]}zirconium dichloride;
diisopropylamidoboranebis{1-[2-n-propyl, 4-(2,3,5-trimethylphenyl)indenyl]}zirconium dichloride;
diisopropylamidoboranebis{1-[2-isopropyl, 4-(2,3,5-trimethylphenyl)indenyl]}zirconium dichloride;
diisopropylamidoboranebis{1-[2-n-butyl, 4-(2,3,5-trimethylphenyl)indenyl]}zirconium dichloride;
diisopropylamidoboranebis{1-[2-isobutyl, 4-(2,3,5-trimethylphenyl)indenyl]}zirconium dichloride;
diisopropylamidoboranebis{1-[2-sec-butyl, 4-(2,3,5-trimethylphenyl)indenyl]}zirconium dichloride;
diisopropylamidoboranebis{1-[2-tert-butyl, 4-(2,3,5-trimethylphenyl)indenyl]}zirconium dichloride;
diisopropylamidoboranebis{1-[2-phenyl, 4-(2,3,5-trimethylphenyl)indenyl]}zirconium dichloride;
diisopropylamidoboranebis{1-[2-n-propyl, 4-(2-methylphenyl)indenyl]}zirconium dimethyl;
diisopropylamidoboranebis{1-[2-isopropyl, 4-(2-methylphenyl)indenyl]}zirconium dimethyl;
diisopropylamidoboranebis{1-[2-n-butyl, 4-(2-methylphenyl)indenyl]}zirconium dimethyl;
diisopropylamidoboranebis{1-[2-isobutyl, 4-(2-methylphenyl)indenyl]}zirconium dimethyl;
diisopropylamidoboranebis{1-[2-sec-butyl, 4-(2-methylphenyl)indenyl]}zirconium dimethyl;
diisopropylamidoboranebis{1-[2-tert-butyl, 4-(2-methylphenyl)indenyl]}zirconium dimethyl;
diisopropylamidoboranebis{1-[2-phenyl, 4-(2-methylphenyl)indenyl]}zirconium dimethyl;
diisopropylamidoboranebis{1-[2-n-propyl, 4-(2-ethylphenyl)indenyl]}zirconium dimethyl;
diisopropylamidoboranebis{1-[2-isopropyl, 4-(2-ethylphenyl)indenyl]}zirconium dimethyl;
diisopropylamidoboranebis{1-[2-n-butyl, 4-(2-ethylphenyl)indenyl]}zirconium dimethyl;
diisopropylamidoboranebis{1-[2-isobutyl, 4-(2-ethylphenyl)indenyl]}zirconium dimethyl;
diisopropylamidoboranebis{1-[2-sec-butyl, 4-(2-ethylphenyl)indenyl]}zirconium dimethyl;
diisopropylamidoboranebis{1-[2-tert-butyl, 4-(2-ethylphenyl)indenyl]}zirconium dimethyl;
diisopropylamidoboranebis{1-[2-phenyl, 4-(2-ethylphenyl)indenyl]}zirconium dimethyl;
diisopropylamidoboranebis{1-[2-n-propyl, 4-(2-n-propylphenyl)indenyl]}zirconium dimethyl;
diisopropylamidoboranebis{1-[2-isopropyl, 4-(2-n-propylphenyl)indenyl]}zirconium dimethyl;
diisopropylamidoboranebis{1-[2-n-butyl, 4-(2-n-propylphenyl)indenyl]}zirconium dimethyl;
diisopropylamidoboranebis{1-[2-isobutyl, 4-(2-n-propylphenyl)indenyl]}zirconium dimethyl;
diisopropylamidoboranebis{1-[2-sec-butyl, 4-(2-n-propylphenyl)indenyl]}zirconium dimethyl;
diisopropylamidoboranebis{1-[2-tert-butyl, 4-(2-n-propylphenyl)indenyl]}zirconium dimethyl;
diisopropylamidoboranebis{1-[2-phenyl, 4-(2-n-propylphenyl)indenyl]}zirconium dimethyl;
diisopropylamidoboranebis{1-[2-n-propyl, 4-(2-isopropylphenyl)indenyl]}zirconium dimethyl;
diisopropylamidoboranebis{1-[2-isopropyl, 4-(2-isopropylphenyl)indenyl]}zirconium dimethyl;
diisopropylamidoboranebis{1-[2-n-butyl, 4-(2-isopropylphenyl)indenyl]}zirconium dimethyl;
diisopropylamidoboranebis{1-[2-isobutyl, 4-(2-isopropylphenyl)indenyl]}zirconium dimethyl;
diisopropylamidoboranebis{1-[2-sec-butyl, 4-(2-isopropylphenyl)indenyl]}zirconium dimethyl;

diisopropylamidoboranebis{1-[2-tert-butyl, 4-(2-isopropylphenyl)indenyl]}zirconium dimethyl;
diisopropylamidoboranebis{1-[2-phenyl, 4-(2-isopropylphenyl)indenyl]}zirconium dimethyl;
diisopropylamidoboranebis{1-[2-n-propyl, 4-(2-n-butylphenyl)indenyl]}zirconium dimethyl;
diisopropylamidoboranebis{1-[2-isopropyl, 4-(2-n-butylphenyl)indenyl]}zirconium dimethyl;
diisopropylamidoboranebis{1-[2-n-butyl, 4-(2-n-butylphenyl)indenyl]}zirconium dimethyl;
diisopropylamidoboranebis{1-[2-isobutyl, 4-(2-n-butylphenyl)indenyl]}zirconium dimethyl;
diisopropylamidoboranebis{1-[2-sec-butyl, 4-(2-n-butylphenyl)indenyl]}zirconium dimethyl;
diisopropylamidoboranebis{1-[2-tert-butyl, 4-(2-n-butylphenyl)indenyl]}zirconium dimethyl;
diisopropylamidoboranebis{1-[2-phenyl, 4-(2-n-butylphenyl)indenyl]}zirconium dimethyl;
diisopropylamidoboranebis{1-[2-n-propyl, 4-(2-isobutylphenyl)indenyl]}zirconium dimethyl;
diisopropylamidoboranebis{1-[2-isopropyl, 4-(2-isobutylphenyl)indenyl]}zirconium dimethyl;
diisopropylamidoboranebis{1-[2-n-butyl, 4-(2-isobutylphenyl)indenyl]}zirconium dimethyl;
diisopropylamidoboranebis{1-[2-isobutyl, 4-(2-isobutylphenyl)indenyl]}zirconium dimethyl;
diisopropylamidoboranebis{1-[2-sec-butyl, 4-(2-isobutylphenyl)indenyl]}zirconium dimethyl;
diisopropylamidoboranebis{1-[2-tert-butyl, 4-(2-isobutylphenyl)indenyl]}zirconium dimethyl;
diisopropylamidoboranebis{1-[2-phenyl, 4-(2-isobutylphenyl)indenyl]}zirconium dimethyl;
diisopropylamidoboranebis{1-[2-n-propyl, 4-(2-sec-butylphenyl)indenyl]}zirconium dimethyl;
diisopropylamidoboranebis{1-[2-isopropyl, 4-(2-sec-butylphenyl)indenyl]}zirconium dimethyl;
diisopropylamidoboranebis{1-[2-n-butyl, 4-(2-sec-butylphenyl)indenyl]}zirconium dimethyl;
diisopropylamidoboranebis{1-[2-isobutyl, 4-(2-sec-butylphenyl)indenyl]}zirconium dimethyl;
diisopropylamidoboranebis{1-[2-sec-butyl, 4-(2-sec-butylphenyl)indenyl]}zirconium dimethyl;
diisopropylamidoboranebis{1-[2-tert-butyl, 4-(2-sec-butylphenyl)indenyl]}zirconium dimethyl;
diisopropylamidoboranebis{1-[2-phenyl, 4-(2-sec-butylphenyl)indenyl]}zirconium dimethyl;
diisopropylamidoboranebis{1-[2-n-propyl, 4-(2-tert-butylphenyl)indenyl]}zirconium dimethyl;
diisopropylamidoboranebis{1-[2-isopropyl, 4-(2-tert-butylphenyl)indenyl]}zirconium dimethyl;
diisopropylamidoboranebis{1-[2-n-butyl, 4-(2-tert-butylphenyl)indenyl]}zirconium dimethyl;
diisopropylamidoboranebis{1-[2-isobutyl, 4-(2-tert-butylphenyl)indenyl]}zirconium dimethyl;
diisopropylamidoboranebis{1-[2-sec-butyl, 4-(2-tert-butylphenyl)indenyl]}zirconium dimethyl;
diisopropylamidoboranebis{1-[2-tert-butyl, 4-(2-tert-butylphenyl)indenyl]}zirconium dimethyl;
diisopropylamidoboranebis{1-[2-phenyl, 4-(2-tert-butylphenyl)indenyl]}zirconium dimethyl;
diisopropylamidoboranebis{1-[2-n-propyl, 4-(2-biphenyl)indenyl]}zirconium dimethyl;
diisopropylamidoboranebis{1-[2-isopropyl, 4-(2-biphenyl)indenyl]}zirconium dimethyl;
diisopropylamidoboranebis{1-[2-n-butyl, 4-(2-biphenyl)indenyl]}zirconium dimethyl;
diisopropylamidoboranebis{1-[2-isobutyl, 4-(2-biphenyl)indenyl]}zirconium dimethyl;
diisopropylamidoboranebis{1-[2-sec-butyl, 4-(2-biphenyl)indenyl]}zirconium dimethyl;
diisopropylamidoboranebis{1-[2-tert-butyl, 4-(2-biphenyl)indenyl]}zirconium dimethyl;
diisopropylamidoboranebis{1-[2-phenyl, 4-(2-biphenyl)indenyl]}zirconium dimethyl;
diisopropylamidoboranebis{1-[2-n-propyl, 4-(2-α-naphthylphenyl)indenyl]}zirconium dimethyl;
diisopropylamidoboranebis{1-[2-isopropyl, 4-(2-α-naphthylphenyl)indenyl]}zirconium dimethyl;
diisopropylamidoboranebis{1-[2-n-butyl, 4-(2-α-naphthylphenyl)indenyl]}zirconium dimethyl;
diisopropylamidoboranebis{1-[2-isobutyl, 4-(2-α-naphthylphenyl)indenyl]}zirconium dimethyl;
diisopropylamidoboranebis{1-[2-sec-butyl, 4-(2-α-naphthylphenyl)indenyl]}zirconium dimethyl;
diisopropylamidoboranebis{1-[2-tert-butyl, 4-(2-α-naphthylphenyl)indenyl]}zirconium dimethyl;
diisopropylamidoboranebis{1-[2-phenyl, 4-(2-α-naphthylphenyl)indenyl]}zirconium dimethyl;
diisopropylamidoboranebis{1-[2-n-propyl, 4-(2-β-naphthylphenyl)indenyl]}zirconium dimethyl;
diisopropylamidoboranebis{1-[2-isopropyl, 4-(2-β-naphthylphenyl)indenyl]}zirconium dimethyl;
diisopropylamidoboranebis{1-[2-n-butyl, 4-(2-β-naphthylphenyl)indenyl]}zirconium dimethyl;
diisopropylamidoboranebis{1-[2-isobutyl, 4-(2-β-naphthylphenyl)indenyl]}zirconium dimethyl;
diisopropylamidoboranebis{1-[2-sec-butyl, 4-(2-β-naphthylphenyl)indenyl]}zirconium dimethyl;
diisopropylamidoboranebis{1-[2-tert-butyl 4-(2-β-naphthylphenyl)indenyl]}zirconium dimethyl;
diisopropylamidoboranebis{1-[2-phenyl, 4-(2-β-naphthylphenyl)indenyl]}zirconium dimethyl;
diisopropylamidoboranebis{1-[2-n-propyl, 4-(2-trifluoromethylphenyl)indenyl]}-zirconium dimethyl;
diisopropylamidoboranebis{1-[2-isopropyl, 4-(2-trifluoromethylphenyl)indenyl]}-zirconium dimethyl;
diisopropylamidoboranebis{1-[2-n-butyl, 4-(2-trifluoromethylphenyl)indenyl]}-zirconium dimethyl;
diisopropylamidoboranebis{1-[2-isobutyl, 4-(2-trifluoromethylphenyl)indenyl]}-zirconium dimethyl;
diisopropylamidoboranebis{1-[2-sec-butyl, 4-(2-trifluoromethylphenyl)indenyl]}-zirconium dimethyl;
diisopropylamidoboranebis{1-[2-tert-butyl, 4-(2-trifluoromethylphenyl)indenyl]}-zirconium dimethyl;
diisopropylamidoboranebis{1-[2-phenyl, 4-(2-trifluoromethylphenyl)indenyl]}-zirconium dimethyl;
diisopropylamidoboranebis{1-[2-n-propyl, 4-(2,3-dimethylphenyl)indenyl]}zirconium dimethyl;
diisopropylamidoboranebis{1-[2-isopropyl, 4-(2,3-dimethylphenyl)indenyl]}zirconium dimethyl;
diisopropylamidoboranebis{1-[2-n-butyl, 4-(2,3-dimethylphenyl)indenyl]}zirconium dimethyl;
diisopropylamidoboranebis{1-[2-isobutyl, 4-(2,3-dimethylphenyl)indenyl]}zirconium dimethyl;
diisopropylamidoboranebis{1-[2-sec-butyl, 4-(2,3-dimethylphenyl)indenyl]}zirconium dimethyl;
diisopropylamidoboranebis{1-[2-tert-butyl, 4-(2,3-dimethylphenyl)indenyl]}zirconium dimethyl;
diisopropylamidoboranebis{1-[2-phenyl, 4-(2,3-dimethylphenyl)indenyl]}zirconium dimethyl;
diisopropylamidoboranebis{1-[2-n-propyl, 4-(2,3,4-trimethylphenyl)indenyl]}zirconium dimethyl;
diisopropylamidoboranebis{1-[2-isopropyl, 4-(2,3,4-trimethylphenyl)indenyl]}zirconium dimethyl;
diisopropylamidoboranebis{1-[2-n-butyl, 4-(2,3,4-trimethylphenyl)indenyl]}zirconium dimethyl;

diisopropylamidoboranebis{1-[2-isobutyl, 4-(2,3,4-trimethylphenyl)indenyl]}zirconium dimethyl;
diisopropylamidoboranebis{1-[2-sec-butyl, 4-(2,3,4-trimethylphenyl)indenyl]}zirconium dimethyl;
diisopropylamidoboranebis{1-[2-tert-butyl, 4-(2,3,4-trimethylphenyl)indenyl]}zirconium dimethyl;
diisopropylamidoboranebis{1-[2-phenyl, 4-(2,3,4-trimethylphenyl)indenyl]}zirconium dimethyl;
diisopropylamidoboranebis{1-[2-n-propyl, 4-(2,3,5-trimethylphenyl)indenyl]}zirconium dimethyl;
diisopropylamidoboranebis{1-[2-isopropyl, 4-(2,3,5-trimethylphenyl)indenyl]}zirconium dimethyl;
diisopropylamidoboranebis{1-[2-n-butyl, 4-(2,3,5-trimethylphenyl)indenyl]}zirconium dimethyl;
diisopropylamidoboranebis{1-[2-isobutyl, 4-(2,3,5-trimethylphenyl)indenyl]}zirconium dimethyl;
diisopropylamidoboranebis{1-[2-sec-butyl, 4-(2,3,5-trimethylphenyl)indenyl]}zirconium dimethyl;
diisopropylamidoboranebis{1-[2-tert-butyl, 4-(2,3,5-trimethylphenyl)indenyl]}zirconium dimethyl;
diisopropylamidoboranebis{1-[2-phenyl, 4-(2,3,5-trimethylphenyl)indenyl]}zirconium dimethyl;
bis(trimethylsilyl)amidoboranebis{1-[2-n-propyl, 4-(2-methylphenyl)indenyl]}zirconium dichloride;
bis(trimethylsilyl)amidoboranebis{1-[2-isopropyl, 4-(2-methylphenyl)indenyl]}zirconium dichloride;
bis(trimethylsilyl)amidoboranebis{1-[2-n-butyl, 4-(2-methylphenyl)indenyl]}zirconium dichloride;
bis(trimethylsilyl)amidoboranebis{1-[2-isobutyl, 4-(2-methylphenyl)indenyl]}zirconium dichloride;
bis(trimethylsilyl)amidoboranebis{1-[2-sec-butyl, 4-(2-methylphenyl)indenyl]}zirconium dichloride;
bis(trimethylsilyl)amidoboranebis{1-[2-tert-butyl, 4-(2-methylphenyl)indenyl]}zirconium dichloride;
bis(trimethylsilyl)amidoboranebis{1-[2-phenyl, 4-(2-methylphenyl)indenyl]}zirconium dichloride;
bis(trimethylsilyl)amidoboranebis{1-[2-n-propyl, 4-(2-ethylphenyl)indenyl]}zirconium dichloride;
bis(trimethylsilyl)amidoboranebis{1-[2-isopropyl, 4-(2-ethylphenyl)indenyl]}zirconium dichloride;
bis(trimethylsilyl)amidoboranebis{1-[2-n-butyl, 4-(2-ethylphenyl)indenyl]}zirconium dichloride;
bis(trimethylsilyl)amidoboranebis{1-[2-isobutyl, 4-(2-ethylphenyl)indenyl]}zirconium dichloride;
bis(trimethylsilyl)amidoboranebis{1-[2-sec-butyl, 4-(2-ethylphenyl)indenyl]}zirconium dichloride;
bis(trimethylsilyl)amidoboranebis{1-[2-tert-butyl, 4-(2-ethylphenyl)indenyl]}zirconium dichloride;
bis(trimethylsilyl)amidoboranebis{1-[2-phenyl, 4-(2-ethylphenyl)indenyl]}zirconium dichloride;
bis(trimethylsilyl)amidoboranebis{1-[2-n-propyl, 4-(2-n-propylphenyl)indenyl]}zirconium dichloride;
bis(trimethylsilyl)amidoboranebis{1-[2-isopropyl, 4-(2-n-propylphenyl)indenyl]}zirconium dichloride;
bis(trimethylsilyl)amidoboranebis{1-[2-n-butyl, 4-(2-n-propylphenyl)indenyl]}zirconium dichloride;
bis(trimethylsilyl)amidoboranebis{1-[2-isobutyl, 4-(2-n-propylphenyl)indenyl]}zirconium dichloride;
bis(trimethylsilyl)amidoboranebis{1-[2-sec-butyl, 4-(2-n-propylphenyl)indenyl]}zirconium dichloride;
bis(trimethylsilyl)amidoboranebis{1-[2-tert-butyl, 4-(2-n-propylphenyl)indenyl]}zirconium dichloride;
bis(trimethylsilyl)amidoboranebis{1-[2-phenyl, 4-(2-n-propylphenyl)indenyl]}zirconium dichloride;
bis(trimethylsilyl)amidoboranebis{1-[2-n-propyl, 4-(2-isopropylphenyl)indenyl]}zirconium dichloride;
bis(trimethylsilyl)amidoboranebis{1-[2-isopropyl, 4-(2-isopropylphenyl)indenyl]}zirconium dichloride;
bis(trimethylsilyl)amidoboranebis{1-[2-n-butyl, 4-(2-isopropylphenyl)indenyl]}zirconium dichloride;
bis(trimethylsilyl)amidoboranebis{1-[2-isobutyl, 4-(2-isopropylphenyl)indenyl]}zirconium dichloride;
bis(trimethylsilyl)amidoboranebis{1-[2-sec-butyl, 4-(2-isopropylphenyl)indenyl]}zirconium dichloride;
bis(trimethylsilyl)amidoboranebis{1-[2-tert-butyl, 4-(2-isopropylphenyl)indenyl]}zirconium dichloride;
bis(trimethylsilyl)amidoboranebis{1-[2-phenyl, 4-(2-isopropylphenyl)indenyl]}zirconium dichloride;
bis(trimethylsilyl)amidoboranebis{1-[2-n-propyl, 4-(2-n-butylphenyl)indenyl]}zirconium dichloride;
bis(trimethylsilyl)amidoboranebis{1-[2-isopropyl, 4-(2-n-butylphenyl)indenyl]}zirconium dichloride;
bis(trimethylsilyl)amidoboranebis{1-[2-n-butyl, 4-(2-n-butylphenyl)indenyl]}zirconium dichloride;
bis(trimethylsilyl)amidoboranebis{1-[2-isobutyl, 4-(2-n-butylphenyl)indenyl]}zirconium dichloride;
bis(trimethylsilyl)amidoboranebis{1-[2-sec-butyl, 4-(2-n-butylphenyl)indenyl]}zirconium dichloride;
bis(trimethylsilyl)amidoboranebis{1-[2-tert-butyl, 4-(2-n-butylphenyl)indenyl]}zirconium dichloride;
bis(trimethylsilyl)amidoboranebis{1-[2-phenyl, 4-(2-n-butylphenyl)indenyl]}zirconium dichloride;
bis(trimethylsilyl)amidoboranebis{1-[2-β-propyl, 4-(2-isobutylphenyl)indenyl]}zirconium dichloride;
bis(trimethylsilyl)amidoboranebis{1-[2-isopropyl, 4-(2-isobutylphenyl)indenyl]}zirconium dichloride;
bis(trimethylsilyl)amidoboranebis{1-[2-n-butyl, 4-(2-isobutylphenyl)indenyl]}zirconium dichloride;
bis(trimethylsilyl)amidoboranebis{1-[2-isobutyl, 4-(2-isobutylphenyl)indenyl]}zirconium dichloride;
bis(trimethylsilyl)amidoboranebis{1-[2-sec-butyl, 4-(2-isobutylphenyl)indenyl]}zirconium dichloride;
bis(trimethylsilyl)amidoboranebis{1-[2-tert-butyl, 4-(2-isobutylphenyl)indenyl]}zirconium dichloride;
bis(trimethylsilyl)amidoboranebis{1-[2-phenyl, 4-(2-isobutylphenyl)indenyl]}zirconium dichloride;
bis(trimethylsilyl)amidoboranebis{1-[2-n-propyl, 4-(2-sec-butylphenyl)indenyl]}zirconium dichloride;
bis(trimethylsilyl)amidoboranebis{1-[2-isopropyl, 4-(2-sec-butylphenyl)indenyl]}zirconium dichloride;
bis(trimethylsilyl)amidoboranebis{1-[2-n-butyl, 4-(2-sec-butylphenyl)indenyl]}zirconium dichloride;
bis(trimethylsilyl)amidoboranebis{1-[2-isobutyl, 4-(2-sec-butylphenyl)indenyl]}zirconium dichloride;
bis(trimethylsilyl)amidoboranebis{1-[2-sec-butyl, 4-(2-sec-butylphenyl)indenyl]}zirconium dichloride;
bis(trimethylsilyl)amidoboranebis{1-[2-tert-butyl, 4-(2-sec-butylphenyl)indenyl]}zirconium dichloride;
bis(trimethylsilyl)amidoboranebis{1-[2-phenyl, 4-(2-sec-butylphenyl)indenyl]}zirconium dichloride;
bis(trimethylsilyl)amidoboranebis{1-[2-n-propyl, 4-(2-tert-butylphenyl)indenyl]}zirconium dichloride;
bis(trimethylsilyl)amidoboranebis{1-[2-isopropyl, 4-(2-tert-butylphenyl)indenyl]}zirconium dichloride;
bis(trimethylsilyl)amidoboranebis{1-[2-n-butyl, 4-(2-tert-butylphenyl)indenyl]}zirconium dichloride;
bis(trimethylsilyl)amidoboranebis{1-[2-isobutyl, 4-(2-tert-butylphenyl)indenyl]}zirconium dichloride;
bis(trimethylsilyl)amidoboranebis{1-[2-sec-butyl, 4-(2-tert-butylphenyl)indenyl]}zirconium dichloride;
bis(trimethylsilyl)amidoboranebis{1-[2-tert-butyl, 4-(2-tert-butylphenyl)indenyl]}zirconium dichloride;
bis(trimethylsilyl)amidoboranebis{1-[2-phenyl, 4-(2-tert-butylphenyl)indenyl]}zirconium dichloride;
bis(trimethylsilyl)amidoboranebis{1-[2-n-propyl, 4-(2-biphenyl)indenyl]}zirconium dichloride;

bis(trimethylsilyl)amidoboranebis{1-[2-isopropyl, 4-(2-biphenyl)indenyl]}zirconium dichloride;
bis(trimethylsilyl)amidoboranebis{1-[2-n-butyl, 4-(2-biphenyl)indenyl]}zirconium dichloride;
bis(trimethylsilyl)amidoboranebis{1-[2-isobutyl, 4-(2-biphenyl)indenyl]}zirconium dichloride;
bis(trimethylsilyl)amidoboranebis{1-[2-sec-butyl, 4-(2-biphenyl)indenyl]}zirconium dichloride;
bis(trimethylsilyl)amidoboranebis{1-[2-tert-butyl, 4-(2-biphenyl)indenyl]}zirconium dichloride;
bis(trimethylsilyl)amidoboranebis{1-[2-phenyl, 4-(2-biphenyl)indenyl]}zirconium dichloride;
bis(trimethylsilyl)amidoboranebis{1-[2-n-propyl, 4-(2-α-naphthylphenyl)indenyl]}zirconium dichloride;
bis(trimethylsilyl)amidoboranebis{1-[2-isopropyl, 4-(2-α-naphthylphenyl)indenyl]}zirconium dichloride;
bis(trimethylsilyl)amidoboranebis{1-[2-n-butyl, 4-(2-α-naphthylphenyl)indenyl]}zirconium dichloride;
bis(trimethylsilyl)amidoboranebis{1-[2-isobutyl, 4-(2-α-naphthylphenyl)indenyl]}zirconium dichloride;
bis(trimethylsilyl)amidoboranebis{1-[2-sec-butyl, 4-(2-α-naphthylphenyl)indenyl]}zirconium dichloride;
bis(trimethylsilyl)amidoboranebis{1-[2-tert-butyl, 4-(2-α-naphthylphenyl)indenyl]}zirconium dichloride;
bis(trimethylsilyl)amidoboranebis{1-[2-phenyl, 4-(2-α-naphthylphenyl)indenyl]}zirconium dichloride;
bis(trimethylsilyl)amidoboranebis{1-[2-n-propyl, 4-(2-β-naphthylphenyl)indenyl]}zirconium dichloride;
bis(trimethylsilyl)amidoboranebis{1-[2-isopropyl, 4-(2-β-naphthylphenyl)indenyl]}zirconium dichloride;
bis(trimethylsilyl)amidoboranebis{1-[2-n-butyl, 4-(2-β-naphthylphenyl)indenyl]}zirconium dichloride;
bis(trimethylsilyl)amidoboranebis{1-[2-isobutyl, 4-(2-β-naphthylphenyl)indenyl]}zirconium dichloride;
bis(trimethylsilyl)amidoboranebis{1-[2-sec-butyl, 4-(2-β-naphthylphenyl)-indenyl]}zirconium dichloride;
bis(trimethylsilyl)amidoboranebis{1-[2-tert-butyl, 4-(2-β-naphthylphenyl)indenyl]}zirconium dichloride;
bis(trimethylsilyl)amidoboranebis{1-[2-phenyl, 4-(2-β-naphthylphenyl)indenyl]}zirconium dichloride;
bis(trimethylsilyl)amidoboranebis{1-[2-n-propyl, 4-(2-trifluoromethylphenyl)indenyl]}zirconium dichloride;
bis(trimethylsilyl)amidoboranebis{1-[2-isopropyl, 4-(2-trifluoromethylphenyl)indenyl]}zirconium dichloride;
bis(trimethylsilyl)amidoboranebis{1-[2-n-butyl, 4-(2-trifluoromethylphenyl)indenyl]}zirconium dichloride;
bis(trimethylsilyl)amidoboranebis{1-[2-isobutyl, 4-(2-trifluoromethylphenyl)indenyl]}zirconium dichloride;
bis(trimethylsilyl)amidoboranebis{1-[2-sec-butyl, 4-(2-trifluoromethylphenyl)indenyl]}zirconium dichloride;
bis(trimethylsilyl)amidoboranebis{1-[2-tert-butyl, 4-(2-trifluoromethylphenyl)indenyl]}zirconium dichloride;
bis(trimethylsilyl)amidoboranebis{1-[2-phenyl, 4-(2-trifluoromethylphenyl)indenyl]}zirconium dichloride;
bis(trimethylsilyl)amidoboranebis{1-[2-n-propyl, 4-(2,3-dimethylphenyl)indenyl]}zirconium dichloride;
bis(trimethylsilyl)amidoboranebis{1-[2-isopropyl, 4-(2,3-dimethylphenyl)indenyl]}zirconium dichloride;
bis(trimethylsilyl)amidoboranebis{1-[2-n-butyl, 4-(2,3-dimethylphenyl)indenyl]}zirconium dichloride;
bis(trimethylsilyl)amidoboranebis{1-[2-isobutyl, 4-(2,3-dimethylphenyl)indenyl]}zirconium dichloride;
bis(trimethylsilyl)amidoboranebis{1-[2-sec-butyl, 4-(2,3-dimethylphenyl)indenyl]}zirconium dichloride;
bis(trimethylsilyl)amidoboranebis{1-[2-tert-butyl, 4-(2,3-dimethylphenyl)indenyl]}zirconium dichloride;
bis(trimethylsilyl)amidoboranebis{1-[2-phenyl, 4-(2,3-dimethylphenyl)indenyl]}zirconium dichloride;
bis(trimethylsilyl)amidoboranebis{1-[2-n-propyl, 4-(2,3,4-trimethylphenyl)indenyl]}zirconium dichloride;
bis(trimethylsilyl)amidoboranebis{1-[2-isopropyl, 4-(2,3,4-trimethylphenyl)indenyl]}zirconium dichloride;
bis(trimethylsilyl)amidoboranebis{1-[2-n-butyl, 4-(2,3,4-trimethylphenyl)indenyl]}zirconium dichloride;
bis(trimethylsilyl)amidoboranebis{1-[2-isobutyl, 4-(2,3,4-trimethylphenyl)indenyl]}zirconium dichloride;
bis(trimethylsilyl)amidoboranebis{1-[2-sec-butyl, 4-(2,3,4-trimethylphenyl)indenyl]}zirconium dichloride;
bis(trimethylsilyl)amidoboranebis{1-[2-tert-butyl, 4-(2,3,4-trimethylphenyl)indenyl]}zirconium dichloride;
bis(trimethylsilyl)amidoboranebis{1-[2-phenyl, 4-(2,3,4-trimethylphenyl)indenyl]}zirconium dichloride;
bis(trimethylsilyl)amidoboranebis{1-[2-n-propyl, 4-(2,3,5-trimethylphenyl)indenyl]}zirconium dichloride;
bis(trimethylsilyl)amidoboranebis{1-[2-isopropyl, 4-(2,3,5-trimethylphenyl)indenyl]}zirconium dichloride;
bis(trimethylsilyl)amidoboranebis{1-[2-n-butyl, 4-(2,3,5-trimethylphenyl)indenyl]}zirconium dichloride;
bis(trimethylsilyl)amidoboranebis{1-[2-isobutyl, 4-(2,3,5-trimethylphenyl)indenyl]}zirconium dichloride;
bis(trimethylsilyl)amidoboranebis{1-[2-sec-butyl, 4-(2,3,5-trimethylphenyl)indenyl]}zirconium dichloride;
bis(trimethylsilyl)amidoboranebis{1-[2-tert-butyl, 4-(2,3,5-trimethylphenyl)indenyl]}zirconium dichloride;
bis(trimethylsilyl)amidoboranebis{1-[2-phenyl, 4-(2,3,5-trimethylphenyl)indenyl]}zirconium dichloride;
bis(trimethylsilyl)amidoboranebis{1-[2-n-propyl, 4-(2-methylphenyl)indenyl]}zirconium dimethyl;
bis(trimethylsilyl)amidoboranebis{1-[2-isopropyl, 4-(2-methylphenyl)indenyl]}zirconium dimethyl;
bis(trimethylsilyl)amidoboranebis{1-[2-n-butyl, 4-(2-methylphenyl)indenyl]}zirconium dimethyl;
bis(trimethylsilyl)amidoboranebis{1-[2-isobutyl, 4-(2-methylphenyl)indenyl]}zirconium dimethyl;
bis(trimethylsilyl)amidoboranebis{1-[2-sec-butyl, 4-(2-methylphenyl)indenyl]}zirconium dimethyl;
bis(trimethylsilyl)amidoboranebis{1-[2-tert-butyl, 4-(2-methylphenyl)indenyl]}zirconium dimethyl;
bis(trimethylsilyl)amidoboranebis{1-[2-phenyl, 4-(2-methylphenyl)indenyl]}zirconium dimethyl;
bis(trimethylsilyl)amidoboranebis{1-[2-n-propyl, 4-(2-ethylphenyl)indenyl]}zirconium dimethyl;
bis(trimethylsilyl)amidoboranebis{1-[2-isopropyl, 4-(2-ethylphenyl)indenyl]}zirconium dimethyl;
bis(trimethylsilyl)amidoboranebis{1-[2-n-butyl, 4-(2-ethylphenyl)indenyl]}zirconium dimethyl;
bis(trimethylsilyl)amidoboranebis{1-[2-isobutyl, 4-(2-ethylphenyl)indenyl]}zirconium dimethyl;
bis(trimethylsilyl)amidoboranebis{1-[2-sec-butyl, 4-(2-ethylphenyl)indenyl]}zirconium dimethyl;
bis(trimethylsilyl)amidoboranebis{1-[2-tert-butyl, 4-(2-ethylphenyl)indenyl]}zirconium dimethyl;
bis(trimethylsilyl)amidoboranebis{1-[2-phenyl, 4-(2-ethylphenyl)indenyl]}zirconium dimethyl;
bis(trimethylsilyl)amidoboranebis{1-[2-n-propyl, 4-(2-n-propylphenyl)indenyl]}zirconium dimethyl;
bis(trimethylsilyl)amidoboranebis{1-[2-isopropyl, 4-(2-n-propylphenyl)indenyl]}zirconium dimethyl;
bis(trimethylsilyl)amidoboranebis{1-[2-n-butyl, 4-(2-n-propylphenyl)indenyl]}zirconium dimethyl;
bis(trimethylsilyl)amidoboranebis{1-[2-isobutyl, 4-(2-n-propylphenyl)indenyl]}zirconium dimethyl;
bis(trimethylsilyl)amidoboranebis{1-[2-sec-butyl, 4-(2-n-propylphenyl)indenyl]}zirconium dimethyl;
bis(trimethylsilyl)amidoboranebis{1-[2-tert-butyl, 4-(2-n-propylphenyl)indenyl]}zirconium dimethyl;

bis(trimethylsilyl)amidoboranebis{1-[2-phenyl, 4-(2-n-propylphenyl)indenyl]}zirconium dimethyl;
bis(trimethylsilyl)amidoboranebis{1-[2-n-propyl, 4-(2-isopropylphenyl)indenyl]}zirconium dimethyl;
bis(trimethylsilyl)amidoboranebis{1-[2-isopropyl, 4-(2-isopropylphenyl)indenyl]}zirconium dimethyl;
bis(trimethylsilyl)amidoboranebis{1-[2-n-butyl, 4-(2-isopropylphenyl)indenyl]}zirconium dimethyl;
bis(trimethylsilyl)amidoboranebis{1-[2-isobutyl, 4-(2-isopropylphenyl)indenyl]}zirconium dimethyl;
bis(trimethylsilyl)amidoboranebis{1-[2-sec-butyl, 4-(2-isopropylphenyl)indenyl]}zirconium dimethyl;
bis(trimethylsilyl)amidoboranebis{1-[2-tert-butyl, 4-(2-isopropylphenyl)indenyl]}zirconium dimethyl;
bis(trimethylsilyl)amidoboranebis{1-[2-phenyl, 4-(2-isopropylphenyl)indenyl]}zirconium dimethyl;
bis(trimethylsilyl)amidoboranebis{1-[2-n-propyl, 4-(2-n-butylphenyl)indenyl]}zirconium dimethyl;
bis(trimethylsilyl)amidoboranebis{1-[2-isopropyl, 4-(2-n-butylphenyl)indenyl]}zirconium dimethyl;
bis(trimethylsilyl)amidoboranebis{1-[2-n-butyl, 4-(2-n-butylphenyl)indenyl]}zirconium dimethyl;
bis(trimethylsilyl)amidoboranebis{1-[2-isobutyl, 4-(2-n-butylphenyl)indenyl]}zirconium dimethyl;
bis(trimethylsilyl)amidoboranebis{1-[2-sec-butyl, 4-(2-n-butylphenyl)indenyl]}zirconium dimethyl;
bis(trimethylsilyl)amidoboranebis{1-[2-tert-butyl, 4-(2-n-butylphenyl)indenyl]}zirconium dimethyl;
bis(trimethylsilyl)amidoboranebis{1-[2-phenyl, 4-(2-n-butylphenyl)indenyl]}zirconium dimethyl;
bis(trimethylsilyl)amidoboranebis{1-[2-n-propyl, 4-(2-isobutylphenyl)indenyl]}zirconium dimethyl;
bis(trimethylsilyl)amidoboranebis{1-[2-isopropyl, 4-(2-isobutylphenyl)indenyl]}zirconium dimethyl;
bis(trimethylsilyl)amidoboranebis{1-[2-n-butyl, 4-(2-isobutylphenyl)indenyl]}zirconium dimethyl;
bis(trimethylsilyl)amidoboranebis{1-[2-isobutyl, 4-(2-isobutylphenyl)indenyl]}zirconium dimethyl;
bis(trimethylsilyl)amidoboranebis{1-[2-sec-butyl, 4-(2-isobutylphenyl)indenyl]}zirconium dimethyl;
bis(trimethylsilyl)amidoboranebis{1-[2-tert-butyl, 4-(2-isobutylphenyl)indenyl]}zirconium dimethyl;
bis(trimethylsilyl)amidoboranebis{1-[2-phenyl, 4-(2-isobutylphenyl)indenyl]}zirconium dimethyl;
bis(trimethylsilyl)amidoboranebis{1-[2-n-propyl, 4-(2-sec-butylphenyl)indenyl]}zirconium dimethyl;
bis(trimethylsilyl)amidoboranebis{1-[2-isopropyl, 4-(2-sec-butylphenyl)indenyl]}zirconium dimethyl;
bis(trimethylsilyl)amidoboranebis{1-[2-n-butyl, 4-(2-sec-butylphenyl)indenyl]}zirconium dimethyl;
bis(trimethylsilyl)amidoboranebis{1-[2-isobutyl, 4-(2-sec-butylphenyl)indenyl]}zirconium dimethyl;
bis(trimethylsilyl)amidoboranebis{1-[2-sec-butyl, 4-(2-sec-butylphenyl)indenyl]}zirconium dimethyl;
bis(trimethylsilyl)amidoboranebis{1-[2-tert-butyl, 4-(2-sec-butylphenyl)indenyl]}zirconium dimethyl;
bis(trimethylsilyl)amidoboranebis{1-[2-phenyl, 4-(2-sec-butylphenyl)indenyl]}zirconium dimethyl;
bis(trimethylsilyl)amidoboranebis{1-[2-n-propyl, 4-(2-tert-butylphenyl)indenyl]}zirconium dimethyl;
bis(trimethylsilyl)amidoboranebis{1-[2-isopropyl, 4-(2-tert-butylphenyl)indenyl]}zirconium dimethyl;
bis(trimethylsilyl)amidoboranebis{1-[2-n-butyl, 4-(2-tert-butylphenyl)indenyl]}zirconium dimethyl;
bis(trimethylsilyl)amidoboranebis{1-[2-isobutyl, 4-(2-tert-butylphenyl)indenyl]}zirconium dimethyl;
bis(trimethylsilyl)amidoboranebis{1-[2-sec-butyl, 4-(2-tert-butylphenyl)indenyl]}zirconium dimethyl;
bis(trimethylsilyl)amidoboranebis{1-[2-tert-butyl, 4-(2-tert-butylphenyl)indenyl]}zirconium dimethyl;
bis(trimethylsilyl)amidoboranebis{1-[2-phenyl, 4-(2-tert-butylphenyl)indenyl]}zirconium dimethyl;
bis(trimethylsilyl)amidoboranebis{1-[2-n-propyl, 4-(2-biphenyl)indenyl]}zirconium dimethyl;
bis(trimethylsilyl)amidoboranebis{1-[2-isopropyl, 4-(2-biphenyl)indenyl]}zirconium dimethyl;
bis(trimethylsilyl)amidoboranebis{1-[2-n-butyl, 4-(2-biphenyl)indenyl]}zirconium dimethyl;
bis(trimethylsilyl)amidoboranebis{1-[2-isobutyl, 4-(2-biphenyl)indenyl]}zirconium dimethyl;
bis(trimethylsilyl)amidoboranebis{1-[2-sec-butyl, 4-(2-biphenyl)indenyl]}zirconium dimethyl;
bis(trimethylsilyl)amidoboranebis{1-[2-tert-butyl, 4-(2-biphenyl)indenyl]}zirconium dimethyl;
bis(trimethylsilyl)amidoboranebis{1-[2-phenyl, 4-(2-biphenyl)indenyl]}zirconium dimethyl;
bis(trimethylsilyl)amidoboranebis{1-[2-n-propyl, 4-(2-α-naphthylphenyl)indenyl]}zirconium dimethyl;
bis(trimethylsilyl)amidoboranebis{1-[2-isopropyl, 4-(2-α-naphthylphenyl)indenyl]}zirconium dimethyl;
bis(trimethylsilyl)amidoboranebis{1-[2-n-butyl, 4-(2-α-naphthylphenyl)indenyl]}zirconium dimethyl;
bis(trimethylsilyl)amidoboranebis{1-[2-isobutyl, 4-(2-α-naphthylphenyl)indenyl]}zirconium dimethyl;
bis(trimethylsilyl)amidoboranebis{1-[2-sec-butyl, 4-(2-α-naphthylphenyl)indenyl]}zirconium dimethyl;
bis(trimethylsilyl)amidoboranebis{1-[2-tert-butyl, 4-(2-α-naphthylphenyl)indenyl]}zirconium dimethyl;
bis(trimethylsilyl)amidoboranebis{1-[2-phenyl, 4-(2-α-naphthylphenyl)indenyl]}zirconium dimethyl;
bis(trimethylsilyl)amidoboranebis{1-[2-n-propyl, 4-(2-β-naphthylphenyl)indenyl]}zirconium dimethyl;
bis(trimethylsilyl)amidoboranebis{1-[2-isopropyl, 4-(2-β-naphthylphenyl)indenyl]}zirconium dimethyl;
bis(trimethylsilyl)amidoboranebis{1-[2-n-butyl, 4-(2-β-naphthylphenyl)indenyl]}zirconium dimethyl;
bis(trimethylsilyl)amidoboranebis{1-[2-isobutyl, 4-(2-β-naphthylphenyl)indenyl]}zirconium dimethyl;
bis(trimethylsilyl)amidoboranebis{1-[2-sec-butyl, 4-(2-β-naphthylphenyl)indenyl]}zirconium dimethyl;
bis(trimethylsilyl)amidoboranebis{1-[2-tert-butyl, 4-(2-β-naphthylphenyl)indenyl]}zirconium dimethyl;
bis(trimethylsilyl)amidoboranebis{1-[2-phenyl, 4-(2-β-naphthylphenyl)indenyl]}zirconium dimethyl;
bis(trimethylsilyl)amidoboranebis{1-[2-n-propyl, 4-(2-trifluoromethylphenyl)indenyl]}zirconium dimethyl;
bis(trimethylsilyl)amidoboranebis{1-[2-isopropyl, 4-(2-trifluoromethylphenyl)indenyl]}zirconium dimethyl;
bis(trimethylsilyl)amidoboranebis{1-[2-n-butyl, 4-(2-trifluoromethylphenyl)indenyl]}zirconium dimethyl;
bis(trimethylsilyl)amidoboranebis{1-[2-isobutyl, 4-(2-trifluoromethylphenyl)indenyl]}zirconium dimethyl;
bis(trimethylsilyl)amidoboranebis{1-[2-sec-butyl, 4-(2-trifluoromethylphenyl)indenyl]}zirconium dimethyl;
bis(trimethylsilyl)amidoboranebis{1-[2-tert-butyl, 4-(2-trifluoromethylphenyl)indenyl]}zirconium dimethyl;
bis(trimethylsilyl)amidoboranebis{1-[2-phenyl, 4-(2-trifluoromethylphenyl)indenyl]}zirconium dimethyl;
bis(trimethylsilyl)amidoboranebis{1-[2-n-propyl, 4-(2,3-dimethylphenyl)indenyl]}zirconium dimethyl;
bis(trimethylsilyl)amidoboranebis{1-[2-isopropyl, 4-(2,3-dimethylphenyl)indenyl]}zirconium dimethyl;
bis(trimethylsilyl)amidoboranebis{1-[2-n-butyl, 4-(2,3-dimethylphenyl)indenyl]}zirconium dimethyl;
bis(trimethylsilyl)amidoboranebis{1-[2-isobutyl, 4-(2,3-dimethylphenyl)indenyl]}zirconium dimethyl;

bis(trimethylsilyl)amidoboranebis{1-[2-sec-butyl, 4-(2,3-dimethylphenyl)indenyl]}zirconium dimethyl;
bis(trimethylsilyl)amidoboranebis{1-[2-tert-butyl, 4-(2,3-dimethylphenyl)indenyl]}zirconium dimethyl;
bis(trimethylsilyl)amidoboranebis{1-[2-phenyl, 4-(2,3-dimethylphenyl)indenyl]}zirconium dimethyl;
bis(trimethylsilyl)amidoboranebis{1-[2-n-propyl, 4-(2,3,4-trimethylphenyl)indenyl]}zirconium dimethyl;
bis(trimethylsilyl)amidoboranebis{1-[2-isopropyl, 4-(2,3,4-trimethylphenyl)indenyl]}zirconium dimethyl;
bis(trimethylsilyl)amidoboranebis{1-[2-n-butyl, 4-(2,3,4-trimethylphenyl)indenyl]}zirconium dimethyl;
bis(trimethylsilyl)amidoboranebis{1-[2-isobutyl, 4-(2,3,4-trimethylphenyl)indenyl]}zirconium dimethyl;
bis(trimethylsilyl)amidoboranebis{1-[2-sec-butyl, 4-(2,3,4-trimethylphenyl)indenyl]}zirconium dimethyl;
bis(trimethylsilyl)amidoboranebis{1-[2-tert-butyl, 4-(2,3,4-trimethylphenyl)indenyl]}zirconium dimethyl;
bis(trimethylsilyl)amidoboranebis{1-[2-phenyl, 4-(2,3,4-trimethylphenyl)indenyl]}zirconium dimethyl;
bis(trimethylsilyl)amidoboranebis{1-[2-n-propyl, 4-(2,3,5-trimethylphenyl)indenyl]}zirconium dimethyl;
bis(trimethylsilyl)amidoboranebis{1-[2-isopropyl, 4-(2,3,5-trimethylphenyl)indenyl]}zirconium dimethyl;
bis(trimethylsilyl)amidoboranebis{1-[2-n-butyl, 4-(2,3,5-trimethylphenyl)indenyl]}zirconium dimethyl;
bis(trimethylsilyl)amidoboranebis{1-[2-isobutyl, 4-(2,3,5-trimethylphenyl)indenyl]}zirconium dimethyl;
bis(trimethylsilyl)amidoboranebis{1-[2-sec-butyl, 4-(2,3,5-trimethylphenyl)indenyl]}zirconium dimethyl;
bis(trimethylsilyl)amidoboranebis{1-[2-tert-butyl, 4-(2,3,5-trimethylphenyl)indenyl]}zirconium dimethyl;
bis(trimethylsilyl)amidoboranebis{1-[2-phenyl, 4-(2,3,5-trimethylphenyl)indenyl]}zirconium dimethyl;
dimethylsilanediylbis{1-[2-n-propyl, 4-(2-methylphenyl)indenyl}zirconium $\eta^4$-1,4-diphenyl-1,3-butadiene;
dimethylsilanediylbis{1-[2-isopropyl, 4-(2-methylphenyl)indenyl]}zirconium $\eta^4$-1,4-diphenyl-1,3-butadiene;
dimethylsilanediylbis{1-[2-n-butyl, 4-(2-methylphenyl)indenyl]}zirconium $\eta^4$-1,4-diphenyl-1,3-butadiene;
dimethylsilanediylbis{1-[2-isobutyl, 4-(2-methylphenyl)indenyl]}zirconium $\eta^4$-1,4-diphenyl-1,3-butadiene;
dimethylsilanediylbis{1-[2-sec-butyl, 4-(2-methylphenyl)indenyl]}zirconium $\eta^4$-1,4-diphenyl-1,3-butadiene;
dimethylsilanediylbis{1-[2-tert-butyl, 4-(2-methylphenyl)indenyl]}zirconium $\eta^4$-1,4-diphenyl-1,3-butadiene;
dimethylsilanediylbis{1-[2-phenyl, 4-(2-methylphenyl)indenyl]}zirconium $\eta^4$-1,4-diphenyl-1,3-butadiene;
dimethylsilanediylbis{1-[2-n-propyl, 4-(2-ethylphenyl)indenyl]}zirconium $\eta^4$-1,4-diphenyl-1,3-butadiene;
dimethylsilanediylbis{1-[2-isopropyl, 4-(2-ethylphenyl)indenyl]}zirconium $\eta^4$-1,4-diphenyl-1,3-butadiene;
dimethylsilanediylbis{1-[2-n-butyl, 4-(2-ethylphenyl)indenyl]}zirconium $\eta^4$-1,4-diphenyl-1,3-butadiene;
dimethylsilanediylbis{1-[2-isobutyl, 4-(2-ethylphenyl)indenyl]}zirconium $\eta^4$-1,4-diphenyl-1,3-butadiene;
dimethylsilanediylbis{1-[2-sec-butyl, 4-(2-ethylphenyl)indenyl]}zirconium $\eta^4$-1,4-diphenyl-1,3-butadiene;
dimethylsilanediylbis{1-[2-tert-butyl, 4-(2-ethylphenyl)indenyl]}zirconium $\eta^4$-1,4-diphenyl-1,3-butadiene;
dimethylsilanediylbis{1-[2-phenyl, 4-(2-ethylphenyl)indenyl]}zirconium $\eta^4$-1,4-diphenyl-1,3-butadiene;
dimethylsilanediylbis{1-[2-n-propyl, 4-(2-n-propylphenyl)indenyl]}zirconium $\eta^4$-1,4-diphenyl-1,3-butadiene;
dimethylsilanediylbis{1-[2-isopropyl, 4-(2-n-propylphenyl)indenyl]}zirconium $\eta^4$-1,4-diphenyl-1,3-butadiene;
dimethylsilanediylbis{1-[2-n-butyl, 4-(2-n-propylphenyl)indenyl]}zirconium $\eta^4$-1,4-diphenyl-1,3-butadiene;
dimethylsilanediylbis{1-[2-isobutyl, 4-(2-n-propylphenyl)indenyl]}zirconium $\eta^4$-1,4-diphenyl-1,3-butadiene;
dimethylsilanediylbis{1-[2-sec-butyl, 4-(2-n-propylphenyl)indenyl]}zirconium $\eta^4$-1,4-diphenyl-1,3-butadiene;
dimethylsilanediylbis{1-[2-tert-butyl, 4-(2-n-propylphenyl)indenyl]}zirconium $\eta^4$-1,4-diphenyl-1,3-butadiene;
dimethylsilanediylbis{1-[2-phenyl, 4-(2-n-propylphenyl)indenyl]}zirconium $\eta^4$-1,4-diphenyl-1,3-butadiene;
dimethylsilanediylbis{1-[2-n-propyl, 4-(2-isopropylphenyl)indenyl]}zirconium $\eta^4$-1,4-diphenyl-1,3-butadiene;
dimethylsilanediylbis{1-[2-isopropyl, 4-(2-isopropylphenyl)indenyl]}zirconium $\eta^4$-1,4-diphenyl-1,3-butadiene;
dimethylsilanediylbis{1-[2-n-butyl, 4-(2-isopropylphenyl)indenyl]}zirconium $\eta^4$-1,4-diphenyl-1,3-butadiene;
dimethylsilanediylbis{1-[2-isobutyl, 4-(2-isopropylphenyl)indenyl]}zirconium $\eta^4$-1,4-diphenyl-1,3-butadiene;
dimethylsilanediylbis{1-[2-sec-butyl, 4-(2-isopropylphenyl)indenyl]}zirconium $\eta^4$-1,4-diphenyl-1,3-butadiene;
dimethylsilanediylbis{1-[2-tert-butyl, 4-(2-isopropylphenyl)indenyl]}zirconium $\eta^4$-1,4-diphenyl-1,3-butadiene;
dimethylsilanediylbis{1-[2-phenyl, 4-(2-isopropylphenyl)indenyl]}zirconium $\eta^4$-1,4-diphenyl-1,3-butadiene;
dimethylsilanediylbis{1-[2-n-propyl, 4-(2-n-butylphenyl)indenyl]}zirconium $\eta^4$-1,4-diphenyl-1,3-butadiene;
dimethylsilanediylbis{1-[2-isopropyl, 4-(2-n-butylphenyl)indenyl]}zirconium $\eta^4$-1,4-diphenyl-1,3-butadiene;
dimethylsilanediylbis{1-[2-n-butyl, 4-(2-n-butylphenyl)indenyl]}zirconium $\eta^4$-1,4-diphenyl-1,3-butadiene;
dimethylsilanediylbis{1-[2-isobutyl, 4-(2-n-butylphenyl)indenyl]}zirconium $\eta^4$-1,4-diphenyl-1,3-butadiene;
dimethylsilanediylbis{1-[2-sec-butyl, 4-(2-n-butylphenyl)indenyl]}zirconium $\eta^2$-1,4-diphenyl-1,3-butadiene;
dimethylsilanediylbis{1-[2-tert-butyl, 4-(2-n-butylphenyl)indenyl]}zirconium $\eta^4$-1,4-diphenyl-1,3-butadiene;
dimethylsilanediylbis{1-[2-phenyl, 4-(2-n-butylphenyl)indenyl]}zirconium $\eta^4$-1,4-diphenyl-1,3-butadiene;
dimethylsilanediylbis{1-[2-n-propyl, 4-(2-isobutylphenyl)indenyl]}zirconium $\eta^4$-1,4-diphenyl-1,3-butadiene;
dimethylsilanediylbis{1-[2-isopropyl, 4-(2-isobutylphenyl)indenyl]}zirconium $\eta^4$-1,4-diphenyl-1,3-butadiene;
dimethylsilanediylbis{1-[2-n-butyl, 4-(2-isobutylphenyl)indenyl]}zirconium $\eta^4$-1,4-diphenyl-1,3-butadiene;
dimethylsilanediylbis{1-[2-isobutyl, 4-(2-isobutylphenyl)indenyl]}zirconium $\eta^4$-1,4-diphenyl-1,3-butadiene;
dimethylsilanediylbis{1-[2-sec-butyl, 4-(2-isobutylphenyl)indenyl]}zirconium $\eta^2$-1,4-diphenyl-1,3-butadiene;
dimethylsilanediylbis{1-[2-tert-butyl, 4-(2-isobutylphenyl)indenyl]}zirconium $\eta^4$-1,4-diphenyl-1,3-butadiene;
dimethylsilanediylbis{1-[2-phenyl, 4-(2-isobutylphenyl)indenyl]}zirconium $\eta^4$-1,4-diphenyl-1,3-butadiene;
dimethylsilanediylbis{1-[2-n-propyl, 4-(2-sec-butylphenyl)indenyl]}zirconium $\eta^4$-1,4-diphenyl-1,3-butadiene;
dimethylsilanediylbis{1-[2-isopropyl, 4-(2-sec-butylphenyl)indenyl]}zirconium $\eta^4$-1,4-diphenyl-1,3-butadiene;
dimethylsilanediylbis{1-[2-n-butyl, 4-(2-sec-butylphenyl)indenyl]}zirconium $\eta^4$-1,4-diphenyl-1,3-butadiene;
dimethylsilanediylbis{1-[2-isobutyl, 4-(2-sec-butylphenyl)indenyl]}zirconium $\eta^4$-1,4-diphenyl-1,3-butadiene;
dimethylsilanediylbis{1-[2-sec-butyl, 4-(2-sec-butylphenyl)indenyl]}zirconium $\eta^4$-1,4-diphenyl-1,3-butadiene;
dimethylsilanediylbis{1-[2-tert-butyl, 4-(2-sec-butylphenyl)indenyl]}zirconium $\eta^4$-1,4-diphenyl-1,3-butadiene;
dimethylsilanediylbis{1-[2-phenyl, 4-(2-sec-butylphenyl)indenyl]}zirconium $\eta^4$-1,4-diphenyl-1,3-butadiene;

dimethylsilanediylbis{1-[2-n-propyl, 4-(2-tert-butylphenyl)indenyl]}zirconium η⁴-1,4-diphenyl-1,3-butadiene;
dimethylsilanediylbis{1-[2-isopropyl, 4-(2-tert-butylphenyl)indenyl]}zirconium η⁴-1,4-diphenyl-1,3-butadiene;
dimethylsilanediylbis{1-[2-n-butyl, 4-(2-tert-butylphenyl)indenyl]}zirconium η⁴-1,4-diphenyl-1,3-butadiene;
dimethylsilanediylbis{1-[2-isobutyl, 4-(2-tert-butylphenyl)indenyl]}zirconium η⁴-1,4-diphenyl-1,3-butadiene;
dimethylsilanediylbis{1-[2-sec-butyl, 4-(2-tert-butylphenyl)indenyl]}zirconium η⁴-1,4-diphenyl-1,3-butadiene;
dimethylsilanediylbis{1-[2-tert-butyl, 4-(2-tert-butylphenyl)indenyl]}zirconium η⁴-1,4-diphenyl-1,3-butadiene;
dimethylsilanediylbis{1-[2-phenyl, 4-(2-tert-butylphenyl)indenyl]}zirconium η⁴-1,4-diphenyl-1,3-butadiene;
dimethylsilanediylbis{1-[2-n-propyl, 4-(2-biphenyl)indenyl]}zirconium η⁴-1,4-diphenyl-1,3-butadiene;
dimethylsilanediylbis{1-[2-isopropyl, 4-(2-biphenyl)indenyl]}zirconium η⁴-1,4-diphenyl-1,3-butadiene;
dimethylsilanediylbis{1-[2-n-butyl, 4-(2-biphenyl)indenyl]} zirconium η⁴-1,4-diphenyl-1,3-butadiene;
dimethylsilanediylbis{1-[2-isobutyl, 4-(2-biphenyl)indenyl]} zirconium η⁴-1,4-diphenyl-1,3-butadiene;
dimethylsilanediylbis{1-[2-sec-butyl, 4-(2-biphenyl)indenyl]}zirconium η⁴-1,4-diphenyl-1,3-butadiene;
dimethylsilanediylbis{1-[2-tert-butyl, 4-(2-biphenyl)indenyl]}zirconium η⁴-1,4-diphenyl-1,3-butadiene;
dimethylsilanediylbis{1-[2-phenyl, 4-(2-biphenyl)indenyl]} zirconium η⁴-1,4-diphenyl-1,3-butadiene;
dimethylsilanediylbis{1-[2-n-propyl, 4-(2-α-naphthylphenyl)indenyl]}zirconium η⁴-1,4-diphenyl-1,3-butadiene;
dimethylsilanediylbis{1-[2-isopropyl, 4-(2-α-naphthylphenyl)indenyl]}zirconium η⁴-1,4-diphenyl-1,3-butadiene;
dimethylsilanediylbis{1-[2-n-butyl, 4-(2-α-naphthylphenyl)indenyl]}zirconium η⁴-1,4-diphenyl-1,3-butadiene;
dimethylsilanediylbis{1-[2-isobutyl, 4-(2-α-naphthylphenyl)indenyl]}zirconium η⁴-1,4-diphenyl-1,3-butadiene;
dimethylsilanediylbis{1-[2-sec-butyl, 4-(2-α-naphthylphenyl)indenyl]}zirconium η⁴-1,4-diphenyl-1,3-butadiene;
dimethylsilanediylbis{1-[2-tert-butyl, 4-(2-α-naphthylphenyl)indenyl]}zirconium η⁴-1,4-diphenyl-1,3-butadiene;
dimethylsilanediylbis{1-[2-phenyl, 4-(2-α-naphthylphenyl)indenyl]}zirconium η⁴-1,4-diphenyl-1,3-butadiene;
dimethylsilanediylbis{1-[2-n-propyl, 4-(2-β-naphthylphenyl)indenyl]}zirconium η⁴-1,4-diphenyl-1,3-butadiene;
dimethylsilanediylbis{1-[2-isopropyl, 4-(2-β-naphthylphenyl)indenyl]}zirconium η⁴-1,4-diphenyl-1,3-butadiene;
dimethylsilanediylbis{1-[2-n-butyl, 4-(2-β-naphthylphenyl)indenyl]}zirconium η⁴-1,4-diphenyl-1,3-butadiene;
dimethylsilanediylbis{1-[2-isobutyl, 4-(2-β-naphthylphenyl)indenyl]}zirconium η⁴-1,4-diphenyl-1,3-butadiene;
dimethylsilanediylbis{1-[2-sec-butyl, 4-(2-β-naphthylphenyl)indenyl]}zirconium η⁴-1,4-diphenyl-1,3-butadiene;
dimethylsilanediylbis{1-[2-tert-butyl, 4-(2-β-naphthylphenyl)indenyl]}zirconium η⁴-1,4-diphenyl-1,3-butadiene;
dimethylsilanediylbis{1-[2-phenyl, 4-(2-β-naphthylphenyl)indenyl]}zirconium η⁴-1,4-diphenyl-1,3-butadiene;
dimethylsilanediylbis{1-[2-n-propyl, 4-(2-trifluoromethylphenyl)indenyl]}zirconium η⁴-1,4-diphenyl-1,3-butadiene;
dimethylsilanediylbis{1-[2-isopropyl, 4-(2-trifluoromethylphenyl)indenyl]}zirconium η⁴-1,4-diphenyl-1,3-butadiene;
dimethylsilanediylbis{1-[2-n-butyl, 4-(2-trifluoromethylphenyl)indenyl]}zirconium η⁴-1,4-diphenyl-1,3-butadiene;
dimethylsilanediylbis{1-[2-isobutyl, 4-(2-trifluoromethylphenyl)indenyl]}zirconium η⁴-1,4-diphenyl-1,3-butadiene;
dimethylsilanediylbis{1-[2-sec-butyl, 4-(2-trifluoromethylphenyl)indenyl]}zirconium η⁴-1,4-diphenyl-1,3-butadiene;
dimethylsilanediylbis{1-[2-tert-butyl, 4-(2-trifluoromethylphenyl)indenyl]}zirconium η⁴-1,4-diphenyl-1,3-butadiene;
dimethylsilanediylbis{1-[2-phenyl, 4-(2-trifluoromethylphenyl)indenyl]}zirconium η⁴-1,4-diphenyl-1,3-butadiene;
dimethylsilanediylbis{1-[2-n-propyl, 4-(2,3-dimethylphenyl)indenyl]}zirconium η⁴-1,4-diphenyl-1,3-butadiene;
dimethylsilanediylbis{1-[2-isopropyl, 4-(2,3-dimethylphenyl)indenyl]}zirconium η⁴-1,4-diphenyl-1,3-butadiene;
dimethylsilanediylbis{1-[2-n-butyl, 4-(2,3-dimethylphenyl)indenyl]}zirconium η⁴-1,4-diphenyl-1,3-butadiene;
dimethylsilanediylbis{1-[2-isobutyl, 4-(2,3-dimethylphenyl)indenyl]}zirconium η⁴-1,4-diphenyl-1,3-butadiene;
dimethylsilanediylbis{1-[2-sec-butyl, 4-(2,3-dimethylphenyl)indenyl]}zirconium η⁴-1,4-diphenyl-1,3-butadiene;
dimethylsilanediylbis{1-[2-tert-butyl, 4-(2,3-dimethylphenyl)indenyl]}zirconium η⁴-1,4-diphenyl-1,3-butadiene;
dimethylsilanediylbis{1-[2-phenyl, 4-(2,3-dimethylphenyl)indenyl]}zirconium η⁴-1,4-diphenyl-1,3-butadiene;
dimethylsilanediylbis{1-[2-n-propyl, 4-(2,3,4-trimethylphenyl)indenyl]}zirconium η⁴-1,4-diphenyl-1,3-butadiene;
dimethylsilanediylbis{1-[2-isopropyl, 4-(2,3,4-trimethylphenyl)indenyl]}zirconium η⁴-1,4-diphenyl-1,3-butadiene;
dimethylsilanediylbis{1-[2-n-butyl, 4-(2,3,4-trimethylphenyl)indenyl]}zirconium η⁴-1,4-diphenyl-1,3-butadiene;
dimethylsilanediylbis{1-[2-isobutyl, 4-(2,3,4-trimethylphenyl)indenyl]} η⁴-1,4-diphenyl-1,3-butadiene;
dimethylsilanediylbis{1-[2-sec-butyl, 4-(2,3,4-trimethylphenyl)indenyl]}zirconium η⁴-1,4-diphenyl-1,3-butadiene;
dimethylsilanediylbis{1-[2-tert-butyl, 4-(2,3,4-trimethylphenyl)indenyl]}zirconium η⁴-1,4-diphenyl-1,3-butadiene;
dimethylsilanediylbis{1-[2-phenyl, 4-(2,3,4-trimethylphenyl)indenyl]}zirconium η⁴-1,4-diphenyl-1,3-butadiene;
dimethylsilanediylbis{1-[2-n-propyl, 4-(2,3,5-trimethylphenyl)indenyl]}zirconium η⁴-1,4-diphenyl-1,3-butadiene;
dimethylsilanediylbis{1-[2-isopropyl, 4-(2,3,5-trimethylphenyl)indenyl]}zirconium η⁴-1,4-diphenyl-1,3-butadiene;

dimethylsilanediylbis{1-[2-n-butyl, 4-(2,3,5-trimethylphenyl)indenyl]}zirconium η⁴-1,4-diphenyl-1,3-butadiene;
dimethylsilanediylbis{1-[2-isobutyl, 4-(2,3,5-trimethylphenyl)indenyl]}zirconium η⁴-1,4-diphenyl-1,3-butadiene;
dimethylsilanediylbis{1-[2-sec-butyl, 4-(2,3,5-trimethylphenyl)indenyl]}zirconium η⁴-1,4-diphenyl-1,3-butadiene;
dimethylsilanediylbis{1-[2-tert-butyl, 4-(2,3,5-trimethylphenyl)indenyl]}zirconium η⁴-1,4-diphenyl-1,3-butadiene;
dimethylsilanediylbis{1-[2-phenyl, 4-(2,3,5-trimethylphenyl)indenyl]}zirconium η⁴-1,4-diphenyl-1,3-butadiene;
dimethylsilanediylbis{1-[2-n-propyl, 4-(2-methylphenyl)indenyl]}hafnium η⁴-1,4-diphenyl-1,3-butadiene;
dimethylsilanediylbis{1-[2-isopropyl, 4-(2-methylphenyl)indenyl]}hafnium η⁴-1,4-diphenyl-1,3-butadiene;
dimethylsilanediylbis{1-[2-n-butyl, 4-(2-methylphenyl)indenyl]}hafnium η⁴-1,4-diphenyl-1,3-butadiene;
dimethylsilanediylbis{1-[2-isobutyl, 4-(2-methylphenyl)indenyl]}hafnium η⁴-1,4-diphenyl-1,3-butadiene;
dimethylsilanediylbis{1-[2-sec-butyl, 4-(2-methylphenyl)indenyl]}hafnium η⁴-1,4-diphenyl-1,3-butadiene;
dimethylsilanediylbis{1-[2-tert-butyl, 4-(2-methylphenyl)indenyl]}hafnium η⁴-1,4-diphenyl-1,3-butadiene;
dimethylsilanediylbis{1-[2-phenyl, 4-(2-methylphenyl)indenyl]}hafnium η⁴-1,4-diphenyl-1,3-butadiene;
dimethylsilanediylbis{1-[2-n-propyl, 4-(2-ethylphenyl)indenyl]}hafnium η⁴-1,4-diphenyl-1,3-butadiene;
dimethylsilanediylbis{1-[2-isopropyl, 4-(2-ethylphenyl)indenyl]}hafnium η⁴-1,4-diphenyl-1,3-butadiene;
dimethylsilanediylbis{1-[2-n-butyl, 4-(2-ethylphenyl)indenyl]}hafnium η⁴-1,4-diphenyl-1,3-butadiene;
dimethylsilanediylbis{1-[2-isobutyl, 4-(2-ethylphenyl)indenyl]}hafnium η⁴-1,4-diphenyl-1,3-butadiene;
dimethylsilanediylbis{1-[2-sec-butyl, 4-(2-ethylphenyl)indenyl[}hafnium η⁴-1,4-diphenyl-1,3-butadiene;
dimethylsilanediylbis{1-[2-tert-butyl, 4-(2-ethylphenyl)indenyl]}hafnium η⁴-1,4-diphenyl-1,3-butadiene;
dimethylsilanediylbis{1-[2-phenyl, 4-(2-ethylphenyl)indenyl]}hafnium η⁴-1,4-diphenyl-1,3-butadiene;
dimethylsilanediylbis{1-[2-n-propyl, 4-(2-n-propylphenyl)indenyl]}hafnium ⁴-1,4-diphenyl-1,3-butadiene;
dimethylsilanediylbis{1-[2-isopropyl, 4-(2-n-propylphenyl)indenyl]}hafnium η⁴-1,4-diphenyl-1,3-butadiene;
dimethylsilanediylbis{1-[2-n-butyl, 4-(2-n-propylphenyl)indenyl]}hafnium η⁴-1,4-diphenyl-1,3-butadiene;
dimethylsilanediylbis{1-[2-isobutyl, 4-(2-n-propylphenyl)indenyl]}hafnium η⁴-1,4-diphenyl-1,3-butadiene;
dimethylsilanediylbis{1-[2-sec-butyl, 4-(2-n-propylphenyl)indenyl]}hafnium η⁴-1,4-diphenyl-1,3-butadiene;
dimethylsilanediylbis{1-[2-tert-butyl, 4-(2-n-propylphenyl)indenyl]}hafnium η⁴-1,4-diphenyl-1,3-butadiene;
dimethylsilanediylbis{1-[2-phenyl, 4-(2-n-propylphenyl)indenyl]}hafnium η⁴-1,4-diphenyl-1,3-butadiene;
dimethylsilanediylbis{1-[2-n-propyl, 4-(2-isopropylphenyl)indenyl]}hafnium η⁴-1,4-diphenyl-1,3-butadiene;
dimethylsilanediylbis{1-[2-isopropyl, 4-(2-isopropylphenyl)indenyl]}hafnium η⁴-1,4-diphenyl-1,3-butadiene;
dimethylsilanediylbis{1-[2-n-butyl, 4-(2-isopropylphenyl)indenyl]}hafnium η⁴-1,4-diphenyl-1,3-butadiene;
dimethylsilanediylbis{1-[2-isobutyl, 4-(2-isopropylphenyl)indenyl]}hafnium η⁴-1,4-diphenyl-1,3-butadiene;
dimethylsilanediylbis{1-[2-sec-butyl, 4-(2-isopropylphenyl)indenyl]}hafnium η⁴-1,4-diphenyl-1,3-butadiene;
dimethylsilanediylbis{1-[2-tert-butyl, 4-(2-isopropylphenyl)indenyl]}hafnium η⁴-1,4-diphenyl-1,3-butadiene;
dimethylsilanediylbis{1-[2-phenyl, 4-(2-isopropylphenyl)indenyl]}hafnium η⁴-1,4-diphenyl-1,3-butadiene;
dimethylsilanediylbis{1-[2-n-propyl, 4-(2-n-butylphenyl)indenyl]}hafnium η⁴-1,4-diphenyl-1,3-butadiene;
dimethylsilanediylbis{1-[2-isopropyl, 4-(2-n-butylphenyl)indenyl]}hafnium η⁴-1,4-diphenyl-1,3-butadiene;
dimethylsilanediylbis{1-[2-n-butyl, 4-(2-n-butylphenyl)indenyl]}hafnium η⁴-1,4-diphenyl-1,3-butadiene;
dimethylsilanediylbis{1-[2-isobutyl, 4-(2-n-butylphenyl)indenyl]}hafnium η⁴-1,4-diphenyl-1,3-butadiene;
dimethylsilanediylbis{1-[2-sec-butyl, 4-(2-n-butylphenyl)indenyl]}hafnium η⁴-1,4-diphenyl-1,3-butadiene;
dimethylsilanediylbis{1-[2-tert-butyl, 4-(2-n-butylphenyl)indenyl]}hafnium η⁴-1,4-diphenyl-1,3-butadiene;
dimethylsilanediylbis{1-[2-phenyl, 4-(2-n-butylphenyl)indenyl]}hafnium η⁴-1,4-diphenyl-1,3-butadiene;
dimethylsilanediylbis{1-[2-n-propyl, 4-(2-isobutylphenyl)indenyl]}hafnium η⁴-1,4-diphenyl-1,3-butadiene;
dimethylsilanediylbis{1-[2-isopropyl, 4-(2-isobutylphenyl)indenyl]}hafnium η⁴-1,4-diphenyl-1,3-butadiene;
dimethylsilanediylbis{1-[2-n-butyl, 4-(2-isobutylphenyl)indenyl]}hafnium η⁴-1,4-diphenyl-1,3-butadiene;
dimethylsilanediylbis{1-[2-isobutyl, 4-(2-isobutylphenyl)indenyl]}hafnium η⁴-1,4-diphenyl-1,3-butadiene;
dimethylsilanediylbis{1-[2-sec-butyl, 4-(2-isobutylphenyl)indenyl]}hafnium η⁴-1,4-diphenyl-1,3-butadiene;
dimethylsilanediylbis{1-[2-tert-butyl, 4-(2-isobutylphenyl)indenyl]}hafnium η⁴-1,4-diphenyl-1,3-butadiene;
dimethylsilanediylbis{1-[2-phenyl, 4-(2-isobutylphenyl)indenyl]}hafnium η⁴-1,4-diphenyl-1,3-butadiene;
dimethylsilanediylbis{1-[2-n-propyl, 4-(2-sec-butylphenyl)indenyl]}hafnium η⁴-1,4-diphenyl-1,3-butadiene;
dimethylsilanediylbis{1-[2-isopropyl, 4-(2-sec-butylphenyl)indenyl]}hafnium η⁴-1,4-diphenyl-1,3-butadiene;
dimethylsilanediylbis{1-[2-n-butyl, 4-(2-sec-butylphenyl)indenyl]}hafnium η⁴-1,4-diphenyl-1,3-butadiene;
dimethylsilanediylbis{1-[2-isobutyl, 4-(2-sec-butylphenyl)indenyl]}hafnium η⁴-1,4-diphenyl-1,3-butadiene;
dimethylsilanediylbis{1-[2-sec-butyl, 4-(2-sec-butylphenyl)indenyl]}hafnium η⁴-1,4-diphenyl-1,3-butadiene;
dimethylsilanediylbis{1-[2-tert-butyl, 4-(2-sec-butylphenyl)indenyl]}hafnium η⁴-1,4-diphenyl-1,3-butadiene;
dimethylsilanediylbis{1-[2-phenyl, 4-(2-sec-butylphenyl)indenyl]}hafnium η⁴-1,4-diphenyl-1,3-butadiene;
dimethylsilanediylbis{1-[2-n-propyl, 4-(2-tert-butylphenyl)indenyl]}hafnium η⁴-1,4-diphenyl-1,3-butadiene;
dimethylsilanediylbis{1-[2-isopropyl, 4-(2-tert-butylphenyl)indenyl]}hafnium η⁴-1,4-diphenyl-1,3-butadiene;
dimethylsilanediylbis{1-[2-n-butyl, 4-(2-tert-butylphenyl)indenyl]}hafnium η⁴-1,4-diphenyl-1,3-butadiene;
dimethylsilanediylbis{1-[2-isobutyl, 4-(2-tert-butylphenyl)indenyl]}hafnium η⁴-1,4-diphenyl-1,3-butadiene;
dimethylsilanediylbis{1-[2-sec-butyl, 4-(2-tert-butylphenyl)indenyl]}hafnium η⁴-1,4-diphenyl-1,3-butadiene;
dimethylsilanediylbis{1-[2-tert-butyl, 4-(2-tert-butylphenyl)indenyl]}hafnium η⁴-1,4-diphenyl-1,3-butadiene;
dimethylsilanediylbis{1-[2-phenyl, 4-(2-tert-butylphenyl)indenyl]}hafnium η⁴-1,4-diphenyl-1,3-butadiene;
dimethylsilanediylbis{1-[2-n-propyl, 4-(2-biphenyl)indenyl]}hafnium η⁴-1,4-diphenyl-1,3-butadiene;
dimethylsilanediylbis{1-[2-isopropyl, 4-(2-biphenyl)indenyl]}hafnium η⁴-1,4-diphenyl-1,3-butadiene;

dimethylsilanediylbis{1-[2-n-butyl, 4-(2-biphenyl) indenyl]} hafnium $\eta^4$-1,4-diphenyl-1,3-butadiene;
dimethylsilanediylbis{1-[2-isobutyl, 4-(2-biphenyl) indenyl]} hafnium $\eta^4$-1,4-diphenyl-1,3-butadiene;
dimethylsilanediylbis{1-[2-sec-butyl, 4-(2-biphenyl) indenyl]}hafnium $\eta^4$-1,4-diphenyl-1,3-butadiene;
dimethylsilanediylbis{1-[2-tert-butyl, 4-(2-biphenyl) indenyl]}hafnium $\eta^4$-1,4-diphenyl-1,3-butadiene;
dimethylsilanediylbis{1-[2-phenyl, 4-(2-biphenyl)indenyl]} hafnium $\eta^4$-1,4-diphenyl-1,3-butadiene;
dimethylsilanediylbis{1-[2-n-propyl, 4-(2-α-naphthylphenyl)indenyl]}hafnium $\eta^4$-1,4-diphenyl-1,3-butadiene;
dimethylsilanediylbis{1-[2-isopropyl, 4-(2-α-naphthylphenyl)indenyl]}hafnium $\eta^4$-1,4-diphenyl-1,3-butadiene;
dimethylsilanediylbis{1-[2-n-butyl, 4-(2-α-naphthylphenyl)indenyl]}hafnium $\eta^4$-1,4-diphenyl-1,3-butadiene;
dimethylsilanediylbis{1-[2-isobutyl, 4-(2-α-naphthylphenyl)indenyl]}hafnium $\eta^4$-1,4-diphenyl-1,3-butadiene;
dimethylsilanediylbis{1-[2-sec-butyl, 4-(2-α-naphthylphenyl)indenyl]}hafnium $\eta^4$-1,4-diphenyl-1,3-butadiene;
dimethylsilanediylbis{1-[2-tert-butyl, 4-(2-α-naphthylphenyl)indenyl]}hafnium $\eta^4$-1,4-diphenyl-1,3-butadiene;
dimethylsilanediylbis{1-[2-phenyl, 4-(2-α-naphthylphenyl) indenyl]}hafnium $\eta^4$-1,4-diphenyl-1,3-butadiene;
dimethylsilanediylbis{1-[2-n-propyl, 4-(2-β-naphthylphenyl)indenyl]}hafnium $\eta^4$-1,4-diphenyl-1,3-butadiene;
dimethylsilanediylbis{1-[2-isopropyl, 4-(2-β-naphthylphenyl)indenyl]}hafnium $\eta^4$-1,4-diphenyl-1,3-butadiene;
dimethylsilanediylbis{1-[2-n-butyl, 4-(2-β-naphthylphenyl) indenyl]}hafnium $\eta^4$-1,4-diphenyl-1,3-butadiene;
dimethylsilanediylbis{1-[2-isobutyl, 4-(2-β-naphthylphenyl)indenyl]}hafnium $\eta^4$-1,4-diphenyl-1,3-butadiene;
dimethylsilanediylbis{1-[2-sec-butyl, 4-(2-β-naphthylphenyl)indenyl]}hafnium $\eta^4$-1,4-diphenyl-1,3-butadiene;
dimethylsilanediylbis{1-[2-tert-butyl, 4-(2-β-naphthylphenyl)indenyl]}hafnium $\eta^4$-1,4-diphenyl-1,3-butadiene;
dimethylsilanediylbis{1-[2-phenyl, 4-(2-β-naphthylphenyl) indenyl]}-hafnium $\eta^4$-1,4-diphenyl-1,3-butadiene;
dimethylsilanediylbis{1-[2-n-propyl, 4-(2-trifluoromethylphenyl)indenyl]}-hafnium $\eta^4$-1,4-diphenyl-1,3-butadiene;
dimethylsilanediylbis{1-[2-isopropyl, 4-(2-trifluoromethylphenyl)indenyl]}-hafnium $\eta^4$-1,4-diphenyl-1,3-butadiene;
dimethylsilanediylbis{1-[2-n-butyl, 4-(2-trifluoromethylphenyl)indenyl]}-hafnium $\eta^4$-1,4-diphenyl-1,3-butadiene;
dimethylsilanediylbis{1-[2-isobutyl, 4-(2-trifluoromethylphenyl)indenyl]}-hafnium $\eta^4$-1,4-diphenyl-1,3-butadiene;
dimethylsilanediylbis{1-[2-sec-butyl, 4-(2-trifluoromethylphenyl)indenyl]}-hafnium $\eta^4$-1,4-diphenyl-1,3-butadiene;
dimethylsilanediylbis{1-[2-tert-butyl, 4-(2-trifluoromethylphenyl)indenyl]}-hafnium $\eta^4$-1,4-diphenyl-1,3-butadiene;
dimethylsilanediylbis{1-[2-phenyl, 4-(2-trifluoromethylphenyl)indenyl]}-hafnium $\eta^4$-1,4-diphenyl-1,3-butadiene;
dimethylsilanediylbis{1-[2-n-propyl, 4-(2,3-dimethylphenyl)indenyl]}hafnium $\eta^4$-1,4-diphenyl-1,3-butadiene;
dimethylsilanediylbis{1-[2-isopropyl, 4-(2,3-dimethylphenyl)indenyl]}hafnium $\eta^4$-(1,4-diphenyl-1,3-butadiene;
dimethylsilanediylbis{1-[2-n-butyl, 4-(2,3-dimethylphenyl) indenyl]}hafnium $\eta^4$-1,4-diphenyl-1,3-butadiene;
dimethylsilanediylbis{1-[2-isobutyl, 4-(2,3-dimethylphenyl)indenyl]}hafnium $\eta^4$-1,4-diphenyl-1,3-butadiene;
dimethylsilanediylbis{1-[2-sec-butyl, 4-(2,3-dimethylphenyl)indenyl]}hafnium $\eta^4$-1,4-diphenyl-1,3-butadiene;
dimethylsilanediylbis{1-[2-tert-butyl, 4-(2,3-dimethylphenyl)indenyl]}hafnium $\eta^4$-1,4-diphenyl-1,3-butadiene;
dimethylsilanediylbis{1-[2-phenyl, 4-(2,3-dimethylphenyl) indenyl]}hafnium $\eta^4$-1,4-diphenyl-1,3-butadiene;
dimethylsilanediylbis{1-[2-n-propyl, 4-(2,3,4-trimethylphenyl)indenyl]}hafnium $\eta^4$-1,4-diphenyl-1,3-butadiene;
dimethylsilanediylbis{1-[2-isopropyl, 4-(2,3,4-trimethylphenyl)indenyl]}hafnium $\eta^4$-1,4-diphenyl-1,3-butadiene;
dimethylsilanediylbis{1-[2-n-butyl, 4-(2,3,4-trimethylphenyl)indenyl]}hafnium $\eta^4$-1,4-diphenyl-1,3-butadiene;
dimethylsilanediylbis{1-[2-isobutyl, 4-(2,3,4-trimethylphenyl)indenyl]}hafnium $\eta^4$-1,4-diphenyl-1,3-butadiene;
dimethylsilanediylbis{1-[2-sec-butyl, 4-(2,3,4-trimethylphenyl)indenyl]}hafnium $\eta^4$-1,4-diphenyl-1,3-butadiene;
dimethylsilanediylbis{1-[2-tert-butyl, 4-(2,3,4-trimethylphenyl)indenyl]}hafnium $\eta^4$-1,4-diphenyl-1,3-butadiene;
dimethylsilanediylbis{1-[2-phenyl, 4-(2,3,4-trimethylphenyl)indenyl]}hafnium $\eta^4$-1,4-diphenyl-1,3-butadiene;
dimethylsilanediylbis{1-[2-n-propyl, 4-(2,3,5-trimethylphenyl)indenyl]}hafnium $\eta^4$-1,4-diphenyl-1,3-butadiene;
dimethylsilanediylbis{1-[2-isopropyl, 4-(2,3,5-trimethylphenyl)indenyl]}hafnium $\eta^4$-1,4-diphenyl-1,3-butadiene;
dimethylsilanediylbis{1-[2-n-butyl, 4-(2,3,5-trimethylphenyl)indenyl]}hafnium $\eta^4$-1,4-diphenyl-1,3-butadiene;
dimethylsilanediylbis{1-[2-isobutyl, 4-(2,3,5-trimethylphenyl)indenyl]}hafnium $\eta^4$-1,4-diphenyl-1,3-butadiene;
dimethylsilanediylbis{1-[2-sec-butyl, 4-(2,3,5-trimethylphenyl)indenyl]}hafnium $\eta^4$-1,4-diphenyl-1,3-butadiene;
dimethylsilanediylbis{1-[2-tert-butyl, 4-(2,3,5-trimethylphenyl)indenyl]}hafnium $\eta^4$-1,4-diphenyl-1,3-butadiene;
dimethylsilanediylbis{1-[2-phenyl, 4-(2,3,5-trimethylphenyl)indenyl]}hafnium $\eta^4$-1,4-diphenyl-1,3-butadiene;
9-silafluorenediylbis{1-[2-n-propyl, 4-(2-methylphenyl) indenyl]}zirconium $\eta^4$-1,4-diphenyl-1,3-butadiene;
9-silafluorenediylbis{1-[2-isopropyl, 4-(2-methylphenyl) indenyl]}zirconium $\eta^4$-1,4-diphenyl-1,3-butadiene;
9-silafluorenediylbis{1-[2-n-butyl, 4-(2-methylphenyl) indenyl]}zirconium $\eta^4$-1,4-diphenyl-1,3-butadiene;

9-silafluorenediylbis{1-[2-isobutyl, 4-(2-methylphenyl) indenyl]}zirconium η$^4$-1,4-diphenyl-1,3-butadiene;
9-silafluorenediylbis{1-[2-sec-butyl, 4-(2-methylphenyl) indenyl]}zirconium η$^4$-1,4-diphenyl-1,3-butadiene;
9-silafluorenediylbis{1-[2-tert-butyl, 4-(2-methylphenyl) indenyl]}zirconium η$^4$-1,4-diphenyl-1,3-butadiene;
9-silafluorenediylbis{1-[2-phenyl, 4-(2-methylphenyl) indenyl]}zirconium η$^4$-1,4-diphenyl-1,3-butadiene;
9-silafluorenediylbis{1-[2-n-propyl, 4-(2-ethylphenyl) indenyl]}zirconium η$^4$-1,4-diphenyl-1,3-butadiene;
9-silafluorenediylbis{1-[2-isopropyl, 4-(2-ethylphenyl) indenyl]}zirconium η$^4$-1,4-diphenyl-1,3-butadiene;
9-silafluorenediylbis{1-[2-n-butyl, 4-(2-ethylphenyl) indenyl]}zirconium η$^4$-1,4-diphenyl-1,3-butadiene;
9-silafluorenediylbis{1-[2-isobutyl, 4-(2-ethylphenyl) indenyl]}zirconium η$^4$-1,4-diphenyl-1,3-butadiene;
9-silafluorenediylbis{1-[2-sec-butyl, 4-(2-ethylphenyl) indenyl]}zirconium η$^4$-1,4-diphenyl-1,3-butadiene;
9-silafluorenediylbis{1-[2-tert-butyl, 4-(2-ethylphenyl) indenyl]}zirconium η$^4$-1,4-diphenyl-1,3-butadiene;
9-silafluorenediylbis{1-[2-phenyl, 4-(2-ethylphenyl) indenyl]}zirconium η$^4$-1,4-diphenyl-1,3-butadiene;
9-silafluorenediylbis{1-[2-n-propyl, 4-(2-n-propylphenyl) indenyl]}zirconium η$^4$-1,4-diphenyl-1,3-butadiene;
9-silafluorenediylbis{1-[2-isopropyl, 4-(2-n-propylphenyl) indenyl]}zirconium η$^4$-1,4-diphenyl-1,3-butadiene;
9-silafluorenediylbis{1-[2-n-butyl, 4-(2-n-propylphenyl) indenyl]}zirconium η$^4$-1,4-diphenyl-1,3-butadiene;
9-silafluorenediylbis{1-[2-isobutyl, 4-(2-n-propylphenyl) indenyl]}zirconium η$^4$-1,4-diphenyl-1,3-butadiene;
9-silafluorenediylbis{1-[2-sec-butyl, 4-(2-n-propylphenyl) indenyl]}zirconium η$^4$-1,4-diphenyl-1,3-butadiene;
9-silafluorenediylbis{1-[2-tert-butyl, 4-(2-n-propylphenyl) indenyl]}zirconium η$^4$-1,4-diphenyl-1,3-butadiene;
9-silafluorenediylbis{1-[2-phenyl, 4-(2-n-propylphenyl) indenyl]}zirconium η$^4$-1,4-diphenyl-1,3-butadiene;
9-silafluorenediylbis{1-[2-n-propyl, 4-(2-isopropylphenyl) indenyl]}zirconium η$^4$-1,4-diphenyl-1,3-butadiene;
9-silafluorenediylbis{1-[2-isopropyl, 4-(2-isopropylphenyl) indenyl]}zirconium η$^4$-1,4-diphenyl-1,3-butadiene;
9-silafluorenediylbis{1-[2-n-butyl, 4-(2-isopropylphenyl) indenyl]}zirconium η$^4$-1,4-diphenyl-1,3-butadiene;
9-silafluorenediylbis{1-[2-isobutyl, 4-(2-isopropylphenyl) indenyl]}zirconium η$^4$-1,4-diphenyl-1,3-butadiene;
9-silafluorenediylbis{1-[2-sec-butyl, 4-(2-isopropylphenyl) indenyl]}zirconium η$^4$-1,4-diphenyl-1,3-butadiene;
9-silafluorenediylbis{1-[2-tert-butyl, 4-(2-isopropylphenyl) indenyl]}zirconium η$^4$-1,4-diphenyl-1,3-butadiene;
9-silafluorenediylbis{1-[2-phenyl, 4-(2-isopropylphenyl) indenyl]}zirconium η$^4$-1,4-diphenyl-1,3-butadiene;
9-silafluorenediylbis{1-[2-n-propyl, 4-(2-n-butylphenyl) indenyl]}zirconium η$^4$-1,4-diphenyl-1,3-butadiene;
9-silafluorenediylbis{1-[2-isopropyl, 4-(2-n-butylphenyl) indenyl]}zirconium η$^4$-1,4-diphenyl-1,3-butadiene;
9-silafluorenediylbis{1-[2-n-butyl, 4-(2-n-butylphenyl) indenyl]}zirconium η$^4$-1,4-diphenyl-1,3-butadiene;
9-silafluorenediylbis{1-[2-isobutyl, 4-(2-n-butylphenyl) indenyl]}zirconium η$^4$-1,4-diphenyl-1,3-butadiene;
9-silafluorenediylbis{1-[2-sec-butyl, 4-(2-n-butylphenyl) indenyl]}zirconium η$^4$-1,4-diphenyl-1,3-butadiene;
9-silafluorenediylbis{1-[2-tert-butyl, 4-(2-n-butylphenyl) indenyl]}zirconium η$^4$-1,4-diphenyl-1,3-butadiene;
9-silafluorenediylbis{1-[2-phenyl, 4-(2-n-butylphenyl) indenyl]}zirconium η$^4$-1,4-diphenyl-1,3-butadiene;
9-silafluorenediylbis{1-[2-n-propyl, 4-(2-isobutylphenyl) indenyl]}zirconium η$^4$-1,4-diphenyl-1,3-butadiene;
9-silafluorenediylbis{1-[2-isopropyl, 4-(2-isobutylphenyl) indenyl]}zirconium η$^4$-1,4-diphenyl-1,3-butadiene;
9-silafluorenediylbis{1-[2-n-butyl, 4-(2-isobutylphenyl) indenyl]}zirconium η$^4$-1,4-diphenyl-1,3-butadiene;
9-silafluorenediylbis{1-[2-isobutyl, 4-(2-isobutylphenyl) indenyl]}zirconium η$^4$-1,4-diphenyl-1,3-butadiene;
9-silafluorenediylbis{1-[2-sec-butyl, 4-(2-isobutylphenyl) indenyl]}zirconium η$^4$-1,4-diphenyl-1,3-butadiene;
9-silafluorenediylbis{1-[2-tert-butyl, 4-(2-isobutylphenyl) indenyl]}zirconium η$^4$-1,4-diphenyl-1,3-butadiene;
9-silafluorenediylbis{1-[2-phenyl, 4-(2-isobutylphenyl) indenyl]}zirconium η$^4$-1,4-diphenyl-1,3-butadiene;
9-silafluorenediylbis{1-[2-n-propyl, 4-(2-sec-butylphenyl) indenyl]}zirconium η$^4$-1,4-diphenyl-1,3-butadiene;
9-silafluorenediylbis{1-[2-isopropyl, 4-(2-sec-butylphenyl) indenyl]}zirconium η$^4$-1,4-phenyl-1,3-butadiene;
9-silafluorenediylbis{1-[2-n-butyl, 4-(2-sec-butylphenyl) indenyl]}zirconium η$^4$-1,4-diphenyl-1,3-butadiene;
9-silafluorenediylbis{1-[2-isobutyl, 4-(2-sec-butylphenyl) indenyl]}zirconium η$^4$-1,4-diphenyl-1,3-butadiene;
9-silafluorenediylbis{1-[2-sec-butyl, 4-(2-sec-butylphenyl) indenyl]}zirconium η$^4$-1,4-diphenyl-1,3-butadiene;
9-silafluorenediylbis{1-[2-tert-butyl, 4-(2-sec-butylphenyl) indenyl]}zirconium η$^4$-1,4-diphenyl-1,3-butadiene;
9-silafluorenediylbis{1-[2-phenyl, 4-(2-sec-butylphenyl) indenyl]}zirconium η$^4$-1,4-diphenyl-1,3-butadiene;
9-silafluorenediylbis{1-[2-n-propyl, 4-(2-tert-butylphenyl) indenyl]}zirconium η$^4$-1,4-diphenyl-1,3-butadiene;
9-silafluorenediylbis{1-[2-isopropyl, 4-(2-tert-butylphenyl) indenyl]}zirconium η$^4$-1,4-diphenyl-1,3-butadiene;
9-silafluorenediylbis{1-[2-n-butyl, 4-(2-tert-butylphenyl) indenyl]}zirconium η$^4$-1,4-diphenyl-1,3-butadiene;
9-silafluorenediylbis{1-[2-isobutyl, 4-(2-tert-butylphenyl) indenyl]}zirconium η$^4$-1,4-diphenyl-1,3-butadiene;
9-silafluorenediylbis{1-[2-sec-butyl, 4-(2-tert-butylphenyl) indenyl]}zirconium η$^4$-1,4-diphenyl-1,3-butadiene;
9-silafluorenediylbis{1-[2-tert-butyl, 4-(2-tert-butylphenyl) indenyl]}zircorium η$^4$-1,4-diphenyl-1,3-butadiene;
9-silafluorenediylbis{1-[2-phenyl, 4-(2-tert-butylphenyl) indenyl]}zirconium η$^4$-1,4-diphenyl-1,3-butadiene;
9-silafluorenediylbis{1-[2-n-propyl, 4-(2-biphenyl)indenyl]}zirconium η$^4$-1,4-diphenyl-1,3-butadiene;
9-silafluorenediylbis{1-[2-isopropyl, 4-(2-biphenyl) indenyl]}zirconium η$^4$-1,4-diphenyl-1,3-butadiene;
9-silafluorenediylbis{1-[2-n-butyl, 4-(2-biphenyl)indenyl]}zirconium η$^4$-1,4-diphenyl-1,3-butadiene;
9-silafluorenediylbis{1-[2-isobutyl, 4-(2-biphenyl) indenyl]} zirconium η$^4$-1,4-diphenyl-1,3-butadiene;
9-silafluorenediylbis{1-[2-sec-butyl, 4-(2-biphenyl) indenyl]} zirconium η$^4$-1,4-diphenyl-1,3-butadiene;
9-silafluorenediylbis{1-[2-tert-butyl, 4-(2-biphenyl) indenyl]}zirconium η$^4$-1,4-diphenyl-1,3-butadiene;
9-silafluorenediylbis{1-[2-phenyl, 4-(2-biphenyl)indenyl]} zirconium η$^4$-1,4-diphenyl-1,3-butadiene;
9-silafluorenediylbis{1-[2-n-propyl, 4-(2-α-naphthylphenyl)indenyl]}zirconium η$^4$-1,4-diphenyl-1,3-butadiene;
9-silafluorenediylbis{1-[2-isopropyl, 4-(2-α-naphthylphenyl))indenyl]}zirconium η$^4$-1,4-diphenyl-1,3-butadiene;
9-silafluorenediylbis{1-[2-n-butyl, 4-(2-α-naphthylphenyl) indenyl]}zirconium η$^4$-1,4-diphenyl-1,3-butadiene;
9-silafluorenediylbis{1-[2-isobutyl, 4-(2-α-naphthylphenyl) indenyl]}zirconium η$^4$-1,4-diphenyl-1,3-butadiene;
9-silafluorenediylbis{1-[2-sec-butyl, 4-(2-α-naphthylphenyl)indenyl]}zirconium η$^4$-1,4-diphenyl-1,3-butadiene;
9-silafluorenediylbis{1-[2-tert-butyl, 4-(2-α-naphthylphenyl)indenyl]}zirconium η$^4$-1,4-diphenyl-1,3-butadiene;

9-silafluorenediylbis{1-[2-phenyl, 4-(2-α-naphthylphenyl)indenyl]}zirconium η⁴-1,4-diphenyl-1,3-butadiene;
9-silafluorenediylbis{1-[2-n-propyl, 4-(2-α-naphthylphenyl)indenyl]}zirconium η⁴-1,4-diphenyl-1,3-butadiene;
9-silafluorenediylbis{1-[2-isopropyl, 4-(2-α-naphthylphenyl)indenyl]}zirconium η⁴-1,4-diphenyl-1,3-butadiene;
9-silafluorenediylbis{1-[2-n-butyl, 4-(2-α-naphthylphenyl)indenyl]}zirconium η⁴-1,4-diphenyl-1,3-butadiene;
9-silafluorenediylbis{1-[2-isobutyl, 4-(2-β-naphthylphenyl)indenyl]}zirconium η⁴-1,4-diphenyl-1,3-butadiene;
9-silafluorenediylbis{1-[2-sec-butyl, 4-(2-β-naphthylphenyl)indenyl]}zirconium η⁴-1,4-diphenyl-1,3-butadiene;
9-silafluorenediylbis{1-[2-tert-butyl, 4-(2-β-naphthylphenyl)indenyl]}zirconium η⁴-1,4-diphenyl-1,3-butadiene;
9-silafluorenediylbis{1-[2-phenyl, 4-(2-β-naphthylphenyl)indenyl]}zirconium η⁴-1,4-diphenyl-1,3-butadiene;
9-silafluorenediylbis{1-[2-n-propyl, 4-(2-trifluoromethylphenyl)indenyl]}-zirconium η⁴-1,4-diphenyl-1,3-butadiene;
9-silafluorenediylbis{1-[2-isopropyl, 4-(2-trifluoromethylphenyl)indenyl]}-zirconium η⁴-1,4-diphenyl-1,3-butadiene;
9-silafluorenediylbis{1-[2-n-butyl, 4-(2-trifluoromethylphenyl)indenyl]}-zirconium η⁴-1,4-diphenyl-1,3-butadiene;
9-silafluorenediylbis{1-[2-isobutyl, 4-(2-trifluoromethylphenyl)indenyl]}-zirconium η⁴-1,4-diphenyl-1,3-butadiene;
9-silafluorenediylbis{1-[2-sec-butyl, 4-(2-trifluoromethylphenyl)indenyl]}-zirconium η⁴-1,4-diphenyl-1,3-butadiene;
9-silafluorenediylbis{1-[2-tert-butyl, 4-(2-trifluoromethylphenyl)indenyl]}-zirconium η⁴-1,4-diphenyl-1,3-butadiene;
9-silafluorenediylbis{1-[2-phenyl, 4-(2-trifluoromethylphenyl)indenyl]}-zirconium η⁴-1,4-diphenyl-1,3-butadiene;
9-silafluorenediylbis{1-[2-n-propyl, 4-(2,3-dimethylphenyl)indenyl]}zirconium η⁴-1,4-diphenyl-1,3-butadiene;
9-silafluorenediylbis{1-[2-isopropyl, 4-(2,3-dimethylphenyl)indenyl]}zirconium η⁴-1,4-diphenyl-1,3-butadiene;
9-silafluorenediylbis{1-[2-n-butyl, 4-(2,3-dimethylphenyl)indenyl]}zirconium η⁴-1,4-diphenyl-1,3-butadiene;
9-silafluorenediylbis{1-[2-isobutyl, 4-(2,3-dimethylphenyl)indenyl]}zirconium η⁴-1,4-diphenyl-1,3-butadiene;
9-silafluorenediylbis{1-[2-sec-butyl, 4-(2,3-dimethylphenyl)indenyl]}zirconium η⁴-1,4-diphenyl-1,3-butadiene;
9-silafluorenediylbis{1-[2-tert-butyl, 4-(2,3-dimethylphenyl)indenyl]}zirconium η⁴-1,4-diphenyl-1,3-butadiene;
9-silafluorenediylbis{1-[2-phenyl, 4-(2,3-dimethylphenyl)indenyl]}zirconium η⁴-1,4-diphenyl-1,3-butadiene;
9-silafluorenediylbis{1-[2-n-propyl, 4-(2,3,4-trimethylphenyl)indenyl]}zirconium η⁴-1,4-diphenyl-1,3-butadiene;
9-silafluorenediylbis{1-[2-isopropyl, 4-(2,3,4-trimethylphenyl)indenyl]}zirconium η⁴-1,4-diphenyl-1,3-butadiene;
9-silafluorenediylbis{1-[2-n-butyl, 4-(2,3,4-trimethylphenyl)indenyl]}zirconium η⁴-1,4-diphenyl-1,3-butadiene;
9-silafluorenediylbis{1-[2-isobutyl, 4-(2,3,4-trimethylphenyl)indenyl]}zirconium η⁴-1,4-diphenyl-1,3-butadiene;
9-silafluorenediylbis{1-[2-sec-butyl, 4-(2,3,4-trimethylphenyl)indenyl]}zirconium η⁴-1,4-diphenyl-1,3-butadiene;
9-silafluorenediylbis{1-[2-tert-butyl, 4-(2,3,4-trimethylphenyl)indenyl]}zirconium η⁴-1,4-diphenyl-1,3-butadiene;
9-silafluorenediylbis{1-[2-phenyl, 4-(2,3,4-trimethylphenyl)indenyl]}zirconium η⁴-1,4-diphenyl-1,3-butadiene;
9-silafluorenediylbis{1-[2-n-propyl, 4-(2,3,5-trimethylphenyl)indenyl]}zirconium η⁴-1,4-diphenyl-1,3-butadiene;
9-silafluorenediylbis{1-[2-isopropyl, 4-(2,3,5-trimethylphenyl)indenyl]}zirconium η⁴-1,4-diphenyl-1,3-butadiene;
9-silafluorenediylbis{1-[2-n-butyl, 4-(2,3,5-trimethylphenyl)indenyl]}zirconium η⁴-1,4-diphenyl-1,3-butadiene;
9-silafluorenediylbis{1-[2-isobutyl, 4-(2,3,5-trimethylphenyl)indenyl]}zirconium η⁴-1,4-diphenyl-1,3-butadiene;
9-silafluorenediylbis{1-[2-sec-butyl, 4-(2,3,5-trimethylphenyl)indenyl]}zirconium η⁴-1,4-diphenyl-1,3-butadiene;
9-silafluorenediylbis{1-[2-tert-butyl, 4-(2,3,5-trimethylphenyl)indenyl]}zirconium η⁴-1,4-diphenyl-1,3-butadiene;
9-silafluorenediylbis{1-[2-phenyl, 4-(2,3,5-trimethylphenyl)indenyl]}zirconium η⁴-1,4-diphenyl-1,3-butadiene;
9-silafluorenediylbis{1-[2-n-propyl, 4-(2-methylphenyl)indenyl]}hafnium η⁴-1,4-diphenyl-1,3-butadiene;
9-silafluorenediylbis{1-[2-isopropyl, 4-(2-methylphenyl)indenyl]}hafnium η⁴-1,4-diphenyl-1,3-butadiene;
9-silafluorenediylbis{1-[2-n-butyl, 4-(2-methylphenyl)indenyl]}hafnium η⁴-1,4-diphenyl-1,3-butadiene;
9-silafluorenediylbis{1-[2-isobutyl, 4-(2-methylphenyl)indenyl]}hafnium η⁴-1,4-diphenyl-1,3-butadiene;
9-silafluorenediylbis{1-[2-sec-butyl, 4-(2-methylphenyl)indenyl]}hafnium η⁴-1,4-diphenyl-1,3-butadiene;
9-silafluorenediylbis{1-[2-tert-butyl, 4-(2-methylphenyl)indenyl]}hafnium η⁴-1,4-diphenyl-1,3-butadiene;
9-silafluorenediylbis{1-[2-phenyl, 4-(2-methylphenyl)indenyl]}hafnium η⁴-1,4-diphenyl-1,3-butadiene;
9-silafluorenediylbis{1-[2-n-propyl, 4-(2-ethylphenyl)indenyl]}hafnium η⁴-1,4-diphenyl-1,3-butadiene;
9-silafluorenediylbis{1-[2-isopropyl, 4-(2-ethylphenyl)indenyl]}hafnium η⁴-1,4-diphenyl-1,3-butadiene;
9-silafluorenediylbis{1-[2-n-butyl, 4-(2-ethylphenyl)indenyl]}hafnium η⁴-1,4-diphenyl-1,3-butadiene;
9-silafluorenediylbis{1-[2-isobutyl, 4-(2-ethylphenyl)indenyl]}hafnium η⁴-1,4-diphenyl-1,3-butadiene;
9-silafluorenediylbis{1-[2-sec-butyl, 4-(2-ethylphenyl)indenyl]}hafnium η⁴-1,4-diphenyl-1,3-butadiene;
9-silafluorenediylbis{1-[2-tert-butyl, 4-(2-ethylphenyl)indenyl]}hafnium η⁴-1,4-diphenyl-1,3-butadiene;
9-silafluorenediylbis{1-[2-phenyl, 4-(2-ethylphenyl)indenyl]}hafnium η⁴-1,4-diphenyl-1,3-butadiene;
9-silafluorenediylbis{1-[2-n-propyl, 4-(2-n-propylphenyl)indenyl]}hafnium η⁴-1,4-diphenyl-1,3-butadiene;
9-silafluorenediylbis{1-[2-isopropyl, 4-(2-n-propylphenyl)indenyl]}hafnium η⁴-1,4-diphenyl-1,3-butadiene;
9-silafluorenediylbis{1-[2-n-butyl, 4-(2-n-propylphenyl)indenyl]}hafnium η⁴-1,4-diphenyl-1,3-butadiene;

9-silafluorenediylbis{1-[2-isobutyl, 4-(2-n-propylphenyl) indenyl]}hafnium η⁴-1,4-diphenyl-1,3-butadiene;
9-silafluorenediylbis{1-[2-sec-butyl, 4-(2-n-propylphenyl) indenyl]}hafnium η⁴-1,4-diphenyl-1,3-butadiene;
9-silafluorenediylbis{1-[2-tert-butyl, 4-(2-n-propylphenyl) indenyl]}hafnium η⁴-1,4-diphenyl-1,3-butadiene;
9-silafluorenediylbis{1-[2-phenyl, 4-(2-n-propylphenyl) indenyl]}hafnium η⁴-1,4-diphenyl-1,3-butadiene;
9-silafluorenediylbis{1-[2-n-propyl, 4-(2-isopropylphenyl) indenyl]}hafnium η⁴-1,4-diphenyl-1,3-butadiene;
9-silafluorenediylbis{1-[2-isopropyl, 4-(2-isopropylphenyl) indenyl]}hafnium η⁴-1,4-diphenyl-1,3-butadiene;
9-silafluorenediylbis{1-[2-n-butyl, 4-(2-isopropylphenyl) indenyl]}hafnium η⁴-1,4-diphenyl-1,3-butadiene;
9-silafluorenediylbis{1-[2-isobutyl, 4-(2-isopropylphenyl) indenyl]}hafnium η⁴-1,4-diphenyl-1,3-butadiene;
9-silafluorenediylbis{1-[2-sec-butyl, 4-(2-isopropylphenyl) indenyl]}hafnium η⁴-1,4-diphenyl-1,3-butadiene;
9-silafluorenediylbis{1-[2-tert-butyl, 4-(2-isopropylphenyl) indenyl]}hafnium η⁴-1,4-diphenyl-1,3-butadiene;
9-silafluorenediylbis{1-[2-phenyl, 4-(2-isopropylphenyl) indenyl]}hafnium η⁴-1,4-diphenyl-1,3-butadiene;
9-silafluorenediylbis{1-[2-n-propyl, 4-(2-n-butylphenyl) indenyl]}hafnium η⁴-1,4-diphenyl-1,3-butadiene;
9-silafluorenediylbis{1-[2-isopropyl, 4-(2-n-butylphenyl) indenyl]}hafnium η⁴-1,4-diphenyl-1,3-butadiene;
9-silafluorenediylbis{1-[2-n-butyl, 4-(2-n-butylphenyl) indenyl]}hafnium η⁴-1,4-diphenyl-1,3-butadiene;
9-silafluorenediylbis{1-[2-isobutyl, 4-(2-n-butylphenyl) indenyl]}hafnium η⁴-1,4-diphenyl-1,3-butadiene;
9-silafluorenediylbis{1-[2-sec-butyl, 4-(2-n-butylphenyl) indenyl]}hafnium η⁴-1,4-diphenyl-1,3-butadiene;
9-silafluorenediylbis{1-[2-tert-butyl, 4-(2-n-butylphenyl) indenyl]}hafnium η⁴-1,4-diphenyl-1,3-butadiene;
9-silafluorenediylbis{1-[2-phenyl, 4-(2-n-butylphenyl) indenyl]}hafnium η⁴-1,4-diphenyl-1,3-butadiene;
9-silafluorenediylbis{1-[2-n-propyl, 4-(2-isobutylphenyl) indenyl]}hafnium η⁴-1,4-diphenyl-1,3-butadiene;
9-silafluorenediylbis{1-[2-isopropyl, 4-(2-isobutylphenyl) indenyl]}hafnium η⁴-1,4-diphenyl-1,3-butadiene;
9-silafluorenediylbis{1-[2-n-butyl, 4-(2-isobutylphenyl) indenyl]}hafnium η⁴-1,4-diphenyl-1,3-butadiene;
9-silafluorenediylbis{1-[2-isobutyl, 4-(2-isobutylphenyl) indenyl]}hafnium η⁴-1,4-diphenyl-1,3-butadiene;
9-silafluorenediylbis{1-[2-sec-butyl, 4-(2-isobutylphenyl) indenyl]}hafnium η⁴-1,4-diphenyl-1,3-butadiene;
9-silafluorenediylbis{1-[2-tert-butyl, 4-(2-isobutylphenyl) indenyl]}hafnium η⁴-1,4-diphenyl-1,3-butadiene;
9-silafluorenediylbis{1-[2-phenyl, 4-(2-isobutylphenyl) indenyl]}hafnium η⁴-1,4-diphenyl-1,3-butadiene;
9-silafluorenediylbis{1-[2-n-propyl, 4-(2-sec-butylphenyl) indenyl]}hafnium η⁴-1,4-diphenyl-1,3-butadiene;
9-silafluorenediylbis{1-[2-isopropyl, 4-(2-sec-butylphenyl) indenyl]}hafnium η⁴-1,4-diphenyl-1,3-butadiene;
9-silafluorenediylbis{1-[2-n-butyl, 4-(2-sec-butylphenyl) indenyl]}hafnium η⁴-1,4-diphenyl-1,3-butadiene;
9-silafluorenediylbis{1-[2-isobutyl, 4-(2-sec-butylphenyl) indenyl]}hafnium η⁴-1,4-diphenyl-1,3-butadiene;
9-silafluorenediylbis{1-[2-sec-butyl, 4-(2-sec-butylphenyl) indenyl]}hafnium η⁴-1,4-diphenyl-1,3-butadiene;
9-silafluorenediylbis{1-[2-tert-butyl, 4-(2-sec-butylphenyl) indenyl]}hafnium η⁴-1,4-diphenyl-1,3-butadiene;
9-silafluorenediylbis{1-[2-phenyl, 4-(2-sec-butylphenyl) indenyl]}hafnium η⁴-1,4-diphenyl-1,3-butadiene;
9-silafluorenediylbis{1-[2-n-propyl, 4-(2-tert-butylphenyl) indenyl]}hafnium η⁴-1,4-diphenyl-1,3-butadiene;
9-silafluorenediylbis{1-[2-isopropyl, 4-(2-tert-butylphenyl) indenyl]}hafnium η⁴-1,4-diphenyl-1,3-butadiene;
9-silafluorenediylbis{1-[2-n-butyl, 4-(2-tert-butylphenyl) indenyl]}hafnium η⁴-1,4-diphenyl-1,3-butadiene;
9-silafluorenediylbis{1-[2-isobutyl, 4-(2-tert-butylphenyl) indenyl]}hathium η⁴-1,4-diphenyl-1,3-butadiene;
9-silafluorenediylbis{1-[2-sec-butyl, 4-(2-tert-butylphenyl) indenyl]}hafnium η⁴-1,4-diphenyl-1,3-butadiene;
9-silafluorenediylbis{1-[2-tert-butyl, 4-(2-tert-butylphenyl) indenyl]}hafnium η⁴-1,4-diphenyl-1,3-butadiene;
9-silafluorenediylbis{1-[2-phenyl, 4-(2-tert-butylphenyl) indenyl]}hafnium η⁴-1,4-diphenyl-1,3-butadiene;
9-silafluorenediylbis{1-[2-n-propyl, 4-(2-biphenyl) indenyl]} hafnium η⁴-1,4-diphenyl-1,3-butadiene;
9-silafluorenediylbis{1-[2-isopropyl, 4-(2-biphenyl) indenyl]}hafnium η⁴-1,4-diphenyl-1,3-butadiene;
9-silafluorenediylbis{1-[2-n-butyl, 4-(2-biphenyl)indenyl]} hafnium η⁴-1,4-diphenyl-1,3-butadiene;
9-silafluorenediylbis{1-[2-isobutyl, 4-(2-biphenyl) indenyl]} hafnium η⁴-1,4-diphenyl-1,3-butadiene;
9-silafluorenediylbis{1-[2-sec-butyl, 4-(2-biphenyl) indenyl]} hafnium η⁴-1,4-diphenyl-1,3-butadiene;
9-silafluorenediylbis{1-[2-tert-butyl, 4-(2-biphenyl) indenyl]}hafnium η⁴-1,4-diphenyl-1,3-butadiene;
9-silafluorenediylbis{1-[2-phenyl, 4-(2-biphenyl)indenyl]} hafnium η⁴-1,4-diphenyl-1,3-butadiene;
9-silafluorenediylbis{1-[2-n-propyl, 4-(2-α-naphthylphenyl)indenyl]}hafnium η⁴-1,4-diphenyl-1,3-butadiene;
9-silafluorenediylbis{1-[2-isopropyl, 4-(2-α-naphthylphenyl)indenyl]}hafnium η⁴-1,4-diphenyl-1,3-butadiene;
9-silafluorenediylbis{1-[2-n-butyl, 4-(2-α-naphthylphenyl) indenyl]}hafnium η⁴-1,4-diphenyl-1,3-butadiene;
9-silafluorenediylbis{1-[2-isobutyl, 4-(2-α-naphthylphenyl) indenyl]}hafnium η⁴-1,4-diphenyl-1,3-butadiene;
9-silafluorenediylbis{1-[2-sec-butyl, 4-(2-α-naphthylphenyl)indenyl]}hafnium η⁴-1,4-diphenyl-1,3-butadiene;
9-silafluorenediylbis{1-[2-tert-butyl, 4-(2-α-naphthylphenyl)indenyl]}hafnium η⁴-1,4-diphenyl-1,3-butadiene;
9-silafluorenediylbis{1-[2-phenyl, 4-(2-α-naphthylphenyl) indenyl]}hafnium η⁴-1,4-diphenyl-1,3-butadiene;
9-silafluorenediylbis{1-[2-n-propyl, 4-(2-β-naphthylphenyl)indenyl]}hafnium η⁴-1,4-diphenyl-1,3-butadiene;
9-silafluorenediylbis{1-[2-isopropyl, 4-(2-β-naphthylphenyl)indenyl]}hafnium η⁴-1,4-diphenyl-1,3-butadiene;
9-silafluorenediylbis{1-[2-n-butyl, 4-(2-β-naphthylphenyl) indenyl]}hafnium η⁴-1,4-diphenyl-1,3-butadiene;
9-silafluorenediylbis{1-[2-isobutyl, 4-(2-β-naphthylphenyl) indenyl]}hafnium η⁴-1,4-diphenyl-1,3-butadiene;
9-silafluorenediylbis{1-[2-sec-butyl, 4-(2-β-naphthylphenyl)indenyl]}hafnium η⁴-1,4-diphenyl-1,3-butadiene;
9-silafluorenediylbis{1-[2-tert-butyl, 4-(2-β-naphthylphenyl)indenyl]}hafnium η⁴-1,4-diphenyl-1,3-butadiene;
9-silafluorenediylbis{1-[2-phenyl, 4-(2-β-naphthylphenyl) indenyl]}hafnium η⁴-1,4-diphenyl-1,3-butadiene;
9-silafluorenediylbis{1-[2-n-propyl, 4-(2-trifluoromethylphenyl)indenyl]}-hafnium η⁴-1,4-diphenyl-1,3-butadiene;
9-silafluorenediylbis{1-[2-isopropyl, 4-(2-trifluoromethylphenyl)indenyl]}-hafnium η⁴-1,4-diphenyl-1,3-butadiene;
9-silafluorenediylbis{1-[2-n-butyl, 4-(2-trifluoromethylphenyl)indenyl]}-hafnium η⁴-1,4-diphenyl-1,3-butadiene;

9-silafluorenediylbis{1-[2-isobutyl, 4-(2-trifluoromethylphenyl)indenyl]}-hafnium $\eta^4$-1,4-diphenyl-1,3-butadiene;

9-silafluorenediylbis{1-[2-sec-butyl, 4-(2-trifluoromethylphenyl)indenyl]}-hafnium $\eta^4$-1,4-diphenyl-1,3-butadiene;

9-silafluorenediylbis{1-[2-tert-butyl, 4-(2-trifluoromethylphenyl)indenyl]}-hafnium $\eta^4$-1,4-diphenyl-1,3-butadiene;

9-silafluorenediylbis{1-[2-phenyl, 4-(2-trifluoromethylphenyl)indenyl]}-hafnium $\eta^4$-1,4-diphenyl-1,3-butadiene;

9-silafluorenediylbis{1-[2-n-propyl, 4-(2,3-dimethylphenyl)indenyl]}hafnium $\eta^4$-1,4-diphenyl-1,3-butadiene;

9-silafluorenediylbis{1-[2-isopropyl, 4-(2,3-dimethylphenyl)indenyl]}hafnium $\eta^4$-1,4-diphenyl-1,3-butadiene;

9-silafluorenediylbis{1-[2-n-butyl, 4-(2,3-dimethylphenyl)indenyl]}hafnium $\eta^4$-1,4-diphenyl-1,3-butadiene;

9-silafluorenediylbis{1-[2-isobutyl, 4-(2,3-dimethylphenyl)indenyl]}hafnium $\eta^4$-1,4-diphenyl-1,3-butadiene;

9-silafluorenediylbis{1-[2-sec-butyl, 4-(2,3-dimethylphenyl)indenyl]}hafnium $\eta^4$-1,4-diphenyl-1,3-butadiene;

9-silafluorenediylbis{1-[2-tert-butyl, 4-(2,3-dimethylphenyl)indenyl]}hafnium $\eta^4$-1,4-diphenyl-1,3-butadiene;

9-silafluorenediylbis{1-[2-phenyl, 4-(2,3-dimethylphenyl)indenyl]}hafnium $\eta^4$-1,4-diphenyl-1,3-butadiene;

9-silafluorenediylbis{1-[2-n-propyl, 4-(2,3,4-trimethylphenyl)indenyl]}hafnium $\eta^4$-1,4-diphenyl-1,3-butadiene;

9-silafluorenediylbis{1-[2-isopropyl, 4-(2,3,4-trimethylphenyl)indenyl]}hafnium $\eta^4$-1,4-diphenyl-1,3-butadiene;

9-silafluorenediylbis{1-[2-n-butyl, 4-(2,3,4-trimethylphenyl)indenyl]}hafnium $\eta^4$-1,4-diphenyl-1,3-butadiene;

9-silafluorenediylbis{1-[2-isobutyl, 4-(2,3,4-trimethylphenyl)indenyl]}hafnium $\eta^4$-1,4-diphenyl-1,3-butadiene;

9-silafluorenediylbis{1-[2-sec-butyl, 4-(2,3,4-trimethylphenyl)indenyl]}hafnium $\eta^4$-1,4-diphenyl-1,3-butadiene;

9-silafluorenediylbis{1-[2-tert-butyl, 4-(2,3,4-trimethylphenyl)indenyl]}hafnium $\eta^4$-1,4-diphenyl-1,3-butadiene;

9-silafluorenediylbis{1-[2-phenyl, 4-(2,3,4-trimethylphenyl)indenyl]}hafnium $\eta^4$-1,4-diphenyl-1,3-butadiene;

9-silafluorenediylbis{1-[2-n-propyl, 4-(2,3,5-trimethylphenyl)indenyl]}hafnium $\eta^4$-1,4-diphenyl-1,3-butadiene;

9-silafluorenediylbis{1-[2-isopropyl, 4-(2,3,5-trimethylphenyl)indenyl]}hafnium $\eta^4$-1,4-diphenyl-1,3-butadiene;

9-silafluorenediylbis{1-[2-n-butyl, 4-(2,3,5-trimethylphenyl)indenyl]}hafnium $\eta^4$-1,4-diphenyl-1,3-butadiene;

9-silafluorenediylbis{1-[2-isobutyl, 4-(2,3,5-trimethylphenyl)indenyl]}hafnium $\eta^4$-1,4-diphenyl-1,3-butadiene;

9-silafluorenediylbis{1-[2-sec-butyl, 4-(2,3,5-trimethylphenyl)indenyl]}hafnium $\eta^4$-1,4-diphenyl-1,3-butadiene;

9-silafluorenediylbis{1-[2-tert-butyl, 4-(2,3,5-trimethylphenyl)indenyl]}hafnium $\eta^4$-1,4-diphenyl-1,3-butadiene; and 9-silafluorenediylbis{1-[2-phenyl, 4-(2,3,5-trimethylphenyl)indenyl]}hafnium $\eta^4$-1,4-diphenyl-1,3-butadiene.

The above names represent the individual stereoisomers as well as mixtures of any ratios thereof. For example, "dimethylsilanediylbis{1-[2-n-propyl, 4-(2-methylphenyl)indenyl]}zirconium dichloride" represents rac-dimethylsilanediylbis{1-[2-n-propyl, 4-(2-methylphenyl)indenyl]}zirconium dichloride, meso-dimethylsilanediylbis{1-[2-n-propyl, 4-(2-methylphenyl)indenyl]}zirconium dichloride and any mixtures of these compounds.

Moreover, "biphenylyl" in the above names is synonymous with "phenylphenyl".

"9-silafluorenediyl-" refers to a group of the following formula:

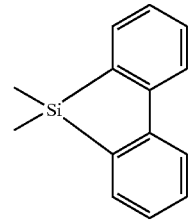

The metallocenes of this invention are prepared according to general techniques known from the literature, for example U.S. Pat. Nos. 5,789,634 and 5,840,644 (both fully incorporated herein by reference).

Generally, metallocenes of this type are synthesized as shown below (for $R^4$=H) where (a) is an aryl-coupling reaction between a 4-halosubstituted indene and an aryl Grignard reagent catalyzed by NiCl$_2$(PPh$_3$)$_2$ in ether-type solvents at room temperature to reflux. Product is usually purified by column chromatography or distillation. (b) is a deprotonation via a metal salt of an alkyl anion (e.g. n-BuLi) to form an indenide followed by reaction with an appropriate bridging precursor (e.g. Me$_2$SiCl$_2$). Reactions are usually done in ether-type solvents at ambient temperatures. The final product is purified by column chromatography or distillation; and (c) is double deprotonation via an alkyl anion (e.g. n-BuLi) to form a dianion followed by reaction with a metal halide (e.g. ZrCl$_4$). The reactions are usually done in ether-type or aromatic solvents at ambient temperatures. The final products are obtained by recrystallization of the crude solids.

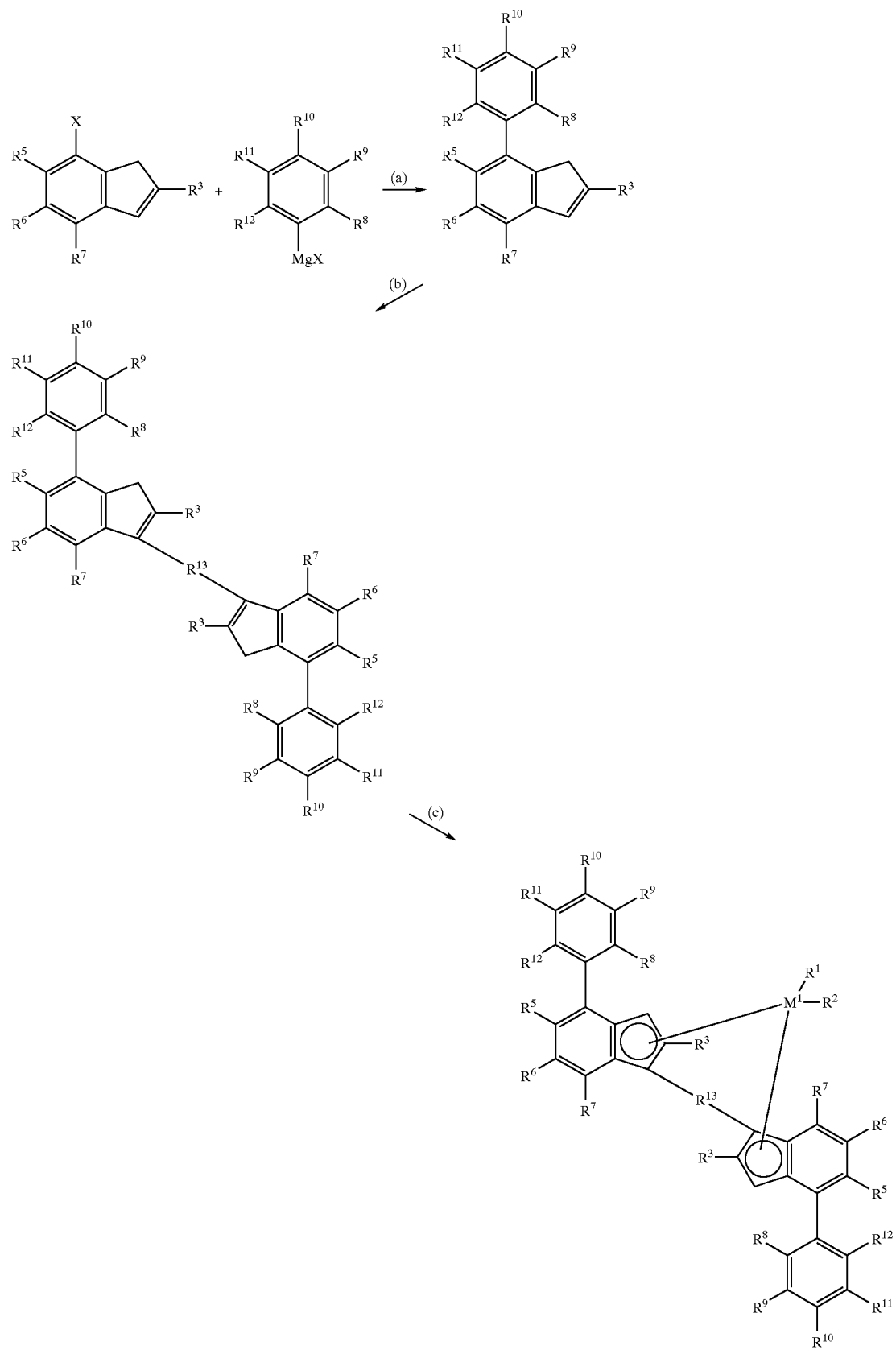

The metallocenes of this invention are highly active catalyst components for the polymerization of olefins. They can form different stereoisomers and are preferably employed as chiral racemates. However, it is also possible to use the individual enantiomers in the (+) or (−) form. The individual stereoisomers allow an optically active polymer to be prepared. In some cases it may be desirable to remove the meso form of the metallocenes, since the polymerization-active center (the metal atom) in these compounds is no longer chiral due to the mirror symmetry at the central metal atom and it is, therefore, not possible to produce a highly isotactic polymer. If the meso form is not removed, atactic polymer is formed in addition to isotactic polymer. For certain applications (e.g., if a random copolymer of propylene and ethylene and/or any other monoolefin and/or diene is to be made) this may be entirely desirable. Accordingly, racemic metallocenes contaminated with not more than about 5%, preferably not more than about 2%, and even more preferred not more than about 1%, of the meso form represent a particularly preferred embodiment of the metallocenes of the present invention. In another preferred embodiment, the meso form of a metallocene of the present invention is contaminated with not more than about 5%, preferably not more than about 2%, and even more preferred not more than about 1%, of the racemic form.

Rac/meso metallocene isomer separation is facilitated when metallocenes containing certain bridging groups are prepared. This has been found to be true when the bridging group, $R^{13}$, is represented by the formula:

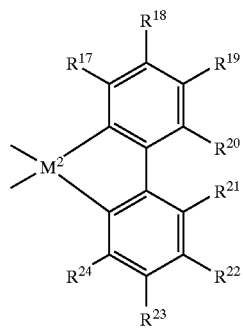

wherein $M^2$ and $R^{17}$ to $R^{24}$ are as defined above.

Metallocenes are generally used in combination with some form of activator in order to create an active catalyst system. The terms "activator" and "cocatalyst" are used interchangeably and are defined herein to mean any compound or component, or combination of compounds or components, capable of enhancing the ability of one or more metallocenes to polymerize olefins.

Alkylalumoxanes such as methylalumoxane (MAO) are commonly used as metallocene activators. The alumoxanes which may be employed according to the present invention are not particularly limited. They include oligomeric linear and/or cyclic alkylalumoxanes of the general formula R—(Al(R)—O)$_n$—AlR$_2$ for oligomeric, linear alumoxanes and (—Al(R)—O—)$_m$ for oligomeric cyclic alumoxanes wherein n usually is 1–40, preferably 10–20, m usually is 3–40, preferably 3–20, and R usually is a $C_1$–$C_8$ alkyl group (e.g., methyl, ethyl, n-propyl, isopropyl, n-butyl and isobutyl), and preferably methyl to provide methylalumoxane (MAO). MAO is a mixture of oligomers with a very wide distribution of molecular weights and usually with an average molecular weight of about 1200. MAO is typically kept in solution in toluene. It is also possible to use, for the present purpose, alumoxanes of the type just described wherein the alkyl groups in the above general formulae are different. A preferred example thereof is modified methylalumoxane (MMAO) wherein in comparison to MAO a part of the methyl groups is replaced by other alkyl groups. Alumoxane solutions, particularly methylalumoxane solutions, may be obtained from commercial vendors as solutions having various concentrations. There are a variety of methods for preparing alumoxane, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,103,031, 6,001,766 and EP-A-0 561 476, EP-B1-0 279 586, EP-A-0 594-218 and WO 94/10180, each fully incorporated herein by reference.

Generally the atomic ratio of Al in the alumoxane to metal in the metallocene compound is at least about 10:1, more preferably at least about 50:1, and most preferred at least about 80:1. On the other hand said ratio is generally not higher than about 1,000:1, particularly not higher than about 500:1, with a ratio of not higher than about 300:1 being particularly preferred.

Ionizing activators may also be used to activate metallocenes. These activators are neutral or ionic, or are compounds such as tri(n-butyl)ammonium tetrakis (pentafluorophenyl)borate, which ionize the neutral metallocene compound. Unlike alumoxane cocatalysts, these ionizing activators can usually be employed in a molar ratio with respect to the metallocene which is much closer to 1:1 (e.g., less than 5:1, less than 2:1, and preferably about 1:1). Such ionizing compounds may contain an active proton, or some other cation associated with, but not coordinated or only loosely coordinated to, the remaining ion of the ionizing compound. Combinations of activators may also be used, for example, alumoxane and ionizing activator combination, see for example, WO 94/07928 (incorporated herein by reference in its entirety).

Descriptions of ionic catalysts for coordination polymerization comprised of metallocene cations activated by non-coordinating anions appear in the early work in EP-A0 277 003, EP-A-0 277 004 and U.S. Pat. No. 5,198,401 and WO-A-92/00333 (each fully incorporated herein by reference). These teach desirable methods of preparation wherein metallocenes are protonated by an anion precursor such that an alkyl/hydride group is abstracted from a transition metal to make it both cationic and charge-balanced by the non-coordinating anion. Suitable ionic salts include tetrakis-substituted borate or aluminum salts having fluorinated aryl-constituents such as phenyl, biphenyl and naphthyl.

The term "noncoordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Non-coordinating anions useful in accordance with this invention are those which are compatible, stabilize the metallocene cation in the sense of balancing its ionic charge at +1, yet retain sufficient lability to permit displacement by an ethylenically or acetylenically unsaturated monomer during polymerization.

The use of ionizing ionic compounds not containing an active proton but capable of producing both the active metallocene cation and a non-coordinating anion is also known. See, for example, EP-A-0 426 637 and EP-A-0 573 403 (each fully incorporated herein by reference). An additional method of making the ionic catalysts uses ionizing anion precursors which are initially neutral Lewis acids but form the cation and anion upon ionizing reaction with the metallocene compounds, for example the use of tris (pentafluorophenyl)borane. See EP-A-0 520732 (incorporated herein by reference in its entirety). Ionic catalysts for addition polymerization can also be prepared by oxidation of the metal centers of transition metal compounds by anion precursors containing metallic oxidizing groups along with the anion groups, see EP-A-0 495 375 (fully incorporated herein by reference).

Where the metal ligands include halogen moieties (for example, chloride) which are not capable of ionizing abstraction under standard conditions, they can be converted via known alkylation reactions with organometallic compounds such as lithium or aluminum hydrides or alkyls, alkylalumoxanes, Grignard reagents, etc. See EP-A-0 500 944 and EP-A1-0 570 982 (each fully incorporated herein by reference) for in situ processes describing the reaction of alkyl aluminum compounds with dihalo-substituted metallocene compounds prior to or with the addition of activating anionic compounds.

Methods for supporting ionic catalysts comprising metallocene cations and NCAs are described in WO 9950311, U.S. Pat. Nos. 5,643,847 and 5,972,823, U.S. patent application Ser. No. 09/184,358, filed Nov. 2, 1998, now U.S. Pat. No. 6,228,795, and U.S. patent application Ser. No. 09/184, 389, filed Nov. 2, 1998 now U.S. Pat. No. 6,143,689, (each fully incorporated herein by reference).

When the activator for the metallocene supported catalyst composition is a NCA, preferably the NCA is first added to the support composition followed by the addition of the metallocene catalyst. When the activator is MAO, preferably the MAO and metallocene catalyst are dissolved together in solution. The support is then contacted with the MAO/metallocene catalyst solution. Other methods and orders of addition will be apparent to those skilled in the art.

The catalyst compositions of this invention preferably comprise a support. Suitable supports include porous particulate materials, such as for example, talc, inorganic oxides, inorganic chlorides such as magnesium chloride, and resinous materials such as polyolefins or other polymers.

Preferably, the support materials are porous inorganic oxide materials, which include those from the Periodic Table of Elements of Groups 2, 3, 4, 5, 13 or 14 metalmetalloid oxides. Silica, alumina, silica-alumina, and mixtures thereof are particularly preferable. Other inorganic oxides that may be employed either alone or in combination with the silica, alumina or silica-alumina are magnesia, titania, zirconia, and the like In one preferred embodiment the support material is porous silica, more preferably porous silica which has a surface area in the range of not less than 10, preferably not less than 50, and most preferred not less than 100 m²/g, but usually not more than 700, preferably not more than 500, and most preferred not more than 400 m²/g. The total pore volume thereof usually is not less than 0.1, preferably not less than 0.5, and most preferred not less than 0.8 cc/g, whereas the pore volume generally is not higher than 4.0, preferably not higher than 3.5, most preferred not higher than 3.0 cc/g. The average particle size of the porous silica should be at least 10, preferably at least 20, and most preferred at least 30 μm, the maximum value thereof usually being not higher than 500, preferably not higher than 200, and most preferred not higher than 100 μm. The average pore size of typical porous support materials usually is at least 10, preferably at least 50, and even more preferably at least 75 Å. Average pore sizes should generally not be higher than 1000, preferably not higher than 500, and most preferred not higher than 350 Å. It may be particularly desirable to dehydrate the silica at a temperature of from 100° C. to 800° C. anywhere from 3 to 24 hours.

The metallocene, activator and support material may be combined in any number of ways. More than one metallocene may also be used. Examples of suitable support techniques are described in U.S. Pat. Nos. 4,808,561 and 4,701,432 (each fully incorporated herein by reference). Preferably metallocene and activator are combined and their contact product is supported on the porous support material as described in U.S. Pat. No. 5,240,894 and WO 94/28034, WO 96/00243, and WO 96/00245 (each fully incorporated herein by reference). Alternatively, the metallocenes may be preactivated separately and then combined with the support material either separately or together. If the metallocenes are separately supported, then preferably, they are dried and then combined as a powder before use in polymerization.

Regardless of whether the metallocene(s) and their activator are separately precontacted or whether the metallocene (s) and activator are combined at once, in some instances it may be preferred that the total volume of reaction solution applied to the porous support is less than 4 times the total pore volume of the porous support, more preferably less than 3 times the total pore volume of the porous support and even more preferably in the range of from more than 1 to less than 2.5 times the total pore volume of the porous support. Procedures for measuring the total pore volume of porous support are well known in the art. One such method is described in Volume 1, Experimental Methods in Catalyst Research, Academic Press, 1968, pages 67–96, fully incorporated herein by reference.

The supported catalyst system may be used directly in polymerization or the catalyst system may be prepolymerized using methods well known in the art. For details regarding prepolymerization, see U.S. Pat. Nos. 4,923,833 and 4,921,825, and EP 0 279 863 and EP 0 354 893 (each fully incorporated herein by reference).

The metallocene catalyst systems described herein are useful in the polymerization of all types of olefins. This includes polymerization processes which produce homopolymers, copolymers, terpolymers and the like as well as block copolymers and impact copolymers. These polymerization processes may be carried out in solution, in suspension or in the gas phase, continuously or batchwise, or any combination thereof, in one or more steps, usually at a temperature not lower than 30, preferably not lower than 50, most preferred not lower than 80° C., and not higher than 200, preferably not higher than 120, most preferred not higher than 100° C. Preferably, the polymerization or copolymerization is carried out using olefins of the formula $R^a$—CH=CH—$R^b$. In this formula, $R^a$ and $R^b$ are identical or different and are a hydrogen atom or an alkyl or alkenyl radical having 1 to 14 carbon atoms. Alternatively, $R^a$ and $R^b$ may form a ring together with the carbon atoms connecting them. Examples of such olefins are ethylene, propylene, 1-butene, 1-hexene, 4-methyl-1-pentene, and 1-octene, vinylcyclohexene, norbornene and norbornadiene. In particular, propylene and ethylene are polymerized. The metallocenes and metallocenes catalyst systems of this invention are most suitable for the polymerization of propylene based polymers.

If necessary, hydrogen is added as a molecular-weight regulator and/or in order to increase the activity. The overall pressure in the polymerization system usually is at least about 0.5 bar, preferably at least about 2 bar, most preferred at least about 5 bar. Pressures higher than about 100, e.g., higher than about 80 bar and, in particular higher than about 64 bar are usually not preferred.

Typically, the metallocene is used in the polymerization in a concentration, based on the transition metal, of not less $10^{-4}$, preferably not less than $10^{-3}$ mol, and not higher than $10^7$, preferably not higher than $10^4$ mol, of transition metal per $dm^3$ of solvent or per $dm^3$ of reactor volume. When alumoxane is used as the cocatalyst, it is used in a concentration of usually not less than $10^{-4}$, preferably not less than $10^{-5}$ mol, and not higher than $10^{-1}$, preferably not higher than $10^{-2}$ mol, per $dm^3$ of solvent or per $dm^3$ of reactor volume. The other cocatalysts mentioned are used in an approximately equimolar amount (e.g., from about 1.2:1 to about 1:1.2) with respect to the metallocene. In principle, however, higher concentrations are also possible.

If the polymerization is carried out as a suspension or solution polymerization, an inert solvent which is customary for the Ziegler low-pressure process is typically used for example, the polymerization is carried out in an aliphatic or cycloaliphatic hydrocarbon; examples of which are propane, butane, hexane, heptane, isooctane, cyclohexane and methylcyclohexane. It is also possible to use mineral spirit or a hydrogenated diesel oil fraction. Toluene can also be used. The polymerization is preferably carried out in the liquid monomer(s). If inert solvents are used, the monomer(s) is (are) metered in gas or liquid form.

Before addition of the catalyst, in particular of the supported catalyst system, another alkylaluminum compound, such as, for example, trimethylaluminum, triethylaluminum, triisobutylaluminum, trioctylaluminum or isoprenylaluminum, may additionally be introduced into the reactor in order to render the polymerization system inert (for example to remove catalyst poisons present in the olefin). This compound is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This allows the molar $Al/M^1$ ratio to be selected at a low level in the synthesis of a supported catalyst system.

In principle, however, the use of further substances for catalysis of the polymerization reaction is unnecessary, i.e., the systems according to the invention can be used as the only catalysts for the polymerization of olefins.

The process according to the invention is distinguished by the fact that the metallocenes described can give propylene polymers of very high molecular weight, melting point, and very high stereotacticity, with high catalyst activities in, e.g., the temperature range from about 40° C. to about 100° C., such as the industrially particularly interesting polymerization temperature range of from about 50° C. to about 80° C.

The catalyst systems of this invention are capable of providing polymers, particularly propylene homopolymers and copolymers, of exceptionally high molecular weight and melting point even when used in processes under commercially relevant conditions of temperature, pressure and catalyst activity. Preferred melting points of olefin polymers comprising at least about 99% by weight, preferably are at least about 99.3% by weight and most preferred at least 99.5% by weight of units derived from propylene (the remainder being preferably derived from one or more compounds selected from ethylene and 1-olefins comprising 4 to 12 carbon atoms, most preferred ethylene) are as high as 155° C., e.g., as high as 156° C., more preferably at least 157° C., even more preferably at least 158° C. and may be as high as 160° C. or even higher (these melting points being determined by DSC according to the procedure described in the Examples below).

With respect to molecular weights, copolymers made with the catalyst systems of the present invention such as, e.g., ethylene/propylene rubbers (EPR's) or ethylene/propylene/diene copolymers (EPDM's), usually have an intrinsic viscosity, measured in decalin at 135° C., of usually at least about 1.8, preferably at least about 2.0, and more preferred at least about 2.1 (e.g., at least about 2.2). This enables the production of very satisfactory impact copolymers (ICP's), such as in situ blends of propylene homopolymer or copolymer as discussed above of high melting point (and preferably also high molecular weight) and propylene copolymers (such as EPR's and/or EPDM's) of high intrinsic viscosity with a single catalyst system (and, preferably, in a single reactor). For this purpose, the copolymers generally will have an ethylene content of at least about 30, preferably at least about 35, more preferred at least about 40 weight % and not more than about 60, preferably not more than about 50 weight %. The ethylene content of the ICP's usually will be at least about 1.5, preferably at least about 3 weight percent and up to about 20, preferably up to about 15, weight %.

The homo- and copolymers made with the catalyst systems of the present invention (e.g., those containing units derived from propylene, or from propylene and ethylene) also have a narrow molecular weight distribution, $M_w/M_n$, usually of not higher than about 3.5, preferably not higher than about 3.0, more preferred not higher than about 2.5 and sometimes even not higher than about 2.2. They also are distinguished by low xylene and n-hexane extractables contents. Often the xylene extractables and/or the n-hexane extractables of these homo- and copolymers will amount to less than about 2.0, preferably less than about 1.5, even more preferred less than about 1.0 weight %. A general description of the procedure for measuring the xylene extractables (solubles) is found in J. C. Randall, J. Poly. Sci.: Part A Polymer Chemistry, Vol. 36, 1527–1542 (1998), incorporated herein by reference in its entirety. Hexane extractions are performed by weighing the polymer sample in a dried soxhlet thimble. Hexane is heated to reflux through the thimble in the soxhlet apparatus. When the extraction is complete the solvent is evaporated, and the sample dried under the appropriate vacuum. The amount of extractables is determined by weight. The thimble containing the insoluble polymer is dried in a vacuum oven and the weight of the recovered polymer is determined.

The polymer compositions of the present invention are also characterized by a relatively narrow molecular weight distribution. Their values of $M_w/M_n$ (as determined by Gel Permeation Chromatography using polystyrene standards, see Examples below) usually are not higher than about 3.5, often not higher than about 3.0, e.g., not higher than about 2.7.

Catalyst systems of this invention are capable of providing propylene polymers having high stereospecificity and regiospecificity. Isotactic propylene polymers prepared according to the processes of this invention may have a proportion of 2,1-inserted propene units of less than about 0.5%, at a triad tacticity of greater than about 98% (see, for example, the results summarized in Table 21C, below). Preferably, there is no measurable proportion of 2,1-inserted propene units. Triad tacticity is determined using $^{13}$C-NMR according to J. C. Randall, Polymer Sequence Determination: Carbon-13 NMR Method, Academic Press New York 1978, incorporated herein by reference in its entirety.

Polymers prepared using the processes described herein find uses in all applications including fibers, injection-molded parts, films, pipes, and wire and cable applications. Non-limiting examples include carpet fibers and primary and secondary carpet backing; slit tape applications such as tarpaulins, erosion abatement screens, sand bags, fertilizer and feed bags, swimming pool covers, intermediate bulk container (IBC) bags; non-woven applications for spunbonded, melt blown and thermobonded carded web applications such as disposable diaper liners, feminine hygiene products, tarpaulins and tent fabrics, and hospital garments; apparel applications such as socks, T-shirts, undergarments, bicycle shorts, sweat bands, football undershirts, hiking socks and other outdoor sporting apparel; cordage applications such as mooring and towing lines and rope applications; netting applications such as safety fences, geogrids for soil stabilization; injection molded applications such as appliance parts in automatic dishwashers and clothes washers, hand tools and kitchen appliances; consumer product applications such as outdoor furniture, luggage, infant car seats, ice coolers, yard equipment; medical applications such as disposable syringes and other hospital and laboratory devices; rigid packaging made by injection molding, blow molding or thermoforming such as margarine tubs, yogurt containers and closures, commercial bottles and ready-to-eat food containers; transportation applications such as automotive interior trim, instrument panels, bumper fascia, grills and external trim parts, battery cases, film applications such as snack packages and other food packaging and film labels, packing tapes and pressure sensitive labels; wire and cable applications such as wire insulation.

While the present invention has been described and illustrated by reference to particular embodiments, it will be appreciated by those of ordinary skill in the art, that the invention lends itself to many different variations not illustrated herein. For these reasons, then, reference should be made solely to the appended claims for purposes of determining the true scope of the present invention.

Although the appendant claims have single appendencies in accordance with U.S. patent practice, each of the features in any of the appendant claims can be combined with each of the features of other appendant claims or the main claim.

EXAMPLES

All air sensitive experiments were carried out in nitrogen purged dry boxes. All solvents were purchased from commercial sources. Aluminum alkyls were purchased as hydrocarbon solutions from commercial sources. The commercial methylalumoxane ("MAO") was purchased from Albemarle as a 30 wt % solution in toluene.

Example 1

Racemic dimethylsilanediylbis{1-[2-methyl, 4-phenylindenyl]}zirconium dichloride was obtained from commercial sources and used as received.

Supported Metallocene Catalyst System 1

In a 100 mL round bottom flask racemic dimethylsilanediylbis{1-[2-methyl, 4-phenylindenyl]} zirconium dichloride (0.055 g) was added to the above MAO solution (6.74 g, 7.2 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes then dried at 40° C. for two minutes under vacuum on a rotary evaporator until the liquid evaporated and then the solid was further dried a total of about 2 hours and twenty two minutes. The supported catalyst was recovered as a light orange, free flowing solid (5.63 g).

Example 2

2-Methyl, 4-(3-methylphenyl)-indene

3-Bromotoluene (10.0 g, 58 mmol) and magnesium turnings (2.0 g, 83 mmol) were taken up in 150 mL of $Et_2O$ (diethyl ether) and stirred at room temperature overnight to form the Grignard solution. In a separate flask, $NiCl_2(PPh_3)_2$ (1.8 g, 2.8 mmol) and 4-chloro-2-methylindene (9.5 g, 58 mmol) were dissolved in 150 mL of $Et_2O$. The Grignard solution was added dropwise to this solution and allowed to stir overnight at reflux. After overnight stirring, the reaction was slowly quenched with $H_2O$ to neutralize unreacted Grignard. The solution was subsequently treated with 100 mL of 10% HCl(aq), and neutralized with saturated sodium bicarbonate aqueous solution. The organic layer was dried with magnesium sulfate and the solvent removed by rotary evaporation. The remaining residue was loaded onto a silica gel column and eluted with hexane. Yield: 6.3 g (48%).

Lithium {1-[2-methyl, 4-(3-methylphenyl) indenide]}

2-Methyl, 4-(3-methylphenyl)-indene (6.3 g, 28 mmol) was dissolved in 100 mL of pentane. To this solution was added 11 mL of n-BuLi (n-butyl lithium; 2.5M in hexane) and the reaction was allowed to stir 5 hours at room temperature. A yellow-white solid precipitated from the solution and was collected by frit filtration and washed with additional pentane. Yield: 6.0 g (95%).

Dimethylsilanediylbis{1-[2-methyl, 4-(3-methylphenyl)indene]}

$Me_2SiCl_2$ (dichlorodimethylsilane; 0.83 g, 6.5 mmol) was dissolved in 80 ml of THF. While stirring, lithium{1-[2-methyl, 4-(3-methylphenyl)indenide]} (3.0 g, 13 mmol) was added as a dry powder and the contents were allowed to stir at reflux overnight. The solvent was removed in vacuo and the residue was taken up in pentane and filtered to remove LiCl salts. The pentane was removed in vacuo, and the crude product was isolated. Yield: 2.4 g (74%)

Dimethylsilanediylbis{1-[2-methyl,4-(3-methylphenyl)indenyl]}zirconium dichloride Dimethylsilanediylbis{1-[2-methyl,4-(3-methylphenyl) indene]} (2.4 g, 4.6 mmol) was dissolved in 50 mL of $Et_2O$. To this solution was added 3.7 mL of n-BuLi (2.5M in hexane) and stirred for 3 hours. The solution was then cooled to −35° C. and $ZrCl_4$ (1.1 g, 5.9 mmol) was added as a dry powder and the reaction was stirred at room temperature overnight. The solvent was removed in vacuo and the residue was taken up in toluene. The solution was filtered through a celite packed frit to remove LiCl, concentrated and cooled to −35° C. to induce crystallization. Yellow-orange crystals of the racemic isomer were isolated. Yield: 260 mg (8.6%).

Supported Metallocene Catalyst System 2

In a 100 mL round bottom flask dimethylsilanediylbis{1-[2-methyl, 4-(3-methylphenyl)indenyl]}zirconium dichloride (0.058 g) was added to the above MAO-toluene solution (6.74 g) and stirred twenty minutes. The resultant mixture was filtered through a medium glass frit funnel and washed with toluene (14 mL). To the combined filtrates were added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and twenty nine minutes. The supported catalyst was recovered as a reddish orange, free flowing solid (5.58 g).

Example 3

2-Methyl, 4-(3,5-dimethylphenyl)-indene

4-Chloro-2-methylindene (8.9 g, 54 mmol) and $NiCl_2(PPh_3)_2$ (1.8 g, 2.8 mmol) were dissolved in 150 mL of $Et_2O$. 3,5-Dimethylphenylmagnesium bromide (10 g, 54 mmol) as $Et_2O$ solution was added to the solution and the reaction was stirred overnight at room temperature. After overnight stirring the reaction was slowly quenched with $H_2O$ to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield. 5.6 g (44%).

Lithium{1-[2-methyl, 4-(3,5-dimethylphenyl) indenide]}

2-Methyl, 4-(3,5-dimethylphenyl)-indene (5.6 g, 23.9 mmol) was dissolved in 80 mL of pentane. To this solution was added 9.6 mL of n-BuLi (2.5M in hexane) and the reaction was allowed to stir 4 hours at room temperature. A white solid precipitated from solution and was collected by frit filtration and washed with additional pentane. Yield: 4.5 g (80%).

Dimethylsilanediylbis{1-[2-methyl, 4-(3,5-dimethylphenyl)indene]}

$Me_2SiCl_2$ (1.2 g, 9.4 mmol) was dissolved in 80 mL of THF. While stirring, lithium{1-[2-methyl, 4-(3,5-dimethylphenyl)indenide]} (4.5 g, 18.7 mmol) was added as a dry powder and the contents were allowed to stir overnight at room temperature. The solvent was removed in vacuo and the residue was taken up in pentane and filtered to remove LiCl salts. The pentane was removed in vacuo to yield a flaky white solid (4.23 g, 87%).

Dimethylsilanediylbis{1-[2-methyl, 4-(3,5-dimethylphenyl)indenyl]}zirconium dichloride Dimethylsilanediylbis{1-[2-methyl, 4-(3,5-dimethylphenyl)indene]} (4.23 g, 8.0 mmol) was dissolved in 60 mL of $Et_2O$. While stirring, 6.4 mL of n-BuLi (2.5M in hexane) was added and allowed to stir at room temperature for 2 hours. After this time, the solution was cooled to −35° C. and $ZrCl_4$ (1.58 g, 8.0 mmol) was added and allowed to stir at room temperature for 3 hours. The solvent was then removed in vacuo and the residue was taken up in a mixture of methylene chloride and pentane and filtered to remove LiCl salts. The filtrate was then concentrated and chilled to −35° C. to induce crystallization. 0.23 g (5.0%) of pure racemic compound was obtained.

Supported Metallocene Catalyst System 3

In a 100 mL round bottom flask dimethylsilanediylbis{1-[2-methyl, 4-(3,5-dimethylphenyl)indenyl]}zirconium dichloride (0.061 g) was added to the above MAO-toluene solution (6.74 g, 7.35 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration) This slurry was stirred for twenty minutes, then dried at 40° C. for two minutes under vacuum on a rotary evaporator until the liquid evaporated and then the solid was further dried a total of about two hours and twenty six minutes. The supported catalyst was recovered as a light orange, free flowing solid (5.36 g).

Example 4

2-Methyl, 4-(2-methylphenyl)-indene

2-Bromotoluene (8.8 g, 51 mmol) and magnesium turnings (24 g, 102 mmol) were taken up in 100 mL of $Et_2O$ (diethyl ether) and stirred at room temperature for 4 hours to form the Grignard solution. In a separate flask, $NiCl_2(PPh_3)_2$ (1.8 g, 2.8 mmol) and 4-chloro-2-methylindene (8.4 g, 51 mmol) were dissolved in 300 mL of $Et_2O$. The Grignard solution was added dropwise to this solution and allowed to stir overnight at reflux. After overnight stirring, the reaction was slowly quenched with $H_2O$ to neutralize unreacted Grignard. The solution was subsequently treated with 100 mL of 10% HCl(aq) and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 5.3 g (47%).

Lithium{1-[2-methyl, 4-(2-methylphenyl)indenide]}

2-Methyl, 4-(2-methylphenyl)indene (5.3 g, 5.9 mmol) was dissolved in 100 mL of pentane. To this solution was added 9.6 mL of n-BuLi (2.5M in hexane) and the reaction was allowed to stir 5 hours at room temperature. A yellow-white solid precipitated from solution and was collected by frit filtration and washed with additional pentane. Yield: 4.6 g (87%).

Dimethylsilanediylbis{1-[2-methyl, 4-(2-methylphenyl)indene]}

$Me_2SiCl_2$ (1.3 g, 10 mmol) was dissolved in 80 mL of pentane and 60 ml of THF. While stirring, lithium{1-[2-methyl, 4-(2-methylphenyl)-indenide]} (4.6 g, 20 mmol) was added as a dry powder and the contents were allowed to stir at reflux for 4 hours. The solvent was removed in vacuo and the residue was taken up in pentane and filtered to remove LiCl salts. The pentane was removed in vacuo, and the crude product was isolated as a viscous oil. Yield: 3.5 g (69%).

Dilithium dimethylsilanediylbis{1-[2-methyl, 4-(2-methylphenyl)indenide]}

Dimethylsilanediylbis{1-[2-methyl, 4-(2-methylphenyl) indene]} (3.5 g, 4.8 mmol) was dissolved in 80 mL of $Et_2O$. To this solution was added 5.4 mL of n-BuLi (2.5M in hexane) and the reaction was allowed to stir for 3 hours. The solution was filtered through a celite-packed frit and the solvent was removed in vacuo to produce a flaky white solid, which was washed with pentane. Yield of solid: 3.0 g (86%).

Dimethylsilanediylbis{1-[2-methyl, 4-(2-methylphenyl)indenyl]}zirconium dichloride Dilithiumdimethylsilanediylbis{1-[2-methyl,4-(2-methylphenyl)indenide]}(3.0 g, 5.9 mmol) was dissolved in 80 mL of Et$_2$O and cooled to −30° C. To this solution was added ZrCl$_4$ (1.37 g, 5.9 mmol) as a dry powder and the reaction was stirred at room temperature overnight. The solvent was removed in vacuo and the residue was taken up in toluene. The solution was filtered through a celite packed frit to remove LiCl, concentrated and cooled to −35° C. to induce crystallization. Yellow-orange crystals of the racemic isomer were isolated. Yield: 220 mg (5.1%)

Supported Metallocene Catalyst System 4

In a 100 mL round bottom flask dimethylsilanediylbis{1-[2-methyl,4-(2-methylphenyl)indenyl]}zirconium dichloride (0.058 g) was added to the above MAO-toluene solution (6.74 g, 7.35 mL) and stirred for twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and thirty two minutes. The supported catalyst was recovered as a salmon orange, free flowing solid (5.34 g).

Example 5

2-Methyl, 4-(2-ethylphenyl)-indene

2-Ethylphenylbromide (10.0 g, 46 mmol) and magnesium turnings (2.0 g, 83 mmol) were taken up in 150 mL of Et$_2$O and stirred at room temperature for 4 hours to form the Grignard solution. In a separate flask, NiCl$_2$(PPh$_3$)$_2$ (1.8 g, 2.8 mmol) and 4-chloro-2-methylindene (7.5 g, 46 mmol) were dissolved in 150 mL of Et$_2$O. The Grignard solution was added dropwise to this solution and allowed to stir overnight at reflux. After overnight stirring, the reaction was slowly quenched with H$_2$O to neutralize unreacted Grignard. Thereafter the solution was treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 7.6 g (71%).

Lithium{1-[2-methyl, 4-(2-ethylphenyl)indenide]}

2-Methyl, 4-(2-ethylphenyl)-indene (7.6 g, 32 mmol) was dissolved in 80 mL of pentane. To this solution was added 13 mL of n-BuLi (2.5M in hexane) and the reaction was allowed to stir 5 hours at room temperature. A yellow-white solid precipitated from solution and was collected by frit filtration and washed with additional pentane. Yield: 7.0 g (92%).

Dimethylsilanediylbis{1-[2-methyl, 4-(2-ethylphenyl)indene]}

Me$_2$SiCl$_2$ (0.82 g, 6.4 mmol) was dissolved in 80 mL of pentane and 50 ml of THF. While stirring, lithium{1-[2-methyl, 4-(2-ethylphenyl)indenide]} (3.0 g, 13 mmol) was added as a dry powder and the contents were allowed to stir at reflux overnight. The solvent was removed in vacuo and the residue was taken up in pentane and filtered to remove LiCl salts. The pentane was removed in vacuo, and the crude product was isolated as a fluffy white solid. Yield: 2.8 g (86%).

Dimethylsilanediylbis{1-[2-methyl, 4-(2-ethylphenyl)indenyl]}zirconium dichloride Dimethylsilanediylbis{1-[2-methyl, 4-(2-ethylphenyl)indene]} (2.5 g, 4.7 mmol) was dissolved in 50 mL of Et$_2$O. To this solution was added 4.4 mL of n-BuLi (2.5M in hexane) and the solution was allowed to stir at room temperature for 2 hours. After this time, the solution was cooled to −35° C. and ZrCl$_4$ (1.1 g, 4.7 mmol) was added as a dry powder. The reaction was allowed to warm to room temperature and was stirred overnight. The solution was filtered through a celite-packed frit to remove LiCl, concentrated, and cooled to −35° C. to induce crystallization. Yellow-orange crystals of the racemic isomer were obtained. Yield: 170 mg (5.2%).

Supported Metallocene Catalyst System 5

In a 100 mL round bottom flask dimethylsilanediylbis{1-[2-methyl, 4-(2-ethylphenyl)indenyl]}zirconium dichloride (0.061 g) was added to the above MAO-toluene solution (6.74 g) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about two hours and thirty three minutes. The supported catalyst was recovered as a pink, free flowing solid (5.57 g).

Example 6

2-Methyl, 4-(2-isopropylphenyl)-indene

2-Isopropylbromobenzene (10 g, 45 mmol) and magnesium (2.4 g, 100 mmol) were combined in 200 mL of diethyl ether and stirred at room temperature overnight to form a Grignard solution. 4-Chloro-2-methylindene (7.4 g, 45 mmol) and NiCl$_2$(PPh$_3$)$_2$ (1.8 g, 2.8 mmol) were dissolved in 150 mL of Et$_2$O. To this was added the Grignard solution and the reaction was stirred overnight at room temperature. After overnight stirring, the reaction was slowly quenched with H$_2$O to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 4.4 g (39%).

Lithium{1-[2-methyl, 4-(2-isopropylphenyl) indenide]}

2-Methyl, 4-(2-isopropylphenyl)-indene (4.4 g, 18 mmol) was dissolved in 80 mL of pentane. To this solution was added 7.0 mL of n-BuLi (2.5M in hexane) and the reaction was allowed to stir 4 hours at room temperature. A white solid precipitated from solution and was collected by frit filtration and washed with additional pentane. Yield: 4.0 g (90%).

Dimethylsilanediylbis{1-[2-methyl, 4-(2-isopropylphenyl)indene]}

Me$_2$SiCl$_2$ (1.0 g, 7.7 mmol) was dissolved in 80 mL of THF. While stirring, lithium{1-[2-methyl, 4-(2-isopropylphenyl)indenide]} (4.0 g, 15.5 mmol) was added as a dry powder and the contents were allowed to stir overnight at room temperature. The solvent was removed in vacuo and the residue was taken up in pentane and filtered to remove LiCl salts. The pentane was removed in vacuo to yield a flaky white solid (2.1 g, 48%).

Dimethylsilanediylbis{1-[2-methyl, 4-(2-isopropylphenyl)indenyl]}zirconium dichloride Dimethylsilanediylbis{1-[2-methyl, 4-(2-isopropylphenyl)indene]} (2.1 g, 3.8 mmol) was dissolved in 60 mL of Et$_2$O. While stirring, 3.0 mL of n-BuLi (2.5M in hexane) was added and allowed to stir at room temperature for 2 hours. After this time, the solution was cooled to −35° C. and ZrCl$_4$ (0.88 g, 3.8 mmol) was added and allowed to stir at room temperature for 3 hours. The solvent was then removed in vacuo and the residue was taken up in a mixture of methylene chloride and pentane and filtered to remove LiCl salts. The filtrate was then concentrated and chilled to −35° C. to induce crystallization. 0.34 g (13%) of pure racemic compound was obtained.

Supported Metallocene Catalyst System 6

In a 100 mL round bottom flask dimethylsilanediylbis{1-[2-methyl, 4-(2-isopropylphenyl)indenyl]}zirconium dichloride (0.063 g) was added to the above MAO-toluene solution (6.74 g, 7.2 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about two hours and twenty two minutes. The supported catalyst was recovered as a light orange, free flowing solid (5.56 g).

Example 7

2-Methyl, 4-(2-biphenylyl)-indene

Magnesium (2.0 g, 83 mmol), 2-bromobiphenyl (10 g, 43 mmol) were added together in 100 mL of diethyl ether and allowed to stir overnight at reflux to form a Grignard solution. 4-Chloro-2-methylindene (6.4 g, 43 mmol) and NiCl$_2$(PPh$_3$)$_2$ (1.5 g, 2.3 mmol) were dissolved in 150 mL of Et$_2$O. The Grignard solution was added and the reaction was stirred overnight at reflux. After overnight stirring, the reaction was slowly quenched with H$_2$O to neutralize unreacted Grignard. The solution was subsequently treated with 100 ml, of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 3.9 g (32%).

Lithium{1-[2-methyl, 4-(2-biphenylyl)indenide]}

2-Methyl, 4-(2-biphenylyl)-indene (3.9 g, 14 mmol) was dissolved in 100 mL of pentane. To this solution was added 5.6 mL of n-BuLi (2.5M in hexane) and the reaction was allowed to stir 4 hours at room temperature. A white solid precipitated from solution and was collected by frit filtration and washed with additional pentane. Yield: 3.0 g (76%).

Dimethylsilanediylbis{1-[2-methyl, 4-(2-biphenylyl)indene]}

Me$_2$SiCl$_2$ (0.67 g, 5.2 mmol) was dissolved in 60 mL of diethyl ether. While stirring, lithium{1-[2-methyl, 4-(2-biphenylyl)indenide]} (3.0 g, 10 mmol) was added as a dry powder and a few drops of THF were added to catalyze the reaction. The contents were allowed to stir overnight at room temperature. The solvent was removed in vacuo and the residue was taken up in pentane and filtered to remove LiCl salts. The pentane was removed in vacuo to yield a flaky white solid. Yield: 2.3 g (72%).

Dimethylsilanediylbis{1-[2-methyl, 4-(2-biphenylyl)indenyl]}zirconium dichloride Dimethylsilanediylbis{1-[2-methyl, 4-(2-biphenylyl)indene]} (2.3 g, 3.7 mmol) was dissolved in 50 mL of Et$_2$O.

While stirring, 3.0 mL of n-BuLi (2.5M in hexane) was added and allowed to stir at room temperature for 0.5 hours. After this time, the solution was cooled to −35° C. and ZrCl$_4$ (0.87 g, 3.7 mmol) was added and allowed to stir at room temperature for 3 hours. The solvent was then removed in vacuo and the residue was taken up in a mixture of methylene chloride and pentane and filtered to remove LiCl salts. The filtrate was then concentrated and chilled to −35° C. to induce crystallization. 0.22 g (7.5%) of pure racemic isomer was isolated.

Supported Metallocene Catalyst System 7

In a 100 mL round bottom flask dimethylsilanediylbis{1-[2-methyl, 4-(2-biphenylyl)indenyl]}zirconium dichloride (0.058 g) was added to the above MAO-toluene solution (5.68 g, 6.05 mL) and stirred twenty minutes. The resultant mixture was filtered through a medium glass frit funnel and washed with toluene (11.8 mL). To the combined filtrates was added dehydrated silica (3.37 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and twelve minutes. The supported catalyst was recovered as a pink-red, free flowing solid (4.58 g).

Example 8

2-Methyl, 4-(4-biphenylyl)indene

4-Bromobiphenyl (10 g, 39 mmol) and magnesium (2.0 g, 83 mmol) were combined in 100 mL of diethyl ether and stirred at room temperature overnight to form a Grignard solution. 4-Chloro-2-methylindene (6.4 g, 39 mmol) and NiCl$_2$(PPh$_3$)$_2$ (1.8 g, 2.8 mmol) were dissolved in 150 mL of Et$_2$O. To this was added the Grignard solution and the reaction was stirred overnight at room temperature. After overnight stirring, the reaction was slowly quenched with H$_2$O to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 5.3 g (44%).

Lithium{1-[2-methyl, 4-(4-biphenylyl)indenide]}

2-Methyl, 4-(4-biphenylyl)-indene (5.3 g, 19 mmol) was dissolved in 80 mL of pentane. To this solution was added 7.5 mL of n-BuLi (2.5M in hexane) and the reaction was allowed to stir 4 hours at room temperature. A white solid precipitated from solution and was collected by frit filtration and washed with additional pentane. Yield: 3.4 g (64%).

Dimethylsilanediylbis{1-[2-methyl, 4-(4-biphenylyl)indene]}

Me$_2$SiCl$_2$ (0.77 g, 5.9 mmol) was dissolved in 80 mL of THF. While stirring, lithium{1-[2-methyl, 4-(4-biphenylyl)indenide]} (3.4 g, 12 mmol) was added as a dry powder and the contents were allowed to stir overnight at room temperature. The solvent was removed in vacuo and the residue was taken up in pentane and filtered to remove LiCl salts. The pentane was removed in vacuo to yield a flaky white solid (1.8 g, 49%).

Dimethylsilanediylbis{1-[2-methyl, 4-(4-biphenylyl)indenyl]}zirconium dichloride Dimethylsilanediylbis{1-[2-methyl, 4-(4-biphenylyl)indene]} (1.8 g, 2.9 mmol) was dissolved in 60 mL of Et$_2$O.

While stirring, 2.3 mL of n-BuLi (2.5M in hexane) was added and allowed to stir at room temperature for 2 hours. After this time, the solution was cooled to −35° C. and ZrCl$_4$ (0.67 g, 5.2 mmol) was added and allowed to stir at room temperature for 3 hours. The solvent was then removed in vacuo and the residue was taken up in a mixture of methylene chloride and pentane and filtered to remove LiCl salts. The filtrate was then concentrated and chilled to −35° C. to induce crystallization. 0.093 g (4.1%) of pure racemic compound was obtained.

Supported Metallocene Catalyst System 8

In a 100 mL round bottom flask dimethylsilanediylbis{1-[2-methyl, 4-(4-biphenylyl)indenyl]}zirconium dichloride (0.075 g) was mixed with the above MAO-toluene solution (7.2 g, 7.8 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and twenty seven minutes. The supported catalyst was recovered as a reddish pink, free flowing solid (5.25 g).

Example 9

2-Methyl, 4-(4-tert-butylphenyl)-indene

Magnesium (3.4 g, 141 mmol) and 4-tert-butylbromobenzene (20 g, 94 mmol) were added together in 200 mL of diethyl ether and allowed to stir overnight at reflux to form a Grignard solution. 4-Chloro-2-methylindene (15.4 g, 94 mmol) and NiCl$_2$(PPh$_3$)$_2$ (1.5 g, 2.3 mmol) were dissolved in 200 mL of Et$_2$O. The Grignard solution was added and the reaction was stirred overnight at reflux. After overnight stirring, the reaction was slowly quenched with H$_2$O to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 9.8 g (40%).

Lithium {1-[2-methyl, 4-(4-tert-butylphenyl)indenide]}

2-Methyl, 4-(4-tert-butylphenyl)-indene (4.0 g, 15 mmol) was dissolved in 100 mL of pentane. To this solution was added 6.1 mL of n-BuLi (2.5M in hexane) and the reaction was allowed to stir 4 hours at room temperature. A white solid precipitated from solution and was collected by frit filtration and washed with additional pentane. Yield: 4.0 g (99%).

Dimethylsilanediylbis{1-[2-methyl, 4-(4-tert-butylphenyl)indene]}

Me$_2$SiCl$_2$ (0.98 g, 7.6 mmol) was dissolved in 50 mL of diethyl ether. While stirring, lithium{1-[2-methyl, 4-(4-tert-butylphenyl)indenide]} (4.0 g, 15 mmol) was added as a dry powder and a few drops of THF were added to catalyze the reaction. The contents were allowed to stir overnight at room temperature. The solvent was removed in vacuo and the residue was taken up in pentane and filtered to remove LiCl salts. The pentane was removed in vacuo to yield an oil. The crude oil was loaded onto a silica gel column and eluted with hexane. Yield of product was 2.4 g (54%).

Dimethylsilanediylbis{1-[2-methyl, 4-(4-tert-butylphenyl)indenyl]}zirconium dichloride Dimethylsilanediylbis{1-[2-methyl, 4-(4-tert-butylphenyl)indene]} (2.4 g, 4.1 mmol) was dissolved in 40 mL of Et$_2$O. While stirring, 5.6 mL of n-BuLi (2.5M in hexane) was added and allowed to stir at room temperature for 0.5 hours. After this time, the solution was cooled to −35° C. and ZrCl$_4$ (0.96 g, 4.1 mmol) was added and allowed to stir at room temperature for 3 hours. The solvent was then removed in vacuo and the residue was taken up in a mixture of methylene chloride and pentane and filtered to remove LiCl salts. The filtrate was then concentrated and chilled to −35° C. to induce crystallization. Yield of product was 1.4 g (46%) as 1:1 mixture of racemic and meso isomers.

Supported Metallocene Catalyst System 9

In a 100 mL round bottom flask a racemic/meso mixture of dimethylsilanediylbis{1-[2-methyl,4-(4-tert-butylphenyl)indenyl]}zirconium dichloride (0.030 g) was added to the above MAO-toluene solution (3.37 g, 3.6 mL) and stirred twenty minutes. The resultant mixture was filtered through a medium glass frit funnel and washed with toluene (7 mL). To the combined filtrates was added dehydrated silica (2.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and fifteen minutes. The supported catalyst was recovered as a pinkish, free flowing solid (2.55 g).

Example 10

2-Methyl, 4-(2,3-dimethylphenyl)-indene

3-Bromo-o-xylene (12.0 g, 64 mmol) and magnesium turnings (2.3 g, 96 mmol) were taken up in 200 mL of Et$_2$O and stirred at room temperature overnight to form a Grignard solution. In a separate flask, NiCl$_2$(PPh$_3$)$_2$ (1.8 g, 2.8 mmol) and 4-chloro-2-methylindene (11 g, 64 mmol) were dissolved in 100 mL of Et$_2$O. The Grignard solution was added dropwise to this solution and allowed to stir overnight at reflux. After overnight stirring, the reaction was slowly quenched with H$_2$O to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 6.6 g (44%).

Lithium{1-[2-methyl, 4-(2,3-dimethylphenyl)indenide]}

2-Methyl, 4-(2,3-dimethylphenyl)indene (6.6 g, 28 mmol) was dissolved 20 in 200 mL of pentane. To this solution was added 11 mL of n-BuLi (2.5M in hexane) and 3 mL of diethyl ether and the reaction was allowed to stir 1 hour at room temperature. A yellow-white solid precipitated from solution and was collected by frit filtration and washed with additional pentane. Yield: 6.5 g (99%).

Dimethylsilanediylbis{1-[2-methyl, 4-(2,3-dimethylphenyl)indene]}

Me$_2$SiCl$_2$ (0.81 g, 6.3 mmol) was dissolved in 40 ml of THF. While stirring, lithium{1-[2-methyl, 4-(2,3-dimethylphenyl)indenide]} (3.0 g, 13 mmol) was added as a dry powder and the contents were allowed to stir at reflux overnight. The solvent was removed in vacuo and the residue was taken up in pentane and filtered to remove LiCl salts. The pentane solution was cooled and white crystals of the product precipitated from solution. Yield: 3.3 g (100%).

Dimethylsilanediylbis{1-[2-methyl, 4-(2,3-dimethylphenyl)indenyl]}zirconium dichloride Dimethylsilanediylbis{1-[2-methyl, 4-(2,3-dimethylphenyl)indene]} (3.3 g, 6.3 mmol) was dissolved in 50 mL of $Et_2O$. To this solution was added 5.0 mL of n-BuLi (2.5M in hexane) and stirred for 3 hours. The solution was then cooled to −30° C. and $ZrCl_4$ (1.5 g, 6.3 mmol) was added as a dry powder and the reaction was stirred at room temperature overnight. The solvent was removed in vacuo and the residue was taken up in toluene. The solution was filtered through a celite packed frit to remove LiCl, concentrated and cooled to −35 C to induce crystallization. Yellow-orange crystals of the racemic isomer were isolated. Yield: 220 mg (5.1%).

Supported Metallocene Catalyst System 10

In a 100 mL round bottom flask dimethylsilanediylbis{1-[2-methyl, 4-(2,3-dimethylphenyl)indenyl]}zirconium dichloride (0.061 g) was added to the above MAO-toluene solution (6.74 g, 7.2 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and thirty minutes. The supported catalyst was recovered as a pink, free flowing solid (5.53 g).

Example 11

2-Methyl, 4-(2,4-dimethylphenyl)-indene

4-Bromo-m-xylene (15 g, 80 mmol) and magnesium turnings (2.9 g, 120 mmol) were taken up in 200 mL of diethyl ether and stirred at room temperature overnight to form a Grignard solution. In a separate flask, $NiCl_2(PPh_3)_2$ (1.8 g, 2.8 mmol) and 4chloro-2-methylindene (13 g, 80 mmol) were dissolved in 100 mL of $Et_2O$. The Grignard solution was added dropwise to this solution and allowed to stir overnight at reflux. After overnight stirring, the reaction was slowly quenched with $H_2O$ to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 11 g (59%).

Lithium{1-[2-methyl, 4-(2,4-dimethylphenyl)indenide]}

2-Methyl, 4-(2,4-dimethylphenyl)-indene (11 g, 28 mmol) was dissolved in 200 mL of pentane. To this solution was added 19 mL of n-BuLi (2.5M in hexane) and 3 mL of diethyl ether and the reaction was allowed to stir 1 hour at room temperature. A yellow-white solid precipitated from solution and was collected by frit filtration and washed with additional pentane. Yield: 11 g (99%).

Dimethylsilanediylbis{1-[2-methyl, 4-(2,4-dimethylphenyl)indene]}

$Me_2SiCl_2$ (0.83 g, 6.4 mmol) was dissolved in 40 ml of THF. While stirring, lithium{1-[2-methyl, 4-(2,4-dimethylphenyl)indenide]} (3.0 g, 13 mmol) was added as a dry powder and the contents were allowed to stir at reflux overnight. The solvent was removed in vacuo and the residue was taken up in pentane and filtered to remove LiCl salts. The pentane solution was cooled and white crystals of the product precipitated from solution. Yield: 3.3 g (100%).

Dimethylsilanediylbis{1-[2-methyl, 4-(2,4-dimethylphenyl)indenyl]}zirconium dichloride Dimethylsilanediylbis{1-[2-methyl, 4-(2,4-dimethylphenyl)indene]} (3.3 g, 6.3 mmol) was dissolved in 50 mL of $Et_2O$. To this solution was added 5.0 mL of n-BuLi (2.5M in hexane) and stirred for 3 hours. The solution was then cooled to −30° C. and $ZrCl_4$ (1.5 g, 6.3 mmol) was added as a dry powder and the reaction was stirred at room temperature overnight. The solvent was removed in vacuo and the residue was taken up in toluene. The solution was filtered through a celite packed frit to remove LiCl, concentrated and cooled to −35° C. to induce crystallization. Yellow-orange crystals of the racemic isomer were isolated. Yield: 700 mg (16%).

Supported Metallocene Catalyst System 11

In a 100 mL round bottom flask dimethylsilanediylbis{1-[2-methyl, 4-(2,4-dimethylphenyl)indenyl]}zirconium dichloride (0.061 g) was added to the above MAO-toluene solution (6.74 g, 7.2 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about two hours and fifteen minutes. The supported catalyst was recovered as a pinkish red, free flowing solid (5.68 g).

Example 12

2-Methyl, 4-(2,6-dimethylphenyl)-indene

2-Bromo-m-xylene (10.0 g, 54 mmol) and magnesium turnings (2.4 g, 100 mmol) were taken up in 150 mL of $Et_2O$ and stirred at room temperature for 4 hours to form a Grignard solution. In a separate flask, $NiCl_2(PPh_3)_2$ (1.8 g, 2.8 mmol) and 4-chloro-2-methylindene (8.9 g, 54 mmol) were dissolved in 150 mL of $Et_2O$. The Grignard solution was added dropwise to this solution and allowed to stir overnight at reflux. After overnight stirring, the reaction was slowly quenched with $H_2O$ to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 4.0 g (32%).

Lithium{1-[2-methyl, 4-(2,6-dimethylphenyl)indenide]}

2-Methyl, 4-(2,6-dimethylphenyl)-indene (4.0 g, 17 mmol) was dissolved in 80 mL of pentane. To this solution was added 6.8 mL of n-BuLi (2.5M in hexane) and the reaction was allowed to stir 2 hours at room temperature. A yellow-white solid precipitated from solution and was collected by frit filtration and washed with additional pentane. Yield: 4.0 g (100%).

Dimethylsilanediylbis{1-[2-methyl, 4-(2,6-dimethylphenyl)indene]}

$Me_2SiCl_2$ (1.1 g, 8.5 mmol) was dissolved in 80 ml of THF. While stirring, lithium{1-[2-methyl, 4-(2,6- dimethylphenyl)indenide]} (4.0 g, 17 mmol) was added as a dry powder and the contents were allowed to stir at reflux overnight. The solvent was removed in vacuo and the residue was taken up in pentane and filtered to remove LiCl salts. The pentane solution was cooled and white crystals of the product precipitated from solution. Yield: 1.7 g (86%).

Dimethylsilanediylbis{1-[2-methyl, 4-(2,6-dimethylphenyl)indenyl]}zirconium dichloride Dimethylsilanediylbis{1-[2-methyl, 4-(2,6-dimethylphenyl)indene]} (1.4 g, 2.7 mmol) was dissolved in 80 mL of Et$_2$O. To this solution was added 2.2 mL of n-BuLi (2.5M in hexane) and the solution was allowed to stir at room temperature for 2 hours. After this time, the solution was cooled to −35° C. and ZrCl$_4$ (0.63 g, 2.7 mmol) was added as a dry powder. The reaction was allowed to warm to room temperature and was stirred overnight. The solution was filtered through a celite-packed frit to remove LiCl, concentrated, and cooled to −35° C. to induce crystallization. Yellow-orange crystals of the racemic isomer were obtained. Yield: 450 mg (24%).

Supported Metallocene Catalyst System 12

In a 100 mL round bottom flask dimethylsilanediylbis{1-[2-methyl, 4-(2,6-dimethylphenyl)indenyl]}zirconium dichloride (0.061 g) was added to the above MAO-toluene solution (6.74 g, 7.3 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about two hours and forty one minutes. The supported catalyst was recovered as a reddish orange, free flowing solid (5.39 g).

Example 13

2-Methyl, 4-(2,5-dimethylphenyl)indene

2-Bromo-p-xylene (20 g, 108 mmol) and magnesium turnings (4.0 g, 162 mmol) were taken up in 300 mL of Et$_2$O and stirred at room temperature overnight to form a Grignard solution. In a separate flask, NiCl$_2$(PPh$_3$)$_2$ (1.8 g, 2.8 mmol) and 4-chloro-2-methylindene (18 g, 108 mmol) were dissolved in 200 mL of Et$_2$O. The Grignard solution was added dropwise to this solution and allowed to stir overnight at reflux. After overnight stirring, the reaction was slowly quenched with H$_2$O to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 9.2 g (36%).

Dimethylsilanediylbis{1-[2-methyl, 4-(2,5-dimethylphenyl)indene]}

2-Methyl, 4-(2,5-dimethylphenyl)-indene (4.0 g, 17 mmol) was dissolved in 30 mL of Et$_2$O and cooled to −30° C. To this solution was added 6.8 mL of n-BuLi (2.5M in hexane) and the reaction was allowed to stir 1 hour at room temperature. Me$_2$SiCl$_2$ (1.1 g, 8.5 mmol) was dissolved in 20 ml of THF and added dropwise to the reaction and the contents were allowed to stir at reflux overnight. The solvent was removed in vacuo and the residue was taken up in pentane and filtered to remove LiCl salts. The pentane was removed in vacuo and the remaining residue was loaded onto a silica gel column and eluted with hexane. Yield of product was 2.8 g (62%).

Dimethylsilanediylbis{1-[2-methyl, 4-(2,5-dimethylphenyl)indenyl]}zirconium dichloride Dimethylsilanediylbis{1-[2-methyl, 4-(2,5-dimethylphenyl)indene]} (2.8 g, 5.3 mmol) was dissolved in 50 mL of Et$_2$O. To this solution was added 4.3 mL of n-BuLi (2.5M in hexane) and stirred for 3 hours. The solution was then cooled to −30° C. and ZrCl$_4$ (1.2 g, 5.3 mmol) was added as a dry powder and the reaction was stirred at room temperature overnight. The solvent was removed in vacuo and the residue was taken up in toluene. The solution was filtered through a celite packed frit to remove LiCl, and concentrated and cooled to −35° C. to induce crystallization. Yellow-orange crystals of the racemic isomer were isolated. Yield: 60 mg (1.6%).

Supported Metallocene Catalyst System 13

In a 100 mL round bottom flask dimethylsilanediylbis{1-[2-methyl, 4-(2,5-dimethylphenyl)indenyl]}zirconium dichloride (0.061 g) was added to the above MAO-toluene solution (6.74 g, 7.3 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about two hours and thirty three minutes. The supported catalyst was recovered as a reddish pink, free flowing solid (5.48 g).

Example 14

2-Methyl, 4-(2,3,4-trimethylphenyl)-indene 2,3,4-Trimethylbromobenzene (10 g, 50 mmol) and magnesium turnings (2.4 g, 100 mmol) were taken up in 150 mL of Et$_2$O and stirred at room temperature overnight to form a Grignard solution. In a separate flask, NiCl$_2$(PPh$_3$)$_2$ (1.8 g, 2.8 mmol) and 4chloro-2-methylindene (8.3 g, 50 mmol) were dissolved in 200 mL of Et$_2$O. The Grignard solution was added dropwise to this solution and allowed to stir overnight at reflux. After overnight stirring, the reaction was slowly quenched with H2O to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 5.5 g (44%).

Lithium{1-[2-methyl, 4-(2,3,4-trimethylphenyl)indenide]}

2-Methyl, 4-(2,3,4-trimethylphenyl)-indene (5.5 g, 22 mmol) was dissolved in 200 mL of pentane. To this solution was added 8.9 mL of n-BuLi (2.5M in hexane) and 3 mL of diethyl ether and the reaction was allowed to stir 1 hour at room temperature. A yellow-white solid precipitated from solution and was collected by frit filtration and washed with additional pentane. Yield: 5.3 g (97%).

Dimethylsilanediylbis{1-[2-methyl, 4-(2,3,4-trimethylphenyl)indene]}

Me$_2$SiCl$_2$ (0.76 g, 5.9 mmol) was dissolved in 40 ml of THF. While stirring, lithium{1-[2-methyl, 4-(2,3,4- trimethylphenyl)indenide]} (3.0 g, 12 mmol) was added as a dry powder and the contents were allowed to stir at reflux overnight. The solvent was removed in vacuo and the residue was taken up in pentane and filtered to remove LiCl salts. The pentane was removed in vacuo, and the crude product was isolated. Yield: 3.5 g (100%).

Dimethylsilanediylbis{1-[2-methyl, 4-(2,3,4-trimethylphenyl)indenyl]}zirconium dichloride Dimethylsilanediylbis{1-[2-methyl, 4-(2,3,4-trimethylphenyl)indene]} (3.5 g, 5.9 mmol) was dissolved in 50 mL of $Et_2O$. To this solution was added 9.4 mL of n-BuLi (2.5M in hexane) and stirred for 1 hour. The solution was then cooled to −30° C. and $ZrCl_4$ (1.4 g, 5.9 mmol) was added as a dry powder and the reaction was stirred at room temperature overnight. The solvent was removed in vacuo and the residue was taken up in toluene. The solution was filtered through a celite packed frit to remove LiCl, concentrated and cooled to −35° C. to induce crystallization. Yellow-orange crystals of the racemic isomer were isolated. Yield: 350 mg (8.0%).

Supported Metallocene Catalyst System 14

In a 100 mL round bottom flask dimethylsilanediylbis{1-[2-methyl, 4-(2,3,4-trimethylphenyl)indenyl]}zirconium dichloride (0.063 g) was added to the above MAO-toluene solution (6.74 g, 7.2 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about two hours and twenty minutes. The supported catalyst was recovered as an orange, free flowing solid (5.29 g).

Example 15

2-Methyl, 4-(2,4,5-trimethylphenyl)-indene 2,4,5-Trimethylbromobenzene (10 g, 50 mmol) and magnesium (2.4 g, 100 mmol) were combined in 200 mL of diethyl ether and stirred at room temperature overnight to form a Grignard solution. 4-Chloro-2-methylindene (8.3 g, 50 mmol) and $NiCl_2(PPh_3)_2$ (1.8 g, 2.8 mmol) were dissolved in 150 mL of $Et_2O$. To this was added the Grignard solution and the reaction was stirred overnight at room temperature. After overnight stirring, the reaction was slowly quenched with $H_2O$ to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 6.0 g (48%).

Lithium{1-[2-methyl, 4-(2,4,5-trimethylphenyl) indenide]}

2-Methyl, 4-(2,4,5-trimethylphenyl)-indene (6.0 g, 24 mmol) was dissolved in 80 mL of pentane. To this solution was added 9.7 mL of n-BuLi (2.5M in hexane) and the reaction was allowed to stir 4 hours at room temperature. A white solid precipitated from solution and was collected by frit filtration and washed with additional pentane. Yield: 5.5 g (92%).

Dimethylsilanediylbis{1-[2-methyl, 4-(2,4,5-trimethylphenyl)indene]}

$Me_2SiCl_2$ (0.76 g, 5.9 mmol) was dissolved in 80 mL of THF. While stirring, lithium{1-[2-methyl, 4-(2,4,5- trimethylphenyl)indenide]} (3.0 g, 12 mmol) was added as a dry powder and the contents were allowed to stir overnight at room temperature. The solvent was removed in vacuo and the residue was taken up in pentane and filtered to remove LiCl salts. The pentane was removed in vacuo to yield a flaky white solid (2.9 g, 88%).

Dimethylsilanediylbis{1-[2-methyl, 4-(2,4,5-trimethylphenyl)indenyl]}zirconium dichloride Dimethylsilanediylbis{1-[2-methyl, 4-(2,4,5-trimethylphenyl)indene]} (2.9 g, 5.2 mmol) was dissolved in 60 mL of $Et_2O$. While stirring, 4.1 mL of n-BuLi (2.5M in hexane) was added and allowed to stir at room temperature for 2 hours. After this time, the solution was cooled to −35° C. and $ZrCl_4$ (1.2 g, 5.2 mmol) was added and allowed to stir at room temperature for 3 hours. The solvent was then removed in vacuo and the residue was taken up in a mixture of methylene chloride and pentane and filtered to remove LiCl salts. The filtrate was then concentrated and chilled to −35° C. to induce crystallization. 0.52 g (14%) of pure racemic compound was obtained.

Supported Metallocene Catalyst System 15

In a 100 mL round bottom flask dimethylsilanediylbis{1-[2-methyl, 4-(2,4,5-trimethylphenyl)indenyl]}zirconium dichloride (0.063 g) was added to the above MAO-toluene solution (6.74 g, 7.3 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about two hours and thirty minutes. The supported catalyst was recovered as an orangish, free flowing solid (5.54 g).

Example 16

2-Methyl, 4-(2,3,5,6-tetramethylphenyl)-indene 2,3,5,6-Tetramethylbromobenzene (10 g, 47 mmol) and magnesium (2.4 g, 100 mmol) were combined in 200 mL of diethyl ether and stirred at room temperature overnight to form a Grignard solution. 4-Chloro-2-methylindene (7.7 g, 47 mmol) and $NiCl_2(PPh_3)_2$ (1.8 g, 2.8 mmol) were dissolved in 150 mL of $Et_2O$. To this was added the Grignard solution and the reaction was stirred overnight at room temperature. After overnight stirring, the reaction was slowly quenched with $H_2O$ to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 8.4 g (68%).

Lithium {1-[2-methyl, 4-(2,3,5,6-tetramethylphenyl) indenide]}

2-Methyl, 4-(2,3,5,6-tetramethylphenyl)-indene (8.4 g, 32 mmol) was dissolved in 80 mL of pentane. To this solution was added 13 mL of n-BuLi (2.5M in hexane) and the reaction was allowed to stir 4 hours at room temperature. A white solid precipitated from solution and was collected by frit filtration and washed with additional pentane. Yield: 8.0 g (95%).

Dimethylsilanediylbis{1-[2-methyl, 4-(2,3,5,6-tetramethylphenyl)indene]}

$Me_2SiCl_2$ (0.72 g, 5.5 mmol) was dissolved in 80 mL of THF. While stirring, lithium{1-[2-methyl, 4-(2,3,5,6- tetramethylphenyl)indenide]} (3.0 g, 11 mmol) was added as a dry powder and the contents were allowed to stir overnight at room temperature. The solvent was removed in vacuo and the residue was taken up in pentane and filtered to remove LiCl salts. The pentane was removed in vacuo to yield a flaky white solid (2.6 g, 81%).

Dimethylsilanediylbis{1-[2-methyl, 4-(2,3,5,6-tetramethylphenyl)indenyl]}zirconium dichloride Dimethylsilanediylbis{1-[2-methyl, 4-(2,3,5,6-tetramethylphenyl)indene]} (2.6 g, 4.4 mmol) was dissolved in 60 mL of $Et_2O$. While stirring, 3.8 mL of n-BuLi (2.5M in hexane) was added and allowed to stir at room temperature for 2 hours. After this time, the solution was cooled to −35° C. and $ZrCl_4$ (1.0 g, 4.4 mmol) was added and allowed to stir at room temperature for 3 hours. The solvent it was then removed in vacuo and the residue was taken up in a mixture of methylene chloride and pentane and filtered to remove LiCl salts. The filtrate was then concentrated and chilled to −35° C. to induce crystallization. 0.71 g (22%) of pure racemic compound was obtained.

Supported Metallocene Catalyst System 16

In a 100 mL round bottom flask dimethylsilanediylbis{1-[2-methyl, 4-(2,3,5,6-tetramethylphenyl)indenyl]}zirconium dichloride (0.66 g) was added to the above MAO-toluene solution (6.74 g, 7.3 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about two hours and twenty minutes. The supported catalyst was recovered as a reddish pink, free flowing solid (5.77 g).

Example 17

2-Isopropyl, 4-(3-biphenylyl)-indene

Magnesium (3.0 g, 125 mmol) and 3-bromobiphenyl (15 g, 65 mmol) were added together in 100 mL of diethyl ether and allowed to stir overnight at reflux to form a Grignard solution. 4-Chloro-2-isopropylindene (12.4 g, 65 mmol) and $NiCl_2PPh_3)_2$ (1.5 g, 2.3 mmol) were dissolved in 150 mL of $Et_2O$. The Grignard solution formed was added and the reaction was stirred overnight at reflux. After overnight stirring, the reaction was slowly quenched with $H_2O$ to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 8.9 g (45%).

Lithium{1-[2-isopropyl, 4-(3-biphenylyl)indenide]}

2-Isopropyl, 4-(3-biphenylyl)-indene (8.9 g, 29 mmol) was dissolved in 150 mL of pentane. To this solution was added 11.5 mL of n-BuLi (2.5M in hexane) and the reaction was allowed to stir 4 hours at room temperature. A white solid precipitated from solution and was collected by frit filtration and washed with additional pentane. Yield: 7.5 g (84%).

Dimethylsilanediylbis{1-[2-isopropyl, 4-(3-biphenylyl)indene]}

$Me_2SiCl_2$ (0.62 g, 4.8 mmol) was dissolved in 60 mL of diethyl ether. While stirring, lithium{1-[2-isopropyl, 4-(3-biphenylyl)indenide]} (3.0 g, 9.5 mmol) was added as a dry powder and a few drops of THF was added to catalyze the reaction. The contents were allowed to stir overnight at room temperature. The solvent was removed in vacuo and the residue was taken up in pentane and filtered to remove LiCl salts. The pentane was removed in vacuo to yield a flaky white solid. Yield: 3.2 g (100%).

Dimethylsilanediylbis{1-[2-isopropyl, 4-(3-biphenylyl)indenyl]}zirconium dichloride Dimethylsilanediylbis{1-[2-isopropyl, 4-(3-biphenylyl)indene]} (3.2 g, 4.7 mmol) was dissolved in 50 mL of $Et_2O$. While stirring, 3.8 mL of n-BuLi (2.5M in hexane) was added and allowed to stir at room temperature for 0.5 hours. After this time, the solution was cooled to −35° C. and $ZrCl_4$ (1.1 g, 4.7 mmol) was added and allowed to stir at room temperature for 3 hours. The solvent was then removed in vacuo and the residue was taken up in a mixture of methylene chloride and pentane and filtered to remove LiCl salts. The filtrate was then concentrated and chilled to −35° C. to induce crystallization. 1.2 g (30%) of pure racemic isomer was isolated.

Supported Metallocene Catalyst System 17

In a 100 mL round bottom flask dimethylsilanediylbis{1-[2-isopropyl, 4-(3-biphenylyl)indenyl]}zirconium dichloride (0.070 g) was added to the above MAO-toluene solution (6.74 g, 7.3 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about two hours and twenty seven minutes. The supported catalyst was recovered as a light purple, free flowing solid (5.46 g).

Example 18

2-Isopropyl, 4-(2-methylphenyl)-indene

4-Chloro-2-isopropylindene (9.8 g, 51 mmol) and $NiCl_2(PPh_3)_2$ (1.8 g, 2.8 mmol) were dissolved in 150 mL of $Et_2O$. 2-Methylphenylmagnesium bromide (51 mmol) as a $Et_2O$ solution was added to the solution and the reaction was stirred overnight at room temperature. After overnight stirring, the reaction was slowly quenched with $H_2O$ to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 6.6 g (52%).

Lithium{1-[2-isopropyl, 4-(2-methylphenyl)indenide]}

2-Isopropyl, 4-(2-methylphenyl)-indene (6.6 g, 26.5 mmol) was dissolved in 80 mL of pentane. To this solution was added 10.6 mL of n-BuLi (2.5M in hexane) and the reaction was allowed to stir 4 hours at room temperature. A white solid precipitated from solution and was collected by frit filtration and washed with additional pentane. Yield: 5.8 g (88%).

Dimethylsilanediylbis{1-[2-isopropyl, 4-(2-methylphenyl)indene]}

$Me_2SiCl_2$ (0.88 g, 6.8 mmol) was dissolved in 60 mL of THF. While stirring, lithium{1-[2-isopropyl, 4-(2- methylphenyl)indenide]} (3.5 g, 13.7 mmol) was added as a dry powder and the contents were allowed to stir overnight at room temperature. The solvent was removed in vacuo and the residue was taken up in pentane and filtered to remove LiCl salts. The pentane was removed in vacuo to yield a flaky white solid (3.0 g).

Dimethylsilanediylbis{1-[2-isopropyl, 4-(2-methylphenyl)indenyl]}zirconium dichloride Dimethylsilanediylbis{1-[2isopropyl, 4-(2-methylphenyl)indene]} (3.0 g, 5.4 mmol) was dissolved in 60 mL of $Et_2O$. While stirring, 4.5 mL of n-BuLi (2.5M in hexane) was added and allowed to stir at room temperature for 2 hours. After this time, the solution was cooled to −35° C. and $ZrCl_4$ (1.25 g, 5.4 mmol) was added and allowed to stir at room temperature for 3 hours. The solvent was then removed in vacuo and the residue was taken up in a mixture of methylene chloride and pentane and filtered to remove LiCl salts. The filtrate was then concentrated and chilled to −35° C. to induce crystallization. 0.26 g (6.7%) of pure racemic compound was obtained.

Supported Metallocene Catalyst System 18

In a 100 mL round bottom flask dimethylsilanediylbis{1-[2-isopropyl, 4-(2-methylphenyl)indenyl]}zirconium dichloride (0.064 g) was added to the above MAO-toluene solution (6.74 g, 7.15 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about two hours and seventeen minutes. The supported catalyst was recovered as a pink-purple, free flowing solid (5.36 g).

Example 19

2-Isopropyl, 4-(2,3-dimethylphenyl)-indene

4-Chloro-2-isopropylindene (10.4 g, 54 mmol) and $NiCl_2(PPh_3)_2$ (1.5 g, 2.3 mmol) were dissolved in 80 mL of $Et_2O$. 2,3-Dimethylphenylmagnesium bromide (54 mmol) as a $Et_2O$ solution was added to the solution and the reaction was stirred overnight at room temperature. After overnight stirring, the reaction was slowly quenched with $H_2O$ to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield: 5.3 g (3 7%).

Lithium{1-[2-isopropyl, 4-(2,3-dimethylphenyl) indenide]}

2-Isopropyl, 4-(2,3-dimethylphenyl)-indene (5.3 g, 20 mmol) was dissolved in 80 mL of pentane. To this solution was added 8.1 mL of n-BuLi (2.5M in hexane) and the reaction was allowed to stir 4 hours at room temperature. A white solid precipitated from solution and was collected by frit filtration and washed with additional pentane. Yield: 4.8 g (90%).

Dimethylsilanediylbis{1-[2-isopropyl, 4-(2,3-dimethylphenyl)indene]}

$Me_2SiCl_2$ (1.2 g, 8.9 mmol) was dissolved in 80 mL of diethyl ether. While stirring, lithium{1-[2-isopropyl, 4-(2,3-dimethylphenyl)indenide]} (4.8 g, 18 mmol) was added as a dry powder and a few drops of THF were added to catalyze the reaction. The contents were allowed to stir overnight at room temperature. The solvent was removed in vacuo and the residue was taken up in pentane and filtered to remove LiCl salts. The pentane was removed in vacuo to yield a flaky white solid (5.2 g).

Dimethylsilanediylbis{1-[2-isopropyl, 4-(2,3-dimethylphenyl)indenyl]}zirconium dichloride Dimethylsilanediylbis{1-[2-isopropyl,4-(2,3-dimethylphenyl)indene]} (5.2 g, 8.9 mmol) was dissolved in 60 mL of $Et_2O$. While stirring, 7.2 mL of n-BuLi (2.5M in hexane) was added and allowed to stir at room temperature for 2 hours. After this time, the solution was cooled to −35° C. and $ZrCl_4$ (2.1 g, 8.9 mmol) was added and allowed to stir at room temperature for 3 hours. The solvent was then removed in vacuo and the residue was taken up in a mixture of methylene chloride and pentane and filtered to remove LiCl salts. The filtrate was then concentrated and chilled to −35° C. to induce crystallization. 0.23 g (3.5%) of pure racemic compound was obtained.

Supported Metallocene Catalyst System 19

In a 100 mL round bottom flask dimethylsilanediylbis{1-[2-isopropyl, 4-(2,3-dimethylphenyl)indenyl]}zirconium dichloride (0.066 g) was added to the above MAO-toluene solution (6.74 g, 7.2 mL) and stirred twenty minutes. The resultant mixture was filtered through a medium glass frit funnel and washed wvith toluene (14 mL). To the combined filtrates was added dehydrated silica (4.0 g, Davison 948 Regular, 600° C. dehydration). This slurry was stirred for twenty minutes then dried at 40° C. for two minutes under vacuum on a rotary evaporator until the liquid evaporated and then the solid was further dried a total of about two hours and twenty eight minutes. The supported catalyst was recovered as a red-purple, free flowing solid (5.81 g).

Example 20

Supported Metallocene Catalyst System 20

In a 10-ml vial 2.71 g (0.535 mmol) of an 11.05 wt % solution of tris(perfluorophenyl)borane in toluene was massed. 0.10 g (0.615 mmol) of N,N-dimethylaniline (Aldrich, 98+%) was added followed by 5.0 g of toluene. A pink solution resulted. This solution was pipetted into a 250 ml round bottom flask containing 5.0 g of silica (Grace Davison, calcined at 500° C. with 3-wt % $(NH_4)_2SiF_6$) and a magnetic stir bar. 10 g of toluene was used to rinse the vial, pipette, and the sides of the flask. The flask was heated to 50° C. in an oil bath. The mixture was stirred for 38 minutes. 0.057 g (0.065 mmol) of dimethylsilanediylbis{1-[2-isopropyl,4-(2-biphenylyl)indenyl]}zirconium dimethyl was added to the flask as a solid to produce a brown slurry. Stirring was continued for 35 minutes at 50° C. After this time, the stirring and heating were discontinued. The solvent was stripped in vacuo to give 5.25 g. Composition by mass balance: Zirconium: 0.012 mmol/g catalyst, Boron: 0.12 mmol/g catalyst.

Example 21

Supported Metallocene Catalyst System 21

In a 100 mL round bottom flask dimethylsilanediyl{1-[2-isopropyl-4-(2-biphenylyl)indenyl]}zirconium dichloride (0.074 g) was added to the above MAO-toluene solution (6.74 g, 7.2 mL) and stirred twenty minutes. The resultant mixture was filtered through a medium glass frit funnel and washed with toluene. (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and thirty one minutes. The supported catalyst was recovered as a light reddish purple, free flowing solid (5.28 g).

Example 22

2-Isopropyl, 4-(2-biphenylyl)-indene

Magnesium (2.0 g, 83 mmol) and 2-bromobiphenyl (10 g, 43 mmol) were added together in 100 mL of diethyl ether and allowed to stir overnight at reflux to form a Grignard solution. 4-Chloro-2-isopropylindene (7.5 g, 434 mmol) and $NiCl_2(PPh_3)_2$ (1.5 g, 2.3 mmol) were dissolved in 150 mL of $Et_2O$. The Grignard solution was added and the reaction was stirred overnight at reflux. After overnight stirring, the reaction was slowly quenched with $H_2O$ to neutralize unreacted Grignard. The solution was subsequently treated with 100 mL of 10% HCl(aq), and neutralized with saturated sodium bicarbonate aqueous solution. The organic layer was dried with magnesium sulfate and the solvent was removed by rotary evaporation. The remaining residue was loaded onto a silica gel column and eluted with hexane. Yield was 8.1 g (61%).

Lithium{1-[2-isopropyl, 4-(2-biphenylyl)indenide]}

2-Isopropyl, 4-(2-biphenylyl)-indene (4.0 g, 13 mmol) was dissolved in 100 mL of pentane. To this solution was added 5.2 mL of n-BuLi (2.5M in hexane) and the reaction was allowed to stir 4 hours at room temperature. A white solid precipitated from solution and was collected by frit filtration and washed with additional pentane. Yield: 2.7 g (67%).

Dimethylsilanediylbis{1-[2-isopropyl, 4-(2-biphenylyl)indene]}

$Me_2SiCl_2$ (0.55 g, 4.3 mmol) was dissolved in 60 mL of diethyl ether. While stirring, lithium{1-[2-isopropyl, 4-(2-biphenylyl)indenide]} (2.7 g, 8.6 mmol) was added as a dry powder and a few drops of THF were added to catalyze the reaction. The contents were allowed to stir overnight at room temperature. The solvent was removed in vacuo and the residue was taken up in pentane and filtered to remove LiCl salts. The pentane was removed in vacuo to yield a flaky white solid. Yield: 2.1 g (72%).

Dimethylsilanediylbis{1-[2-isopropyl, 4-(2biphenylyl)indenyl]}zirconium dichloride Dimethylsilanediylbis{1-[2-isopropyl, 4-(2-biphenylyl) indene]} (2.1 g, 3.1 mmol) was dissolved in 60 mL of $Et_2O$. While stirring, 2.5 mL of n-BuLi (2.5M in hexane) was added and allowed to stir at room temperature for 0.5 hours. After this time, the solution was cooled to −35° C. and $ZrCl_4$ (0.73 g, 3.1 mmol) was added and allowed to stir at room temperature for 3 hours. The solvent was then removed in vacuo and the residue was taken up in a mixture of methylene chloride and pentane and filtered to remove LiCl salts. The filtrate was then concentrated and chilled to −35° C. to induce crystallization. 0.29 g (11%) of pure racemic isomer was isolated.

Dimethylsilanediylbis{1-[2-isopropyl, 4-(2-biphenylyl)indenyl]}zirconium dimethyl Dimethylsilanediylbis{1-[2-isopropyl, 4-(2-biphenylyl) indenyl]}zirconium dichloride (0.4 g, 490 mmol) was dissolved in 50 mL of toluene. To this solution was added 1.8 mL of MeMgBr (3.0M in $Et_2O$) and the reaction was stirred at 90° C. for 5 hours. After this time, the reaction was cooled to room temperature and 10 mL each of $SiCl_4$ and 1,4-dioxane was added. The solution was filtered through celite and the solvent was removed in vacuo. The resulting solids were washed with pentane. Yield: 0. 1 8 g (44%).

Supported Metallocene Catalyst System 22

In a 100 mL round bottom flask dimethylsilanediylbis{1-[2-isopropyl, 4-(2-biphenylyl)indenyl]}zirconium dimethyl (0.070 g) was added to the above MAO-toluene solution (6.74 g, 7.2 mL) and stirred twenty minutes. The resultant mixture was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and thirty four minutes. The supported catalyst was recovered as a light purple, free flowing solid (5.56 g).

Polymerizations

Isotactic Polypropylene Homopolymer

The polymerization procedure for producing homopolymers with the above supported metallocene catalyst systems was as follows. In a clean, dry two liter autoclave which had been flushed with propylene vapor, TEAL (triethyl aluminum) scavenger (0.3 mL, 1.5M) was added. Hydrogen gas was added at this point. The reactor was closed and filled with 800 mL of liquid propylene. After heating the reactor to 70° C. the catalyst was added by washing in with propylene (200 mL). After the indicated time, typically one hour, the reactor was cooled, and the excess propylene vented. The polymer was removed and dried.

Isotactic Polypropylene Random Copolymer (RCP)

The polymerization procedure for producing ethylene random copolymers (RCP) with the above supported metallocene catalyst systems was as follows. In a clean, dry two liter autoclave which had been flushed with propylene vapor, TEAL scavenger (0.3 mL, 1.5M) was added. Hydrogen gas was added at this point, if used. The reactor was closed and filled with 800 mL of liquid propylene. After heating the reactor to 60° C., an overpressure of ethylene, as indicated by the "delta kPa", was slowly added while maintaining 60° C. The ethylene inlet was closed while the catalyst was added by washing in with propylene (200 mL). Immediately after addition the ethylene inlet was reopened and the desired overpressure of ethylene was maintained. After the indicated time, typically one hour, the reactor was cooled, and the excess propylene vented. The polymer was removed and dried.

Impact Copolymers (ICP)

The polymerization procedure for producing ICP with the above supported metallocene catalyst systems was as follows. In a clean, dry two liter autoclave which had been flushed with propylene vapor, TEAL scavenger (0.3 mL, 1.5M) was added. Hydrogen gas was added at this point. The reactor was closed and filled with 900 mL liquid propylene. After heating the reactor to 70° C., the catalyst was added by washing in with propylene (200 mL). After the indicated time, typically one hour, the reactor was vented to about 170 psig (1172 kPa) pressure and then an ethylene/propylene gas mixture was passed through the reactor at the rates indicated while maintaining 200 psig (1379 kPa). At the end of the gas phase stage, typically 90 to 150 minutes, the reactor was vented and cooled under $N_2$. The granular ICP polymer was removed and dried.

Polymer Analysis

Results are shown in Tables 1–22 (A and B) below. The numbering of the Tables corresponds to the numbering of the above Examples (Supported Metallocene Catalyst Systems). Molecular weight determinations were made by gel permeation chromatography (GPC) according to the following technique. Molecular weights and molecular weight distributions were measured using a Waters 150° C. gel permeation chromatograph equipped with Shodex (Showa Denko) AT-80 M/S columns and a differential refractive index (DRI) detector operating at 145° C. with 1,2,4-trichlorobenzene as the mobile phase at a 1.0 mL/min. flow rate. The sample injection volume was 300 microliters. The columns were calibrated using narrow polystyrene standards to generate a universal calibration curve. The polypropylene calibration curve was established using $k=8.33\times10^{-5}$ and $a=0.800$ as the Mark-Houwink coefficients. The numerical analyses were performed using Waters "Millennium" software.

DSC melting points were determined on commercial DSC instruments and were reported as the second melting point. The polymer sample was heated to 230.0° C. for ten minutes and then cooled from 230° C. to 50° C. at 10° C./minute. The sample was held at 50° C. for five minutes. The second melt was then recorded as the sample was heated from 50° C. to 200° C. at a rate of 10° C./minute. The peak temperature was recorded as the second melting point.

The results summarized in Table 21C were obtained by following the procedures described in J. C. Randall, Polymer Sequence Determination: Carbon-13 NMR Method, Academic Press New York 1978, supra.

ICP Polymer Extraction Method

The ICP polymer was dissolved in hot xylene and then allowed to cool overnight. After filtration the insolubles were dried. The xylene soluble portion was evaporated and the soluble material recovered. The IV (intrinsic viscosity) of the recovered soluble material was measured in decalin at 135° C. by using known methods and instruments such as a Schott A VSPro Viscosity Automatic Sampler.

At very high ICP MFR this method can extract some low molecular weight isotactic PP and thus lower the observed IV.

ICP Polymer Fractionation Method

The ICP samples were sent to Polyhedron Laboratories, Inc. to be fractionated and analyzed by GPC. A general description of the procedure is found in J. C. Randall, J. Poly. Sci.: Part A Polymer Chemistry, Vol. 36, 1527–1542 (1998), supra.

TABLE 1A

Dimethylsilanediylbis{1-[2-methyl,4-phenylindenyl]}zirconium dichloride

| RUN # | TEMP. (° C.) | Cat. Amount (mg) | Yield (g) | Efficiency (Kg/g cat) | $C_2=$ (delta kPa) | $H_2$ (mmole) | Time split (min.) | $C_2^-/C_3^-$ flow rates (l/min.) |
|---|---|---|---|---|---|---|---|---|
| 1 | 60 | 67 | 274.7 | 4.10 | 0 | 0 | 60 | — |
| 2 | 60 | 45 | 71.7 | 1.59 | 0 | 0 | 60 | — |
| 3 | 60 | 40 | 134.1 | 3.35 | 68.9 | 0 | 60 | — |
| 4 | 60 | 42 | 221.5 | 5.27 | 137.9 | 0 | 60 | — |
| 5 | 60 | 30 | 121.3 | 4.04 | 379.2 | 0 | 60 | — |
| 6 | 60 | 30 | 130.2 | 4.34 | 482.6 | 0 | 60 | — |
| 7 | 60 | 30 | 101.8 | 3.39 | 137.9 | 0 | 60 | — |
| 8 | 70 | 45 | 293.5 | 6.52 | — | 77.5 | 60 | — |
| 9 | 70 | 31 | 198.9 | 6.42 | — | 77.5 | 60 | — |
| 10 | 70 | 30 | 291.9 | 9.73 | — | 77.5 | 60/150 | 4.0/1.0 |
| 11 | 70 | 30 | 231.3 | 7.71 | — | 77.5 | 60/90 | 4.0/1.0 |
| 12 | 70 | 30 | 224.8 | 7.49 | — | 77.5 | 60/90 | 4.1/0.9 |
| 13 | 70 | 30 | 209.9 | 7.00 | — | 77.5 | 60/90 | 3.6/1.4 |
| 14 | 70 | 30 | 208.2 | 6.94 | — | 77.5 | 60/90 | 4.0/1.0 |

TABLE 1B

Dimethylsilanediylbis{1-[2-methyl,4-phenylindenyl]}zirconium dichloride

| RUN # | Total Ethylene (wt %) | Ethylene in Rubber (wt %) | Total Rubber (wt %) | Final MFR (g/10 min.) | Melting Point (° C.) | MW ($\times 10^{-3}$) | MWD | IV of Copolymer (dl/g) |
|---|---|---|---|---|---|---|---|---|
| 1 | — | — | — | 0.16 | 149.2 | 600.0 | 2.00 | — |
| 2 | — | — | — | 0.54 | 148.2 | 664.9 | 1.92 | — |
| 3 | 0.67 | — | — | 0.84 | 142.0 | 349.0 | 2.09 | — |
| 4 | 1.28 | — | — | 2.57 | 138.4 | 280.0 | 1.95 | — |
| 5 | 3.77 | — | — | 6.48 | 121.4 | 255.0 | 2.04 | — |
| 6 | 4.43 | — | — | 5.95 | 116.0 | 301.0 | 2.30 | — |
| 7 | 1.44 | — | — | 2.05 | 137.5 | 330.4 | 2.23 | — |

TABLE 1B-continued

Dimethylsilanediylbis{1-[2-methyl,4-phenylindenyl]}zirconium dichloride

| RUN # | Total Ethylene (wt %) | Ethylene in Rubber (wt %) | Total Rubber (wt %) | Final MFR (g/10 min.) | Melting Point (° C.) | MW (× $10^{-3}$) | MWD | IV of Copolymer (dl/g) |
|---|---|---|---|---|---|---|---|---|
| 8  | —     | —     | —     | 99.6   | 150.3  | 120.6 | 3.01 | —     |
| 9  | —     | —     | —     | 58.95  | 150.9  | 135.7 | 3.15 | —     |
| 10 | 13.23 | 49.20 | 26.89 | 178.5  | 151.2  | 81.2  | 3.37 | 0.7520 |
| 11 | 7.58  | 47.37 | 16.00 | 134.05 | 150.6  | 98.4  | 3.25 | 0.687 |
| 12 | 7.82  | 50.04 | 15.63 | 127.16 | 150.0  | 100.4 | 3.11 | 0.708 |
| 13 | 5.3   | 38.96 | 13.60 | 201.9  | 150.43 | 91.2  | 3.28 | 0.779 |
| 14 | 0.47  | 64.32 | 0.73  | 97.1   | 150.8  | 116.8 | 3.42 | Not submitted |

TABLE 2A

Dimethylsilanediylbis{1-[2-methyl,4-(3-methylphenyl)indenyl]}zirconium dichloride

| RUN # | TEMP. (° C.) | Cat. Amount (mg) | Yield (g) | Efficiency (Kg/g cat) | $C_2=$ (delta kPa) | $H_2$ (mmole) | Time split (min.) | $C_2^=/C_3^=$ flow rates (l/min.) |
|---|---|---|---|---|---|---|---|---|
| 15 | 60 | 45 | 106.7 | 2.37  | 0     | 0     | 60    | —       |
| 16 | 60 | 46 | 232.5 | 5.05  | 68.9  | 0     | 60    | —       |
| 17 | 60 | 45 | 285.1 | 6.34  | 137.9 | 0     | 60    | —       |
| 18 | 60 | 21 | 132.0 | 6.29  | 241.3 | 0     | 60    | —       |
| 19 | 70 | 20 | 220.1 | 11.01 | —     | 77.5  | 60/90 | 4.0/1.0 |
| 20 | 70 | 22 | 197.9 | 9.00  | —     | 54.3  | 60/90 | 4.0/1.0 |
| 21 | 70 | 46 | 242.0 | 5.26  | —     | 54.3  | 30    | —       |
| 22 | 70 | 21 | 146.5 | 6.98  | —     | 54.3  | 60    | —       |
| 23 | 70 | 20 | 145.3 | 7.27  | —     | 108.5 | 60    | —       |
| 24 | 70 | 20 | 117.4 | 5.87  | —     | 77.5  | 60    | —       |
| 25 | 70 | 20 | 158.9 | 7.95  | —     | 108.5 | 60/90 | 4.0/1.0 |

TABLE 2B

Dimethylsilanediylbis{1-[2-methyl,4-(3-methylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW (× $10^{-3}$) | MWD | IV of Copolymer (dl/g) |
|---|---|---|---|---|---|---|---|---|
| 15 | —     | —     | —     | 0.08  | 149.43 | 797.1 | 2.05 | —     |
| 16 | 0.15  | —     | —     | 0.87  | 144.10 | 425.0 | 1.82 | —     |
| 17 | 1.1   | —     | —     | 2.48  | 139.97 | 318.2 | 1.82 | —     |
| 18 | 2.0   | —     | —     | 4.50  | 134.17 | 280.6 | 1.93 | —     |
| 19 | 7.431 | 50.60 | 14.69 | 15.68 | 151.1  | 195.7 | 3.37 | 0.684 |
| 20 | 9.699 | 49.32 | 19.67 | 6.27  | 150.7  | 302.9 | 3.82 | 0.772 |
| 21 | —     | —     | —     | 2.48  | 151.03 | 334.5 | 2.26 | —     |
| 22 | —     | —     | —     | 1.61  | 150.97 | 336.3 | 2.22 | —     |
| 23 | —     | —     | —     | 91.78 | 151.90 | 125.0 | 3.24 | —     |
| 24 | —     | —     | —     | 39.82 | 151.63 | 154.3 | 2.76 | —     |
| 25 | 6.454 | 51.06 | 12.64 | Not submitted | 151.3 | 83.6 | 3.11 | 0.832 |

TABLE 3A

Dimethylsilanediylbis{1-[2-methyl,4-(3,5-dimethylphenyl)indenyl]}zirconium dichloride

| RUN # | TEMP. (° C.) | Cat. Amount (mg) | Yield (g) | Efficiency (Kg/g cat) | $C_2=$ (delta kPa) | $H_2$ (mmole) | Time split (min.) | $C_2^-/C_3^-$ flow rates (l/min.) |
|---|---|---|---|---|---|---|---|---|
| 26 | 60 | 45 | 72.7  | 1.6 | 0     | 0    | 60    | — |
| 27 | 60 | 45 | 111.9 | 2.5 | 34.5  | 0    | 60    | — |
| 28 | 60 | 47 | 155.6 | 3.3 | 68.9  | 0    | 60    | — |
| 29 | 60 | 46 | 204.9 | 4.5 | 137.9 | 0    | 60    | — |
| 30 | 60 | 45 | 244.5 | 5.4 | 241.3 | 0    | 60    | — |
| 31 | 70 | 30 | 251.2 | 8.4 | —     | 54.3 | 60/90 | 4.0/1.0 |
| 32 | 70 | 30 | 236.8 | 7.9 | —     | 54.3 | 60/90 | 3.6/1.4 |
| 33 | 70 | 32 | 259.5 | 8.7 | —     | 54.3 | 60/90 | 4.2/0.8 |
| 34 | 70 | 33 | 249.4 | 7.6 | —     | 54.3 | 60/90 | 4.4/0.6 |
| 35 | 70 | 33 | 186.8 | 5.7 | —     | 54.3 | 60    | — |

TABLE 3B

Dimethylsilanediylbis{1-[2-methyl,4-(3,5-dimethylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW ($\times 10^{-3}$) | MWD | IV of Copolymer (dl/g) |
|---|---|---|---|---|---|---|---|---|
| 26 | —     | —     | —    | 0.0245 | 150.9  | 937.7 | 2.10 | — |
| 27 | —     | —     | —    | 0.17   | 148.3  | 671.3 | 2.15 | — |
| 28 | 0.18  | —     | —    | 0.59   | 145.03 | 463.6 | 2.01 | — |
| 29 | 1.1   | —     | —    | 2.68   | 140.9  | 303.8 | 1.89 | — |
| 30 | 1.8   | —     | —    | 3.98   | 135.43 | 255.7 | 1.74 | — |
| 31 | 8.11  | 49.7  | 16.3 | 4.54   | 152.57 | 281.1 | 3.51 | 0.866 |
| 32 | 5.34  | 40.32 | 13.2 | 6.25   | 151.97 | 284.5 | 3.57 | 0.861 |
| 33 | 9.98  | 58.47 | 17.1 | 7.07   | 152.43 | 220.4 | 3.00 | 1.420 |
| 34 | 14.42 | 61.66 | 23.4 | 19.43  | 152.1  | 179.4 | 2.57 | 1.091 |
| 35 | —     | —     | —    | 1.79   | 151.30 | 327.9 | 1.98 | — |

TABLE 4A

Dimethylsilanediylbis{1-[2-methyl,4-(2-methylphenyl)indenyl]}zirconium dichloride

| RUN # | TEMP. (° C.) | Cat. Amount (mg) | Yield (g) | Efficiency (Kg/g cat) | $C_2=$ (delta kPa) | $H_2$ (mmole) | Time split (min.) | $C_2^-/C_3^-$ flow rates (l/min.) |
|---|---|---|---|---|---|---|---|---|
| 36 | 60 | 47 | 33.0  | 0.70  | 0     | 0    | 60     | — |
| 37 | 60 | 45 | 118.7 | 2.64  | 68.9  | 0    | 60     | — |
| 38 | 60 | 45 | 197.7 | 4.39  | 137.9 | 0    | 60     | — |
| 39 | 60 | 47 | 340.7 | 7.25  | 241.3 | 0    | 60     | — |
| 40 | 70 | 33 | 273.4 | 8.28  | —     | 77.5 | 60/90  | 4.0/1.0 |
| 41 | 70 | 20 | 222.9 | 11.15 | —     | 77.5 | 60/90  | 4.0/1.0 |
| 42 | 70 | 22 | 228.0 | 10.36 | —     | 77.5 | 60/90  | 4.1/0.9 |
| 43 | 70 | 20 | 222.3 | 11.12 | —     | 77.5 | 60/90  | 3.6/1.4 |
| 44 | 70 | 20 | 175.4 | 8.77  | —     | 54.3 | 60/90  | 4.0/1.0 |
| 45 | 70 | 20 | 161.0 | 8.05  | —     | 54.3 | 60/90  | 4.1/0.9 |
| 46 | 70 | 20 | 174.0 | 8.70  | —     | 54.3 | 60/90  | 3.6/1.4 |
| 47 | 70 | 21 | 189.6 | 9.03  | —     | 54.3 | 60/120 | 4.0/1.0 |
| 48 | 70 | 20 | 132.1 | 6.61  | —     | 54.3 | 60     | — |
| 49 | 70 | 20 | 159.1 | 7.96  | —     | 77.5 | 60.0   | — |

TABLE 4B

Dimethylsilanediylbis{1-[2-methyl,4-(2-methylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW (× 10⁻³) | MWD | IV of Copolymer (dl/g) |
|---|---|---|---|---|---|---|---|---|
| 36 | — | — | — | 0.09 | 146.5 | 912.2 | 2.17 | — |
| 37 | 0.67 | — | — | 0.52 | 136.63 | 499.0 | 2.33 | — |
| 38 | 1.24 | — | — | 0.61 | 132.57 | 449.8 | 2.22 | — |
| 39 | 2.1 | — | — | 0.69 | 126.77 | 499.8 | 2.01 | — |
| 40 | — | — | — | 111.98 | 144.63 | 115.1 | 2.41 | — |
| 41 | 6.951 | 48.87 | 14.22 | 140.01 | 145.7 | 99.7 | 2.59 | 1.429 |
| 42 | 7.88 | 52.43 | 15.03 | 133.9 | 145.37 | 100.9 | 2.74 | 1.287 |
| 43 | 5.576 | 38.33 | 14.55 | 83.2 | 144.90 | 111.8 | 2.34 | 1.046 |
| 44 | 7.353 | 48.96 | 15.02 | 29.14 | 145.10 | 143.3 | 2.50 | 1.446 |
| 45 | 8.809 | 51.90 | 16.97 | 20.42 | 145.17 | 154.3 | 2.42 | 1.448 |
| 46 | 6.013 | 35.55 | 16.91 | 35.55 | 144.97 | 151.8 | 2.32 | 1.355 |
| 47 | 10.84 | 47.31 | 22.91 | 20.36 | 145.63 | 152.6 | 2.39 | 1.648 |
| 48 | — | — | — | 26.76 | 146.17 | 179.9 | 2.64 | — |
| 49 | — | — | — | 95.55 | 145.97 | 124.3 | 2.96 | — |

TABLE 5A

Dimethylsilanediylbis{1-[2-methyl,4-(2-ethylphenyl)indenyl]}zirconium dichloride

| RUN # | TEMP. (° C.) | Cat. Amount (mg) | Yield (g) | Efficiency (Kg/g cat) | $C_2^=$ (delta kPa) | $H_2$ (mmole) | Time split (min.) | $C_2^=/C_3^=$ flow rates (l/min.) |
|---|---|---|---|---|---|---|---|---|
| 50 | 60 | 48 | 19.5 | 0.41 | 0 | 0 | 60 | — |
| 51 | 60 | 46 | 28.2 | 0.61 | 34.5 | 0 | 60 | — |
| 52 | 60 | 45 | 36.0 | 0.80 | 68.9 | 0 | 60 | — |
| 53 | 60 | 45 | 44.9 | 1.00 | 137.9 | 0 | 60 | — |
| 54 | 60 | 45 | 69.6 | 1.55 | 241.3 | 0 | 60 | — |
| 55 | 70 | 152 | 256.1 | 1.68 | — | 54.3 | 35/90 | 4.0/1.0 |
| 56 | 70 | 75 | 228.9 | 3.05 | — | 54.3 | 60 | — |
| 57 | 70 | 74 | 337.4 | 4.56 | — | 54.3 | 60/90 | 4.0/1.0 |
| 58 | 70 | 33 | 134.7 | 4.08 | — | 54.3 | 60/90 | 4.0/1.0 |
| 59 | 70 | 33 | 118.8 | 3.60 | — | 54.3 | 60/90 | 3.6/1.4 |
| 60 | 70 | 31 | 123.0 | 3.97 | — | 54.3 | 60/90 | 4.4/0.6 |
| 61 | 70 | 31 | 130.8 | 4.22 | — | 54.3 | 60/90 | 4.2/0.8 |
| 62 | 70 | 31 | 85.9 | 2.77 | — | 54.3 | 60 | — |

TABLE 5B

Dimethylsilanediylbis{1-[2-methyl,4-(2-ethylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW (× 10⁻³) | MWD | IV of Copolymer (dl/g) |
|---|---|---|---|---|---|---|---|---|
| 50 | — | — | — | 0.038 | 147.97 | 786.3 | 2.14 | — |
| 51 | Trace | — | — | 0.088 | 144.3 | 670.7 | 2.60 | — |
| 52 | 0.83 | — | — | 0.092 | 139.63 | 635.7 | 2.58 | — |
| 53 | 1.7 | — | — | 0.16 | 134.17 | 621.5 | 2.21 | — |
| 54 | 2.6 | — | — | 0.2 | 127.5 | 642.0 | 2.06 | — |
| 55 | — | — | — | 15.17 | 147.1 | 232.3 | 2.56 | — |
| 56 | — | — | — | 15.72 | 147.10 | 214.4 | 2.42 | — |
| 57 | 12.68, 12.74 | 50.79, 50.59 | 24.97, 25.18 | 18.43 | 147.77 | 160.7 | 2.49 | 1.889 |
| 58 | 7.107 | 48.48 | 14.66 | 97.17 | 145.7 | 103.1 | 2.64 | 1.788 |
| 59 | 6.874 | 38.31 | 17.94 | 31.95 | 145.83 | 136.9 | 2.50 | 1.746 |
| 60 | 12.59 | 60.64 | 20.76 | 48.37 | 145.63 | 130.2 | 2.57 | 2.15 |
| 61 | 9.74 | 52.29 | 18.63 | 52.52 | 146.03 | 133.8 | 2.42 | 2.02 |
| 62 | — | — | — | 34.83 | 146.03 | 172.6 | 2.43 | — |

TABLE 6A

Dimethylsilanediylbis{1-[2-methyl,4-(2-isopropylphenyl)indenyl]}zirconium dichloride

| RUN # | TEMP. (° C.) | Cat. Amount (mg) | Yield (g) | Efficiency (Kg/g cat) | $C_2=$ (delta kPa) | $H_2$ (mmole) | Time split (min.) | $C_2^-/C_3^-$ flow rates (l/min.) |
|---|---|---|---|---|---|---|---|---|
| 63 | 60 | 46 | 15.1  | 0.33 | 0 | 0    | 60    | —       |
| 64 | 70 | 21 | 63.3  | 3.01 | — | 54.3 | 60    | —       |
| 65 | 70 | 60 | 243.1 | 4.05 | — | 54.3 | 60/90 | 4.0/1.0 |
| 66 | 70 | 61 | 159.5 | 2.61 | — | 54.3 | 60    | —       |
| 67 | 70 | 61 | 221.4 | 3.63 | — | 54.3 | 60/90 | 3.6/1.4 |
| 68 | 70 | 61 | 199.8 | 3.28 | — | 54.3 | 60/90 | 4.2/0.8 |

TABLE 6B

Dimethylsilanediylbis{1-[2-methyl,4-(2-isopropylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW ($\times 10^{-3}$) | MWD | IV of Copolymer (dl/g) |
|---|---|---|---|---|---|---|---|---|
| 63 | —     | —     | —     | 0.099 | 148.23 | 690.1 | 2.38 | —    |
| 64 | —     | —     | —     | 125.8 | 144.70 | 115.0 | 2.59 | —    |
| 65 | 14.64 | 51.63 | 28.36 | 9.8   | 145.03 | 167.1 | 2.83 | 2.34 |
| 66 | —     | —     | —     | 40.59 | 144.77 | 146.2 | 3.04 | —    |
| 67 | 9.487 | 41.48 | 22.87 | 24.72 | 144.23 | 158.1 | 2.60 | 1.94 |
| 68 | 13.26 | 54.58 | 24.29 | 15.4  | 145.3  | 167.6 | 2.77 | 2.46 |

TABLE 7A

Dimethylsilanediylbis{1-[2-methyl,4-(2-biphenylyl)indenyl]}zirconium dichloride

| RUN # | TEMP. (° C.) | Cat. Amount (mg) | Yield (g) | Efficiency (Kg/g cat) | $C_2=$ (delta kPa) | $H_2$ (mmole) | Time split (min.) | $C_2^-/C_3^-$ flow rates (l/min.) |
|---|---|---|---|---|---|---|---|---|
| 69 | 60 | 48 | 102.9 | 2.14  | 0 | 0    | 60     | —       |
| 70 | 70 | 23 | 290.6 | 12.63 | — | 54.3 | 60/90  | 4.0/1.0 |
| 71 | 70 | 20 | 216.4 | 10.82 | — | 54.3 | 60     | —       |
| 72 | 70 | 20 | 271.1 | 13.56 | — | 54.3 | 60/120 | 4.0/1.0 |
| 73 | 70 | 20 | 141.5 | 7.08  | — | 54.3 | 60/90  | 4.2/0.8 |
| 74 | 70 | 21 | 260.4 | 12.4  | — | 54.3 | 60/90  | 3.6/1.4 |
| 75 | 70 | 20 | 231.2 | 11.56 | — | 54.3 | 60/90  | 4.2/0.8 |

TABLE 7B

Dimethylsilanediylbis{1-[2-methyl,4-(2-biphenylyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW ($\times 10^{-3}$) | MWD | IV of Copolymer (dl/g) |
|---|---|---|---|---|---|---|---|---|
| 69 | —     | —     | —     | 0.052 | 148.63 | 772.9 | 1.92 | —     |
| 70 | 6.066 | 46.64 | 13.01 | 19.18 | 150.30 | 156.5 | 2.35 | 1.338 |
| 71 | —     | —     | —     | 12.93 | 150.70, minor 136.9 | 194.7 | 2.00 | —     |
| 72 | 7.476 | 45.74 | 16.34 | 14.69 | 149.83 | 167.4 | 2.13 | 1.30  |
| 73 | 6.001 | 53.32 | 11.25 | 62.35 | 149.9  | 126.9 | 1.95 | 1.06  |
| 74 | 4.605 | 35.36 | 13.02 | 13.98 | 151.7  | 186.8 | 2.46 | 1.06  |
| 75 | 7.778 | 53.54 | 14.53 | 13.05 | 150.77 | 166.0 | 2.23 | 1.36  |

TABLE 8A

Dimethylsilanediylbis{1-[2-methyl,4-(4-biphenylyl)indenyl]}zirconium dichloride

| RUN # | TEMP. (°C.) | Cat. Amount (mg) | Yield (g) | Efficiency (Kg/g cat) | $C_2=$ (delta kPa) | $H_2$ (mmole) | Time split (min.) | $C_2^-/C_3^-$ flow rates (l/min.) |
|---|---|---|---|---|---|---|---|---|
| 76 | 60 | 48 | 69.6 | 1.45 | 0 | 0 | 60 | — |
| 77 | 70 | 22 | 110.2 | 5.01 | — | 54.3 | 60 | — |
| 78 | 70 | 21 | 120.9 | 5.76 | — | 54.3 | 60/90 | 4.0/1.0 |
| 79 | 70 | 20 | 131.7 | 6.07 | — | 54.3 | 60/120 | 4.0/1.0 |
| 80 | 70 | 20 | 121.3 | 6.07 | — | 54.3 | 60/90 | 4.2/0.8 |
| 81 | 70 | 23 | 135.0 | 5.87 | — | 54.3 | 60/90 | 3.6/1.4 |

TABLE 8B

Dimethylsilanediylbis{1-[2-methyl,4-(4-biphenylyl)indenyl]}zirconium dichloride

| RUN # | Total Ethylene (wt %) | Ethylene in Rubber (wt %) | Total rubber (wt %) | Final MFR (g/10 min.) | Melting Point (°C.) | MW ($\times 10^{-3}$) | MWD | IV of Copolymer (dl/g) |
|---|---|---|---|---|---|---|---|---|
| 76 | — | — | — | 0.046 | 145.57 | 662.3 | 2.06 | — |
| 77 | — | — | — | 4.36 | 147.3 | 244.6 | 2.23 | — |
| 78 | 4.18 | 56.56 | 7.39 | 13.17 | 148.5 | 185.0 | 3.30 | 0.79 |
| 79 | 8.58 | 52.12 | 16.46 | 29.02 | 148.43 | 191.2 | 3.69 | 0.62 |
| 80 | 10.31 | 56.37 | 18.29 | 23.12 | 149.9 | 177.2 | 2.99 | 0.81 |
| 81 | 5.535 | 42.06 | 13.16 | 18.13 | 148.3 | 218.0 | 3.87 | 0.69 |

TABLE 9A

Dimethylsilanediylbis{1-[2-methyl, 4-(4-tert-butylphenyl)indenyl]} zirconium dichloride

| RUN # | TEMP (°C.) | Cat. Amount (mg) | Yield (g) | Efficiency (Kg/g cat) | $H_2$ (mmole) | Time split (min.) |
|---|---|---|---|---|---|---|
| 82 | 60 | 48 | 9.9 | 0.21 | 0 | 60 |
| 83 | 70 | 30 | 27.2 | 0.91 | 54.3 | 60 |

TABLE 9B

Dimethylsilanediylbis{1-[2-methyl, 4-(4-tert-butylphenyl)indenyl]} zirconium dichloride

| RUN # | Final MFR (g/10 min.) | Melting Point (°C.) | MW ($\times 10^{-3}$) | MWD |
|---|---|---|---|---|
| 82 | 0.0725 | 150.9 | 979.3 | 2.63 |
| 83 | 33.04 | 152.9 | 159.7 | 3.03 |

TABLE 10A

Dimethylsilanediylbis{1-[2-methyl,4-(2,3-dimethylphenyl)indenyl]}zirconium dichloride

| RUN # | TEMP (°C.) | Cat. Amount (mg) | Yield (g) | Efficiency (Kg/g cat) | $C_2=$ (kPa) | $H_2$ (mmole) | Time split (min.) | $C_2^-/C_3^-$ flow rates (l/min.) |
|---|---|---|---|---|---|---|---|---|
| 84 | 60 | 45 | 26.2 | 0.58 | 0 | 0 | 60 | — |
| 85 | 70 | 20 | 67.8 | 3.39 | — | 54.3 | 60/90 | 4.0/1.0 |
| 86 | 70 | 60 | 262.2 | 4.37 | — | 54.3 | 60/90 | 4.0/1.0 |
| 87 | 70 | 60 | 174.8 | 2.91 | — | 54.3 | 60 | — |
| 88 | 70 | 60 | 212.5 | 3.54 | — | 54.3 | 60/90 | 4.1/0.9 |
| 89 | 70 | 60 | 255.1 | 4.25 | — | 54.3 | 60/90 | 3.6/1.4 |
| 90 | 70 | 60 | 264.0 | 4.40 | — | 54.3 | 60/120 | 4.0/1.0 |
| 91 | 70 | 61 | 205.9 | 3.38 | — | 62.0 | 60/90 | 4.0/1.0 |
| 92 | 70 | 62 | 257.8 | 4.16 | — | 69.8 | 60/90 | 4.0/1.0 |

TABLE 10A-continued

Dimethylsilanediylbis{1-[2-methyl,4-(2,3-dimethylphenyl)indenyl]}zirconium dichloride

| RUN # | TEMP (° C.) | Cat. Amount (mg) | Yield (g) | Efficiency (Kg/g cat) | $C_2=$ (kPa) | $H_2$ (mmole) | Time split (min.) | $C_2^-/C_3^-$ flow rates (l/min.) |
|---|---|---|---|---|---|---|---|---|
| 93 | 70 | 61 | 199.5 | 3.27 | — | 77.5 | 60/90 | 4.0/1.0 |
| 94 | 70 | 61 | 213.4 | 3.50 | — | 93 | 60/90 | 4.0/1.0 |

TABLE 10B

Dimethylsilanediylbis{1-[2-methyl,4-(2,3-dimethylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW ($\times 10^{-3}$) | MWD | IV of Copolymer (dl/g) |
|---|---|---|---|---|---|---|---|---|
| 84 | — | — | — | 0.023 | 149.3 | 963.8 | 2.32 | — |
| 85 | 9.417 | 46.86 | 20.10 | 28.72 | 148.37 | 139.0 | 3.39 | 1.92 |
| 86 | 14.21 | 50.48 | 28.15 | 2.31 | 149.63 | 253.4 | 2.58 | 2.21 |
| 87 | — | — | — | 5.02 | 150.37 minor 137.46 | 264.0 | 2.69 | — |
| 88 | 14.65, 14.64 | 52.46, 52.37 | 27.93, 27.95 | 2.54 | 150.37 | 263.8 | 2.75 | 2.232 |
| 89 | 12.99, 13.1 | 38.1, 37.65 | 34.09, 34.79 | 4.56 | 151.17 | 218.0 | 2.72 | 2.487 |
| 90 | 22.8, 22.45 | 53.16, 52.62 | 42.89, 42.66 | 3.64 | 150.3 | 205.8 | 3.30 | 2.268 |
| 91 | 15.81 | 51.87 | 30.48 | 9.77 | 149.57 | 165.6 | 2.54 | 1.968 |
| 92 | 20.94 | 51.96 | 40.30 | 5.47 | 150.37 | 206.4 | 3.14 | 1.558 |
| 93 | 13.24 | 51.07 | 25.93 | 40.22 | 149.83 | 131.2 | 3.58 | 2.007 |
| 94 | 12.18 | 45.24 | 26.92 | 39.73 | 149.03 | 150.3 | 4.28 | 2.711 |

TABLE 11A

Dimethylsilanediylbis{1-[2-methyl,4-(2,4-dimethylphenyl)indenyl]}zirconium dichloride

| RUN # | TEMP (° C.) | Cat. Amount (mg) | Yield (g) | Efficiency (Kg/g cat) | $C_2=$ (kPa) | $H_2$ (mmole) | Time split (min.) | $C_2^-/C_3^-$ flow rates (l/min.) |
|---|---|---|---|---|---|---|---|---|
| 95 | 60 | 47 | 41.6 | 0.89 | 0 | 0 | 60 | — |
| 96 | 70 | 32 | 322.9 | 10.09 | — | 54.3 | 60/120 | 4.0/1.0 |
| 97 | 70 | 20 | 168.2 | 8.41 | — | 54.3 | 60/90 | 4.0/1.0 |
| 98 | 70 | 20 | 180.1 | 9.01 | — | 54.3 | 60/90 | 4.1/0.9 |
| 99 | 70 | 20 | 177.1 | 8.86 | — | 54.3 | 60/90 | 3.6/1.4 |
| 100 | 70 | 20 | 181.0 | 9.05 | — | 54.3 | 60/120 | 4.0/1.0 |
| 101 | 70 | 21 | 138.2 | 6.58 | — | 54.3 | 60 | — |

TABLE 11B

Dimethylsilanediylbis{1-[2-methyl,4-(2,4-dimethylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW ($\times 10^{-3}$) | MWD | IV of Copolymer (dl/g) |
|---|---|---|---|---|---|---|---|---|
| 95 | — | — | — | 0.073 | 145.63 | 954.8 | 2.28 | — |
| 96 | 16.62 | 52.43 | 31.70 | 9.53 | 144.23 | 166.3 | 3.81 | 1.582 |
| 97 | 8.092, | 48.83, | 16.57, | 24.3 | 144.23 | 153.1 | 2.21 | 1.047 |

TABLE 11B-continued

Dimethylsilanediylbis{1-[2-methyl,4-(2,4-dimethylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW (× 10⁻³) | MWD | IV of Copolymer (dl/g) |
|---|---|---|---|---|---|---|---|---|
| | 8.171 | 49.08 | 16.64 | | | | | |
| 98 | 7.83 | 54.21 | 14.44 | 76.69 | 143.1 | 117.7 | 2.36 | 1.89 |
| 99 | 5.484 | 39.52 | 13.88 | 67.85 | 144.03 | 132.6 | 2.66 | 1.28 |
| 100 | 9.509 | 50.14 | 18.96 | 41.15 | 144.3 | 122.4 | 2.43 | 1.46 |
| 101 | — | — | — | 72.39 | 144.83 | 132.3 | 2.25 | — |

TABLE 12A

Dimethylsilanediylbis{1-[2-methyl,4-(2,6-dimethylphenyl)indenyl]}zirconium dichloride

| RUN # | TEMP (° C.) | Cat. Amount (mg) | Yield (g) | Efficiency (Kg/g cat) | $C_2^=$ (kPa) | $H_2$ (mmole) | Time split (min.) | $C_2^-/C_3^-$ flow rates (l/min.) |
|---|---|---|---|---|---|---|---|---|
| 102 | 60 | 46 | 6.9 | 0.15 | 0 | 0 | 60 | — |
| 103 | 60 | 45 | 95.4 | 2.12 | 68.9 | 0 | 60 | |
| 104 | 60 | 46 | 110.0 | 2.39 | 137.9 | 0 | 60 | |
| 105 | 60 | 45 | 99.6 | 2.21 | 241.3 | 0 | 60 | — |
| 106 | 70 | 22 | 37.5 | 1.70 | — | 54.3 | 60 | — |
| 107 | 70 | 77 | 87.7 | 1.14 | — | 54.3 | 60 | — |
| 108 | 70 | 75 | 128.5 | 1.71 | — | 54.3 | 60/60 | 4.0/1.0 |
| 109 | 70 | 150 | 190.0 | 1.27 | — | 46.5 | 60/60 | 4.0/1.0 |
| 110 | 70 | 150 | 174.4 | 1.16 | — | 38.8 | 60/60 | 4.0/1.0 |
| 111 | 70 | 150 | 153.6 | 1.02 | — | 31.0 | 60/60 | 4.0/1.0 |
| 112 | 70 | 151 | 136.1 | | — | 23.3 | 60/60 | 4.0/1.0 |

TABLE 12B

Dimethylsilanediylbis{1-[2-methyl,4-(2,6-dimethylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW (× 10⁻³) | MWD | IV of Copolymer (dl/g) |
|---|---|---|---|---|---|---|---|---|
| 102 | — | — | — | Not det. | 148.1 | 307.0 | 3.52 | — |
| 103 | 1.20 | — | — | 76.15 | 137.7 | 123.0 | 2.34 | — |
| 104 | 2.10 | — | — | 68.21 | 133.63 | 144.2 | 2.59 | — |
| 105 | 3.70 | — | — | 66.58 | 128.43 | 139.2 | 2.38 | — |
| 106 | — | — | — | 344.51 | 148.63 | 121.1 | 3.30 | — |
| 107 | — | — | — | 140.44 | 147.9 | 120.6 | 3.53 | — |
| 108 | 5.044 | 43.14 | 11.69 | 596.49 | 147.3 | 77.3 | 5.66 | 0.678 |
| 109 | 9.546 | 45.29 | 21.08 | 136.53 | 147.9 | 102.6 | 3.63 | 0.844 |
| 110 | 11.86 | 44.81 | 26.47 | 108.99 | 148.17 | 105.2 | 2.33 | 0.778 |
| 111 | 12.06 | 45.83 | 26.31 | 103.02 | 147.03 | 106.1 | 3.69 | 0.834 |
| 112 | 12.89 | 44.96 | 28.67 | 78.06 | 147.57 | 114.1 | 3.12 | 0.456 |

TABLE 13A

Dimethylsilanediylbis{1-[2-methyl,4-(2,5-dimethylphenyl)indenyl]}zirconium dichloride

| RUN # | TEMP (° C.) | Cat. Amount (mg) | Yield (g) | Efficiency (Kg/g cat) | C₂= (kPa) | H₂ (mmole) | Time split (min.) | C₂⁻/C₃⁻ flow rates (l/min.) |
|---|---|---|---|---|---|---|---|---|
| 113 | 60 | 47 | 53.2 | 1.13 | 0 | 0 | 60 | — |
| 114 | 60 | 49 | 95.0 | 1.94 | 34.5 | 0 | 60 | — |
| 115 | 60 | 47 | 110.0 | 2.34 | 68.9 | 0 | 60 | — |
| 116 | 60 | 46 | 139.3 | 3.03 | 137.9 | 0 | 60 | — |
| 117 | 60 | 47 | 184.6 | 3.93 | 241.3 | 0 | 60 | — |
| 118 | 70 | 22 | 96.6 | 4.39 | — | 54.3 | 60 | — |
| 119 | 70 | 30 | 159.6 | 5.32 | — | 54.3 | 60/90 | 4.0/1.0 |
| 120 | 70 | 30 | 164.1 | 5.47 | — | 54.3 | 60/120 | 4.0/1.0 |
| 121 | 70 | 30 | 129.2 | 4.31 | — | 54.3 | 60 | — |
| 122 | 70 | 30 | 169.6 | 5.65 | — | 54.3 | 60/90 | 3.6/1.4 |

TABLE 13B

Dimethylsilanediylbis{1-[2-methyl,4-(2,5-dimethylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW (× 10⁻³) | MWD | IV of Copolymer (dl/g) |
|---|---|---|---|---|---|---|---|---|
| 113 | — | — | — | 0.0275 | 149.77 | 815.9 | 2.09 | — |
| 114 | 0.1 | — | — | 0.225 | 147.23 | 574.2 | 2.31 | — |
| 115 | 0.32 | — | — | 0.51 | 144.03 | 460.2 | 1.90 | — |
| 116 | 1.2 | — | — | 1.22 | 139.70 | 346.0 | 1.99 | — |
| 117 | 2.0 | — | — | 4.78 | 134.83 | 297.2 | 2.00 | — |
| 118 | — | — | — | 1.07 | 151.03 | 385.5 | 2.23 | — |
| 119 | 6.99 | 51.82 | 13.49 | 6.98 | 151.9 | 248.0 | 3.50 | 0.895 |
| 120 | 9.66 | 50.95 | 18.84 | 5.33 | 152.17 | 236.8 | 3.20 | 1.161 |
| 121 | — | — | — | 2.02 | 151.37 | 357.3 | 2.27 | — |
| 122 | 4.968 | 42.16 | 11.78 | 7.77 | 152.03 | 220.0 | 3.28 | 0.826 |

TABLE 14A

Dimethylsilanediylbis{1-[2-methyl,4-(2,3,4-trimethylphenyl)indenyl]}zirconium dichloride

| RUN # | TEMP (° C.) | Cat. Amount (mg) | Yield (g) | Efficiency (Kg/g cat) | C₂= (kPa) | H₂ (mmole) | Time split (min.) | C₂⁻/C₃⁻ flow rates (l/min.) |
|---|---|---|---|---|---|---|---|---|
| 123 | 60 | 45 | 44.8 | 1.00 | 0 | 0 | 60 | — |
| 124 | 70 | 21 | 98.2 | 4.68 | — | 54.3 | 60 | — |
| 125 | 70 | 20 | 131.5 | 6.58 | — | 54.3 | 60/90 | 1.0/4.0 |
| 126 | 70 | 20 | 134.3 | 6.72 | — | 54.3 | 60/90 | 3.6/1.4 |
| 127 | 70 | 21 | 109.4 | 5.21 | — | 54.3 | 60/90 | 4.1/0.9 |
| 128 | 70 | 21 | 137.4 | 6.54 | — | 54.3 | 60/120 | 4.0/1.0 |

TABLE 14B

Dimethylsilanediylbis{1-[2-methyl,4-(2,3,4-trimethylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW (× 10⁻³) | MWD | IV of Copolymer (dl/g) |
|---|---|---|---|---|---|---|---|---|
| 123 | — | — | — | No flow | 148.43 | 820.1 | 2.18 | — |
| 124 | — | — | — | 2.28 | 148.77 | 306.1 | 2.41 | — |
| 125 | 10.9 | 47.12 | 23.13 | 1.12 | 148.70 | 310.4 | 2.60 | 2.08 |
| 126 | 7.221 | 37.00 | 19.51 | 2.04 | 149.23 | 273.7 | 3.21 | 1.82 |
| 127 | 10.50 | 51.77 | 20.28 | 1.23 | 149.50 | 302.4 | 2.90 | 1.99 |
| 128 | 16.71 | 48.63 | 34.36 | 0.91 | 148.97 | 260.1 | 2.43 | 2.63 |

TABLE 15A

Dimethylsilanediylbis{1-[2-methyl,4-(2,4,5-trimethylphenyl)indenyl]}zirconium dichloride

| RUN # | TEMP (° C.) | Cat. Amount (mg) | Yield (g) | Efficiency (Kg/g cat) | $C_2^=$ (kPa) | $H_2$ (mmole) | Time split (min.) | $C_2^=/C_3^=$ flow rates (l/min.) |
|---|---|---|---|---|---|---|---|---|
| 129 | 60 | 47 | 45.6 | 0.97 | 0 | 0 | 60 | — |
| 130 | 60 | 45 | 106.0 | 2.36 | 68.9 | 0 | 60 | — |
| 131 | 60 | 46 | 134.8 | 2.93 | 137.9 | 0 | 60 | — |
| 132 | 60 | 45 | 266.6 | 5.92 | 241.3 | 0 | 60 | — |
| 133 | 60 | 45 | 62.5 | 1.39 | 34.5 | 0 | 60 | — |
| 134 | 70 | 30 | 195.1 | 6.50 | — | 54.3 | 60/90 | 4.0/1.0 |
| 135 | 70 | 30 | 194.0 | 6.47 | — | 54.3 | 60 | — |
| 136 | 70 | 30 | 242.3 | 8.08 | — | 54.3 | 60/90 | 3.6/1.4 |
| 137 | 70 | 31 | 216.0 | 6.97 | — | 54.3 | 60/90 | 4.2/0.8 |
| 138 | 70 | 30 | 231.5 | 7.72 | — | 54.3 | 60/90 | 4.4/0.6 |
| 139 | 70 | 31 | 270.2 | 8.72 | — | 54.3 | 60/120 | 4.0/1.0 |

TABLE 15B

Dimethylsilanediylbis{1-[2-methyl,4-(2,4,5-trimethylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW (× 10⁻³) | MWD | IV of Copolymer (dl/g) |
|---|---|---|---|---|---|---|---|---|
| 129 | — | — | — | 0.048 | 148.60 | 914.8 | 2.46 | — |
| 130 | — | — | — | 0.37 | 139.98 | 625.1 | 3.14 | — |
| 131 | — | — | — | 0.43 | 133.78 | 568.4 | 2.58 | — |
| 132 | — | — | — | 0.52 | 129.92 | 545.2 | 2.32 | — |
| 133 | — | — | — | 0.165 | 144.04 | 672.0 | 3.05 | — |
| 134 | 9.56 | 47.94 | 19.94 | 2.50 | 148.3 | 274.4 | 2.98 | 1.93 |
| 135 | — | — | — | 9.68 | 148.17 | 232.7 | 2.80 | — |
| 136 | 6.492 | 37.9 | 17.13 | 4.54 | 149.77 | 235.0 | 2.55 | 1.676 |
| 137 | 10.69 | 55.99 | 19.09 | 8.04 | 147.85 | 203.2 | 3.06 | 1.880 |
| 138 | 18.17 | 62.73 | 28.97 | 2.24 | 147.17 | 264.9 | 2.70 | 2.077 |
| 139 | 10.56 | 50.91 | 20.74 | 15.56 | 147.30 | 168.9 | 3.04 | 1.825 |

TABLE 16A

Dimethylsilanediylbis{1-[2-methyl,4-(2,3,5,6-tetramethylphenyl)indenyl]}zirconium dichloride

| RUN # | TEMP (° C.) | Cat. Amount (mg) | Yield (g) | Efficiency (Kg/g cat) | $C_2=$ (kPa) | $H_2$ (mmole) | Time split (min.) | $C_2^-/C_3^-$ flow rates (l/min.) |
|---|---|---|---|---|---|---|---|---|
| 140 | 60 | 46 | 7.2 | 0.16 | 0 | 0 | 60 | — |
| 141 | 60 | 45 | 82.6 | 1.84 | 34.5 | 0 | 60 | — |
| 142 | 60 | 45 | 166.5 | 3.70 | 68.9 | 0 | 60 | — |
| 143 | 60 | 45 | 185.6 | 4.12 | 137.9 | 0 | 60 | — |
| 144 | 60 | 45 | 257.3 | 5.72 | 241.3 | 0 | 60 | — |
| 145 | 70 | 31 | 97.2 | 3.14 | — | 54.3 | 60/90 | 4.0/1.0 |
| 146 | 70 | 151 | 333.5 | 2.21 | — | 54.3 | 60/79 | 4.0/1.0 |
| 147 | 70 | 76 | 184.4 | 2.43 | — | 54.3 | 60/90 | 4.0/1.0 |
| 148 | 70 | 75 | 123.1 | 1.64 | — | 23.3 | 60/90 | 4.0/1.0 |
| 149 | 70 | 152 | 240.7 | 1.58 | — | 23.3 | 60/60 | 4.0/1.0 |
| 150 | 70 | 152 | 164.2 | 1.08 | — | 23.3 | 60 | — |
| 151 | 70 | 77 | 176.6 | 2.29 | — | 54.3 | 60 | — |
| 152 | 70 | 150 | 200.2 | 1.33 | — | 15.5 | 60/90 | 4.0/1.0 |
| 153 | 70 | 152 | 202.6 | 1.33 | — | 7.8 | 60/90 | 4.0/1.0 |

TABLE 16B

Dimethylsilanediylbis{1-[2-methyl,4-(2,3,5,6-tetramethylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW ($\times 10^{-3}$) | MWD | IV of Copolymer (dl/g) |
|---|---|---|---|---|---|---|---|---|
| 140 | — | — | — | — | 149.24 | 181.4 | 1.85 | — |
| 141 | — | — | — | 66.43 | 144.10 | 120.8 | 2.00 | — |
| 142 | — | — | — | 70.51 | 139.03 | 118.4 | 1.92 | — |
| 143 | — | — | — | 78.03 | 134.57 | 119.3 | 2.13 | — |
| 144 | — | — | — | 63.79 | 130.23 | 136.4 | 1.92 | — |
| 145 | 4.699 | 47.11 | 9.97 | 1612.72 | 150.03 (155.5 | 65.7 | 2.95 | 0.807 |
| 146 | 8.684 | 44.91 | 19.34 | 248.26 | 150.23 | 102.1 | 2.70 | 0.836 |
| 147 | 6.34 | 45.05 | 14.07 | 343.29 | 149.1 | 67.6 | 1.36 | 0.892 |
| 148 | 12.96 | 42.65 | 30.39 | 81.54 | 149.03 | 107.0 | 2.46 | 0.996 |
| 149 | 12.44 | 45.84 | 27.14 | 124.68 | 149.1 | 93.9 | 2.63 | 0.875 |
| 150 | — | — | — | 100.79 | 151.03 | 108.1 | 1.96 | — |
| 151 | — | — | — | Too fast | 149.63 | 59.6 | 2.41 | — |
| 152 | 19.18 | 45.6 | 42.06 | 90.68 | 148.63 | 106.1 | 2.96 | 0.973 |
| 153 | 20.76 | 44.63 | 46.52 | 95.07 | 148.9 | 114.4 | 3.04 | 0.891 |

TABLE 17A

Dimethylsilanediylbis{1-[2-isopropyl,4-(3-biphenylyl)indenyl]}zirconium dichloride

| RUN # | TEMP (° C.) | Cat. Amount (mg) | Yield (g) | Efficiency (Kg/g cat) | $C_2=$ (delta kPa) | $H_2$ (mmole) | Time split (min.) | $C_2^-/C_3^-$ flow rates (l/min.) |
|---|---|---|---|---|---|---|---|---|
| 154 | 60 | 302 | 16.0 | 0.05 | 0 | 0 | 60 | — |
| 155 | 70 | 61 | 81.8 | 1.34 | — | 46.5 | 60/120 | 4.0/1.0 |
| 156 | 70 | 60 | 74.7 | 1.25 | — | 46.5 | 60/120 | 4.4/0.6 |
| 157 | 70 | 60 | 62.0 | 1.03 | — | 46.5 | 60 | — |
| 158 | 70 | 62 | 48.0 | 0.77 | — | 31.0 | 60 | — |
| 159 | 70 | 60 | 22.0 | 0.37 | — | 15.5 | 60 | — |

TABLE 17B

Dimethylsilanediylbis{1-[2-isopropyl,4-(3-biphenylyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW (× 10⁻³) | MWD | IV Of Copolymer (dl/g) |
|---|---|---|---|---|---|---|---|---|
| 154 | — | — | — | 15.26 | 150.37 | 227.8 | 2.04 | — |
| 155 | 5.011 | 41.67 | 12.03 | 118.14 | 151.97 | 134.6 | 2.88 | 1.88 |
| 156 | 9.911 | 53.91 | 18.38 | 52.09 | 152.77 | 164.9 | 3.71 | 2.95 |
| 157 | — | — | — | 259.61 | 150.83 | 104.3 | 2.38 | — |
| 158 | — | — | — | 116.54 | 150.97 | 125.2 | 2.28 | — |
| 159 | — | — | — | 102.01 | 151.17 | 128.0 | 2.05 | — |

TABLE 18A

Dimethylsilanediylbis{1-[2-isopropyl,4-(2-methylphenyl)indenyl]}zirconium dichloride

| RUN # | TEMP (° C.) | Cat. Amount (mg) | Yield (g) | Efficiency (Kg/g cat) | $C_2=$ (delta kPa) | $H_2$ (mmole) | Time split (min.) | $C_2^=/C_3^=$ flow rates (l/min.) |
|---|---|---|---|---|---|---|---|---|
| 160 | 60 | 46 | 2.7 | 0.06 | 0 | 0 | 60 | — |
| 161 | 60 | 300 | 56.3 | 0.19 | 0 | 0 | 60 | — |
| 162 | 70 | 61 | 158.2 | 2.59 | — | 46.5 | 60/120 | 4.0/1.0 |
| 163 | 70 | 60 | 139.9 | 2.33 | 0 | 46.5 | 60 | — |
| 164 | 70 | 61 | 168.9 | 2.77 | — | 46.5 | 60/120 | 4.4/0.6 |
| 165 | 70 | 60 | 42.3 | 0.70 | 0 | 15.5 | 60 | — |
| 166 | 70 | 61 | 94.7 | 1.55 | 0 | 31.0 | 60 | — |
| 167 | 70 | 300 | 159.8 | 0.53 | 0 | 7.8 | 60 | — |
| 168 | 70 | 300 | 51.4 | 0.17 | 0 | 7.8 | 21 | — |
| 169 | 70 | 300 | 276.2 | 0.92 | — | 7.8 | 64/180 | 4.0/1.0 |

TABLE 18B

Dimethylsilanediylbis{1-[2-isopropyl,4-(2-methylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW (× 10⁻³) | MWD | IV Of Copolymer (dl/g) |
|---|---|---|---|---|---|---|---|---|
| 160 | — | — | — | Not submitted | 153.5 | 178.2 | 2.13 | — |
| 161 | — | — | — | 30.48 | 154.83 | 197.2 | 2.12 | — |
| 162 | 3.584 | 43.25 | 8.29 | 971.02 | 152.17 | 75.6 | 2.50 | 1.121 |
| 163 | — | — | — | 1013.8 | 152.1 (157.17 minor) | 70.9 | 2.27 | — |
| 164 | 4.62 | 57.52 | 8.03 | 954.7 | 151.57 | 69.2 | 2.39 | 2.083 |
| 165 | — | — | — | 142.5 | 152.91 | 120.1 | 2.38 | — |
| 166 | — | — | — | 420.7 | 152.1 | 91.7 | 2.19 | — |
| 167 | — | — | — | 129.85 | 153.23 | 127.3 | 3.62 | — |
| 168 | — | — | — | 268.69 | 152.97 | 108.1 | 4.41 | — |
| 169 | 15.07, 14.24 | 48.96, 47.85 | 30.8, 29.8 | 11.94 | 154.1 | 238.1 | 14.49 | 1.993 |

TABLE 19A

Dimethylsilanediylbis{1-[2-isopropyl,4-(2,3-dimethylphenyl)indenyl]}zirconium dichloride

| RUN # | TEMP (° C.) | Cat. Amount (mg) | Yield (g) | Efficiency (Kg/g cat) | $C_2=$ (delta kPa) | $H_2$ (mmole) | Time split (min.) | $C_2^-/C_3^-$ flow rates (l/min.) |
|---|---|---|---|---|---|---|---|---|
| 170 | 60 | 306 | 55.0 | 0.18 | — | 0 | 60 | — |
| 171 | 70 | 122 | 130.8 | 1.07 | — | 7.8 | 60 | — |
| 172 | 70 | 122 | 123.9 | 1.02 | — | 7.8 | 60/90 | 4.0/1.0 |
| 173 | 70 | 122 | 106.3 | 0.87 | — | 7.8 | 60/90 | 4.1/0.9 |
| 174 | 70 | 122 | 88.9 | 0.73 | — | 7.8 | 60/90 | 3.6/1.4 |
| 175 | 70 | 121 | 108.3 | 0.89 | — | 7.8 | 60/120 | 4.0/1.0 |
| 176 | 70 | 123 | 146.8 | 1.19 | — | 15.5 | 60/90 | 4.0/1.0 |
| 177 | 70 | 124 | 140.7 | 1.13 | — | 15.5 | 60/90 | 4.2/0.8 |
| 178 | 70 | 122 | 92.2 | 0.76 | — | 15.5 | 60 | — |

TABLE 19B

Dimethylsilanediylbis{1-[2-isopropyl,4-(2,3-dimethylphenyl)indenyl]}zirconium dichloride

| RUN # | Total Ethylene (wt %) | Ethylene in Rubber (wt %) | Total rubber (wt %) | Final MFR (g/10 min.) | Melting Point (° C.) | MW ($\times 10^{-3}$) | MWD | IV Of Copolymer (dl/g) |
|---|---|---|---|---|---|---|---|---|
| 170 | — | — | — | 16.93 | 153.1 | 190.3 | 2.09 | — |
| 171 | — | — | — | 70.15 | 151.63 | 157.1 | 2.78 | — |
| 172 | 10.54 | 44.28 | 23.80 | 10.07 | 153.03 | 215.0 | 3.21 | 2.18 |
| 173 | 16.11 | 47.0 | 34.28 | 2.21 | 152.5 | 262.2 | 3.52 | 2.68 |
| 174 | 8.036 | 31.63 | 25.41 | 19.22 | 151.7 | 191.5 | 2.83 | 2.35 |
| 175 | 18.04 | 44.83 | 40.24 | 1.56 | 152.23 | 261.1 | 3.96 | 1.62 |
| 176 | 7.447 | 43.78 | 17.01 | 32.4 | 151.77 | 170.8 | 2.94 | 1.73 |
| 177 | 14.43 | 49.56 | 29.12 | 7.46 | 152.3 | 213.5 | 3.53 | 1.99 |
| 178 | — | — | — | 110.54 | 151.3 | 119.2 | 2.43 | — |

TABLE 20A

Dimethylsilanediylbis{1-[2-isopropyl,4-(2-biphenylyl)indenyl]}zirconium dimethyl/NCA

| RUN # | TEMP (° C.) | Cat. Amount (mg) | Yield (g) | Efficiency (Kg/g cat) | $C_2=$ (delta kPa) | $H_2$ (mmole) | Time split (min.) | $C_2^-/C_3^-$ flow rates (l/min.) |
|---|---|---|---|---|---|---|---|---|
| 179 | 60 | 45 | <0.5 | <0.01 | 0 | 0 | 60 | — |
| 180 | 60 | 303 | <0.5 | <0.01 | 0 | 0 | 60 | — |
| 181 | 70 | 60 | 84.2 | 1.4 | 0 | 46.5 | 60 | — |
| 182 | 70 | 121 | 147.6 | 1.22 | 0 | 46.5 | 60 | — |
| 183 | 70 | 120 | 192.3 | 1.60 | — | 46.5 | 60/120 | 4.0/1.0 |
| 184 | 70 | 122 | 32.8 | 0.27 | 0 | 15.5 | 60 | — |
| 185 | 70 | 120 | 195.6 | 1.63 | — | 46.5 | 60/120 | 4.4/0.6 |
| 186 | 70 | 123 | 198.8 | 1.62 | 0 | 46.5 | 60 | — |
| 187 | 70 | 121 | 42.0 | 0.35 | 0 | 23.3 | 60 | — |

TABLE 20B

Dimethylsilanediylbis{1-[2-isopropyl,4-(2-biphenylyl)indenyl]}zirconium dimethyl/NCA

| RUN # | Total Ethylene (wt %) | Ethylene in Rubber (wt %) | Total rubber (wt %) | Final MFR (g/10 min.) | Melting Point (° C.) | MW (× 10⁻³) | MWD | IV Of Copolymer (dl/g) |
|---|---|---|---|---|---|---|---|---|
| 179 | — | — | — | — | — | — | — | — |
| 180 | — | — | — | — | — | — | — | — |
| 181 | — | — | — | 390.37 | 158.38 | 88.1 | 2.17 | — |
| 182 | — | — | — | 228.3 | 158.3 | 101.0 | 2.19 | — |
| 183 | 4.283 | 37.52 | 11.42 | 165.76 | 157.77 | 103.7 | 2.51 | 1.54 |
| 184 | — | — | — | 99.02 | 158.57 | 132.0 | 2.07 | — |
| 185 | 4.304 | 55.95 | 7.69 | 148.85 | 157.7, minor 160.4 | 107.7 | 2.42 | 1.98 |
| 186 | — | — | — | 511.88 | 156.84, minor 161.44 | 77.4 | 2.23 | — |
| 187 | — | — | — | 126.76 | 158.03 | 132.1 | 2.40 | — |

TABLE 21A

Dimethylsilanediylbis{1-[2-isopropyl,4-(2-biphenylyl)indenyl]}zirconium dichloride/MAO

| RUN # | TEMP (° C.) | Cat. Amount (mg) | Yield (g) | Efficiency (Kg/g cat) | $C_2^=$ (delta kPa) | $H_2$ (mmole) | Time split (min.) | $C_2^=/C_3^=$ flow rates (l/min.) |
|---|---|---|---|---|---|---|---|---|
| 188 | 60 | 45  | 5.6   | 0.12 | 0  | 0    | 60     | —       |
| 189 | 60 | 300 | 83.7  | 0.28 | 0  | 0    | 60     | —       |
| 190 | 70 | 60  | 188.0 | 3.13 | —  | 46.5 | 60/120 | 4.0/1.0 |
| 191 | 70 | 61  | 201.6 | 3.30 | —  | 46.5 | 60     | —       |
| 192 | 70 | 60  | 234.8 | 3.91 | —  | 46.5 | 60/120 | 4.4/0.6 |
| 193 | 70 | 60  | 66.9  | 1.12 | —  | 15.5 | 60     | —       |
| 194 | 70 | 61  | 107.5 | 1.76 | —  | 31.0 | 60     | —       |
| 195 | 70 | 301 | 125.8 | 0.42 | —  | 7.8  | 25     | —       |
| 196 | 70 | 63  | 150.8 | 2.39 | —  | 46.5 | 60     | —       |
| 197 | 70 | 150 | 222.9 | 1.49 | —  | 31.0 | 60     | —       |
| 198 | 70 | 150 | 233.0 | 1.55 | —  | 31.0 | 60     | —       |

TABLE 21B

Dimethylsilanediylbis{1-[2-isopropyl,4-(2-biphenylyl)indenyl]}zirconium dichloride/MAO

| RUN # | Total Ethylene (wt %) | Ethylene in Rubber (wt %) | Total rubber (wt %) | Final MFR (g/10 min.) | Melting Point (° C.) | MW (× 10⁻³) | MWD | IV Of Copolymer (dl/g) |
|---|---|---|---|---|---|---|---|---|
| 188 | — | — | — | — | 158.10 | 266.9 | 2.21 | — |
| 189 | — | — | — | 2.56 | 158.90 | 285.1 | 2.19 | — |
| 190 | 3.588 | 40.79 | 8.80 | 102.36 | 157.77 | 132.3 | 3.26 | 1.86 |
| 191 | — | — | — | 74.31 | 157.10 | 129.1 | 2.53 | — |
| 192 | 5.476 | 55.13 | 9.93 | 82.31 | 157.57 | 142.6 | 3.15 | 2.46 |
| 193 | — | — | — | 11.04 | 157.90 | 211.8 | 2.55 | — |
| 194 | — | — | — | 24.95 | 156.70 | 169.1 | 2.41 | — |
| 195 | — | — | — | 39.42 | 157.57 | 168.4 | 2.12 | — |
| 196 | — | — | — | 158.6 | 156.04, minor 160.7 | 114.3 | 2.43 | — |
| 197 | — | — | — | 33.95 | 156.85, minor 160.14 | 149,7 | 2.30 | — |
| 198 | — | — | — | 35.57 | 157.25 | 150.7 | 2.30 | — |

TABLE 21C

Dimethylsilanediylbis{1-[2-isopropyl,4-(2-biphenylyl)indenyl]}zirconium dichloride/MAO

| RUN # | Meso Run Length (Monomer Units) | Diad (%) | Stereo Misinsertions/ 10000 Monomer Units | 2,1-Misinsertions/ 10000 Monomer Units | 1,3-Misinsertions/ 10000 Monomer Units | Xylene Solubles (wt %) | Xylene Insolubles (wt %) |
|---|---|---|---|---|---|---|---|
| 191 | 245 | 99.6 | 23.9 | 0 | 16.7 | 0.53 | 99.64 |
| 197 | 278 | 99.6 | 20.0 | 0 | 15.9 | 0.87 | 99.09 |

TABLE 22A

Dimethylsilanediylbis{1-[2-isopropyl,4-(2-biphenylyl)indenyl]}zirconium dimethyl/MAO

| RUN # | TEMP (° C.) | Cat. Amount (mg) | Yield (g) | Efficiency (Kg/g cat) | $C_2^=$ (delta kPa) | $H_2$ (mmole) | Time split (min.) | $C_2^=/C_3^=$ flow rates (l/min.) |
|---|---|---|---|---|---|---|---|---|
| 199 | 70 | 61 | 168.4 | 2.76 | 0 | 46.5 | 60 | — |
| 200 | 70 | 101 | 180.2 | 1.78 | 0 | 31.0 | 60 | — |
| 201 | 70 | 101 | 186.1 | 1.84 | — | 31.0 | 60 | — |
| 202 | 70 | 62 | 141.3 | 2.28 | — | 31.0 | 60/120 | 4.4/0.6 |
| 203 | 70 | 60 | 138.5 | 2.31 | — | 31.0 | 60/120 | 4.4/0.6 |

TABLE 22B

Dimethylsilanediylbis{1-[2-isopropyl,4-(2-biphenylyl)indenyl]}zirconium dimethyl/MAO

| RUN # | Total Ethylene (wt %) | Ethylene in Rubber (wt %) | Total rubber (wt %) | Final MFR (g/10 min.) | Melting Point (° C.) | MW (× $10^{-3}$) | MWD | IV Of Copolymer (dl/g) |
|---|---|---|---|---|---|---|---|---|
| 199 | — | — | — | 143.13 | 156.04 minor 160.17 | 175.9 | 21.02 | — |
| 200 | — | — | — | 38.98 | 160.37 | 149.9 | 2.22 | — |
| 201 | — | — | — | 26.82 | 155.71 | 153.4 | 2.31 | — |
| 202 | 5.817 | 55.61 | 10.46 | 26.41 | 157.77 | 172.5 | 3.29 | 3.14 |
| 203 | 5.549 | 56.39 | 9.84 | 44.55 | 157.77 | 165.6 | 2.99 | 2.85 |

The matallocenes in the above Examples and Tables are represented by formula (I) as follows:

$M^1$ = zirconium, $R^1$, $R^2$ = Cl(methyl in Examples 20 and 22), $R^4$, $R^5$, $R^6$, $R^7$ = H $R^{13}$ = $Me_2Si$

| Ex. (Table) | $R^3$ | $R^{12}$ | $R^{11}$ | $R^{10}$ | $R^9$ | $R^8$ |
|---|---|---|---|---|---|---|
| 1 | Me | H | H | H | H | H |
| 2 | Me | H | Me | H | H | H |
| 3 | Me | H | Me | H | Me | H |
| 4 | Me | Me | H | H | H | H |
| 5 | Me | Et | H | H | H | H |
| 6 | Me | iso-Pr | H | H | H | H |
| 7 | Me | Ph | H | H | H | H |
| 8 | Me | H | H | Ph | H | H |
| 9 | Me | H | H | tert-Bu | H | H |
| 10 | Me | Me | Me | H | H | H |
| 11 | Me | Me | H | Me | H | H |
| 12 | Me | Me | H | H | H | Me |
| 13 | Me | Me | H | H | Me | H |
| 14 | Me | Me | Me | Me | H | H |
| 15 | Me | Me | H | Me | Me | H |
| 16 | Me | Me | Me | H | Me | Me |
| 17 | iso-Pr | H | Ph | H | H | H |
| 18 | iso-Pr | Me | H | H | H | H |
| 19 | iso-Pr | Me | Me | H | H | H |
| 20 | iso-Pr | Ph | H | H | H | H |
| 21 | iso-Pr | Ph | H | H | H | H |
| 22 | iso-Pr | Ph | H | H | H | H |

Me = Methyl; Et = Ethyl; iso-Pr = Isopropyl; tert-Bu = tert. Butyl; Ph = Phenyl

What is claimed is:

1. A polymerization process comprising contacting, under polymerization conditions, one or more ethylenically unsaturated monomers and a catalyst composition, said catalyst composition comprising the product of a compound represented by formula (I) and a cocatalyst:

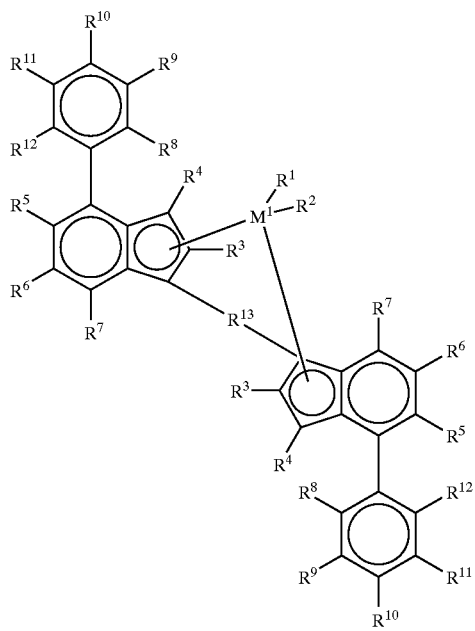

(I)

wherein:

$M^1$ is selected from titanium, zirconium, hafnium, vanadium, niobium, tantalum, chromium, molybdenum and tungsten;

$R^1$ and $R^2$ are selected from chlorine, $C_1$–$C_6$ alkyl groups, $C_6$–$C_{10}$ aryl groups, $C_7$–$C_{12}$ arylalkyl groups and $C_7$–$C_{12}$ alkylaryl groups;

$R^3$ is selected from $C_3$–$C_6$ alkyl groups and phenyl;

$R^4$, $R^5$, $R^6$ and $R^7$ are each independently selected from hydrogen, halogen, $C_1$–$C_{10}$ alkyl groups, $C_6$–$C_{14}$ aryl groups, $C_2$–$C_{10}$ alkenyl groups, $C_7$–$C_{40}$ arylalkyl groups, $C_7$–$C_{40}$ alkylaryl groups, $C_8$–$C_{40}$ arylalkenyl groups, and —NR'$_2$, —SR', —OR', —SiR'$_3$, —OSiR'$_3$ and —PR'$_2$ radicals wherein each R' is independently selected from halogen, $C_1$–$C_{10}$ alkyl groups and $C_6$–$C_{14}$ aryl groups; or two or more adjacent radicals $R^5$, $R^6$ and $R^7$ together with the atoms connecting them may form one or more rings;

$R^8$, $R^9$, $R^{10}$ and $R^{11}$ are each independently as defined for $R^4$, $R^5$, $R^6$ and $R^7$;

$R^{12}$ is selected from halogen, $C_1$–$C_{10}$ alkyl groups, $C_6$–$C_{14}$ aryl groups, $C_2$–$C_{10}$ alkenyl groups, $C_7$–$C_{40}$ arylalkyl groups, $C_7$–$C_{40}$ alkylaryl groups, $C_8$–$C_{40}$ arylalkenyl groups, and —NR'$_2$, —SR', —OR', —SiR'$_3$, —OSiR'$_3$ and —PR'$_2$ radicals wherein each R' is independently selected from halogen, $C_1$–$C_{10}$ alkyl groups and $C_6$–$C_{14}$ aryl groups;

$R^{13}$ is selected from

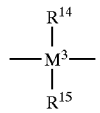

-continued

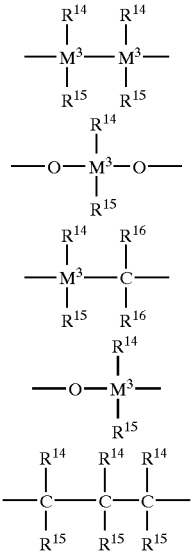

—B($R^{14}$)—, —Al($R^{14}$)—, —Ge—, —Sn—, —O—, —S—, —SO—, —SO$_2$—, —N($R^{14}$)—, —CO—, —P($R^{14}$)— and —P(O)($R^{14}$);

wherein $R^{14}$, $R^{15}$ and $R^{16}$ are each independently selected from hydrogen, halogen, $C_1$–$C_{20}$ alkyl groups, $C_6$–$C_{30}$ aryl groups, $C_1$–$C_{20}$ alkoxy groups, $C_2$–$C_{20}$ alkenyl groups, $C_7$–$C_{40}$ arylalkyl groups, $C_8$–$C_{40}$ arylalkenyl groups and $C_7$–$C_{40}$ alkylaryl groups, or $R^{14}$ and $R^{15}$, together with the atom(s) connecting them, form a ring; and $M^3$ is selected from carbon, silicon, germanium and tin; or $R^{13}$ is represented by the formula

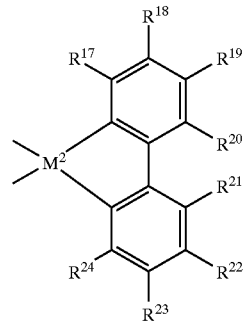

wherein:

$R^{17}$, $R^{18}$, $R^{19}$, $R^{20}$, $R^{21}$, $R^{22}$, $R^{23}$ and $R^{24}$ are each independently selected from hydrogen, halogen, hydroxy, $C_1$–$C_{10}$ alkyl groups, $C_1$–$C_{10}$ alkoxy groups, $C_6$–$C_{14}$ aryl groups, $C_6$–$C_{14}$ aryloxy groups, $C_2$–$C_{10}$ alkenyl groups, $C_7$–$C_{40}$ arylalkyl groups, $C_7$–$C_{40}$ alkylaryl groups and $C_8$–$C_{40}$ arylalkenyl groups; or two or more adjacent radicals $R^{17}$, $R^{18}$, $R^{19}$, $R^{20}$, $R^{21}$, $R^{22}$, $R^{23}$ and $R^{24}$, including $R^{20}$ and $R^{21}$, together with the atoms connecting them, form one or more rings; and $M^2$ represents one or more carbon atoms, or a silicon, germanium or tin atom.

2. The process of claim 1, wherein $R^3$ is selected from branched $C_3$–$C_6$ alkyl groups.

3. The process of claim 1, wherein $R^3$ is an isopropyl group.

4. The process of claim 1, wherein $R^{12}$ is selected from $C_1$–$C_6$ alkyl groups and $C_6$–$C_{10}$ aryl groups.

5. The process of claim 3, wherein $R^{12}$ is phenyl.

6. The process of claim 4, wherein each of $R^4$ and $R^8$ is hydrogen.

7. The process of claim 1, wherein $R^3$ is selected from isopropyl, isobutyl, sec-butyl, tert-butyl and phenyl groups, and $R^{12}$ is selected from n-propyl, isopropyl, n-butyl, isobutyl, sec-butyl, tert-butyl, phenyl, tolyl, benzyl and naphthyl groups.

8. The process of claim 1, wherein the compound of formula (I) comprises not more than 2% of the meso form.

9. The process of claim 1, wherein the cocatalyst is selected from compounds comprising noncoordinating anion, alumoxanes and mixtures thereof.

10. The process of claim 1, wherein the cocatalyst comprises methylalumoxane.

11. The process of claim 1, wherein the cocatalyst comprises a noncoordinating anion.

12. The process of claim 11, wherein the noncoordinating anion comprises at least one unit of the formula —$B(C_6F_5)_3$.

13. The process of claim 1, wherein the catalyst composition further comprises a support material.

14. The process of claim 1, wherein the catalyst composition further comprises an inorganic support material.

15. The process of claim 13, wherein the support material is selected from silica, alumina, silica-alumina, magnesium chloride and mixtures thereof.

16. The process of claim 1, wherein said one or more ethylenically unsaturated monomers are selected from monoolefins, diolefins and mixtures thereof.

17. The process of claim 16, wherein said monoolefins comprise compounds of the formula $R^aCH{=}CHR^b$ wherein $R^a$ and $R^b$ are each independently selected from hydrogen, alkyl and alkenyl radicals having 1 to 14 carbon atoms or, together with the carbon atoms to which they are connected, form a ring having 4 to 8 carbon atoms.

18. The process of claim 16, wherein said monoolefins are selected from ethylene and α-olefins having from 3 to 12 carbon atoms.

19. The process of claim 18, wherein said α-olefins are selected from propylene, 1-butene, 4-methyl-1pentene, 1-hexene, 1-octene and mixtures thereof.

20. The process of claim 1, wherein said ethylenically unsaturated monomers consist essentially of ethylene and propylene.

21. The process of claim 1, wherein said process is carried out at a temperature ranging from 30° C. to 80° C.

22. The process of claim 21, wherein said process is carried out at a pressure ranging from 5 to 64 bar.

23. The process of claim 1, wherein $R^1$ and $R^2$ are selected from chlorine, $C_1$–$C_6$ alkyl groups, $C_6$–$C_{10}$ aryl group, $C_7$–$C_{12}$ arylalkyl groups and $C_7$–$C_{12}$ alkylaryl groups, $R^3$ is selected from $C_3$–$C_6$ alkyl groups and phenyl, each of $R^4$ and $R^8$ is hydrogen, $R^{12}$ is selected from n-propyl, isopropyl, n-butyl, isobutyl, sec-butyl, tert-butyl, phenyl, tolyl, benzyl and naphthyl groups, the cocatalyst comprises noncoordinating anions, alumoxanes or mixtures thereof, wherein the catalyst composition further comprises a support material selected from silica, alumina, silica-alumina, magnesium chloride and mixtures thereof, and wherein said one or more ethylenically unsaturated monomers comprise at least ethylene and propylene.

24. A polymerization process comprising contacting, under polymerization conditions, one or more ethylenically unsaturated monomers and a catalyst composition, said catalyst composition comprising the product of a compound represented by formula (I) and a cocatalyst:

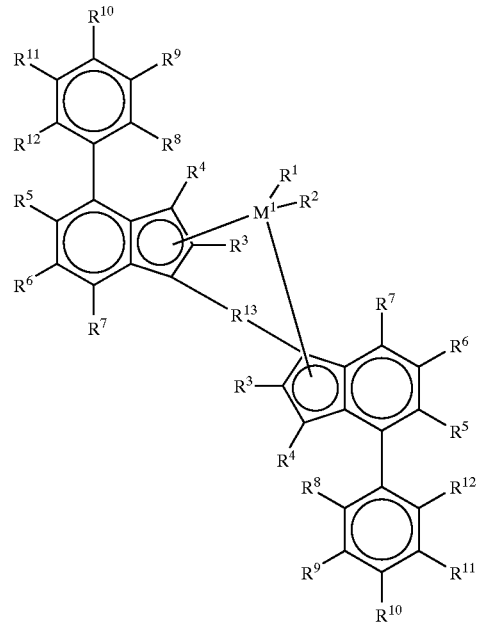

wherein:

$M^1$ is selected from titanium, zirconium, hafnium, vanadium, niobium, tantalum, chromium, molybdenum and tungsten;

$R^1$ and $R^2$ are selected from hydrogen, halogen, hydroxy, $C_1$–$C_{10}$ alkyl groups, $C_1$–$C_{10}$ alkoxy groups, $C_6$–$C_{14}$ aryl groups, $C_6$–$C_{14}$ aryloxy groups, $C_2$–$C_{10}$ alkenyl groups, $C_7$–$C_{40}$ arylalkyl groups, $C_7$–$C_{40}$ alkylaryl groups and $C_7$–$C_{40}$ arylalkenyl groups; or $R^1$ and $R^2$ are joined together to form an alkanediyl group or a conjugated $C_4$–$C_{40}$ diene ligand which is coordinated to $M^1$ in a metallacyclopentene fashion; or $R^1$ and $R^2$ represent a conjugated diene, optionally substituted with one or more groups independently selected from hydrocarbyl, trihydrocarbylsilyl and trihydrocarbylsilylhydrocarbyl groups, said diene having a total of up to 40 atoms not counting hydrogen and forming a π complex with $M^1$;

$R^3$ is selected from hydrogen, halogen, $C_1$–$C_{10}$ alkyl groups, $C_6$–$C_{14}$ aryl groups, $C_2$–$C_{10}$ alkenyl groups, $C_7$–$C_{40}$ arylalkyl groups, $C_7$–$C_{40}$ alkylaryl groups, $C_8$–$C_{40}$ arylalkenyl groups, and —$NR'_2$, —$SR'$, —$OR'$, —$SiR'_3$, —$OSiR'_3$ and —$PR'_2$ radicals wherein each R' is independently selected from halogen, $C_1$–$C_{10}$ alkyl groups and $C_6$–$C_{14}$ aryl groups;

$R^4$, $R^5$, $R^6$ and $R^7$ are each independently selected from hydrogen, halogen, $C_1$–$C_{10}$ alkyl groups, $C_6$–$C_{14}$ aryl groups, $C_2$–$C_{10}$ alkenyl groups, $C_7$–$C_{40}$ arylalkyl groups, $C_7$–$C_{40}$ alkylaryl groups, $C_8$–$C_{40}$ arylalkenyl groups, and —$NR'_2$, —$SR'$, —$OR'$, —$SiR'_3$, —$OSiR'_3$ and —$PR'_2$ radicals wherein each R' is independently selected from halogen, $C_1$–$C_{10}$ alkyl groups and $C_6$–$C_{14}$ aryl groups; or two or more adjacent radicals $R^5$, $R^6$ and $R^7$ together with the atoms connecting them may form one or more rings; $R^8$, $R^9$, $R^{10}$ and $R^{11}$ are each independently as defined for $R^4$, $R^5$, $R^6$ and $R^7$, provided that two or more adjacent radicals $R^8$, $R^9$, $R^{10}$ and $R^{11}$ together with the atoms connecting them may form one or more rings;

$R^{12}$ is selected from halogen, $C_1$–$C_{10}$ alkyl groups, $C_6$–$C_{14}$ aryl groups, $C_2$–$C_{10}$ alkenyl groups, $C_7$–$C_{40}$ arylalkyl groups, $C_7$–$C_{40}$ alkylaryl groups, $C_8$–$C_{40}$ arylalkenyl groups, and —NR'$_2$, —SR', —OR', —SiR'$_3$, —OSiR'$_3$ and —PR'$_2$ radicals wherein each R' is independently selected from halogen, $C_1$–$C_{10}$ alkyl groups and $C_6$–$C_{14}$ aryl groups;

$R^{13}$ is selected from groups of the formula

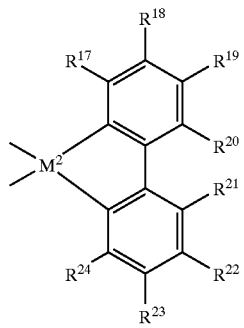

wherein $R^{17}$, $R^{18}$, $R^{19}$, $R^{20}$, $R^{21}$, $R^{22}$, $R^{23}$ and $R^{24}$ are each independently selected from hydrogen, halogen, hydroxy, $C_1$–$C_{10}$ alkyl groups, $C_1$–$C_{10}$ alkoxy groups, $C_6$–$C_{14}$ aryl groups, $C_6$–$C_{14}$ aryloxy groups, $C_2$–$C_{10}$ alkenyl groups, $C_7$–$C_{40}$ arylalkyl groups, $C_7$–$C_{40}$ alkylaryl groups and $C_8$–$C_{40}$ arylalkenyl groups; or two or more adjacent radicals $R^{17}$, $R^{18}$, $R^{19}$, $R^{20}$, $R^{21}$, $R^{22}$, $R^{23}$ and $R^{24}$, including $R^{20}$ and $R^{21}$, together with the atoms connecting them, form one or more rings; and $M^2$ represents a carbon, silicon or germanium atom.

25. The process of claim 24, wherein $R^3$ is selected from $C_3$–$C_6$ alkyl groups and phenyl.

26. The process of claim 25, wherein $R^3$ is an isopropyl group.

27. The process of claim 25, wherein $R^{12}$ is selected from $C_1$–$C_6$ alkyl groups and $C_6$–$C_{10}$ aryl groups.

28. The process of claim 26, wherein $R^{12}$ is phenyl.

29. The process of claim 27, wherein each of $R^4$ and $R^8$ is hydrogen.

30. The process of claim 24, wherein the cocatalyst comprises noncoordinating anions, alumoxanes or mixtures thereof.

31. The process of claim 30, wherein the noncoordinating anion comprises at least one unit of the formula —B(C$_6$F$_5$)$_3$.

32. The process of claim 24, wherein the catalyst composition further comprises a support material.

33. The process of claim 24, wherein said one or more ethylenically unsaturated monomers are selected from monoolefins, diolefins and mixtures thereof.

34. The process of claim 33, wherein said monoolefins comprise compounds of the formula $R^a$CH=CHR$^b$ wherein $R^a$ and $R^b$ are each independently selected from hydrogen, alkyl and alkenyl radicals having 1 to 14 carbon atoms or, together with the carbon atoms to which they are connected, form a ring having 4 to 8 carbon atoms.

35. The process of claim 33, wherein said monoolefins are selected from ethylene, propylene, 1-butene, 4-methyl-1-pentene, 1-hexene, 1-octene and mixtures thereof.

36. The process of claim 30, wherein said ethylenically unsaturated monomers consist essentially of ethylene and propylene.

* * * * *